United States Patent
Brumby et al.

(10) Patent No.: US 7,235,561 B2
(45) Date of Patent: Jun. 26, 2007

(54) COMPOUND AND A COMPOSITION INCLUDING SUCH A COMPOUND

(75) Inventors: Thomas Brumby, Berlin (DE); Rolf Jautelat, Berlin (DE); Olaf Prien, Berlin (DE); Martina Schäfer, Berlin (DE); Gerhard Siemeister, Berlin (DE); Ulrich Lücking, Berlin (DE); Christoph Huwe, Berlin (DE)

(73) Assignee: Schering AG, Berlin (DE)

(*) Notice: Subject to any disclaimer, the term of this patent is extended or adjusted under 35 U.S.C. 154(b) by 56 days.

(21) Appl. No.: 10/156,759

(22) Filed: May 29, 2002

(65) Prior Publication Data

US 2004/0102630 A1 May 27, 2004

(30) Foreign Application Priority Data

May 29, 2001 (DE) .......................... 101 27 581
Mar. 11, 2002 (DE) .......................... 102 12 098

(51) Int. Cl.
*A61K 31/505* (2006.01)
*C07D 239/02* (2006.01)
*A61P 35/00* (2006.01)

(52) U.S. Cl. .................. 514/275; 544/297; 544/242
(58) Field of Classification Search .............. 544/217, 544/242, 323; 514/275; 546/307
See application file for complete search history.

(56) References Cited

U.S. PATENT DOCUMENTS

| | | |
|---|---|---|
| 3,947,467 A | 3/1976 | Verge et al. |
| 4,012,495 A | 3/1977 | Schmiechen et al. |
| 4,015,017 A | 3/1977 | Gazave et al. |
| 4,153,713 A | 5/1979 | Huth et al. |
| 4,193,926 A | 3/1980 | Schmiechen et al. |
| 4,303,649 A | 12/1981 | Jones |
| 4,548,940 A | 10/1985 | Ife |
| 4,694,009 A | 9/1987 | Hubele et al. |
| 4,788,195 A | 11/1988 | Torley et al. |
| 4,792,561 A | 12/1988 | Walker et al. |
| 4,876,252 A | 10/1989 | Torley et al. |
| 4,897,396 A | 1/1990 | Hubele |
| 4,921,862 A | 5/1990 | Walker et al. |
| 4,966,622 A | 10/1990 | Rempfler et al. |
| 4,971,959 A | 11/1990 | Hawkins |
| 4,973,690 A | 11/1990 | Rempfler et al. |
| 4,987,132 A | 1/1991 | Mase et al. |
| 4,988,704 A | 1/1991 | Ito et al. |
| 5,124,455 A | 6/1992 | Lombardo |
| 5,128,358 A | 7/1992 | Saccomano et al. |
| 5,159,078 A | 10/1992 | Rempfler et al. |
| 5,164,372 A | 11/1992 | Matsuo et al. |
| 5,175,167 A | 12/1992 | Zipperer et al. |
| 5,177,085 A | 1/1993 | Naef |
| 5,236,918 A | 8/1993 | Amschler et al. |
| 5,274,002 A | 12/1993 | Hawkins |
| 5,298,511 A | 3/1994 | Waterson |
| 5,326,898 A | 7/1994 | Chandraratna |

(Continued)

FOREIGN PATENT DOCUMENTS

| | | |
|---|---|---|
| DE | 40 29 650 A1 | 3/1992 |
| EP | 0 224 339 T1 | 6/1987 |
| EP | 0 310 550 A1 | 4/1989 |
| JP | 03 127790 A | 5/1991 |
| WO | WO 8706576 A1 | 12/1987 |
| WO | WO 9116892 A1 | 11/1991 |
| WO | WO 9200968 A1 | 1/1992 |
| WO | WO 9206085 A1 | 4/1992 |
| WO | WO 9207567 A1 | 5/1992 |
| WO | WO 9212961 A1 | 8/1992 |

(Continued)

OTHER PUBLICATIONS

S. Ding et al., "A Combunatorial Scaffold Approach Toward Kinase–Directed Heterocycle Libraries," Journal of the American Chemical Society, 2002,124(8), pp. 1594–1596, XP002210160.

Database Chemcats Online! Chemical Abstracts Service, Columbus, OH, US; Jan. 21, 2002, retrieved from STN, XP002210161, Order No. F0487–0047 & "Ambinter Exploratory Library," Ambinter, F–75016 Paris.

Database Chemcats Online! Chemical Abstracts Services, Columbus, OH, US; retrieved fro STN XP002210162 Order No. CD207267, CD207266 & "Oak Samples Product List" Oct. 8, 2001, Oak Samples Ltd., 03680 KIEV–142, Ukraine.

(Continued)

*Primary Examiner*—Kamal A. Saeed
*Assistant Examiner*—Robert Shiao
(74) *Attorney, Agent, or Firm*—Millen, White, Zelano & Branigan

(57) ABSTRACT

This invention relates to pyrimidine derivatives of general formula I (I)

Figure 1:
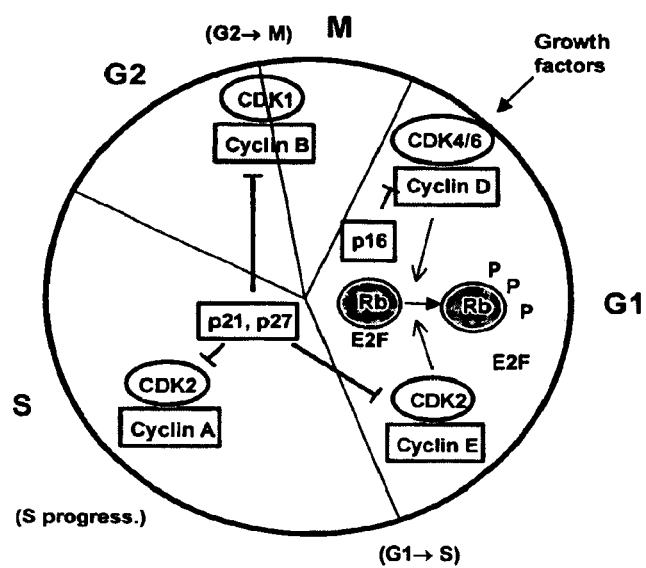

in which $R^1$, $R^2$, X, A and B have the meanings that are contained in the description, as inhibitors of the cyclin-dependent kinases, their production as well as their use as medications for treating various diseases.

58 Claims, 1 Drawing Sheet

U.S. PATENT DOCUMENTS

| | | | |
|---|---|---|---|
| 5,340,827 | A | 8/1994 | Beeley et al. |
| 5,491,147 | A | 2/1996 | Boyd et al. |
| 5,521,184 | A | 5/1996 | Zimmermann |
| 5,550,137 | A | 8/1996 | Beeley et al. |
| 5,580,888 | A | 12/1996 | Warrellow et al. |
| 5,593,997 | A | 1/1997 | Dow et al. |
| 5,608,070 | A | 3/1997 | Alexander et al. |
| 5,622,977 | A | 4/1997 | Warrellow et al. |
| 5,633,257 | A | 5/1997 | Warrellow et al. |
| 5,674,880 | A | 10/1997 | Boyd et al. |
| 5,691,376 | A | 11/1997 | Caggiano et al. |
| 5,693,659 | A | 12/1997 | Head et al. |
| 5,698,711 | A | 12/1997 | Palfreyman |
| 5,716,967 | A | 2/1998 | Kleinman |
| 5,723,460 | A | 3/1998 | Warrellow et al. |
| 5,728,708 | A | 3/1998 | Zimmermann |
| 5,739,144 | A | 4/1998 | Warrellow et al. |
| 5,753,663 | A | 5/1998 | Flippin et al. |
| 5,776,958 | A | 7/1998 | Warrellow et al. |
| 5,780,477 | A | 7/1998 | Head et al. |
| 5,780,478 | A | 7/1998 | Alexander et al. |
| 5,786,354 | A | 7/1998 | Warrellow et al. |
| 5,798,373 | A | 8/1998 | Warrellow |
| 5,849,770 | A | 12/1998 | Head et al. |
| 5,851,784 | A | 12/1998 | Owens et al. |
| 5,859,034 | A | 1/1999 | Warrellow et al. |
| 5,866,593 | A | 2/1999 | Warrellow et al. |
| 5,891,896 | A | 4/1999 | Warrellow et al. |
| 5,922,741 | A | 7/1999 | Davis et al. |
| 5,958,935 | A * | 9/1999 | Davis et al. |
| 6,048,866 | A | 4/2000 | Hutchings et al. |
| 6,080,790 | A | 6/2000 | Boyd et al. |
| 6,093,716 | A | 7/2000 | Davis et al. |
| 6,096,747 | A | 8/2000 | Beeley et al. |
| 6,235,746 | B1 | 5/2001 | Davis et al. |
| 6,337,335 | B1 | 1/2002 | Hutchings et al. |
| 2003/0134838 | A1 | 7/2003 | Bornemann et al. |
| 2003/0171359 | A1 | 9/2003 | Dahmann et al. |
| 2004/0029902 | A1 | 2/2004 | Singh et al. |

FOREIGN PATENT DOCUMENTS

| | | |
|---|---|---|
| WO | WO 9219594 A1 | 11/1992 |
| WO | WO 9319748 A1 | 10/1993 |
| WO | WO 9402465 A1 | 2/1994 |
| WO | WO 9410118 A1 | 5/1994 |
| WO | WO 9412461 A1 | 6/1994 |
| WO | WO 9413361 A1 | 6/1994 |
| WO | WO 9414742 A1 | 7/1994 |
| WO | WO 9420446 A1 | 9/1994 |
| WO | WO 9115451 A1 | 11/1994 |
| WO | WO 9206963 A1 | 12/1994 |
| WO | WO 9504046 A1 | 2/1995 |
| WO | WO 9219602 A1 | 9/1995 |
| WO | WO 9310118 A1 | 10/1995 |
| WO | WO 9533727 A1 | 12/1995 |
| WO | WO 9614843 A2 | 5/1996 |
| WO | WO 9509852 A1 | 8/1996 |
| WO | WO 9531451 A1 | 9/1996 |
| WO | WO 9509847 A1 | 3/1997 |
| WO | WO 9517386 A1 | 3/1997 |
| WO | WO 9709325 A1 | 3/1997 |
| WO | WO 9420455 A1 | 5/1997 |
| WO | WO 9509851 A1 | 1/1998 |
| WO | WO 9509853 A1 | 3/1998 |
| WO | WO 9535281 A1 | 7/1998 |
| WO | WO 9709297 A2 | 7/1998 |
| WO | WO 98 33798 A2 | 8/1998 |
| WO | WO 9841512 A1 | 9/1998 |
| WO | WO 99 50251 A2 | 10/1999 |
| WO | WO 00/27825 A1 | 5/2000 |
| WO | WO 9828281 A1 | 5/2000 |
| WO | WO 00 39101 A1 | 7/2000 |
| WO | WO 00 53595 A1 | 9/2000 |
| WO | WO 9858926 A1 | 10/2000 |
| WO | WO 01 14375 A1 | 3/2001 |
| WO | WO 9535283 A1 | 6/2001 |
| WO | WO 01/64654 A1 | 9/2001 |
| WO | WO 02 04429 A1 | 1/2002 |
| WO | WO 02/059110 A1 | 8/2002 |
| WO | WO 03/030909 A1 | 4/2003 |
| WO | WO 03/032994 A2 | 4/2003 |
| WO | WO 03/032997 A1 | 4/2003 |
| WO | WO 03/063794 A2 | 8/2003 |
| WO | WO 03/066601 A1 | 8/2003 |
| WO | WO 03/078404 A1 | 9/2003 |
| WO | WO 03/094920 A1 | 11/2003 |
| WO | WO 04/046118 A2 | 6/2004 |

OTHER PUBLICATIONS

Database Crossfire Beilstein Online! Beilstein Institut zur Förderung der Chemischen Wissenschaften, Frankfurt am Main, DE; Database Accession No. BRN 249340, 265505, XP002210163 &1. Naito et al., Chem. Pharm. Bull., Bd. 6, 1958, pp. 338–341.

D. Boschelli et al., "Synthesis and Tyrosine Kinase Inhibitory Activity Of A Series of 2–Amino–8–H–Pyridoä2, 3–Düpyrimidines: Identification of Potent, Selective Platelet–Derived Growth Factor Receptor Tyrosine Kinase Inhibitors," Journal of Medicinal Chemistry, American Chemical Society, Washington, US, Bd. 41, Nr. 22, 1998, pp. 4365–4377, XP002191993.

Patent Abstracts of Japan, Patent No. 031277790 A, May 30, 1991.

PCT Search Report for App. No. PCT/EP02/05669 date Dec. 9, 2002.

U.S. Appl. No. 60/353,333, filed Feb. 1, 2002.
U.S. Appl. No. 60/353,267, filed Feb. 1, 2002.
U.S. Appl. No. 60/399,673, filed Jul. 29, 2002.
U.S. Appl. No. 60/434,277, filed Dec. 17, 2002.
U.S. Appl. No. 60/330,128, filed Oct. 17, 2001.
U.S. Appl. No. 60/330,145, filed Oct. 17, 2001.

Amendment and IDS filed Dec. 14, 2005 in U.S. Appl. No. 10/271,763 (filed Oct. 16, 2002); Examiner Deepak R. Rao.

Office Action dated Jan. 13, 2006 in U.S. Appl. No. 11/007,923 (filed Dec. 9, 2004); Examiner Kahsay Habte.

Office Action dated Mar. 10, 2006 in U.S. Appl. No. 10/271,763 (filed Oct. 16, 2002); Examiner Deepak R. Rao.

Response filed by Dahmann et al. in 10/271,763, (US2003/0171359) on Apr. 19, 2005.

Office Action of Jul. 14, 2005 in 10/271,763.

* cited by examiner

COMPOUND AND A COMPOSITION INCLUDING SUCH A COMPOUND

This invention relates to pyrimidine derivatives, their production as well as their use as medications for treating various diseases.

The CDKs (cyclin-dependent kinase) is an enzyme family that plays an important role in the regulation of the cell cycle and thus is an especially advantageous target for the development of small inhibitory molecules. Selective inhibitors of the CDKs can be used for treating cancer or other diseases that cause disruptions of cell proliferation.

Pyrimidines and analogs are already described as active ingredients, such as, for example, the 2-anilino-pyrimidines as fungicides (DE 4029650) or substituted pyrimidine derivatives for treating neurological or neurodegenerative diseases (WO 99/19305). As CDK-inhibitors, the most varied pyrimidine derivatives are described, for example bis (anilino)-pyrimidine derivatives (WO 00/12486), 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

The object of this invention is to provide compounds that have better properties than the inhibitors that are already known. The substances that are described here are more effective, since they already inhibit in the nanomolar range and can be distinguished from other already known CDK-inhibitors such as, e.g., olomoucine and roscovitine.

It has now been found that compounds of general formula I

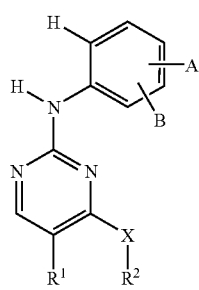

(I)

in which $R^1$ stands for hydrogen, halogen, $C_1$–$C_6$-alkyl, nitro, or for the group —$COR^5$, —$OCF_3$, —$(CH_2)_n R^5$, —S—$CF_3$ or —$SO_2 CF_3$, $R^2$ stands for $C_1$–$C_{10}$-alkyl, $C_2$–$C_{10}$-alkenyl, $C_2$–$C_{10}$-alkinyl, or $C_3$–$C_{10}$-cycloalkyl or for $C_1$–$C_{10}$-alkyl, $C_2$–$C_{10}$-alkenyl, $C_2$–$C_{10}$-alkinyl, or $C_3$–$C_{10}$-cycloalkyl that is substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—$(CH_2)_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkinyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —$NHC_1$—$C_6$-alkyl, —$N(C_1$–$C_6$-alkyl$)_2$, —$SO(C_1$–$C_6$-alkyl), —$SO_2(C_1$–$C_6$-alkyl), $C_1$–$C_6$-alkanoyl, —$CONR^3 R^4$, —$COR^5$, $C_1$–$C_6$-alkylOAc, carboxy, aryl, heteroaryl, —$(CH_2)_n$-aryl, —$(CH_2)_n$-heteroaryl, phenyl-$(CH_2)_n$—$R^5$, —$(CH_2)_n PO_3(R^5)_2$ or with the group —$R^6$ or —$NR^3 R^4$, and the phenyl, $C_3$–$C_{10}$-cycloalkyl, aryl, heteroaryl, —$(CH_2)_n$-aryl and —$(CH_2)_n$-heteroaryl itself optionally can be substituted in one or more places in the same way or differently with halogen, hydroxy, $C_1$–$C_6$-alkyl, $C_1$–$C_6$-alkoxy, heteroaryl, benzoxy or with the group —$CF_3$ or —$OCF_3$, and the ring of the $C_3$–$C_{10}$-cycloalkyl and the $C_1$–$C_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, or $R^2$ stands for the group

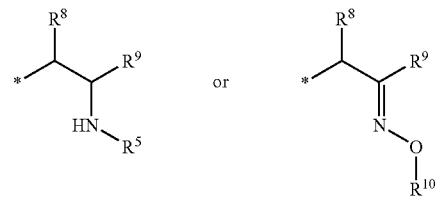

X stands for oxygen or for the group —NH—, —N($C_1$–$C_3$-alkyl) or for —$OC_3$-$C_{10}$-cycloalkyl, which can be substituted in one or more places in the same way or differently with a heteroaromatic compound, or X and $R^2$ together form a $C_3$–$C_{10}$-cycloalkyl ring, which optionally can contain one or more heteroatoms and optionally can be substituted in one or more places with hydroxy, $C_1$–$C_6$-alkyl, $C_1$–$C_6$-alkoxy or halogen, A and B, in each case independently of one another, stand for hydrogen, hydroxy, $C_1$–$C_3$-alkyl, $C_1$–$C_6$-alkoxy or for the group —$SR^7$, —$S(O)R^7$, —$SO_2 R^7$, —$NHSO_2 R^7$, —$CH(OH)R^7$, —$CR^7(OH)$—$R^7$, $C_1$–$C_6$-alkylP(O)$OR^3 OR^4$ or —$COR^7$, or for

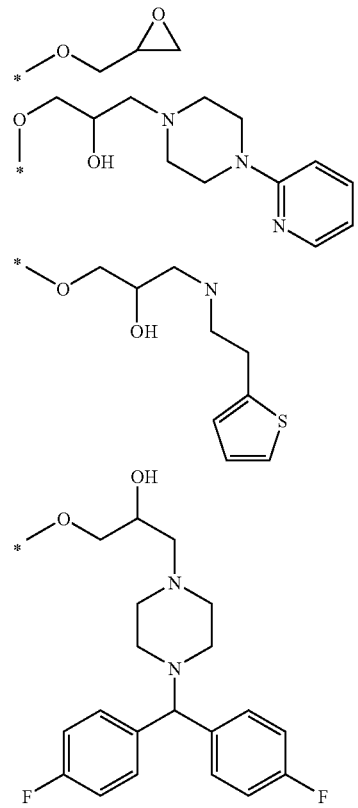

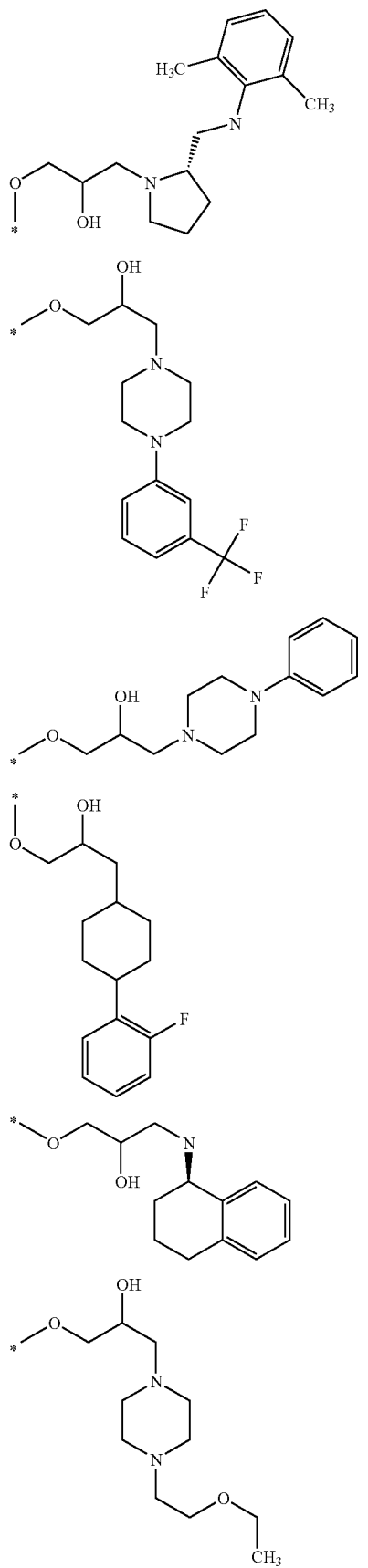
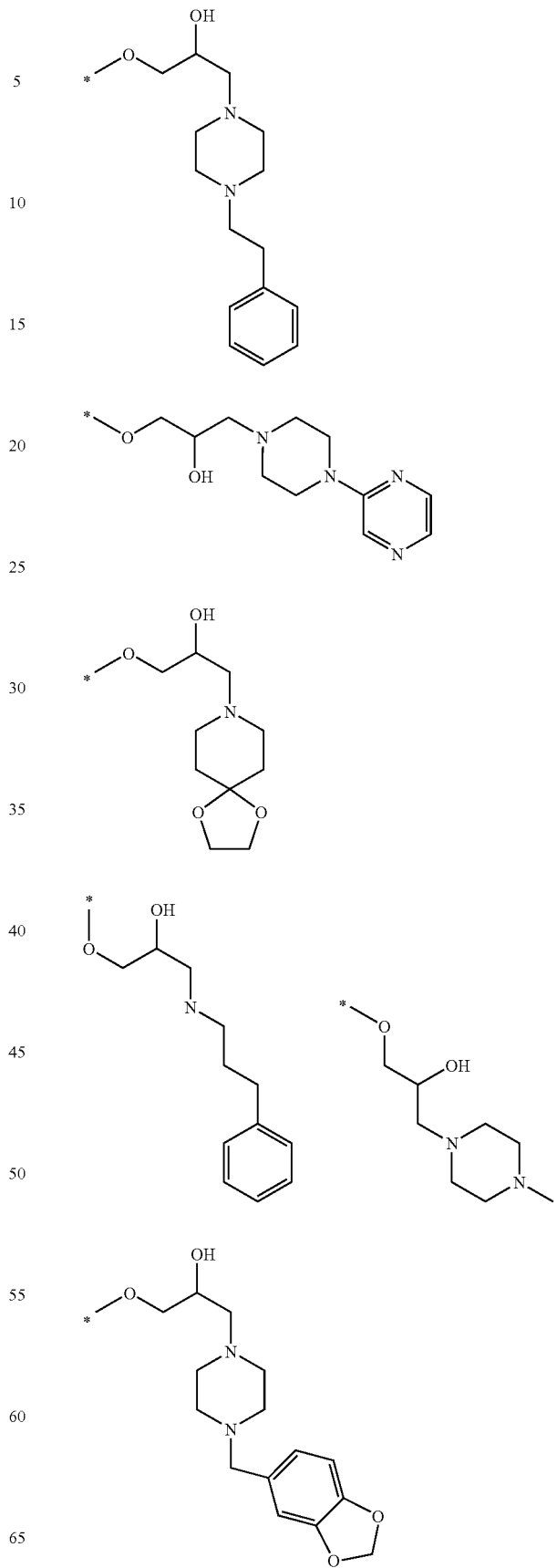

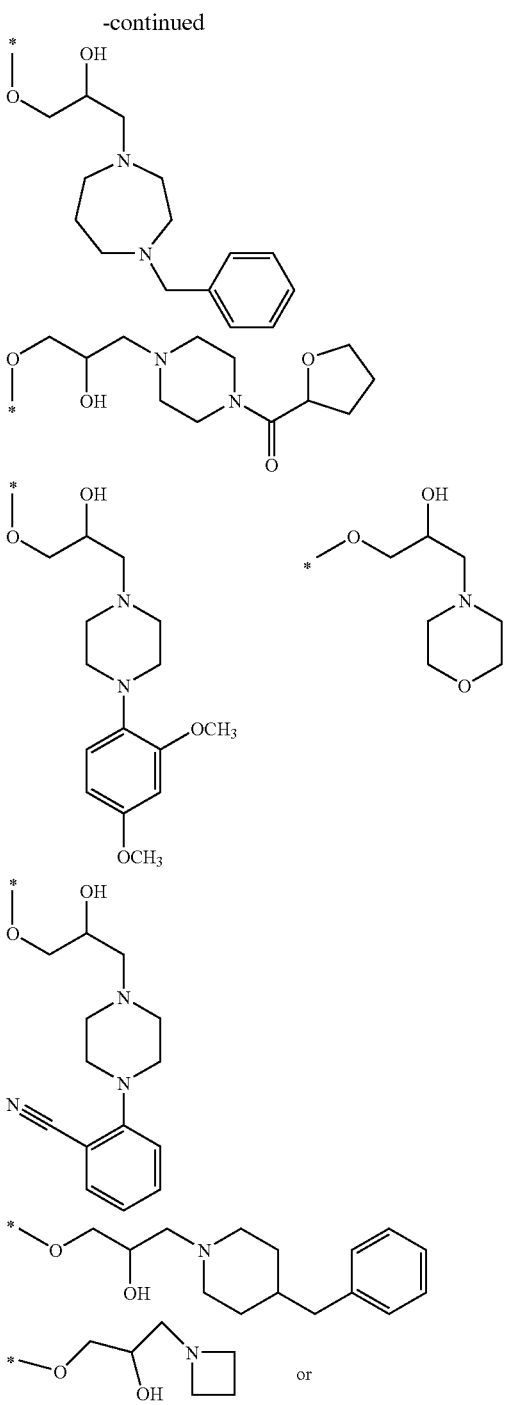

A and B together form a $C_3$–$C_{10}$-cycloalkyl ring that optionally can be interrupted by one or more nitrogen, oxygen and/or sulfur atoms and/or can be interrupted by one or more =C=O or =SO$_2$ groups in the ring and/or optionally one or more possible double bonds can be contained in the ring, and the $C_3$–$C_{10}$-cycloalkyl ring optionally can be substituted in one or more places in the same way or differently with hydroxy, halogen, $C_1$–$C_6$-alkoxy, $C_1$–$C_6$-alkylthio, amino, cyano, $C_1$–$C_6$-alkyl, $C_2$–$C_6$-alkenyl, $C_3$–$C_{10}$-cycloalkyl, $C_1$–$C_6$-alkoxy-$C_1$–$C_6$-alkyl, —NHC$_1$–$C_6$-alkyl, —N($C_1$–$C_6$-alkyl)$_2$, —SO($C_1$–$C_6$-alkyl), —SO$_2$R$^7$, $C_1$–$C_6$-alkanoyl, —CONR$^3$R$^4$, —COR$^5$, $C_1$–$C_6$-alkoxyOAc, phenyl or with the group R$^6$, whereby the phenyl itself optionally can be substituted in one or more places in the same way or differently with halogen, hydroxy, $C_1$–$C_6$-alkyl, $C_1$–$C_6$-alkoxy or with the group —CF$_3$ or —OCF$_3$, R$^3$ and R$^4$, in each case independently of one another, stand for hydrogen, phenyl, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, heteroaryl, heterocyclo-$C_3$–$C_{10}$-alkyl, heteroaryl-$C_1$–$C_3$-alkyl, $C_3$–$C_6$-cycloalkyl-$C_1$–$C_3$-alkyl that is optionally substituted with cyano, or for $C_1$–$C_6$-alkyl that is optionally substituted in one or more places in the same way or differently with phenyl, pyridyl, phenyloxy, $C_3$–$C_6$-cycloalkyl, $C_1$–$C_6$-alkyl or $C_1$–$C_6$-alkoxy, whereby the phenyl itself can be substituted in one or more places in the same way or differently with halogen, $C_1$–$C_6$-alkyl, $C_1$–$C_6$-alkoxy or with the group —SO$_2$NR$^3$R$^4$, or for the group —(CH$_2$)$_n$NR$^3$R$^4$, —CNHNH$_2$ or —NR$^3$R$^4$, or R$^3$ and R$^4$ together form a $C_3$–$C_{10}$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, R$^5$ stands for hydroxy, phenyl, $C_1$–$C_6$-alkyl, $C_3$–$C_6$-cycloalkyl, benzoxy, $C_1$–$C_6$-alkylthio or $C_1$–$C_6$-alkoxy, R$^6$ stands for a heteroaryl or $C_3$–$C_{10}$-cycloalkyl ring, whereby the ring has the above-indicated meaning, R$^7$ stands for halogen, hydroxy, phenyl, $C_1$–$C_6$-alkyl, $C_2$–$C_6$-alkenyl, $C_2$–$C_6$-alkinyl, $C_3$–$C_{10}$-cycloalkyl, with the above-indicated meaning, or for the group —NR$^3$R$^4$, or for a $C_1$–$C_{10}$-alkyl, $C_2$–$C_{10}$-alkenyl, $C_2$–$C_{10}$-alkinyl or $C_3$–$C_7$-cycloalkyl that is substituted in one or more places in the same way or differently with hydroxy, $C_1$–$C_6$-alkoxy, halogen, phenyl, —NR$^3$R$^4$ or phenyl, which itself can be substituted in one or more places in the same way or differently with halogen, hydroxy, $C_1$–$C_6$-alkyl, $C_1$–$C_6$-alkoxy, halo-$C_1$–$C_6$-alkyl, halo-$C_1$–$C_6$-alkoxy, or R$^7$ stands for phenyl, which itself can be substituted in one or more places in the same way or differently with halogen, hydroxy, $C_1$–$C_6$-alkyl or $C_1$–$C_6$-alkoxy, halo-$C_1$–$C_6$-alkyl, or halo-$C_1$–$C_6$-alkoxy, R$^8$, R$^9$ and R$^{10}$, in each case independently of one another, stand for hydrogen, hydroxy, $C_1$–$C_{10}$-alkyl, $C_2$–$C_{10}$-alkenyl, $C_2$–$C_{10}$-alkinyl, $C_3$–$C_{10}$-cycloalkyl, aryl, or heteroaryl or for $C_1$–$C_{10}$-alkyl, $C_2$–$C_{10}$-alkenyl, $C_2$–$C_{10}$-alkinyl or $C_3$–$C_{10}$-cycloalkyl that is substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—(CH$_2$)$_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkinyl, $C_1$–$C_6$-alkoxy, $C_1$–$C_6$-alkyl, $C_1$–$C_6$-alkoxy-$C_1$–$C_6$-alkoxy-$C_1$–$C_6$-alkyl, —NHC$_1$–$C_6$-alkyl, —N($C_1$–$C_6$-alkyl)$_2$, —SO($C_1$–$C_6$-alkyl), —SO$_2$($C_1$–$C_6$-alkyl), $C_1$–$C_6$-alkanoyl, —CONR$^3$R$^4$, —COR$^5$, $C_1$–$C_6$-alkylOAc, carboxy, aryl, heteroaryl, —(CH$_2$)$_n$-aryl, —(CH$_2$)$_n$-heteroaryl, phenyl-(CH$_2$)$_n$—R$^5$, —(CH$_2$)$_n$PO$_3$(R$^5$)$_2$ or with the group —R$^6$ or —NR$^3$R$^4$, and the phenyl, $C_3$–$C_{10}$-cycloalkyl, aryl, heteroaryl, —(CH$_2$)$_n$-aryl and —$(CH_2)_n$-heteroaryl itself optionally can be substituted in one or more places in the same way or differently with halogen, hydroxy, $C_1$–$C_6$-alkyl, $C_1$–$C_6$-alkoxy or with the group —$CF_3$ or —$OCF_3$, and the ring of $C_3$–$C_{10}$-cycloalkyl and the $C_1$–$C_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, and n stands for 0–6, as well as isomers, diastereomers, enantiomers and salts thereof that overcome known drawbacks.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, tert-butyloxy, pentyloxy, isopentyloxy, or hexyloxy.

Alkylthio is defined in each case as a straight-chain or branched alkylthio radical, such as, for example, methylthio, ethylthio, propylthio, isopropylthio, butylthio, isobutylthio, sec-butylthio, tert-butylthio, pentylthio, isopentylthio or hexylthio.

Cycloalkyl is defined in general as monocyclic alkyl rings, such as cyclopropyl, cyclobutyl, cyclopentyl, cyclohexyl, cycloheptyl, cyclooctyl, cyclononyl or cyclodecyl, but also bicyclic rings or tricyclic rings such as, for example, norbornyl, adamantanyl, etc.

The ring systems, in which optionally one or more possible double bonds can be contained in the ring, are defined as, for example, cycloalkenyls, such as cyclopropenyl, cyclobutenyl, cyclopentenyl, cyclohexenyl, or cycloheptenyl, whereby the linkage can be carried out both to the double bond and to the single bonds.

If A and B, $R^3$ and $R^4$, X and $R^2$, in each case independently of one another, together form a $C_3$–$C_{10}$-cycloalkyl ring, which optionally can be interrupted by one or more heteroatoms, such as nitrogen atoms, oxygen atoms and/or sulfur atoms, and/or can be interrupted by one or more =C=O groups in the ring and/or optionally one or more possible double bonds can be contained in the ring, however, the above-mentioned definitions are also intended to include heteroaryl radical or heterocycloalkyl and heterocycloalkenyl.

Halogen is defined in each case as fluorine, chlorine, bromine or iodine.

The alkenyl substituents in each case are straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl 1-en-1-yl, but-1-en-3-yl, ethinyl, prop-1-in-1-yl, but-1-in-1-yl, but-2-in-1-yl, but-3-en-1-yl, and allyl.

Alkinyl is defined in each case as a straight-chain or branched alkinyl radical that contains 2–6, preferably 2–4 C atoms. For example, the following radicals can be mentioned: acetylene, propin-1-yl, propin-3-yl, but-1-in-1-yl, but-1-in-4-yl, but-2-in-1-yl, but-1-in-3-yl, etc.

The aryl radical in each case comprises 3–12 carbon atoms and in each case can be benzocondensed.

For example, there can be mentioned: cyclopropenyl, cyclopentadienyl, phenyl, tropyl, cyclooctadienyl, indenyl, naphthyl, azulenyl, biphenyl, fluorenyl, anthracenyl, etc.

The heteroaryl radical in each case comprises 3–16 ring atoms, and instead of the carbon can contain one or more heteroatoms that are the same or different, such as oxygen, nitrogen or sulfur, in the ring, and can be monocyclic, bicyclic, or tricyclic and in addition in each case can be benzocondensed.

For example, there can be mentioned:

Thienyl, fuiranyl, pyrrolyl, oxazolyl, thiazolyl, imidazolyl, pyrazolyl, isoxazolyl, isothiazolyl, oxadiazolyl, triazolyl, thiadiazolyl, etc. and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc. and benzo derivatives thereof, such as, e.g., quinolyl, isoquinolyl, etc., or azocinyl, indolizinyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, etc.

Heterocycloalkyl stands for an alkyl ring that comprises 3–12 carbon atoms, which instead of the carbon contains one or more heteroatoms that are the same or different, such as, e.g., oxygen, sulfur or nitrogen.

As heterocycloalkyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

Heterocycloalkenyl stands for an alkyl ring that comprises 3–12 carbon atoms, which instead of the carbon contains one or more heteroatoms that are the same or different such as, e.g., oxygen, sulfur or nitrogen, and which is partially saturated.

As heterocycloalkenyls, there can be mentioned, e.g.: pyran, thiin, dihydroacet, etc.

If an acid group is included, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropane diol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, i.a.

Those compounds of general formula (I) in which $R^1$ stands for hydrogen, halogen, $C_1$–$C_6$-alkyl, nitro, or for the group —$COR^5$, —$OCF_3$, —$(CH_2)_nR^5$, —S—$CF_3$ or —$SO_2CF_3$, $R^2$ stands for $C_1$–$C_{10}$-alkyl, $C_2$–$C_{10}$-alkenyl, $C_2$–$C_{10}$-alkinyl, or $C_3$–$C_{10}$-cycloalkyl or for $C_1$–$C_{10}$-alkyl, $C_2$–$C_{10}$-alkenyl, $C_2$–$C_{10}$-alkinyl, or $C_3$–$C_{10}$-cycloalkyl that is substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—$(CH_2)_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkinyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —$NHC_1$–$C_6$-alkyl, —$N(C_1$–$C_6$-alkyl$)_2$, —$SO(C_1$–$C_6$-alkyl), —$SO_2(C_1$–$C_6$-alkyl), $C_1$–$C_6$-alkanoyl, —$CONR^3R^4$, —$COR^5$, $C_1$–$C_6$-alkylOAc, carboxy, aryl, heteroaryl, —$(CH_2)_n$-aryl, —$(CH_2)_n$-heteroaryl, phenyl-$(CH_2)_n$-$R^5$, —$(CH_2)_nPO_3(R^5)_2$ or with the group —$R^6$ or —$NR^3R^4$, and the phenyl, $C_3$–$C_{10}$-cycloalkyl, aryl, heteroaryl, —$(CH_2)_n$-aryl and —$(CH_2)_n$-heteroaryl itself optionally can be substituted in one or more places in the same way or differently with halogen, hydroxy, $C_1$–$C_6$-alkyl, $C_1$–$C_6$ alkoxy, heteroaryl, benzoxy or with the group —$CF_3$ or —$OCF_3$, and the ring of the $C_3$–$C_{10}$-cycloalkyl and the $C_1$–$C_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, or $R^2$ stands for the group

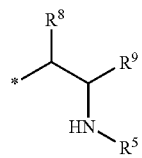 or 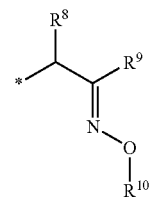

X stands for oxygen or for the group —NH—, —N($C_1$–$C_3$-alkyl) or for —$OC_3$–$C_{10}$-cycloalkyl, which can be substituted in one or more places in the same way or differently with a heteroaromatic compound, or X and $R^2$ together form a $C_3$–$C_{10}$-cycloalkyl ring, which optionally can contain one or more heteroatoms and optionally can be substituted in one or more places with hydroxy, $C_1$–$C_6$-alkyl, $C_1$–$C_6$-alkoxy or halogen, A and B, in each case independently of one another, stand for hydrogen, hydroxy, $C_1$–$C_3$-alkyl, $C_1$–$C_6$-alkoxy or for the group —S—$CH_3$, —$SO_2$—$C_2H_4$—OH, —CO—$CH_3$, —S—$CHF_2$, —S—$(CH_2)_n$CH(OH)$CH_2$N—$R^3R^4$, —$CH_2$P(O)$OR^3OR^4$, —S—$CF_3$, —SO—$CH_3$, —$SO_2CF_3$, —$SO_2$—$(CH_2)_n$—N—$R^3R^4$, —$SO_2$—$NR^3R^4$, —$SO_2R^7$, —CH—(OH)—$CH_3$ or for

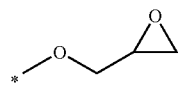

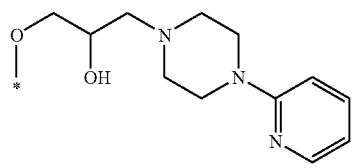

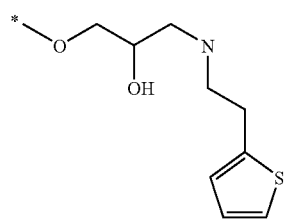

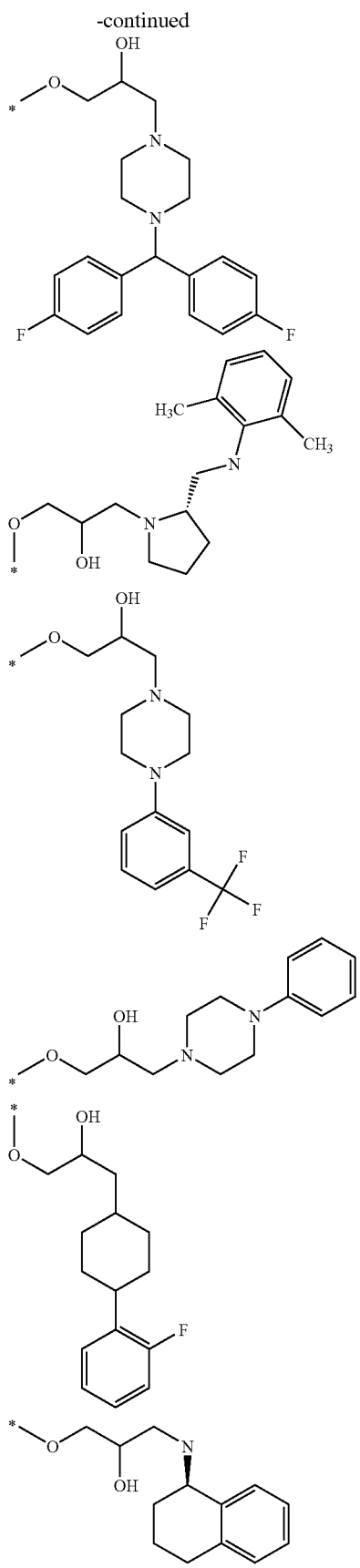

-continued
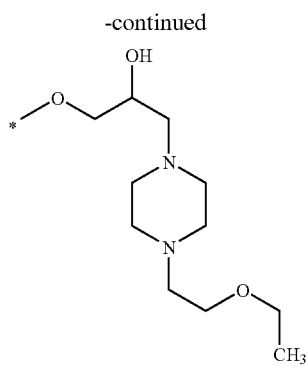
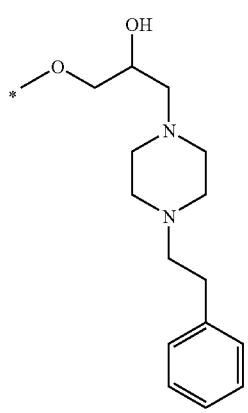
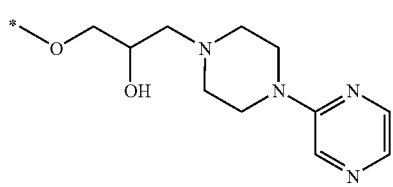
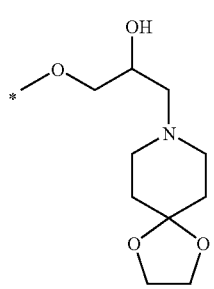
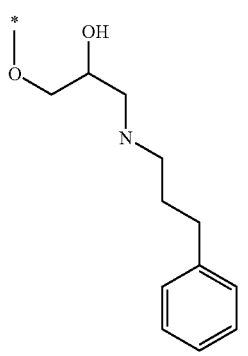
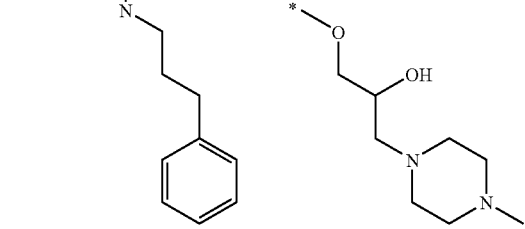
-continued
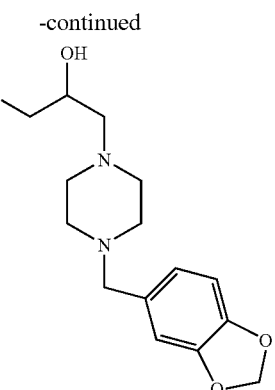
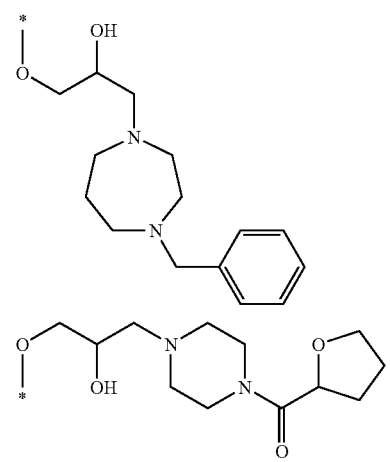
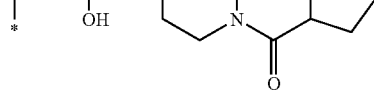
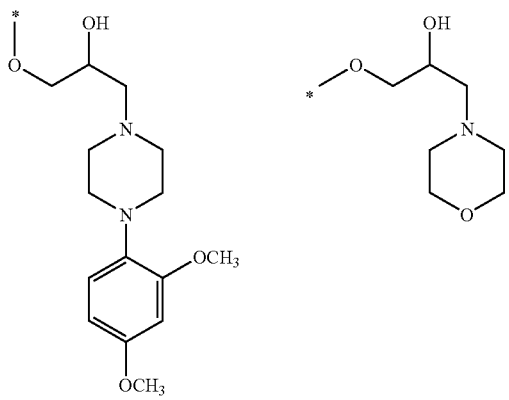
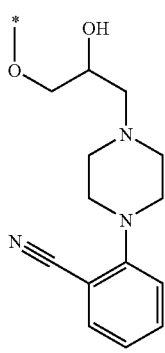
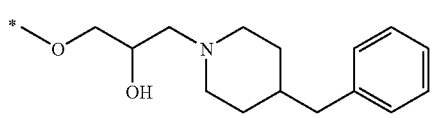

-continued

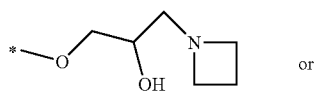

A and B together can form a group

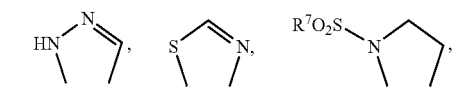

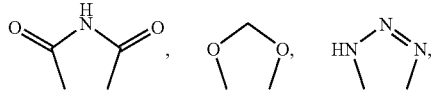

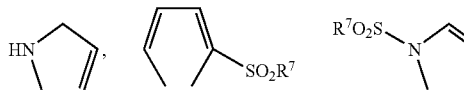

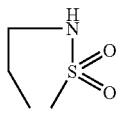

R$^3$ and R$^4$, in each case independently of one another, stand for hydrogen, phenyl, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, heteroaryl, heterocyclo-$C_3$–$C_{10}$-alkyl, heteroaryl-$C_1$–$C_3$-alkyl, $C_3$–$C_6$-cycloalkyl-$C_1$–$C_3$-alkyl optionally substituted with cyano, or for $C_1$–$C_6$-alkyl that is optionally substituted in one or more places in the same way or differently with phenyl, pyridyl, phenyloxy, $C_3$–$C_6$-cycloalkyl, $C_1$–$C_6$-alkyl or $C_1$–$C_6$-alkoxy, whereby the phenyl itself can be substituted in one or more places in the same way or differently with halogen, trifluoromethyl, $C_1$–$C_6$-alkyl, $C_1$–$C_6$-alkoxy or with the group —SO$_2$NR$^3$R$^4$, or for the group —(CH$_2$)$_n$NR$^3$R$^4$, —CNHNH$_2$ or —NR$^3$R$^4$ or for

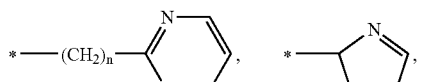

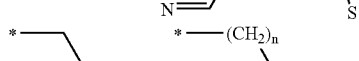

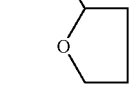

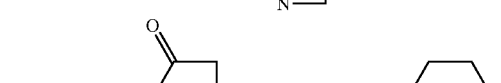

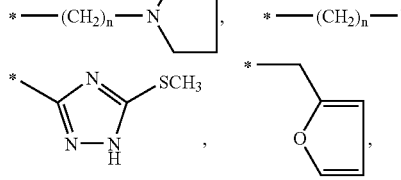

-continued

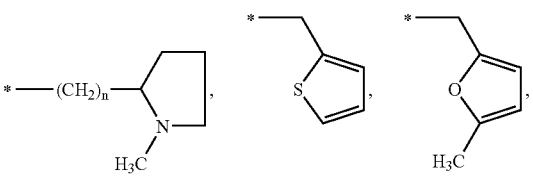

which optionally can be substituted with $C_1$–$C_6$-alkyl,

R$^5$ stands for hydroxy, phenyl, $C_1$–$C_6$-alkyl, $C_3$–$C_6$-cycloalkyl, benzoxy, $C_1$–$C_6$-alkylthio or $C_1$–$C_6$-alkoxy, R$^6$ stands for the group

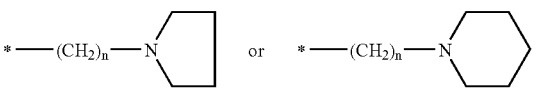

R$^7$ stands for halogen, hydroxy, phenyl, $C_1$–$C_6$-alkyl, —C$_2$H$_4$OH, —NR$^3$R$^4$, or the group

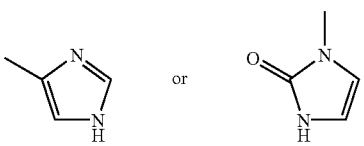

R$^8$, R$^9$ and

R$^{10}$, in each case independently of one another, stand for hydrogen, hydroxy, $C_1$–$C_6$-alkyl, $C_3$–$C_6$-cycloalkyl or for the group

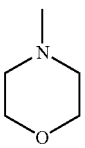

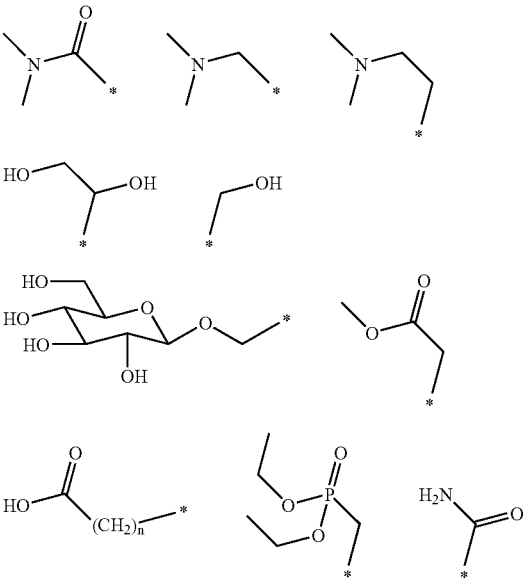

-continued

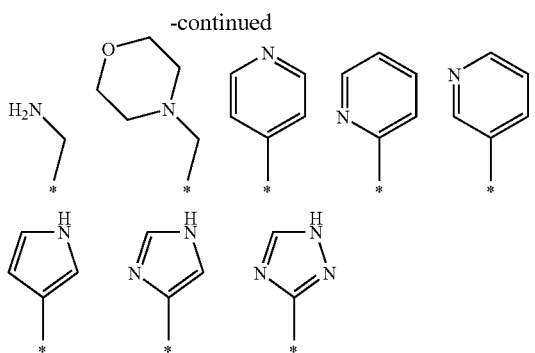

and
n stands for 0–6,
as well as isomers, enantiomers, diastereomers, and salts thereof, are especially effective.

Those compounds of general formula I in which
$R^1$ stands for hydrogen, halogen, $C_1$–$C_3$-alkyl, or for the group —$(CH_2)_n R^5$, $R^2$ stands for —CH($CH_3$)—$(CH_2)_n$—$R^5$, —CH—($CH_2OH$)$_2$, —$(CH_2)_n R^7$, —CH($C_3H_7$)—$(CH_2)_n$—R5, —CH($C_2H_5$)—$(CH_2)_n$—$R^5$, —$CH_2$—CN, —CH($CH_3$) $COCH_3$, —CH($CH_3$)—C(OH)($CH_3$)$_2$, —CH (CH(OH)$CH_3$)$OCH_3$, —CH($C_2H_5$)CO—$R^5$, $C_2$–$C_4$-alkinyl, —$(CH_2)_n$—$COR^5$, —$(CH_2)_n$—CO—$C_1$–$C_6$-alkyl, —$(CH_2)_n$—C(OH)($CH_3$)-phenyl, —CH($CH_3$)—C($CH_3$)—$R^5$, —CH($CH_3$)—C($CH_3$)($C_2H_5$)—$R^5$, —CH($OCH_3$)—$CH_2$—$R^5$, —$CH_2$—CH(OH)—$R^5$, —CH($OCH_3$)—$CHR^5$—$CH_3$, —CH($CH_3$)—CH (OH)—$CH_2$—CH═$CH_2$, —CH($C_2H_5$)—CH(OH)—$(CH_2)_n$—$CH_3$, —CH($CH_3$)—CH(OH)—$(CH_2)_n$—$CH_3$, —CH($CH_3$)—CH(OH)—CH($CH_3$)$_2$, (CH$_2$OAC)$_2$, —$(CH_2)_n$—$R^6$, —$(CH_2)_n$—$(CF_2)_n$—$CF_3$, —CH ($(CH_2)_n$—$R^5$)$_2$, —CH($CH_3$)—CO—$NH_2$, —CH($CH_2OH$)-phenyl, —CH($CH_2OH$)—CH(OH)—$(CH_2)_n R^5$, —CH($CH_2OH$)—CH(OH)-phenyl, —CH($CH_2OH$)—$C_2H_4$—$R^5$, —$(CH_2)_n$—C≡C($CH_3$) ═CH—$COR^5$, —CH(Ph)—$(CH_2)_n R^5$, —$(CH_2)_n$—$COR^5$, —$(CH_2)_n PO_3(R^5)_2$, —$(CH_2)_n$—$COR^5$, —CH (($CH_2)_n OR^5$)CO—$R^5$, —$(CH_2)_n CONHCH(($CH_2)_n R^5)_2$, —$(CH_2)_n NH$—$COR^5$, —CH($(CH_2)_n R^5$—$(CH_2)_n$ $C_3$–$C_{10}$-cycloalkyl, —$(CH_2)_n$—$C_3$–$C_{10}$-cycloalkyl, $C_3$–$C_{10}$-cycloalkyl; $C_1$–$C_6$-alkyl, $C_3$–$C_{10}$-cycloalkyl, —$(CH_2)_n$—O—$(CH_2)_n$—$R^5$, —$(CH_2)_n$—$NR^3R^4$ that is optionally substituted in one or more places in the same way or differently with hydroxy, $C_1$–$C_6$-alkyl or the group —COONH($CH_2)_n CH_3$ or —$NR^3R^4$, —CH($C_3H_7$)—$(CH_2)_n$—OC(O)—$(CH_2)_n$—$CH_3$, —$(CH_2)_n$—$R^5$,
—C($CH_3)_2$—$(CH_2)_n$—$R^5$, —C($(CH_2)_n(CH_3)$)—$(CH_2)_n$ $R^5$,
—C($(CH_2)_n$)—$(CH_2)_n R^5$, —CH(t-butyl)—$(CH_2)_n$—$R^5$, —$CCH_3(C_3H_7)$—$(CH_2)_n R^5$, —CH($C_3H_7$)—$(CH_2)_n$—$R^5$,
—CH($C_3H_7$)—$COR^5$, —CH($C_3H_7$)—$(CH_2)_n$—OC (O)—NH—Ph,
—CH(($CH_2)_n(C_3H_7))$—$(CH_2)_n R^5$,
—CH($C_3H_7$)—$(CH_2)_n$—OC(O)—NH—Ph($OR^5$)$_3$, —$NR^3R^4$,
—NH—$(CH_2)_n$—$NR^3R^4$, $R^5$—$(CH_2)_n$—C*H—CH ($R^5$)—$(CH_2)_n$—$R^5$,
—$(CH_2)_n$—CO—NH—$(CH_2)_n$—CO—$R^5$, —OC(O) NH—$C_1$–$C_6$-alkyl or
—$(CH_2)_n$—CO—NH—$(CH_2)_n$—CH—(($CH_2)_n R^5$)$_2$, or for $C_3$–$C_{10}$-cycloalkyl, which is substituted with the group

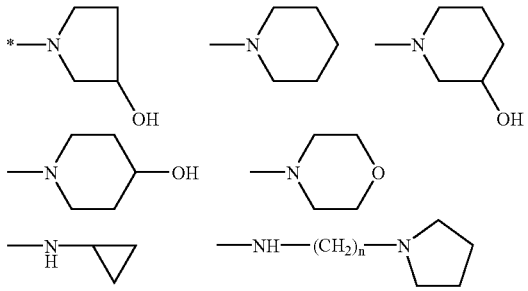

or for the group

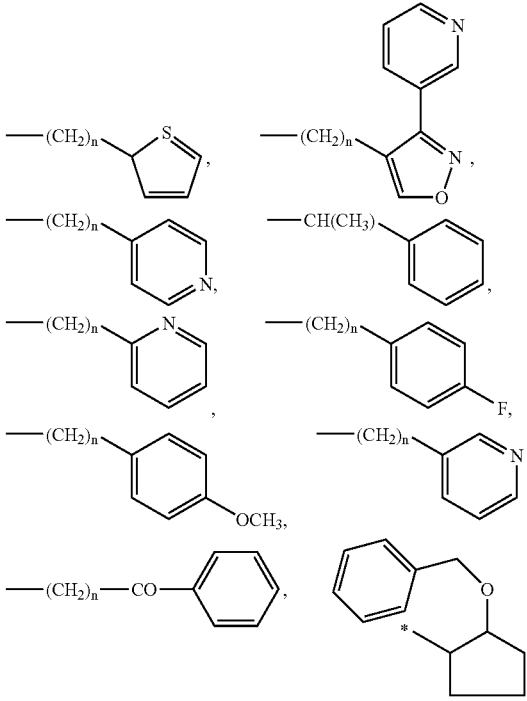

or

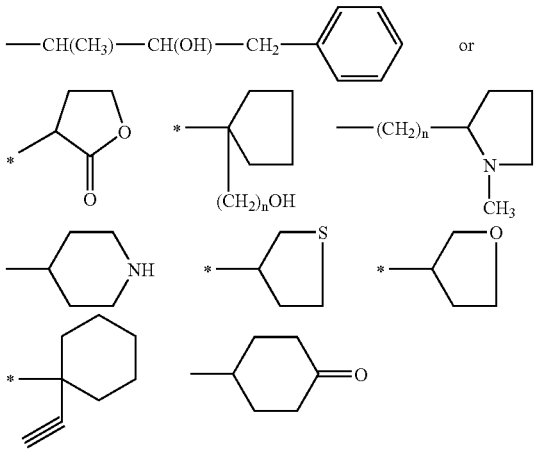

or
X stands for oxygen or for the group —NH—, —N($C_1$–$C_3$-alkyl) or

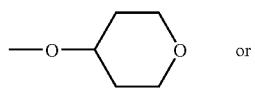 or or
R² stands for the group

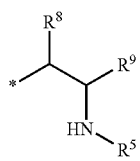 or 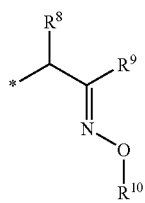

X and R² together form a group

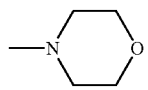 or 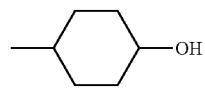

A and B, in each case independently of one another, stand for hydrogen, hydroxy, $C_1$–$C_3$-alkyl, $C_1$–$C_6$-alkoxy or for the group —S—$CH_3$, —$SO_2$—$C_2H_4$—OH, —CO—$CH_3$, —S—$CHF_2$, —S$(CH_2)_n$CH(OH) $CH_2$N—$R^3R^4$, —$CH_2$PO$(OC_2H_5)_2$, —S—$CF_3$, —SO—$CH_3$, —$SO_2CF_3$, —$SO_2$—$(CH_2)_n$—N—$R^3R^4$, —$SO_2$—N$R^3R^4$, —$SO_2R^7$, —CH(OH)—$CH_3$, —COOH, —CH$((CH_2)_nR^5)_2$, —$(CH_2)_nR^5$, —COO—$C_1$–$C_6$-alkyl, —CON$R^3R^4$ or for

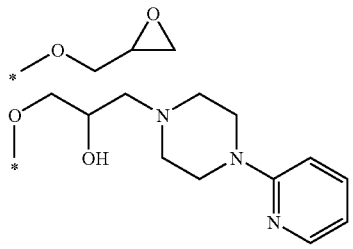

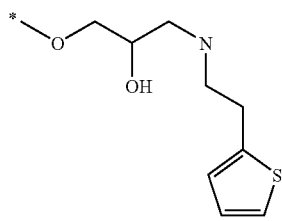

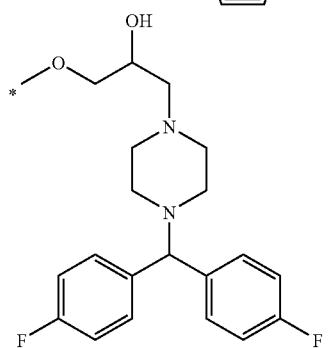

-continued

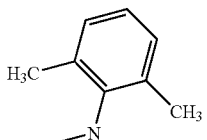

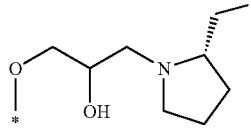

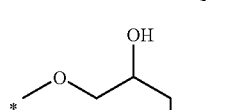

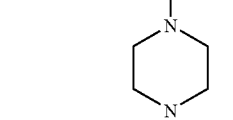

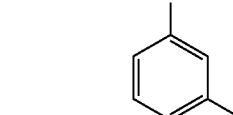

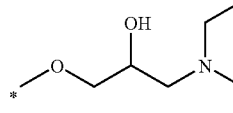

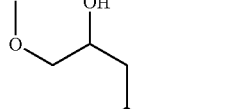

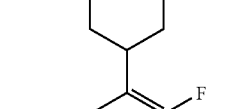

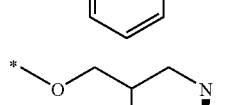

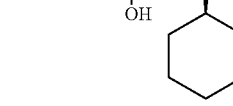

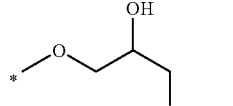

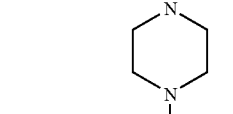

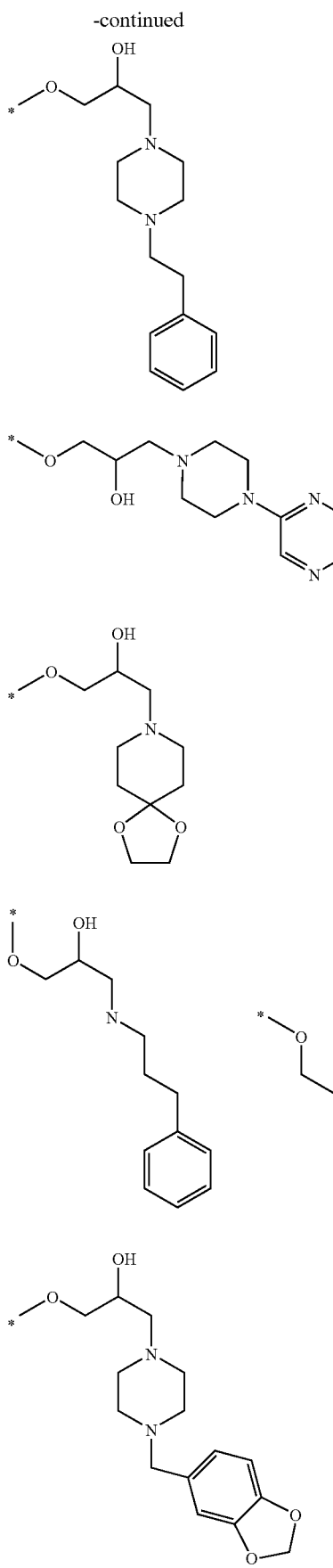
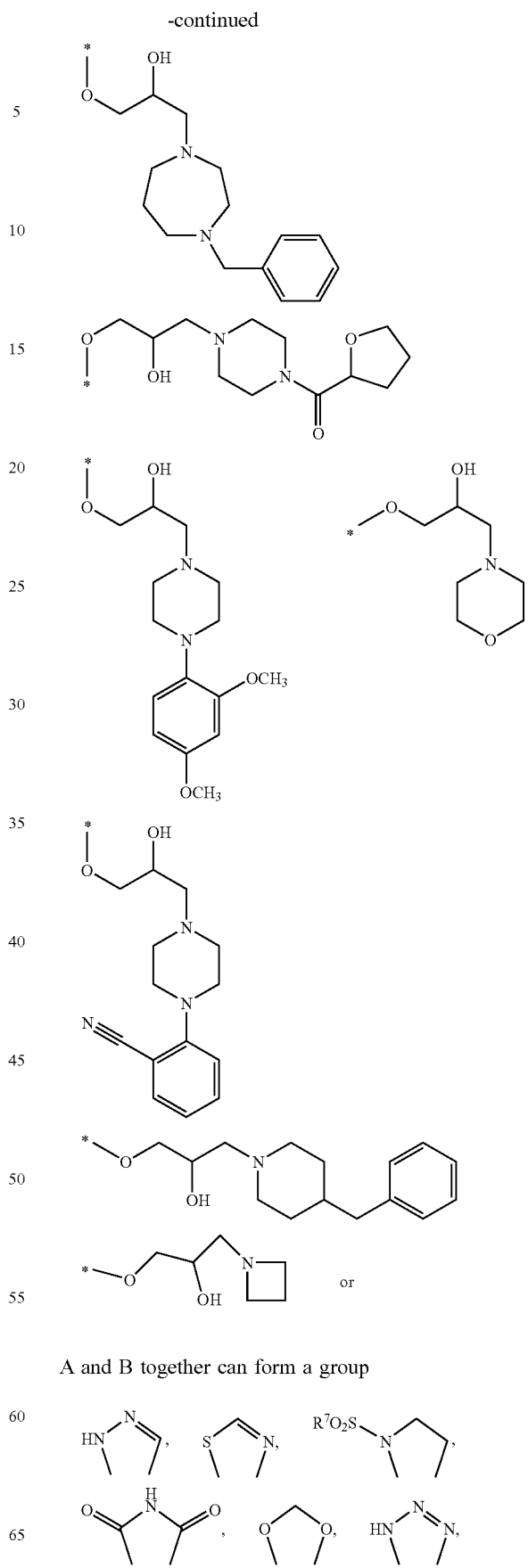
A and B together can form a group

-continued

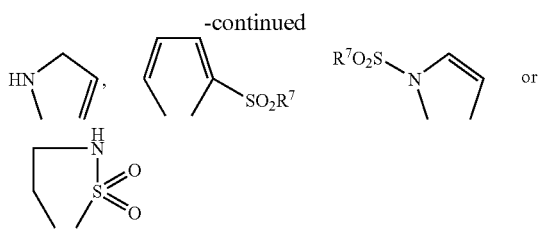

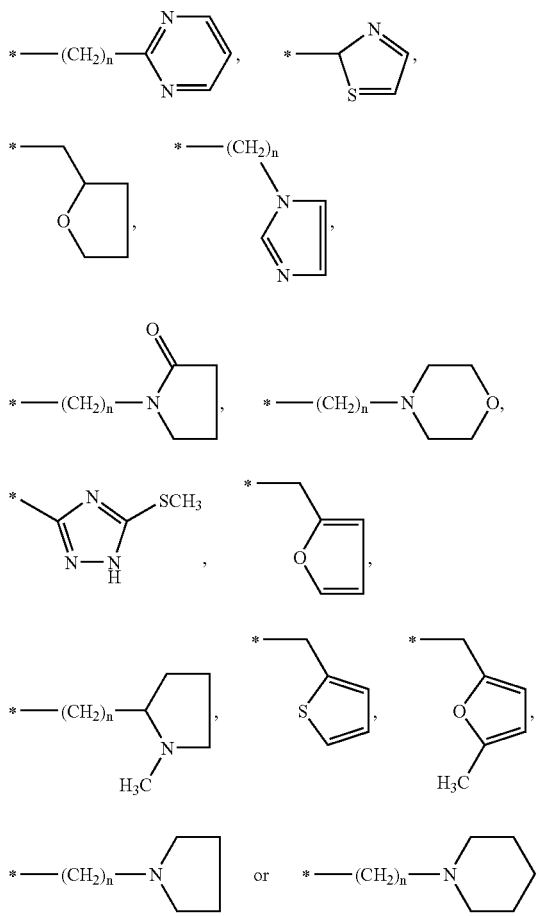

which optionally can be substituted with $C_1-C_6$-alkyl, $R^5$ stands for hydroxy, phenyl, $C_1-C_6$-alkyl, $C_3-C_6$-cycloalkyl, benzoxy, $C_1-C_6$-alkylthio or $C_1-C_6$-alkoxy, $R^3$ and $R^4$, in each case independently of one another, stand for hydrogen, phenyl, benzyloxy, $C_1-C_2$-alkyl, $C_1---C_6$-alkoxy, $C_2-C_4$-alkenyloxy, $C_3-C_6$-cycloalkyl, hydroxy, hydroxy-$C_1-C_6$-alkyl, dihydroxy-$C_1-C_6$-alkyl, heteroaryl, heterocyclo-$C_3-C_{10}$-alkyl, heteroaryl-$C_1-C_3$-alkyl, $C_3-C_6$-cycloalkyl-$C_1-C_3$-alkyl that is optionally substituted with cyano, or for $C_1-C_6$-alkyl that is optionally substituted in one or more places in the same way or differently with phenyl, pyridyl, phenyloxy, $C_3-C_6$-cycloalkyl, $C_1-C_6$-alkyl or $C_1-C_6$-alkoxy, whereby the phenyl itself can be substituted in one or more places in the same way or differently with halogen, trifluoromethyl, $C_1-C_6$-alkyl, $C_1-C_6$-alkoxy or with the group —$SO_2NR^3R^4$, or for the group —$CH_2)_nNR^3R^4$, —$CNHNH_2$ or —$NR^3R^4$ or for $R^6$ stands for the group

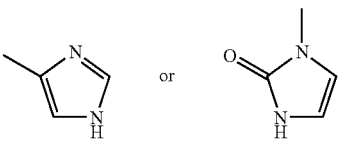

$R^7$ stands for halogen, hydroxy, phenyl, $C_1-C_6$-alkyl, —$(CH_2)_nOH$, —$NR^3R^4$ or the group

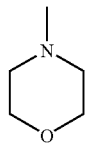

$R^8$, $R^9$ and
$R^{10}$ stand for hydrogen, hydroxy, $C_1-C_6$-alkyl or for the group —$(CH_2)_n$—COOH, and
n stands for 0–6, as well as isomers, diastereomers, enantiomers and salts thereof, have proven quite especially effective.

The compounds according to the invention essentially inhibit cyclin-dependent kinases, upon which is based their action, for example, against cancer, such as solid tumors and leukemia; auto-immune diseases such as psoriasis, alopecia, and multiple sclerosis, chemotherapy-induced alopecia and mucositis; cardiovascular diseases such as stenoses, arterioscleroses and restenoses; infectious diseases, such as, e.g., by unicellular parasites, such as trypanosoma, toxoplasma or plasmodium, or produced by fungi; nephrological diseases, such as, e.g., glomerulonephritis, chronic neurodegenerative diseases, such as Huntington's disease, amyotropic lateral sclerosis, Parkinson's disease, AIDS dementia and Alzheimer's disease; acute neurodegenerative diseases, such as ischemias of the brain and neurotraumas; viral infections, such as, e.g., cytomegalic infections, herpes, Hepatitis B and C, and HIV diseases.

The eukaryotic cell division ensures the duplication of the genome and its distribution to the daughter cells by passing through a coordinated and regulated sequence of events. The cell cycle is divided into four successive phases: the G1 phase represents the time before the DNA replication, in which the cell grows and is sensitive to external stimuli. In the S phase, the cell replicates its DNA, and in the G2 phase, preparations are made for entry into mitosis. In mitosis (M phase), the replicated DNA separates, and cell division is completed.

The cyclin-dependent kinases (CDKs), a family of serine/threonine kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the above-mentioned cell cycle CDKs, while no specific function could be associated with other members of the CDK enzyme family. One of the latter, CDK5, is distinguished in that it has an atypical regulatory subunit (p35) that deviates from the cyclins, and its activity is highest in the brain.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates transcription factors of the E2F type and forms transcriptional repressor complexes with histone-deacetylases (HDAC) (Zhang, H. S. et al. (2000). Exit from G1 and S Phase of the Cell Cycle is Regulated by Repressor Complexes Containing $HDAC_1$-Rb-hSWI/SNF and Rb-hSWI/SNF. *Cell* 101, 79–89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDK's is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory threonine and tyrosine radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1,2,4,6, but inhibit only the complexes that contain CDK1 or CDK2. Members of the p16 family are specific inhibitors of the CDK4 and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. *Science* 288, 1425–1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al. (1999). Selective Killing of Transformed Cells by Cyclin/Cyclin-Dependent Kinase 2 Antagonists. Proc. Natl. Acad. Sci USA 96, 4325–4329).

Changes of the cell cycle control play a role not only in carcinoses. The cell cycle is activated by a number of viruses, both by transforming viruses as well as by non-transforming viruses, to make possible the replication of viruses in the host cell. The false entry into the cell cycle of normally post-mitotic cells is associated with various neurodegenerative diseases. The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. J. Med. Chem. 43, 1–18; Fry, D. W. & Garrett, M. D. (2000). Inhibitors of Cyclin-Dependent Kinases as Therapeutic Agents for the Treatment of Cancer. Curr. Opin. Oncol. Endo. Metab. Invest. Drugs 2, 40–59; Rosiania, G. R. & Chang, Y. T. (2000). Targeting Hyperproliferative Disorders with Cyclin-Dependent Kinase Inhibitors. Exp. Opin. Ther. Patents 10, 215–230; Meijer L. et al. (1999). Properties and Potential Applications of Chemical Inhibitors of Cyclin-Dependent Kinases. Pharmacol. Ther. 82, 279–284; Senderowicz, A. M. & Sausville, E. A. (2000). Preclinical and Clinical Development of Cyclin-Dependent Kinase Modulators. J. Natl. Cancer Inst. 92, 376–387).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure or buffers. These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants such as salts of bile acids or animal or plant phospholipids, but also mixtures thereof, as well as liposomes or their components can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5–1000 mg, preferably 50–200 mg, whereby the dose can be given as a single dose to be administered once or divided into two or more daily doses.

Subjects of this invention also include the use of compounds of general formula I for the production of a pharmaceutical agent for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arterioscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS dementia and Alzheimer's disease; acute neurodegenerative diseases are defined as ischemias of the brain and neurotraumas; and viral infections are defined as cytomegalic infections, herpes, hepatitis B or C, and HIV diseases.

Subjects of this invention also include pharmaceutical agents for treating the above-cited diseases, which contain at least one compound according to general formula I, as well as pharmaceutical agents with suitable formulation substances and vehicles.

The compounds of general formula I according to the invention are, i.a., excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β).

If the production of the starting compounds is not described, these compounds are known or can be produced analogously to known compounds or to processes that are described here. It is also possible to perform all reactions that are described here in parallel reactors or by means of combinatory operating procedures.

The isomer mixtures can be separated into the enantiomers or E/Z isomers according to commonly used methods, such as, for example, crystallization, chromatography or salt formation.

The production of the salts is carried out in the usual way by a solution of the compound of formula I being mixed with the equivalent amount of or excess base or acid, which optionally is in solution, and the precipitate being separated or the solution being worked up in the usual way.

Production of the Compounds According to the Invention

The following examples explain the production of the compounds according to the invention, without the scope of the claimed compounds being limited to these examples.

The compounds of general formula I according to the invention can be produced according to the following general diagrams of the process:

Diagram 1
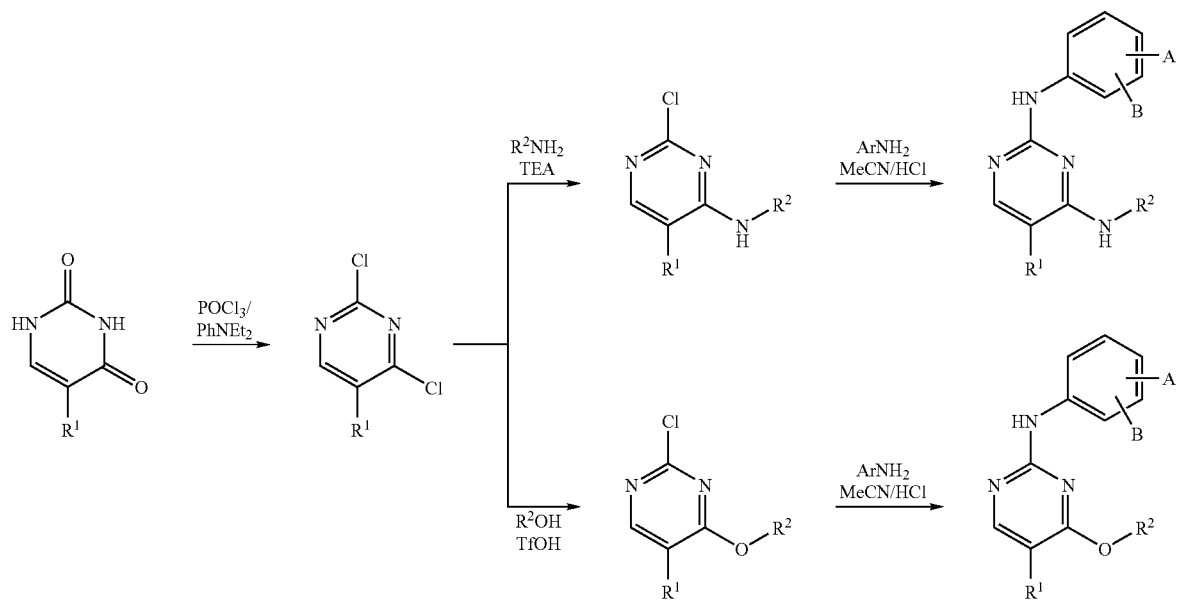
Diagram 2
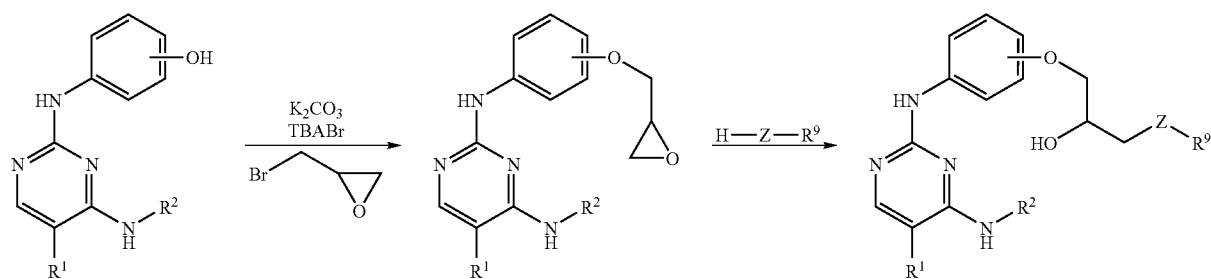
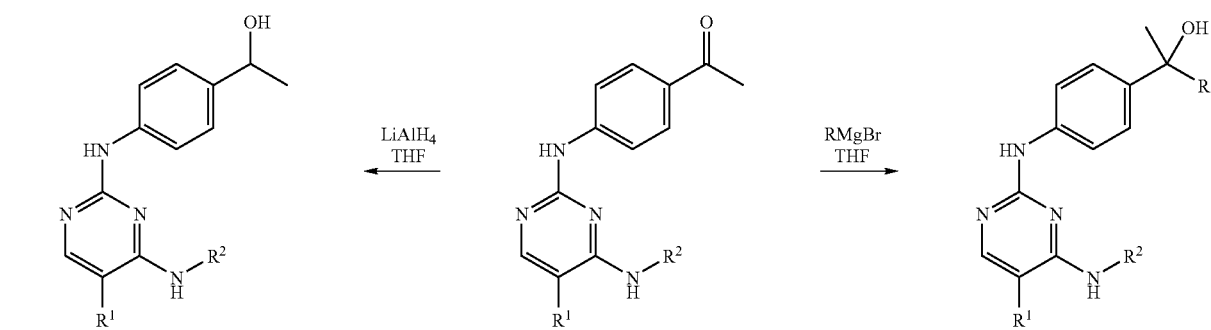
Z = O or NH

Diagram 3

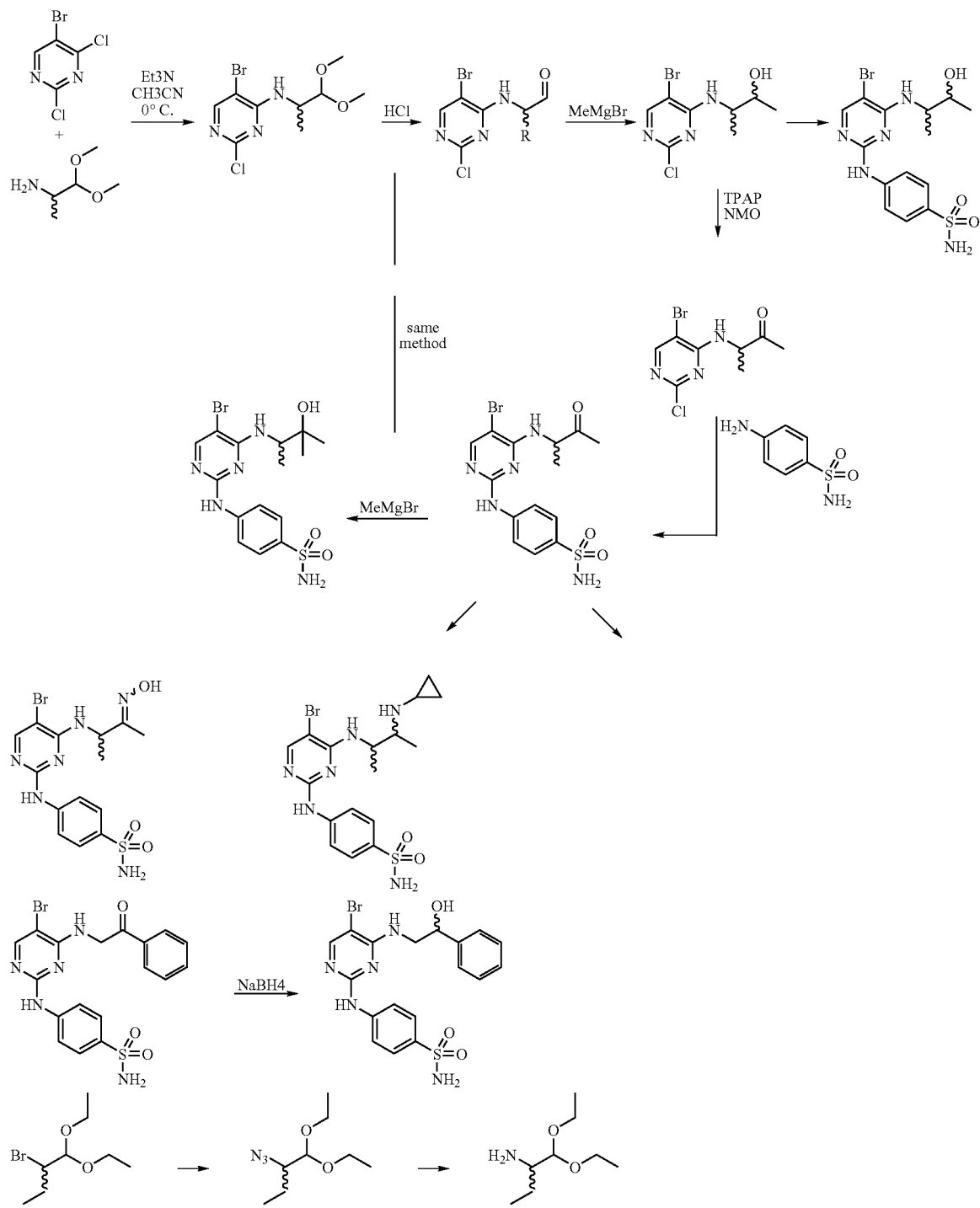

[Key:] gleiche Methode=same method

EXAMPLE 1

Production of 5-Bromo-N2-(4-difluoromethylthiophenyl)-N4-2-propynyl-2,4-pyrimidine diamine (is Carried out According to Process Diagram 1) (Compound 23).

245 mg (1 mmol) of 2-chloro-4-2-propynylaminopyrimidine is dissolved in 2 ml of acetonitrile, and a suspension of 4-(difluoromethylthio)-aniline hydrochloride [produced from 352 mg (2 mmol) of 4-(difluoromethylthio)-aniline, 1 ml of acetonitrile and 0.5 ml of aqueous HCl (4M in dioxane)] is added at room temperature. Then, the reaction mixture is refluxed overnight under $N_2$ atmosphere. After cooling, the mixture is filtered, the remaining solid phase is washed with $H_2O$ and dried. A yield of 328 mg (85%) of the product can be expected

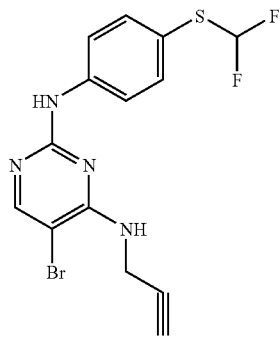

| | | |
|---|---|---|
| 6H | 8.25 (s, 1H) | Yield: |
| 2CH | 7.86 (d, 2H) | 85% |
| | 7.51 (d, 2H) | |
| | 7.38 | |
| | (t, 56.8 Hz, 1H) | Melting point: >235° C. |
| 4CH⁺ | 4.18 (m, 2H) | |
| | 3.16 (sb, 1H) | |
| | 10.24 (sb, 1H) | |
| NH | 8.17 (sb, 1H) | |

EXAMPLE 2

Production of 5-bromo-N-(3-(oxiranylmethoxy)phenyl)-2-(2-propynyloxy)-2-pyrimidinamine (Compound 51) is Carried out According to Process Diagram 2.

1.55 g (4.9 mmol) of compound 20 is dissolved in 5.5 ml of epibromohydrin, and 1.38 g of $K_2CO_3$ and 65 mg of tetrabutylammonium bromide are added to it. The reaction mixture is stirred under nitrogen atmosphere at 100° C. for 1 hour. After ethyl acetate is added, the resulting precipitate is collected and recrystallized from ethanol. The product yield is 1.15 g (62%) as a white powder.

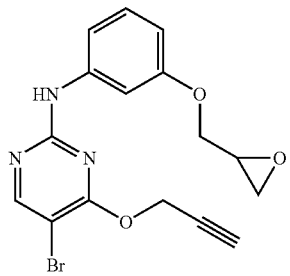

| | | |
|---|---|---|
| 6H | 8.45 (s, 1H) | |
| 2CH | 7.47 (s, 1H) | |
| | 7.32 (d, 1H) | Yield: 62% |
| | 7.20 (t, 1H) | |
| | 6.40 (d, 1H) | Melting point: 173° C. |
| | 4.32 (dd, 1H) | |
| | 3.82 (dd, 1H) | |
| | 3.3–3.4 (m, 1H) | |
| | 2.87 (t, 1H) | |
| | 2.72 (dd, 1H) | |
| 4CH | 5.13 (d, 2H) | |
| | 3.67 (t, 1H) | |
| NH | 9.84 (sb, 1H) | |

Substance 40 is produced analogously to Example 2.

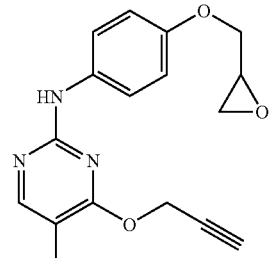

| | | |
|---|---|---|
| 6-H | 8.36 (s, 1H) | Chromatography: |
| 2CH | 7.60 (d, 1H) | H/EA 1:3 0.5% TEA |
| | 6.91 (d, 1H) | |
| | 4.28 (dd, 1H) | |
| | 3.79 (dd, 1H) | Yield: 38% |
| | 3.31 (m, 1H) | Melting point: 140–141° C. |
| | 2.70 (dd, 1H) | |
| 4CH | 5.07 (d, 12H) | |
| | 3.65 (t, 1H) | |
| NH OH | 9.65 (sb, 1H) | |

EXAMPLE 3

Production of 1-(4-((5-bromo-4-(2-propynyloxy)-pyrimidin-2-yl)-amino)phenoxy)-3-(4-phenylpiperazin-1-yl)-2-propanol (Compound 41).

0.2 ml of a 0.5 M 4-phenylpiperazine solution in DMPU is added to a solution of 19 mg (0.05 mmol) of substance 51 in N,N'-dimethylpropylurea (DMPU). The reaction mixture is kept for 18 hours at a temperature of 80° C. After cooling, 3.5 ml of tertiary butyl methyl ether is added, and the organic phase is extracted 5 times with 1.5 ml of $H_2O$ and then evaporated in a vacuum. The remaining residue is chromatographed on 1.7 g (15 μM) of Lichrosphere Si60 (gradient: dichloromethane/hexane 1:1 to DCM and then dichloromethane/methanol 99:1 to 93:7). A product yield of 17 mg (64%) is achieved.

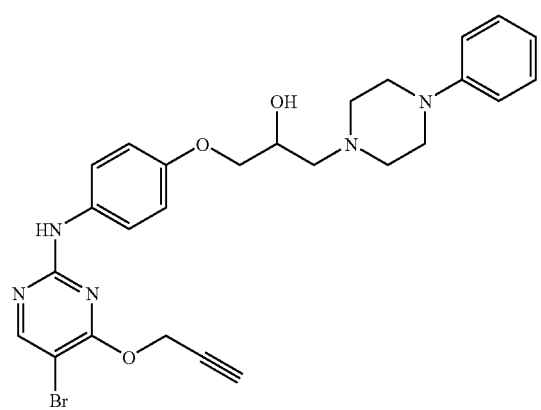

Similarly produced are also the following compounds:
| No. | Structure |
|---|---|
| 96 | 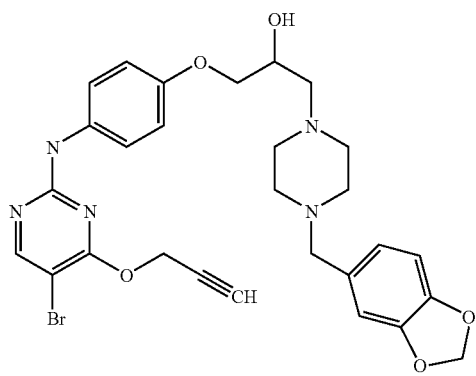 |
| 97 | 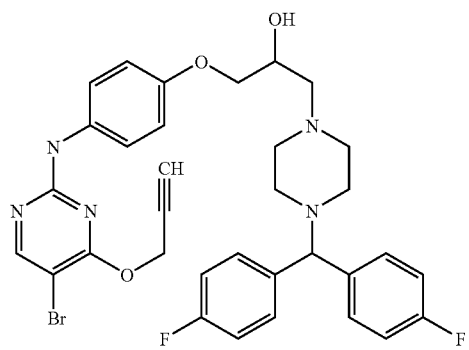 |
| 98 | 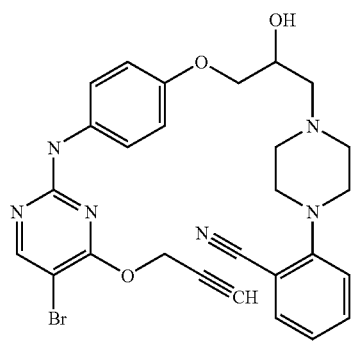 |
| 99 | 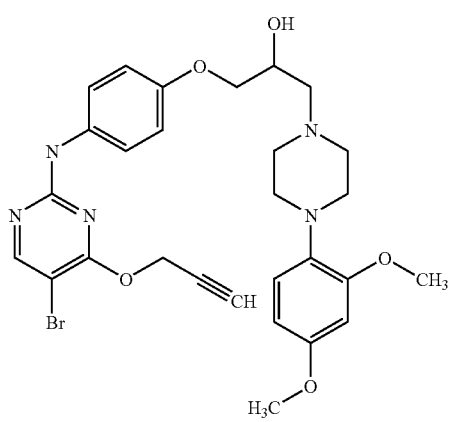 |
-continued
| No. | Structure |
|---|---|
| 100 | 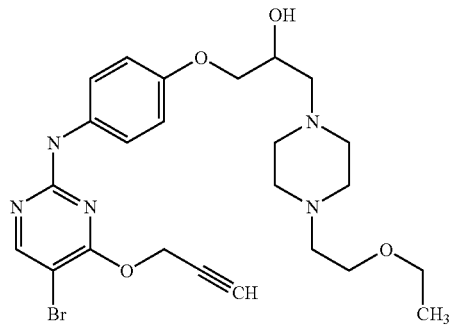 |
| 101 | 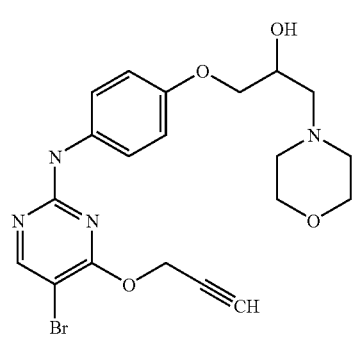 |
| 102 | 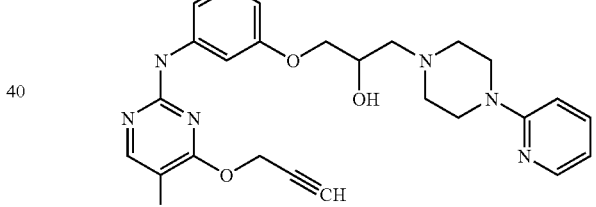 |
| 103 | 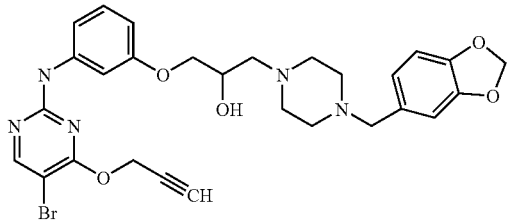 |
| 104 | 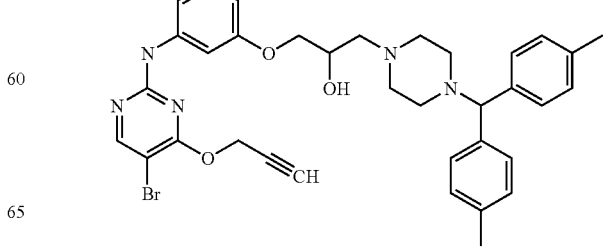 |

-continued
| No. | Structure |
|---|---|
| 105 | 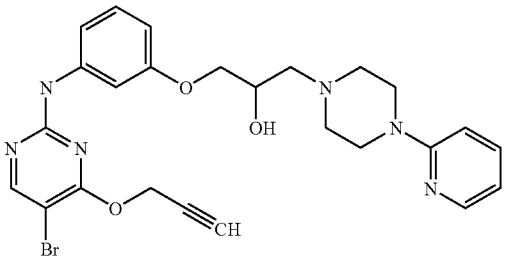 |
| 106 | 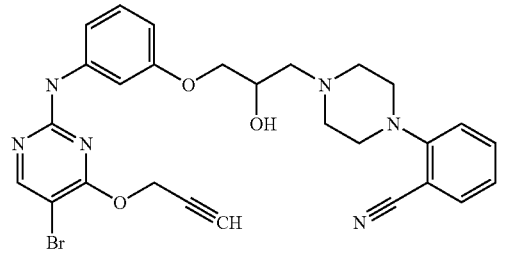 |
| 107 | 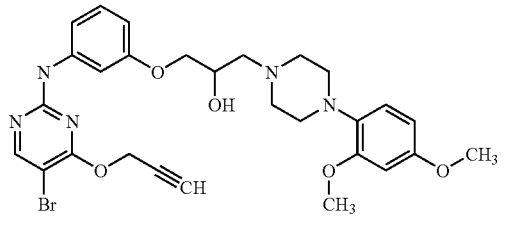 |
| 108 | 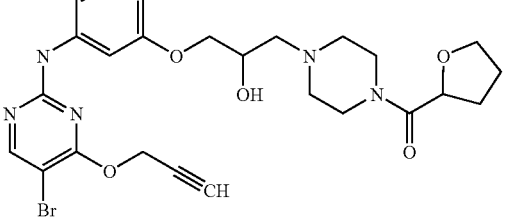 |
| 109 | 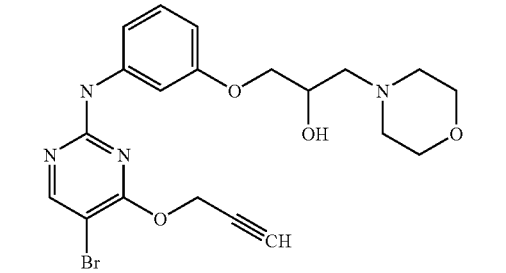 |
| 110 | 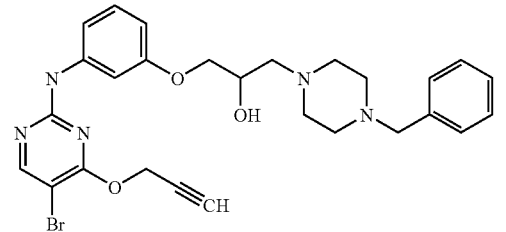 |
-continued
| No. | Structure |
|---|---|
| 111 | 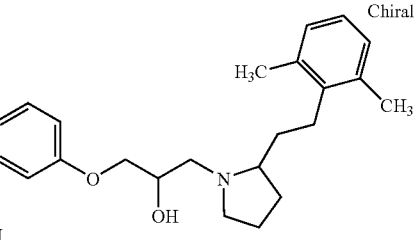 |
| 112 | 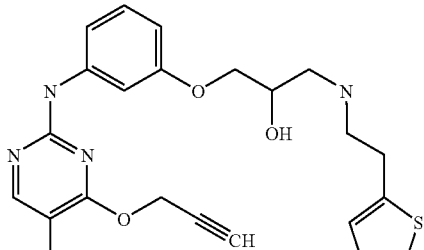 |
| 113 | 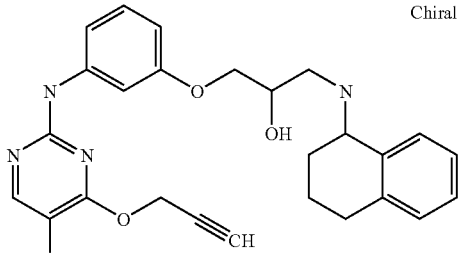 |
| 114 | 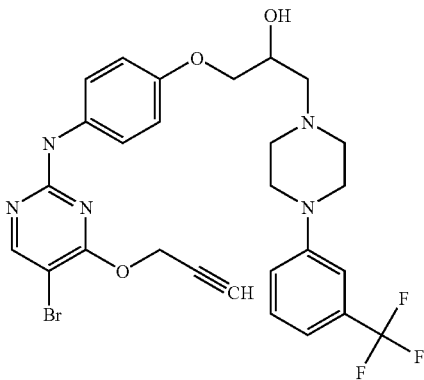 |

-continued
| No. | Structure |
|---|---|
| 115 | 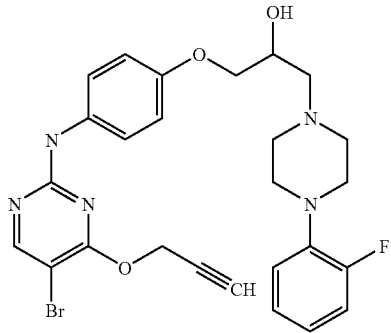 |
| 116 | 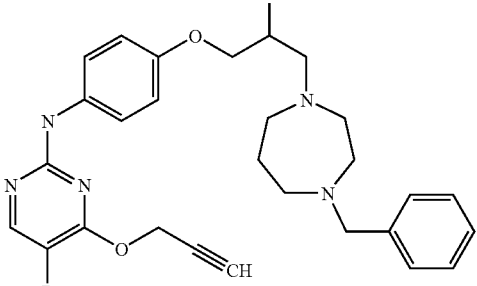 |
-continued
| No. | Structure |
|---|---|
| 117 | 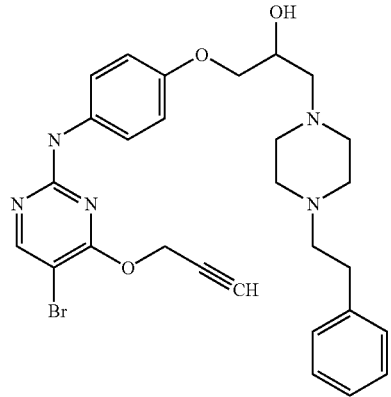 |
| 118 | 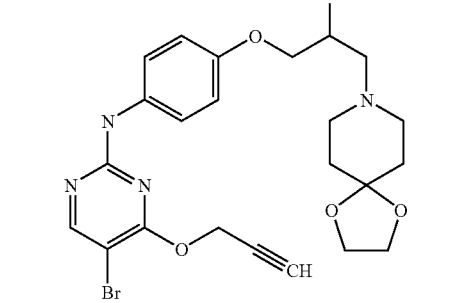 |
| 119 | 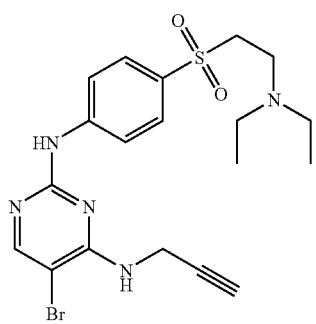 |
The following compounds are similarly produced in the described examples.
| No. | Structure | Name |
|---|---|---|
| 28 | 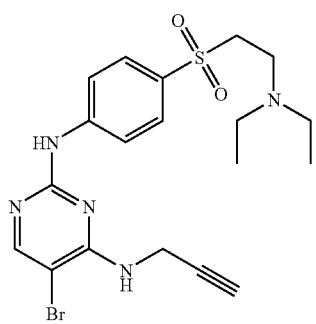 | 5-Bromo-N2-(4-(2-diethylaminoethylsulfonyl)phenyl)-N4-2-propynyl-2,4-pyrimidine diamine |

-continued

| No. | Structure | Name |
|---|---|---|
| 29 | 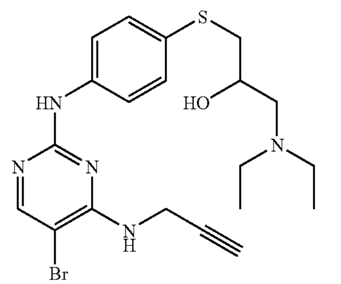 | 1-(4-[5-Bromo-4-(2-propynylamino)-2-pyrimidinyl]amino-phenylthio)-3-(diethylamino)-2-propanol |
| 32 | 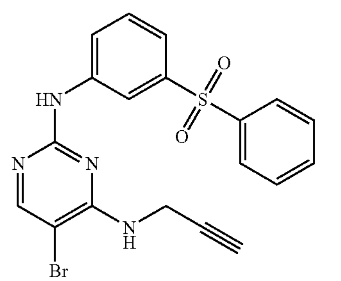 | 5-Bromo-N2-(3-phenylsulfonylphenyl)-N4-2-propynyl-2,4-pyrimidine diamine |
| 33 | 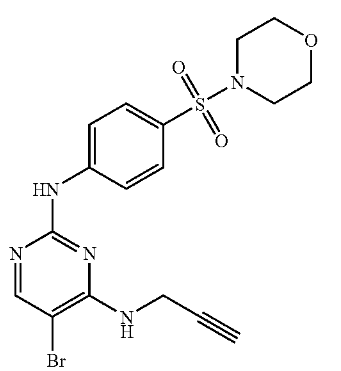 | N-[4-[[5-Bromo-4-(2-propynylamino)-2-pyrimidinyl]amino]-benzenesulfonyl]morpholine |
| 41 | 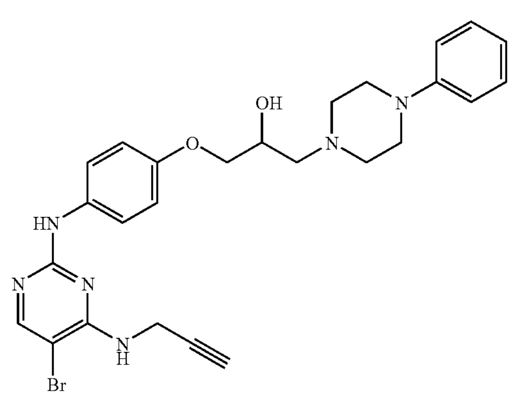 | 1-(4-((5-Bromo-4-(2-propynyloxy)-pyrimidin-2-yl)-amino)phenoxy)-3-(4-phenylpiperazin-1-yl)-2-propanol |

-continued

| No. | Structure | Name |
|---|---|---|
| 57 | 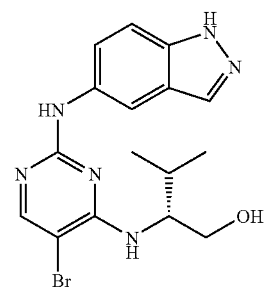 | N-[5-Bromo-4-((2R)-1-hydroxy-4-methyl-2-butylamino)-2-pyrimidinyl]-indazol-5-amine |
| 58 | 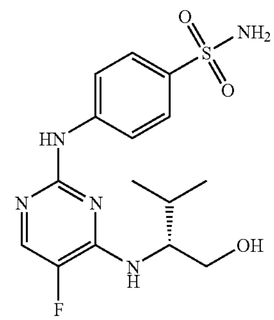 | 4-[[5-Fluoro-4-((2R)-1-hydroxy-3-methyl-2-butylamino)-2-pyrimidinyl]amino]-benzenesulfonamide |
| 59 | 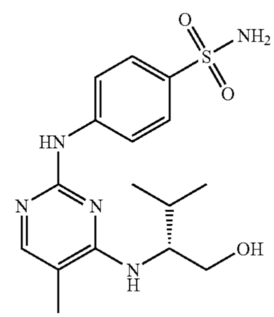 | 4-[[5-Iodo-4-((2R)-1-hydroxy-3-methyl-2-butylamino)-2-pyrimidinyl]amino]-benzenesulfonamide |
| 62 | 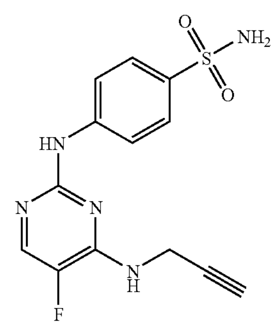 | 4-[[5-Fluoro-4-(2-propynylamino)-2-pyrimidinyl]amino]-benzenesulfonamide |
| 65 | 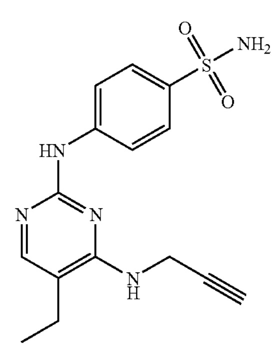 | 4-[[5-Ethyl-4-(2-propynylamino)-2-pyrimidinyl]amino]-benzenesulfonamide |

-continued

| No. | Structure | Name |
|---|---|---|
| 66 | 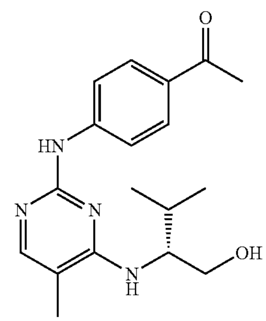 | 1-[4-[(5-Iodo-4-((2R)-1-hydroxy-3-methyl-2-butylamino)-2-pyrimidinyl)amino]phenyl]-ethanone |
| 68 | 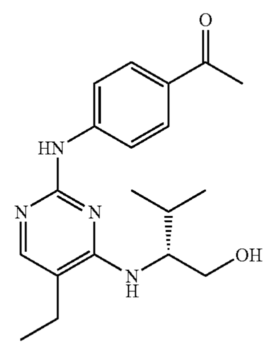 | 1-[4-[(5-Ethyl-4-((2R)-1-hydroxy-3-methyl-2-butylamino)-2-pyrimidinyl)amino]phenyl]-ethanone |
| 72 | 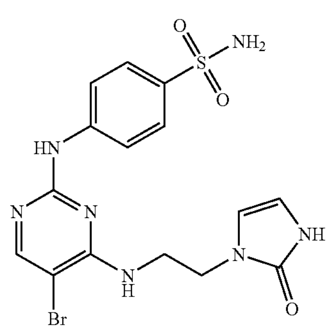 | 4-[[5-Bromo-4-(2-(2-oxo-imidazolin-1-yl)ethylamine)-2-pyrimidinyl]amino]-benzenesulfonamide |
| 73 | 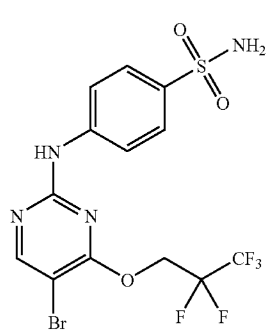 | 4-[[5-Bromo-4-(2,2,3,3,3-pentafluoropropyloxy)-2-pyrimidinyl]amino]-benzenesulfonamide |

| No. | Structure | Name |
|---|---|---|
| 75 | 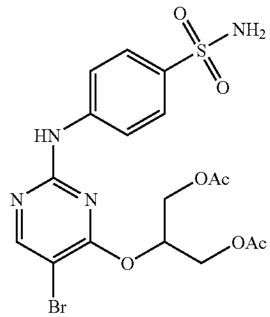 | 4-[[5-Bromo-4-(1,3-bisacetoxy-2-propyloxy)-2-pyrimidinyl]amino]-benzenesulfonamide |
| 76 | 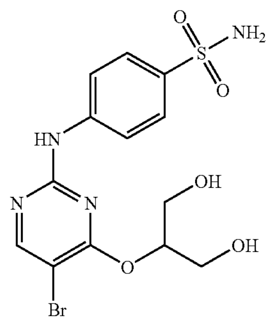 | 4-[[5-Bromo-4-(1,3-dihydroxy-2-propyloxy)-2-pyrimidinyl]amino]-benzenesulfonamide |
| 79 | 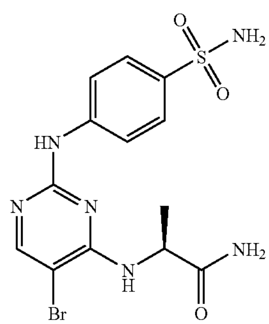 | N□-(5-Bromo-2-(4-sulfamoylphenyl)amino-pyrimidin-4-yl)-L-alanine amide |
| 83 | 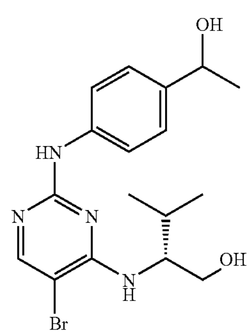 | 1-[4-[(5-Bromo-4-(2-propynylamino)-2-pyrimidinyl)amino]phenyl]-ethanol |

The following compounds are produced analogously to the described synthesis processes according to Diagram 1 or 2:

All NMR spectra are measured in the indicated solvent or in DMSO.

| Ex.-No. | 37 | 38 | 39 | 5 |
|---|---|---|---|---|
| | 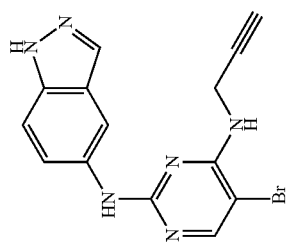 | 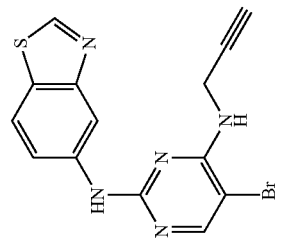 | 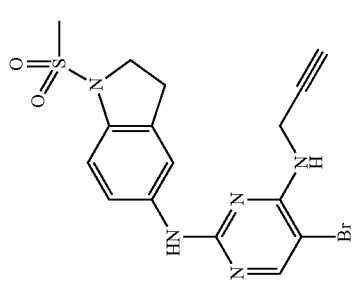 | 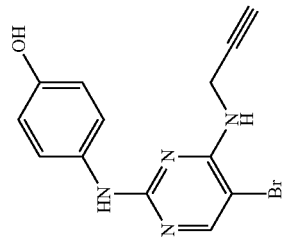 |
| 6-H | 8.34 (s, 1H) | 8.39 (s, 1H) | 8.30 (s, 1H) | 8.00 (s, 1H) |
| 2CH | 12.88 (sb, 1H)<br>8.07 (s, 1H)<br>7.93 (s, 1H)<br>7.41 (d, 1H)<br>7.56 | 9.28 (s, 1H)<br>8.79 (s, 1H)<br>7.70 (d, 1H)<br>8.04 (d, 1H) | 7.74 (s, 1H)<br>7.44 (d, 1H)<br>7.22 (d, 1H)<br>3.98 (t, 2H)<br>3.13 (t, 2H)<br>2.99 (s, 3H) | 7.52 (d, 2H)<br>6.65 (d, 2H) |
| 4CH | 4.15 (dd, 1H)<br>3.22 (sb, 1H) | 4.19 (d, 2H)<br>3.28 (sb, 1H) | 4.16 (d, 2H)<br>3.09 (s, 1H) | 4.09 (d, 2H) |
| NH | 4.15 (dd, 2H)<br>3.18 (t, 1H)<br>9.30 (sb, 1H)<br>7.39 (tb, 1H) | 10.43 (sb, 1H)<br>8.45 (sb, 1H) | 10.6 (1H)<br>8.75 (1H) | 9.00 (s, 1H)<br>8.96 (s, 1H)<br>7.31 (t, 1H) |
| Chromatography | EA + 0.5% TEA | — | Crystallized MeOH | — |
| Yield | 10% | 36% | 73% | 20% |
| Melting Point | 231° C. | >235° C. | 237° C. | 157° C. |

-continued

| Example No. | 16 | 24 | 36 | 35 |
|---|---|---|---|---|
| 6-H | 8.80 (s, 1H) | 8.30 (s, 1H) | 8.18 (s, 1H) | 8.14 (s, 1H) |
| 2CH | 7.67 (d, 2H)<br>7.27 (d, 2H)<br>2.47 (s, 3H) | 7.94 (d, 2H)<br>7.63 (d, 2H) | 7.67 (s, 1H)<br>7.54 (d, 1H)<br>7.24 (t, 1H)<br>6.92 (d, 1H) | 8.28 (s, 1H)<br>7.98 (d, 1H)<br>7.41 (t, 1H)<br>7.25 (d, 1H) |
| 4CH | 4.17 (dd, 2H)<br>3.75 (t, 1H) | 4.17 (dd, 2H)<br>3.18 (t, 1H) | 4.20 (dd, 2H)<br>3.12 (sb, 1H) | 4.14 (dd, 2H)<br>3.04 (sb, 1H) |
| NH | 10.55 (sb, 1H)<br>8.68 (sb, 1H) | 10.45 (sb, 1H)<br>8.22 (sb, 1H) | 9.78 (sb, 1H)<br>7.95 (sb, 1H) | 9.58 (sb, 1H)<br>7.46 (sb, 1H) |
| Chrom. Yield | 94% | 86% | 73% | 69% |
| Melting Point | 232–234° C. | 160° C. | 194° C. | 143° C. |

-continued
| Example No. | 27 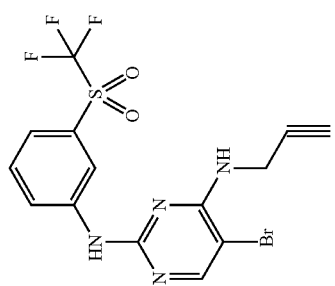 | 36 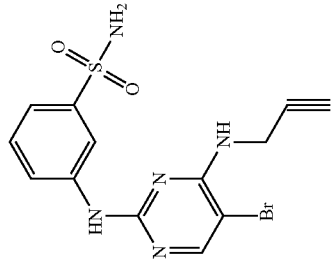 | 34 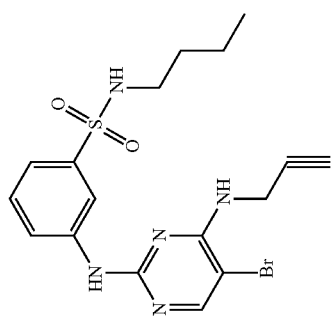 | 21 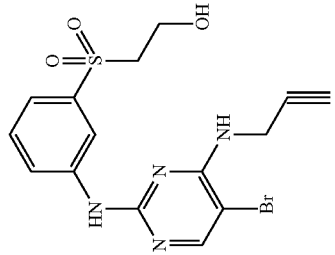 |
|---|---|---|---|---|
| 6-H | 8.18 (s, 1H) | 8.26 (s, 1H) | 8.25 (s, 1H) | 8.17 (s, 1H) |
| 2CH | 8.73 (s, 1H)<br>7.62 (d, 1H)<br>7.72 (t, 1H)<br>8.31 (d, 1H) | 8.12 (s, 1H)<br>7.35–<br>7.55 (m, 3H)<br>8.06 (d, 1H) | 8.16 (s, 1H)<br>7.43 (d, 1H)<br>7.52 (t, 1H)<br>8.01 (d, 1H)<br>2.78 (m, 2H)<br>1.35 (mc, 2H)<br>1.24 (mc, 2H)<br>0.80 (t, 3H) | 8.74 (s, 1H)<br>7.43 (d, 1H)<br>7.52 (t, 1H)<br>8.08 (d, 1H)<br>3.43 (t, 2H)<br>3.70 (t, 2H) |
| 4CH | 4.18 (dd, 2H)<br>3.06 (t, 1H) | | 4.21 (d, 2H)<br>3.09 (sb, 1H) | 3.08 (t, 1H) |
| NH | 10.02 (s, 1H)<br>7.49 (sb, 1H) | 9.68 (sb, 1H) | 10.3 (sb, 1H)<br>8.13 (sb, 1H) | 9.79 (s, 1H)<br>7.55 (tb, 1H) |
| OH | | 7.30 (sb, 2H) | | 4.90 (sb, 1H) |
| Chrom. Yield | —<br>69% | Cryst. EtOH<br>64% | —<br>87% | —<br>59% |
| Melting Point | 144° C. | 219° C. | 220° C. | 192.5–193.5° C. |

-continued
| Example No. | 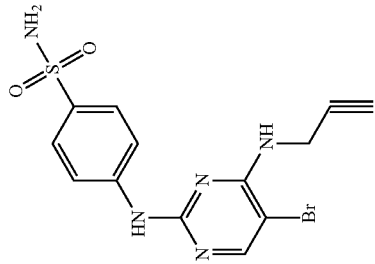 31 | 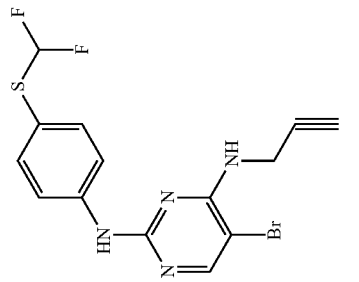 25 | 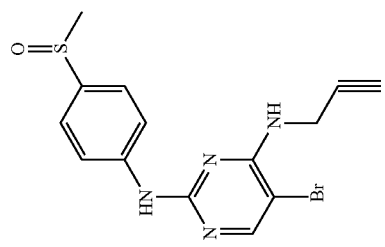 23 | 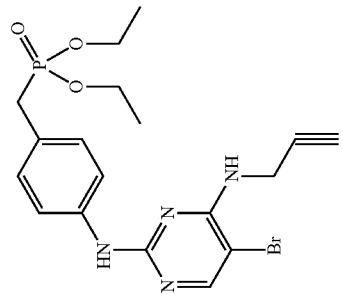 11 |
|---|---|---|---|---|
| 6-H | 8.25 (s, 1H) | 8.14 (s, 1H) | 8.25 (s, 1H) | 8.29 (s, 1H) |
| 2CH | 7.65 (d, 2H)<br>7.24 (d, 2H)<br>3.19 (d, 21.3 Hz, 2H)<br>3.95 | 8.01 (d, 2H)<br>7.56 (d, 2H)<br>2.70 (s, 3H) | 7.86 (d, 2H)<br>7.51 (d, 2H)<br>7.38 (t, 56.8 Hz, 1H) | 7.95 (d, 2H)<br>7.78 (d, 2H) |
| 4CH | (mc, 4H)<br>1.20 (t, 6H) | 4.15 (dd, 2H)<br>3.14 (t, 1H) | 4.18 (m, 2H)<br>3.16 (sb, 1H) | 4.19 (d, 2H)<br>3.18 (sb, 1H) |
| NH | 4.17 (sb, 2H)<br>3.15 (sb, 1H)<br>10.19 (sb, 1H)<br>8.34 (sb, 1H) | 9.69 (sb, 1H)<br>7.55 (tb, 1H) | 10.24 (sb, 1H)<br>8.17 (sb, 1H) | 10.40 (sb, 1H)<br>8.24 (sb, 1H)<br>7.15 (sb, 2H) |
| Chrom.<br>Yield | EA Cryst.<br>H/DIPE<br>23% | DCM/MeOH<br>95:5<br>25% | —<br>85% | Cryst.<br>DIPE/EtOH<br>17 |
| Melting Point | 198° C. | 217–218° C. | >235° C. | >235° C. |

-continued
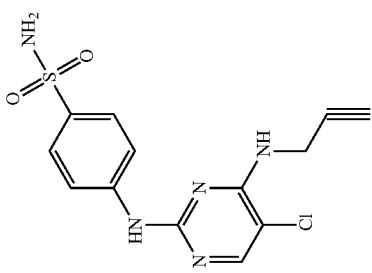
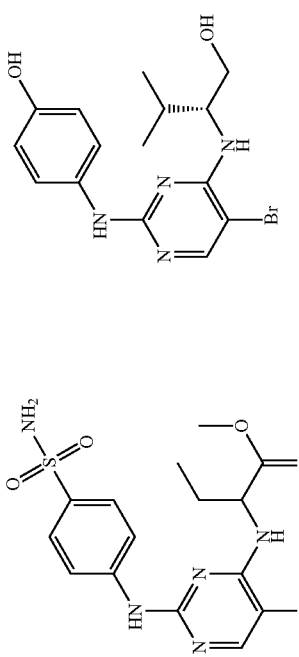
| Example No. | 44 | 45 | 46 |
|---|---|---|---|
| 6-H | 8.34 (s, 1H) | 8.34 (s, 1H) | 8.23 n(sb, 1H) |
| 2CH | 7.93 (d, 2H)<br>7.79 (d, 2H) | 7.74 (mc, 4H) | 7.39 (d, 2H)<br>6.79 (d, 2H) |
| 4CH | 4.20 (sb, 2H)<br>3.31 (sb, 1H) | 4.55 (q, 1H)<br>1.98 (dq, 2H)<br>0.94 (t, 3H)<br>3.61 (s, 3H) | 3.52–3.71 (2H)<br>3.97 (mc, 1H)<br>1.96 (mc, 1H)<br>0.91 (d, 3H) |
| NH | 11.03 (sb, 1H)<br>9.04 (sb, 1H)<br>7.34 (sb, 2H) | 10.60 (s, 1H)<br>7.97 (d, 1H)<br>7.31 (db, 2H) | 0.85 (d, 3H)<br>10.35 (sb, 1H)<br>7.76 (sb, 1H) |
| Chrom.<br>Yield | Cryst. EtOH<br>27% | Cryst. EtOH<br>48% | —<br>52% |
| Melting<br>Point | 252° C. | 235° C. | 252–253° C. |

-continued
| Example No. | 10 | 15 | 3 | 19 |
|---|---|---|---|---|
| | 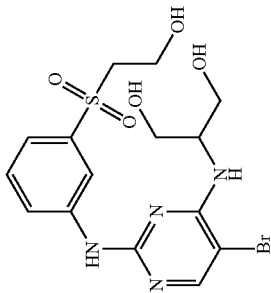 | 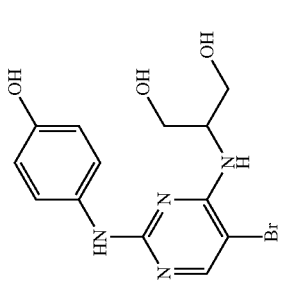 | | 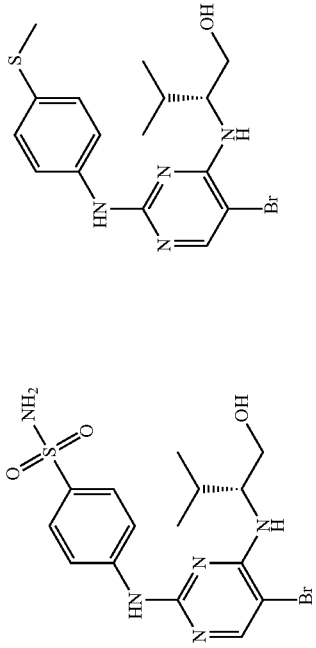 |
| 6-H | 8.27 (s, 1H) | 8.17 (s, 1H) | 7.97 (s, 1H) | 8.20-8.35 (2H) |
| 2H | 7.80 (mc, 4H) | 7.60 (d, 2H) 7.24 (d, 2H) 2.44 (s, 3H) | 7.44 (d, 2H) 6.67 (d, 2H) | 7.90 (sb, 1H) 7.50–7.64 (2H) 3.46 (t, 2H) |
| 4H | 3.66 (mc, 2H) n. obs. 2.04 | 3.5–3.7 (2H) 40.1 (mc, 1H) 1.98 (mc, 1H) 0.94 (d, 3H) 0.90 (d, 3H) | 3.50–3.65 (4H) 4.12 (mc, 1H) | 3.70 (t, 2H) 3–56–3.66 (4H) 4.28 (mc, 1H) |
| NH | (mc, 1H) | 9.95 (sb, 1H) | | |
| OH | 0.97 (d, 3H) 0.94 (d, 3H) 10.40 (sb, 1H) 7.18 (sb, 2H) n. obs. | 6.96 (sb, 1H) about 4, very broad | 8.98 (sb, 1H) 5.97 (db, 1H) 8.90 (sb, 1H) 4.80 (tb, 2H) | NH and OH are very broad |
| Chrom. | — | — | — | Crystallized Water |
| Yield | 43% | 27% | 76% | 52% |
| Melting Point | 252–253° C. | 192–193° C. | 257 . 258° C. | 209–210° C. |

-continued

| Example No. | 9 | 14 | 55 | 50 |
|---|---|---|---|---|
| 6-H | 8.30 (s, 1H) | 8.30 (s, 1H) | 8.11 (s, 1H) | 8.17 (s, 1H) |
| 2H | 7.82 (mc, 4H) | 7.55 (d, 2H)<br>7.30 (d, 2H)<br>2.48 (s, 3H) | 7.87 (s, 4H)<br>2.50 (s) | 7.95 (d, 2H)<br>7.86 (d, 2H)<br>2.50 (s) |
| 4H | 3.63 (mc, 4H) | 3.54–3.68 (4H)<br>4.24 (mc, 1H) | 4.19 (mc, 1H)<br>3.61 (mc, 4H) | 4.17 (dd, 2H)<br>3.13 (t, 1H) |
| NH | 4.24 (mc, 1H) | | 9.73 (s, 1H) | 9.81 (s, 1H) |
| OH | 10.59 (b, 1H)<br>7.2 (sb)<br>6.1 (sb) | 10.63 (sb, 1H)<br>7.60 (sb, 1H)<br>4.4 (b) | 6.20 (sb, 1H)<br>4.88 (t, 2H) | 7.58 (t, 1H) |
| Chrom. Yield | Crystallized MeOH 24% | 91 | Crystallized MeOH/DIPE 27% | — 56% |
| Melting Point | 247–247° C. | 233–234° C. | 228–229° C. | 241° C. |

-continued

| Example No. | 46 | 13 | 52 | 53 |
|---|---|---|---|---|
| Structure | 4-sulfamoylphenyl NH-pyrimidine(5-Br)-NH-CH2-cyclopropyl | 4-(methylthio)phenyl NH-pyrimidine(5-Br)-NH-CH2CH2-morpholine | 4-acetylphenyl NH-pyrimidine(5-Br)-NH-CH2-cyclopropyl | 4-acetylphenyl NH-pyrimidine(5-Br)-NH-CH(iPr)-CH2OH |
| 6-H | 8.07/s, 1H | 8.00 (s, 1H) | 8.09 (s, 1H) | 8.11 (s, 1H) |
| 2H | 7.91 (d, 2H)<br>7.69 (d, 2H) | 7.68 (d, 2H)<br>7.18 (d, 2H)<br>2.44 (s, 3H) | 7.88 (s, 4H) | 7.86 (s, 4H)<br>not obs. |
| 4H | 3.30 (t, 2H)<br>n.obs. (mc, 1 H)<br>0.45 (mc, 2H) | 3.54 (q, 2h9<br>2.53 (t, 2H)<br>2.40–2.45 (4H)<br>3.58 (t, 4H) | 3.32 (t, 2H)<br>1.20 (mc, 1H)<br>0.44 (mc, 2H)<br>0.30 (mc, 2H) | 3.62 (mc, 2H)<br>4.06 (mc, 1H)<br>2.02 (mc, 1H)<br>0.97 (d, 3H)<br>0.92 (d, 3H) |
| NH | 0.30 | 9.20 (sb, 1H)<br>6.81 (tb, 1H) | 9.70 (s, 1H) | 9.70 (s, 1H) |
| OH | 9.94 (s, 1H)<br>7.21 (t, 1H)<br>7.18 (s, 2H) | | 7.21 (t, 1H) | 6.24 (d, 1H)<br>4.80 (sb, 1H) |
| Chrom. Yield | H/EA 1:2<br>20% | —<br>28% | —<br>53% | H/EA 1:2<br>9% |
| Melting Point | 256° C. | 185–186° C. | 183° C. | 170° C. |

-continued
| Example No | 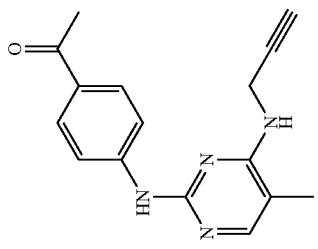 1 | 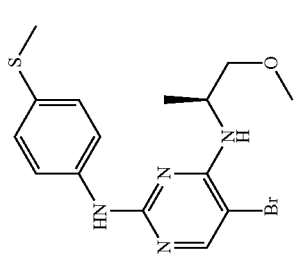 54 | 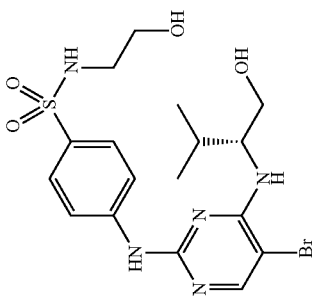 12 | 60 |
|---|---|---|---|---|
| 6-H | 7.96 (s, 1H) | 8.22 (s, 1H) | 8.03 (s, 1H) | 8.10 (s, 1H) |
| 2H | 7.43 (d, 2H)<br>6.67 (d, 2H) | 7.93 (d, 2H)<br>7.85 (d, 2H) | 7.68 (d, 2H)<br>7.19 (d, 2H)<br>2.43 (s, 3H) | 7.92 (d, 2H)<br>7.66 (d, 2H)<br>not. obs.<br>2.74 (t, 2H) |
| 4H | 1.20 (d, 3H)<br>4.38 (mc, 1H)<br>3.37 (dd, 1H)<br>3.48 (dd, 1H) | 4.26 (d, 2H)<br>3.12 (sb, 1H) | 1.20 (d, 3H)<br>4.42 (mc, 1H)<br>3.37 (dd, 1H)<br>3.50 (dd, 1H)<br>3.34 (s, 3H) | 3.61 (mc, 2H)<br>4.04 (mc, 1H)<br>2.01 (mc, 1H)<br>0.94 (d, 3H)<br>0.91 (d, 3H) |
| NH | 3.28 (s, 3H)<br>8.92 (sb, 1H)<br>8.81 (sb, 1H) | 9.78 (s, 1H) | 9.26 (s, 1H) | 9.72 (s, 1H)<br>7.65 (s, 1H)<br>6.27 (d, 1H) |
| OH | 6.20 (tb, 1H) | 7.21 (t, 1H) | 6.42 (d, 1H) | 4.80 (sb, 1H)<br>4.70 (sb, 1H) |
| Chrom. Yield | Crystallized EA 64% | Crystallized DIPE/MeOH 52% | Crystallized EA 36% | |
| Melting Point | 165.5–166° C. | 210° C. | 91° C. | 150–151° C. |

-continued

| Example No. | 7 | 17 | 2 | 18 | 8 (D₂O) |
|---|---|---|---|---|---|
| 6-H | 8.32 (s, 1H) | 8.08 (s, 1H) | 7.95 (s, 1H) | 8.32 (s, 1H) | 8.14 (s, 1H) |
| 4CH | 1.22 (d, 3H)<br>4.46 (mc, 1H)<br>3.40 (dd, 1H)<br>3.57 (dd, 1H) | 1.21 (d, 3H)<br>4.53 (mc, 1H)<br>3.41 (dd, 1H)<br>3.51 (dd, 1H)<br>3.27 (s, 3H) | 3.50 (q, 2H)<br>2.50 (t, 2H)<br>2.40 (t, 4H)<br>3.59 (t, 4H) | 3.10 (m, 2H)<br>3.52 (m, 4H)<br>3.77–3.97 (6H) | 3.06 (sb, 2H)<br>3.39 (t, 4H)<br>3.71 (sb, 2H)<br>3.85 (sb, 2H)<br>3.94 (t, 2H) |
| 2CH | 3.28 (s, 3H)<br>7.80 (s, 4H) | 8.53 (s, 1H)<br>7.40 (d, 1H)<br>7.50 (t, 1H)<br>7.86 (d, 1H)<br>3.40 (t, 2H)<br>3.68 (t, 2H) | 7.45 (d, 2H)<br>6.66 (d, 2H)<br>7.55–7.70 | 8.40 (s, 1H)<br>(2H)<br>7.85 (sb, 2H)<br>3.48 (m, 2H) | 8.00 (d, 2H)<br>7.72 (d, 2H) |
| NH | 10.79 (sb, 1H)<br>7.84 (db, 1H)<br>7.31 (sb, 2H) | 9.65 (sb, 1H)<br>6.47 (db, 1H) | 8.94 (sb, 1H)<br>8.79 (db, 1H) | 11.16 (sb, 1H)<br>10.60 (sb, 1H)<br>8.20 (sb, 1H) | |
| OH | | 4.84 (tb, 1H) | 6.70 (tb, 1H) | | |
| Chrom. Yield | 25% | 10% | 62% | Crystall. MeOH | Cryst. Water 25% |
| Melting Point | 247° Dec. | 201–202° C. | 227.5–228.5° C. | 245° C. Dec. >275° C. | |

-continued
| Example No. | 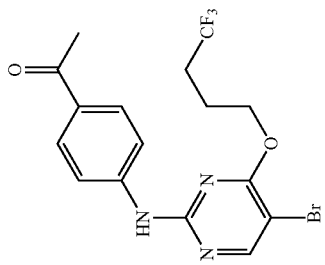 47 | 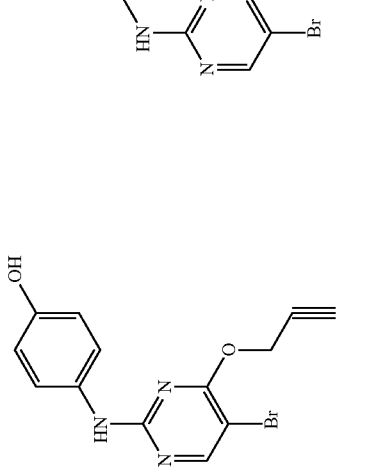 6 | 22 | 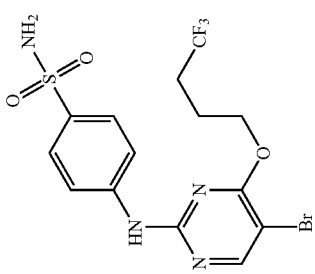 84 |
|---|---|---|---|---|
| 5-H | 8.74 (s, 1H) | 8.31 (s, 1H) | 8.31 (s, 1H) | 8.47 (s, 1H) |
| 2CH | 7.87 (d, 2H)<br>7.74 (d, 2H) | 7.47 (d, 2H)<br>6.71 (d, 2H) | 7.76 (d, 2H)<br>7.72 (d, 2H)<br>2.58 (s, 3H) | 4.48 (t, 2H)<br>2.01 (mc, 2H)<br>2.44 (mc, 2H) |
| 4CH | 4.50 (t, 2H)<br>2.03 (mc, 2H)<br>2.44 (mc, 2H) | 5.04 (d, 2H)<br>3.59 (t, 1H) | 5.05 (d, 2H)<br>2.57 (t, 1H) | 7.91 (d, 2H) |
| 2NH | 10.14 (s, 1H)<br>7.21 (s, 2H) | 9.02 (sb, 1H)<br>9.40 (sb, 1H) | 7.47 (sb, 1H) | 7.85 (d, 2H)<br>2.50 (s)<br>10.19 (s, 1H) |
| Chrom.<br>Yield | MeOH/DCM<br>1:9<br>4% | —<br>66% | —<br>8% | —<br>11% |
| Melting<br>Point | 186–187° C. | 146° C. | 165–166° C. | 152° C. |

-continued
| Example No. | 86 | 77 |
|---|---|---|
| | 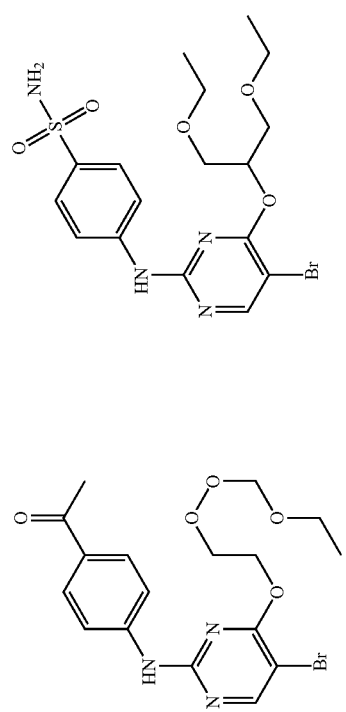 | 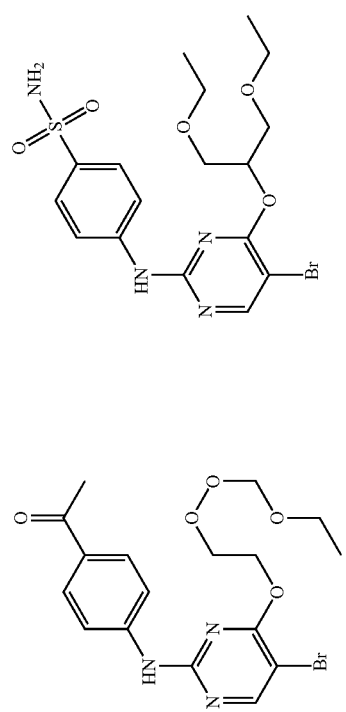 |
| 5-H | 8.47 (s, 1H) | 8.48 (s, 1H) |
| 2CH | 4.07 (mc, 2H)<br>3.81 (mc, 2H)<br>3.60 (mc, 2H) | 5.52 (m, 1H)<br>3.68 (d, 4H)<br>3.48 (mc, 4H) |
| 4CH | 3.48 (mc, 2H)<br>3.41 (t, 2H)<br>1.07 (t, 3H) | 1.09 (t, 6H)<br>7.84 (d, 2H) |
| 2NH | 7.84 (d, 2H)<br>7.91 (d, 2H)<br>10.18 (s2, H) | 7.74 (d, 2H)<br>8.05 (vb)<br>3.40 (vb) |
| Chrom. Yield | 2% | 74% |
| Melting | 85° C. | 132° C. |

-continued
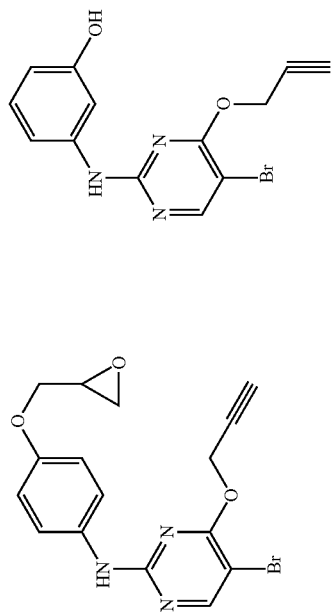
| | | |
|---|---|---|
| Example No. | 40 | 20 |
| 6-H | 8.36 (s, 1H) | 8.40 (s, 1H) |
| 2CH | 7.60 (d, 1H)<br>6.91 (d, 1H)<br>4.28 (dd, 1H)<br>3.79 (dc, 1H)<br>3.31 (m, 1H)<br>2.84 (dd, 1H)<br>2.70 (dd, 1H) | 7.23 (s, 1H)<br>6.42 (d, 1H)<br>7.06 (t, 1H)<br>7.18 (d, 1H) |
| 4CH | 5.07 (d, 12H)<br>3.65 (t, 1H) | 5.12 (d, 2H)<br>3.60 (sb, 1H) |
| NH | 9.65 (sb, 1H) | 9.60 (sb, 1H) |
| OH | | 9.21 (sb, 1H) |
| Chrom.<br>Yield | H/EA 1:3<br>0.5% TEA<br>38% | Cryst. DIPE<br>35% |
| Melting Point | 140–141° C. | 174° C. |

-continued
| Example No. | 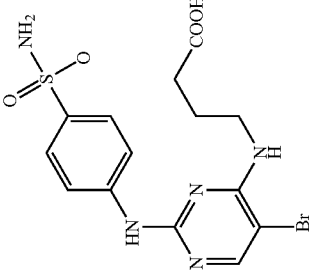 49 | 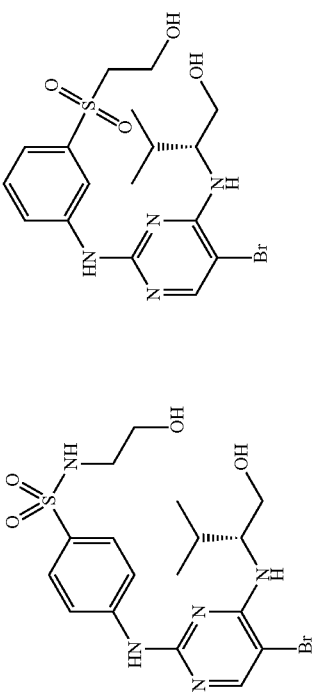 48 | 29 | 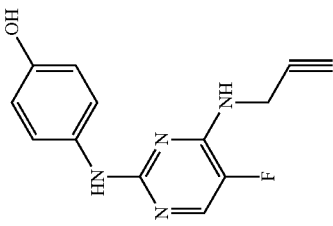 42 |
|---|---|---|---|---|
| 6-H | 8.14 (s, 1H) | 8.10 (s, 1H) | 8.09 (s, 1H) | 7.87 (d, 3.4, 1H) |
| 2H | 7.88 (d, 2H) 7.69 (d, 2H) 2.74 (t, 2H) | 7.92 (d, 2H) 7.66 (d, 2H) not. obs. 7.40 (d, 1H) | 8.50 (s, 1H) 7.86 (d, 1H) 7.50 (t, 1H) | 7.51 (d, 2H) 6.66 (d, 2H) |
| 4H | 3.41 (q, 2H) 2.20 (t, 2H) 1.81 (q, 2H) | 3.61 (mc, 2H) 4.04 (mc, 1H) 2.01 (mc, 1H) 0.94 (d, 3H) 0.91 (d, 3H) | 3.40 (t, 2H) 3.52–3.73 (4H) 4.09 (mc, 1H) 1.98 (mcAH) 0.97 (d, 3H) | 4.13 (dd, 2H) 3.08 (t, 1H) |
| NH | 9.64 (s, 1H) 7.64 (t, 1H) | 9.72 (s, 1H) 7.65 (t, 1H) | 0.89 (d, 3H) 9.68 (s, 1H) | 8.76 (s, 1H) 7.74 (tb, 1H) |
| OH | 3.5 (vb | 6.27 (d, 1H) 4.80 (sb, 1H) 4.70 (sb, 1H) | 6.17 (d, 1H) 4.74 (t, 1H) 4.93 (sb, 1H) | 8.88 (s, 1H) |
| Chrom. Yield | — 9% | Cryst. MeOH/DIPE 16% | DCM/EA 2:1 26% | H/EA 1:2 29% |
| Melting Point | 262° C. | 150–151° C. | | 163° C. |

-continued
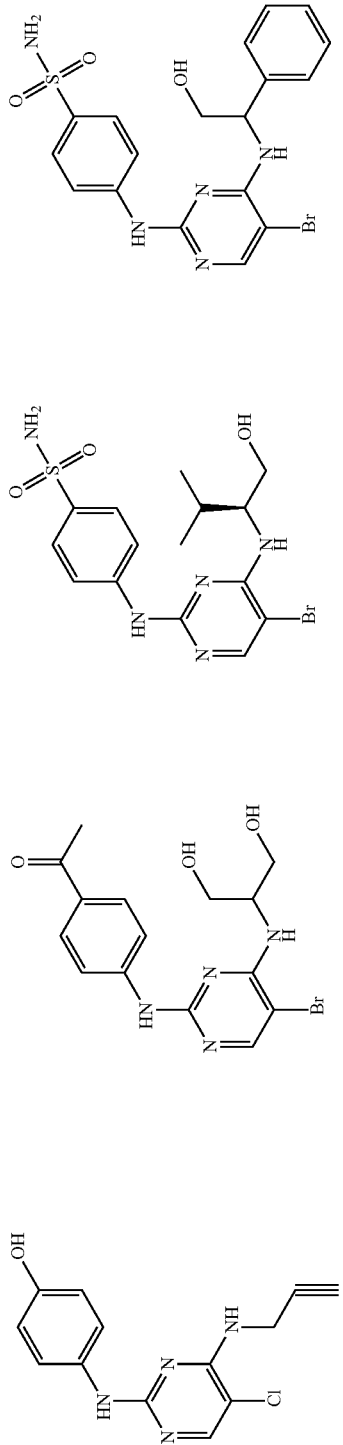
| Example No. | 43 | 55 | 89 | 88 |
|---|---|---|---|---|
| 6-H | 7.93 (s, 1H) | 8.11 (s, 1H) | 8.36 (s, 1H) | 8.29 (s, 1H) |
| 2H | 7.52 (d, 2H)<br>6.68 (d, 2H) | 7.87 (s, 4H)<br>2.50 (s) | 7.7–7.8 (5H) | 7.73 (d, 2H)<br>7.57 (d, 2H) |
| 4H | 3.09 (s, 1H)<br>4.14 (d, 2H) | 4.19 (mc, 1H)<br>3.61 (mc, 4H) | 3.66 (mc, 2H)<br>4.04 (m, 1H)<br>1.99 (mc, 1H)<br>0.94 (d, 3H)<br>0.89 (d, 3H) | 3.7–3.9 (2H)<br>5.19 (m, 1H)<br>7.2–7.4 (5H) |
| NH | 8.98 (sb, 2H)<br>7.50 (s, 1H) | 9.73 (s, 1H)<br>6.20 (s, 1H) | 11.11 (sb, 1H) | 10.50 (s, 1H)<br>5.029 (vb) |
| OH |  | 4.88 (t, 2H) | 7.34 (sb, 2H)<br>n. obs. |  |
| Chrom.<br>Yield | H/EA 1:2<br>35% | Cryst. MeOH/<br>DIPE<br>27% | —<br>74% | —<br>27% |
| Melting<br>Point | 168° C. | 228° C. | 248° C. Dec. | 159° C. Dec. |

-continued
| Example No. | 87 | 92 | 91 | 96 |
|---|---|---|---|---|
| | 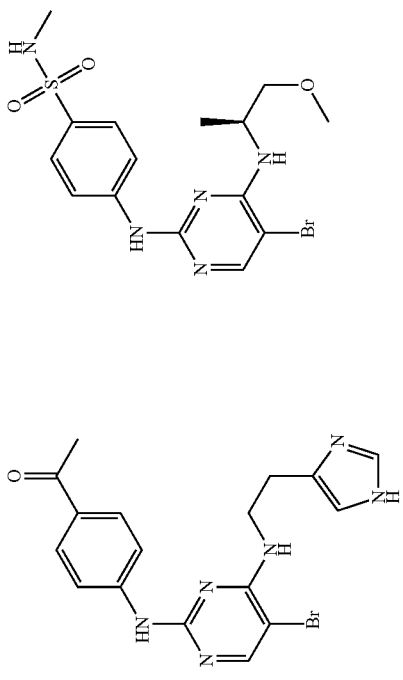 | 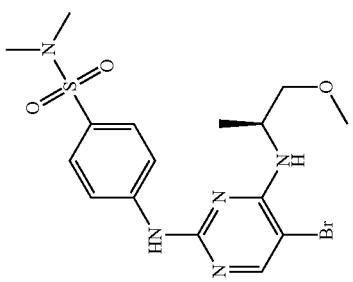 | 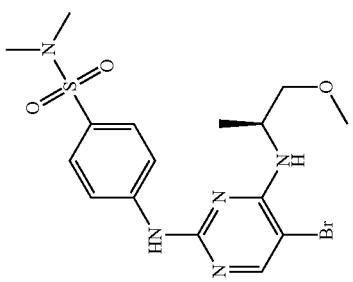 | 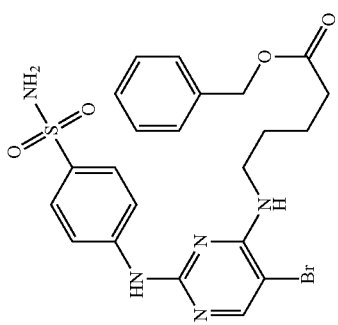 |
| 6-H | 8.09 (s, 1H) | 8.10 (s, 1H) | 8.09 (s, 1H) | 8.06 (s, 1H) |
| 2H | 7.90 (d, 2H) 7.82 (d, 2H) not. obs | 7.91 (d, 2H) 7.63 (d, 2H) 2.39 (s, 3H) | 7.98 (d, 2H) 7.61 (d, 2H) 2.54 (s, 6H) | 7.88 (d, 2H) 7.69 (d, 2H) |
| 4H | 3.69 (d, 2H) 2.84 (t, 2H) 7.60 (s, 1H) 6.86 (s, 1H) | 1.21 (d, 3H) 4.45 (mc, 1H) 3.38 (dd, 1H) 3.51 (dd, 1H) | 1.20 (d, 3H) 4.46 (mc, 1H) 3.47 (dd, 1H) 3.51 (dd, 1H) 3.38 (s, 3H) | 3.41 (m, 2H) 1.62 (m, 4H) 2.41 (m, 2H) 5.07 (s, 2H) |
| NH | 7.34 (tb, 1H) 9.72 (s, 1H) | 9.73 (sb, 1H) 7.20 (q, 1H) | 9.81 (sb, 1H) 6.58 (db, 1H) | 7.32 (s, 5H) 9.64 (s, 1H) 7.16 (sb, 2H) |
| OH | 11.91 (sb, 1H) | 6.57 (d, 1H) | | |
| Chrom. Yield | — 16% | H to H/EA 1:1 21% | H to H/EA 1:1 7% | — 33% |
| Melting Point | 210° C. | 167–168° C. | 105° C. | 202° C. |

-continued
| Example No. | 97 | 98 | | 90 | 85 |
|---|---|---|---|---|---|
| | 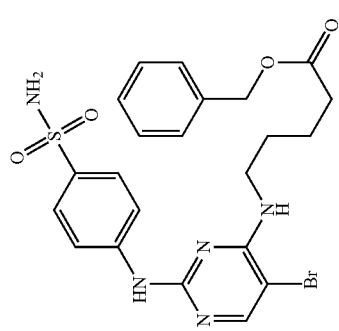 | 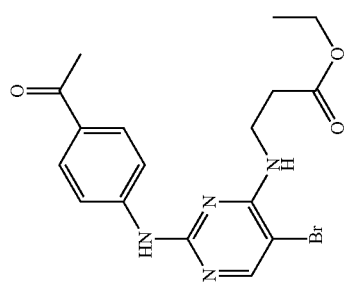 | | 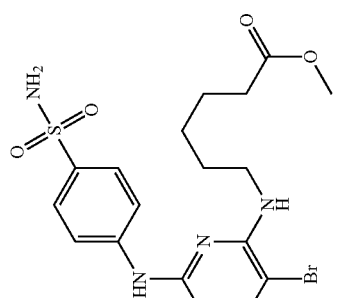 | 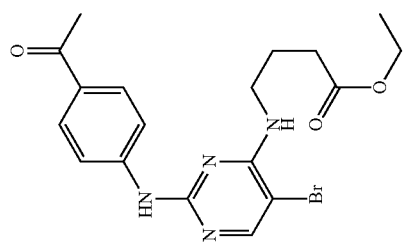 |
| 6-H | 8.07 (s, 1H) | 8.10 (s, 1H) | | | 8.30 (s, 1H) |
| 2H | 7.87 (s, 4H)<br>2.50 (s, 3H) | 7.86 (mc, 4H)<br>n. obs. | | | 7.95 (d, 2H)<br>7.69 (d, 2H)<br>2.48 (s, 3H) |
| 4H | 3.41 (m, 2H)<br>1.61 (m, 4H)<br>2.41 (m, 2H)<br>5.07 (s, 2H) | 3.68 (t, 2H)<br>2.68 (t, 2H)<br>4.08 (q, 2H)<br>1.17 (t, §H) | | | 3.50 (q, 2H)<br>1.87 (m, 2H)<br>2.38 (t, 2H)<br>4.03 (q, 2H)<br>1.13 (t, 3H) |
| NH | 7.32 (s, 5H)<br>9.70 (s, 1H)<br>7.19 (t, 1H) | 9.74 (s, 1H)<br>7.18 (t, 1H) | | | 10.86 (s, 1H)<br>8.28 (sb, 2H) |
| Chrom. Yield | 23% | 32% | | | 53% |
| Melting Point | 152° C. | 172 | | | 184° C. |

| Example No. | 63 | 94 | 93 | 80 |
|---|---|---|---|---|
| | 9.73 (s, 1H)<br>8.25 (s, 1H)<br>7.95 (d, 2H)<br>7.67 (d, 2H)<br>7.21 (s, 3H)<br>4.12 (s, 2H)<br>3.12 (s, 1H) | 10.91 (s, 1H)<br>8.34 (s, 1H)<br>7.80 (s, 4H)<br>7.30 (s, 2H)<br>4.35 (m, 1H)<br>3.58 (m, 2H)<br>2.47 (m, 2H)<br>2.03 (s, 3H)<br>1.91 (m, 2H) | 10.80 (s, 1H)<br>8.30 (s, 1H)<br>7.81 (d, 2H)<br>7.65 (d, 2H)<br>7.30 (m, 8H)<br>4.95 (d, 1H)<br>4.38 (m, 1H)<br>3.59 (d, 1H) | 10.88 (s, 1H)<br>8.40 (s, 1H)<br>8.29 (m, 1H)<br>7.79 (s, 4H)<br>7.31 (s, 2H)<br>4.75 (dd, 1H)<br>3.65 (m, 1H)<br>3.49 (m, 1H)<br>2.10 (m, 2H) |
| Yield | 61% | 24% | 70% | 51% |
| Melting Point | 220 | 168 | 243 | |
| Mass | 428 (EI) | 462 (ES) | 494 (ES) | 427 (EI) |

| Example No. | 120 | 121 | 122 | 123 |
|---|---|---|---|---|
| | 9.65 (s, 1H) | 9.68 (s, 1H) | 11.30 (s, 1H) | 10.79 (s, 1H) |

| | |
|---|---|
| 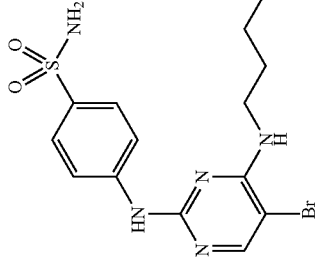 | 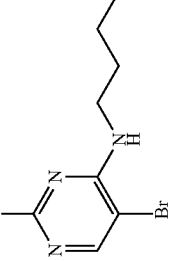 |
| 8.12 (s, 1H)<br>7.89 (d, 2H)<br>7.65 (s, 2H)<br>7.15 (d, 2H)<br>6.06 (d, 1H)<br>4.71 (t, 1H)<br>4.18 (m, 1H)<br>3.67 (t, 1H)<br>0.95 (s, 9H) | 8.11 (s, 1H)<br>7.93 (t, 1H)<br>7.90 (d, 2H)<br>7.65 (d, 2H)<br>7.15 (s, 2H)<br>7.07 (t, 1H)<br>3.65 (m, 2H)<br>3.56 (s, 3H)<br>3.07 (q, 2H)<br>2.45 (t, 2H)<br>2.30 (t, 2H)<br>1.65 (p, 2H) |
| Yield 49%<br>Melting Point<br>Mass 445 (EI) | Yield 24%<br>Melting Point<br>Mass 516 (EI) |

| Example No. | 95 | 124 |
|---|---|---|
| | 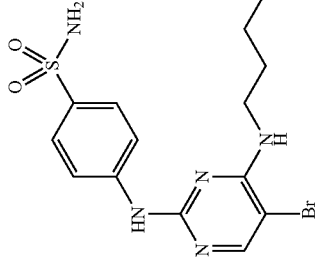 | 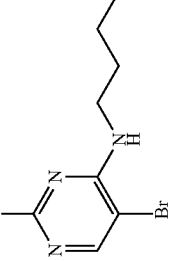 |
| | 11.19 (s, 1H)<br>8.37 (s, 1H)<br>8.11 (d, 4H)<br>7.80 (s, 2H)<br>7.31 (s, 2H)<br>3.91 (m, 4H)<br>1.89 (m, 4H)<br>1.67 (m, 1H)<br>1.55 (m, 2H)<br>1.34 (m, 2H)<br>1.15 (m, 1H) | 9.62 (s, 1H)<br>8.04 (s, 1H)<br>7.88 (m, 3H)<br>7.66 (d, 2H)<br>7.13 (s, 3H)<br>3.58 (s, 3H)<br>3.40 (m, 2H)<br>3.05 (m, 2H)<br>2.25 (m, 2H)<br>2.05 (m, 2H)<br>1.32 (m, 3H) |
| Yield<br>Melting Point<br>Mass | 29%<br>255<br>425 (EI) | 25%<br>557 (ES) |

| | |
|---|---|
| 8.35 (s, 1H)<br>8.25 (s, 1H)<br>7.80 (s, 4H)<br>7.30 (s, 2H)<br>3.41 (m, 2H)<br>2.22 (t, 2H)<br>1.60 (m, 4H)<br>1.30 (m, 2H) | |
| 73%<br>252<br>459 (EI) | |

| | |
|---|---|
| 8.11 (d, 1H)<br>7.85 (d, 2H)<br>7.72 (d, 2H)<br>7.31 (s, 2H)<br>6.71 (d, 1H)<br>3.85 (m, 8H) | |
| 80%<br>334 (EI) | |

-continued

| Example No. | 125 | 126 |
|---|---|---|
|  | 9.62 (s, 1H)<br>8.04 (s, 1H)<br>7.86 (d, 2H)<br>7.66 (d, 2H)<br>7.12 (s, 3H)<br>3.58 (s, 3H)<br>3.40 (m, 2H)<br>2.30 (t, 2H)<br>1.60 (m, 4H)<br>1.32 (m, 2H)<br>1.60 (m, 5H) | 10.91 (s, 1H)<br>8.38 (s, 1H)<br>7.83 (d, 2H)<br>7.77 (d, 2H)<br>7.28 (s, 2H)<br>7.04 (d, 1H)<br>6.40 (br, 3H)<br>4.35 (m, 1H)<br>3.87 (m, 1H)<br>3.60 (d, 2H)<br>3.41 (dd, 1H)<br>3.28 (dd, 1H) |
| Yield | 27% | 46% |
| Melting Point | 218 |  |
| Mass | 471 (EI) | 449 (EI) |

-continued

| Example No. | 127 | 128 | 129 | 130 |
|---|---|---|---|---|
| | 9.96 (s, 1H)<br>8.12 (s, 1H)<br>7.85 (d, 2H)<br>7.69 (d, 2H)<br>7.20 (s, 2H)<br>6.78 (d, 1H)<br>4.35 (m, 2H)<br>3.48 (m, 2H)<br>1.65 (m, 7H)<br>1.10 (m, 6H)<br>1.55 (m, 4H)<br>1.30 (m, 2H) | 9.60 (s, 1H)<br>8.05 (s, 1H)<br>7.90 (d, 2H)<br>7.69 (d, 2H)<br>7.42 (d, 1H)<br>7.16 (m, 3H)<br>4.57 (t, 2H)<br>3.70 (m, 1H)<br>3.4 (m, 5H)<br>2.10 (t, 2H) | 9.67 (s, 1H)<br>8.07 (s, 1H)<br>7.87 (d, 2H)<br>7.75 (d, 2H)<br>7.13 (s, 2H)<br>6.40 (d, 1H)<br>4.91 (br, 1H)<br>4.23 (m, 1H)<br>3.52 (m, 2H)<br>1.21 (d, 3H)<br>1.50 (m, 2H)<br>1.30 (m, 2H) | 9.65 (s, 1H)<br>8.08 (s, 1H)<br>7.87 (d, 2H)<br>7.64 (d, 2H)<br>7.14 (s, 2H)<br>6.53 (d, 1H)<br>4.62 (d, 1H)<br>3.90 (br, 1H)<br>3.40 (br, 1H)<br>1.88 (m, 4H) |
| Yield | 18% | 94% | 61% | 58% |
| Melting Point | 220 | | 259 | 262 |
| Mass | 485 (EI) | 531 (ES) | 403 (EI) | 443 (EI) |

-continued
| Example No. | 131 | 132 | 133 | 134 |
|---|---|---|---|---|
| | 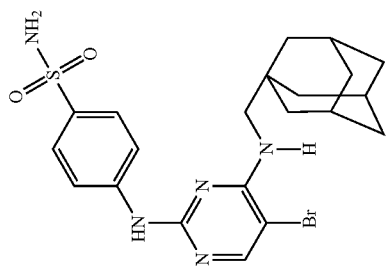 | 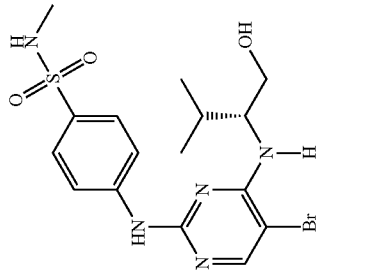 | 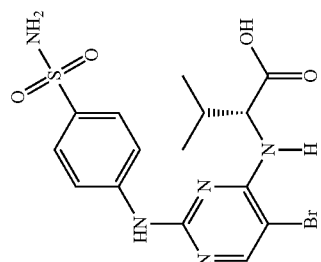 | 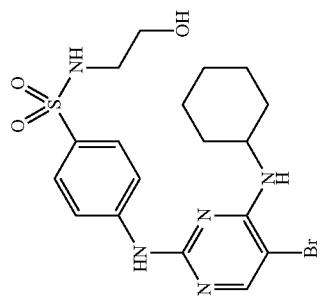 |
| | 9.62 (s, 1H)<br>8.08 (s, 1H)<br>7.92 (d, 2H)<br>7.67 (d, 2H)<br>7.23 (s, 2H)<br>6.75 (t, 1H)<br>3.22 (d, 2H)<br>1.95 (s, 3H)<br>1.60 (m, 12H) | 9.70 (s, 1H)<br>8.11 (s, 1H)<br>7.90 (d, 2H)<br>7.60 (d, 2H)<br>7.21 (q, 1H)<br>5.25 (d, 1H)<br>4.77 (t, 1H)<br>4.02 (m, 1H)<br>3.60 (m, 2H)<br>2.39 (s, 3H)<br>2.02 (m, 1H)<br>0.95 (dd, 6H) | 9.69 (s, 1H)<br>8.11 (s, 1H)<br>7.88 (d, 2H)<br>7.66 (d, 2H)<br>7.15 (s, 2H)<br>6.52 (d, 1H)<br>4.35 (dd, 1H)<br>2.29 (m, 1H)<br>1.07 (d, 3H)<br>0.91 (d, 3H) | 10.85 (s, 1H)<br>8.31 (s, 1H)<br>7.90 (d, 1H)<br>7.85 (d, 2H)<br>7.75 (d, 2H)<br>7.54 (s, 1H)<br>3.90 (m, 1H)<br>3.38 (t, 2H)<br>2.78 (br, 2H)<br>1.50 (m, 11H) |
| Yield | 9% | 42% | 25% | 64% |
| Melting Point | 229 | 141 | | |
| Mass | 491 (EI) | 443 (EI) | 444 (FAB) | |

| Example No. | 135 | 136 | 137 | 138 |
|---|---|---|---|---|
| | 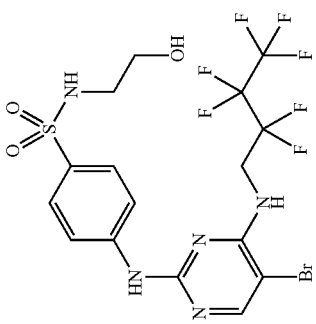 | 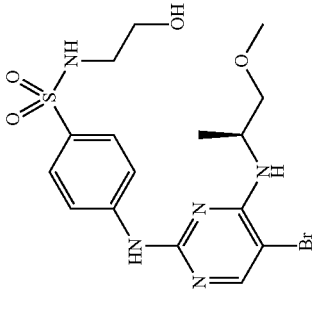 | 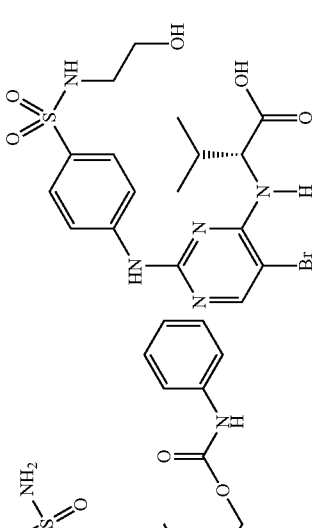 | 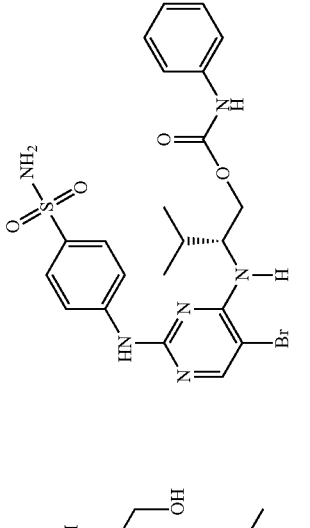 |
| | 10.01 (s, 1H)<br>8.28 (s, 1H)<br>7.81 (d, 2H)<br>7.71 (t, 1H)<br>7.63 (d, 2H)<br>7.45 (br, 1H)<br>4.34 (dt, 2H)<br>3.32 (t, 2H)<br>2.71 (br, 2H) | 9.70 (s, 1H)<br>8.11 (s, 1H)<br>7.90 (d, 2H)<br>7.64 (d, 2H)<br>7.35 (t, 1H)<br>6.55 (d, 1H)<br>4.65 (t, 1H)<br>4.45 (m, 1H)<br>3.53 (m, 6H)<br>3.44 (m, 6H)<br>2.75 (q, 2H)<br>1.20 (d, 3H) | 9.65 (s, 1H)<br>9.58 (s, 1H)<br>8.10 (s, 1H)<br>7.85 (d, 2H)<br>7.68 (d, 2H)<br>7.40 (m, 4H)<br>7.18 (m, 4H)<br>6.94 (t, 1H)<br>6.75 (d, 1H)<br>4.40 (m, 3H)<br>2.05 (m, 1H)<br>0.96 (dd, 6H) | 9.70 (s, 1H)<br>8.10 (s, 1H)<br>7.89 (d, 2H)<br>7.63 (d, 2H)<br>7.39 (t, 1H)<br>6.68 (d, 1H)<br>4.34 (dd, 1H)<br>3.36 (m, 3H)<br>2.25 (q, 2H)<br>2.29 (m, 1H)<br>1.05 (dd, 6H) |
| Yield | 34% | 53% | 59% | 57% |
| Melting Point | | | | |
| Mass | 570 (ES) | 460 (ES) | 549 (ES) | 488 (ES) |

| Example No. | 139 | 140 | 141 | 142 |
|---|---|---|---|---|
| | 9.82 (s, 1H)<br>8.15 (s, 1H)<br>7.82 (d, 2H)<br>7.64 (d, 2H)<br>7.39 (t, 1H)<br>6.55 (d, 1H)<br>4.50 (t, 1H)<br>3.65 (m, 3H)<br>3.4 (m, 2H)<br>2.75 (m, 2H)<br>2.35 (m, 1H)<br>1.00 (dd, 6H) | 9.82 (s, 1H)<br>8.08 (s, 1H)<br>7.96 (d, 2H)<br>7.75 (t, 1H)<br>7.62 (d, 2H)<br>7.30 (t, 1H)<br>4.64 (t, 1H)<br>4.14 (m, 2H)<br>3.35 (m, 1H)<br>3.16 (m, 2H)<br>2.75 (q, 2H) | 9.58 (s, 1H)<br>8.12 (s, 1H)<br>7.83 (d, 2H)<br>7.68 (d, 2H)<br>7.15 (s, 2H)<br>5.92 (s, 1H)<br>5.28 (t, 1H)<br>3.50 (d, 2H)<br>1.42 (s, 6H) | 9.62 (s, 1H)<br>8.07 (s, 1H)<br>7.87 (d, 2H)<br>7.67 (d, 2H)<br>7.14 (s, 2H)<br>6.36 (d, 1H)<br>4.81 (t, 1H)<br>4.32 (m, 1H)<br>3.47 (m, 2H)<br>1.52 (m, 3H)<br>0.90 (d, 3H)<br>0.86 (d, 3H) |
| Yield | 20% | 63% | 23% | 8% |
| Melting Point | | | | |
| Mass | 502 (ES) | 382 (ES) | 415 (EI) | 443 (EI) |

| Example No. | 143 | 144 | 145 | 78 |
|---|---|---|---|---|
| | 10.6 (s, 1H)<br>8.28 (s, 1H)<br>8.30 (m, 5H)<br>7.48 (d, 1H)<br>7.20 (s, 1H)<br>4.05 (br, 1H)<br>3.60 (br, 2H)<br>2.01 (m, 1H)<br>0.90 (m, 6H) | 10.11 (s, 1H)<br>8.45 (s, 1H)<br>7.86 (d, 2H)<br>7.78 (d, 2H)<br>7.15 (br, 2H)<br>5.32 (m, 1H)<br>3.91 (m, 2H)<br>3.53 (m, 2H)<br>2.05 (m, 2H)<br>1.70 (m, 2H) | 11.05 (s, 1H)<br>8.32 (s, 1H)<br>8.08 (d, 1H)<br>7.80 (m, 4H)<br>7.30 (br, 2H)<br>3.88 (m, 1H)<br>3.65 (m, 1H)<br>1.95 (m, 2H)<br>1.69 (m, 2H)<br>1.35 (m, 4H) | 9.69 (s, 1H)<br>8.06 (s, 1H)<br>7.88 (d, 2H)<br>7.63 (d, 2H)<br>7.18 (s, 2H)<br>7.10 (t, 1H)<br>6.65 (d, 1H)<br>4.47 (m, 1H)<br>3.97 (m, 2H)<br>2.98 (m, 2H)<br>2.00 (m, 4H)<br>1.40 (m, 8H)<br>0.85 (t, 3H) |
| Yield | 13% | 47% | 42% | 20% |
| Melting Point | | | | |
| Mass | 392 (EI) | 428 (EI) | 441 (EI) | 541 (ES) |

-continued

| Example No. | 146 | 147 | 148 | 149 |
|---|---|---|---|---|
|  | 11.13 (s, 1H)<br>8.38 (s, 1H)<br>7.92 (d, 2H)<br>7.75 (m, 3H)<br>4.04 (m, 1H)<br>3.80 (s, 3H)<br>3.65 (m, 2H)<br>2.00 (m, 1H)<br>0.96 (d, 3H)<br>0.89 (d, 3H) | 11.18 (s, 1H)<br>8.35 (s, 1H)<br>7.90 (s, 4H)<br>7.62 (d, 1H)<br>4.02 (m, 1H)<br>3.62 (m, 2H)<br>3.02 (s, 3H)<br>2.00 (m, 1H)<br>0.95 (d, 3H)<br>0.89 (d, 3H) | 11.15 (s, 1H)<br>8.35 (s, 1H)<br>7.90 (d, 2H)<br>7.65 (m, 3H)<br>4.01 (m, 1H)<br>3.60 (m, 6H)<br>2.85 (m, 4H)<br>2.00 (m, 1H)<br>0.95 (d, 3H)<br>0.85 (d, 3H)<br>0.90 (d, 3H) | 9.19 (s, 1H)<br>8.30 (s, 1H)<br>8.02 (s, 1H)<br>7.62 (m, 1H)<br>6.85 (d, 1H)<br>6.05 (d, 1H)<br>4.03 (m, 1H)<br>3.56 (m, 2H)<br>1.96 (m, 1H)<br>0.97 (d, 3H) |
| Yield | 86% | 33% | 79% | 42% |
| Melting Point | 225 | 211 | 232 | 241 |
| Mass | 408 (EI) | 428 (EI) | 501 (EI) | 411 (ES) |

-continued
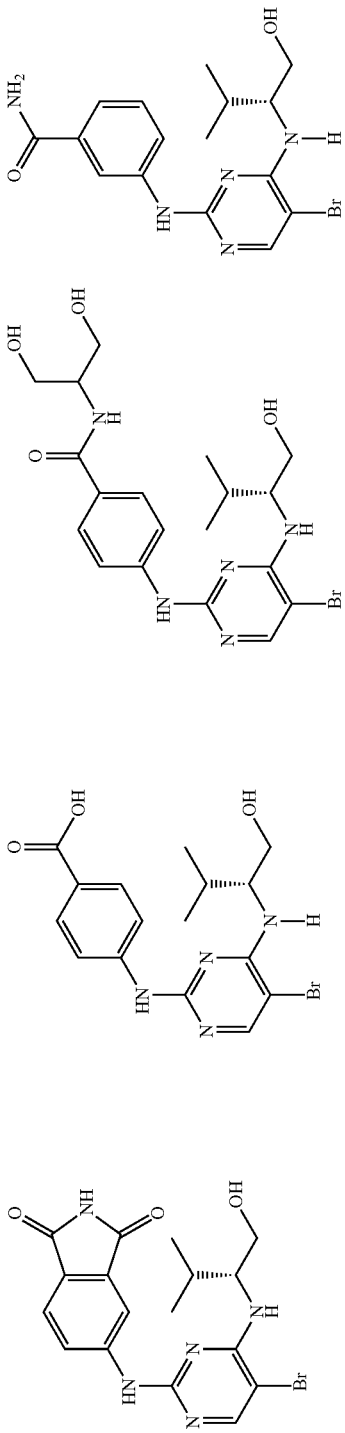
| Example No. | 150 | 151 | 152 | 153 |
|---|---|---|---|---|
|  | 11.19 (s, 1H) | 10.96 (s, 1H) | 9.50 (s, 1H) | 12.90 (s, 1H) |
|  | 10.80 (s, 1H) | 8.35 (s, 1H) | 8.08 (s, 1H) | 9.45 (s, 1H) |
|  | 8.30 (m, 2H) | 7.95 (m, 2H) | 7.75 (m, 5H) | 8.52 (s, 1H) |
|  | 7.85 (d, 1H) | 7.65 (m, 3H) | 6.17 (d, 1H) | 8.05 (s, 1H) |
|  | 7.72 (d, 1H) | 4.04 (m, 1H) | 4.80 (br, 1H) | 7.82 (d, 1H) |
|  | 7.20 (d, 1H) | 3.62 (m, 2H) | 4.64 (br, 2H) | 7.50 (d, 1H) |
|  | 4.02 (m, 1H) | 2.00 (m, 1H) | 4.05 (m, 1H) | 7.32 (t, 1H) |
|  | 3.60 (m, 2H) | 0.90 (M, 6H) | 3.94 (m, 1H) | 6.11 (d, 1H) |
|  | 2.00 (m, 1H) |  | 3.52 (m, 6H) | 4.72 (s, 1H) |
|  | 1.01 (d, 3H) |  | 2.01 (m, 1H) | 4.10 (s, 1H) |
|  | 0.90 (d, 3H) |  | 0.93 (dd, 6H) | 3.60 (m, 2H) |
|  |  |  |  | 2.01 (m, 1H) |
|  |  |  |  | 0.99 (d, 3H) |
|  |  |  |  | 0.92 (d, 3H) |
| Yield | 27% | 65% | 85% | 9% |
| Melting Point |  |  |  | 231 |
| Mass | 420 (ES) | 395 (ES) | 468 (ES) | 395 (ES) |

-continued

| Example No. | 154 | 155 | 156 | 157 |
|---|---|---|---|---|
| | 10.91 (s, 1H)<br>8.38 (s, 1H)<br>7.90 (d, 1H)<br>7.80 (m, 4H)<br>7.05 (m, 1H)<br>4.50 (s, 2H)<br>4.04 (m, 1H)<br>3.62 (m, 2H)<br>1.96 (m, 1H)<br>0.93 (d, 3H)<br>0.85 (d, 3H) | 11.05 (s, 1H)<br>8.34 (m, 2H)<br>7.75 (m, 3H)<br>7.52 (t, 1H)<br>4.04 (m, 1H)<br>3.85 (s, 3H)<br>3.65 (m, 2H)<br>2.00 (m, 1H)<br>0.94 (d, 3H)<br>0.85 (d, 3H) | 10.51 (s, 1H)<br>8.22 (s, 1H)<br>7.71 (d, 1H)<br>7.27 (m, 1H)<br>6.86 (m, 2H)<br>6.06 (s, 2H)<br>3.96 (m, 1H)<br>3.62 (m, 2H)<br>1.99 (m, 1H)<br>0.90 (m, 6H) | 15.5o (s, 1H)<br>9.50 (s, 1H)<br>8.40 (s, 1H)<br>8.11 (s, 1H)<br>7.80 (d, 1H)<br>7.53 (d, 1H)<br>6.16 (d, 1H)<br>4.78 (br, 1H)<br>4.03 (m, 2H)<br>3.60 (m, 2H)<br>2.01 (m, 1H)<br>0.91 (dd, 6H) |
| Yield | 90% | 48% | 77% | 21% |
| Melting Point | 170 | 181 | 177 | 196 |
| Mass | 381 (ES) | 409 (ES) | 394 (EI) | 391 (EI) |

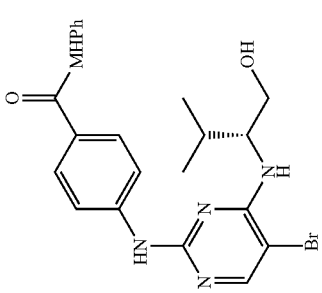

-continued
| Ex. No. | 162 | 163 * | 164 | 165 |
|---|---|---|---|---|
| | 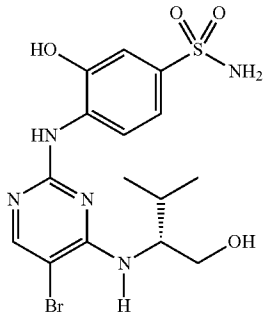 | 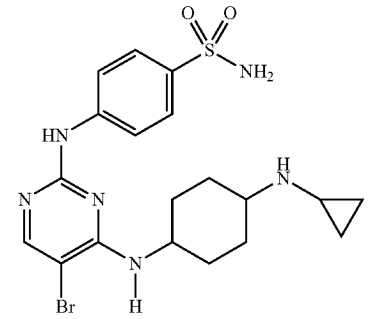  Diastereomers 1/2 (about 1:1) | 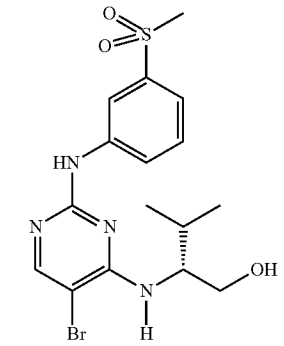 |  |
| | 11.25 (s, 1H) 9.40 (s, 1H) 8.47 (s, 1H) 7.63 (s, 1H) 7.43 (d, 1H) 7.07 (m, 3H) 4.06 (m, 1H) 3.63 (m, 2H) 1.98 (m, 1H) 0.95 (d, 3H) 0.85 (d, 3H) | 10.95 (s, 1H) 10.72 (s, 1H) 9.47 (br, 2H) 9.30 (br, 2H) 8.32 (2xs, 2H) 8.08 (d, 1H) 7.88 (d, 2H) 7.75 (m, 6H) 7.30 (br, 4H) 6.95 (d, 1H) 4.12 (m, 1H) 3.98 (m, 1H) 3.30 (m, 1H) 3.10 (m, 1H) 2.69 (m, 2H) 2.25 (m, 2H) 1.80 (m, 18H) 1.01 (m, 4H) 0.72 (m, 4H) | 9.65 (s, 1H) 8.54 (s, 1H) 8.10 (s, 1H) 7.82 (d, 1H) 7.45 (m, 2H) 6.20 (d, 1H) 4.70 (t, 1H) 4.10 (m, 1H) 3.60 (m, 2H) 3.15 (s, 3H) 2.00 (m, 1H) 0.96 (d, 3H) 0.89 (d, 3H) | |
| Yield | 16% | 33 | 14 | 51% |
| Melting Point | 195 | | | 162–164 |
| Mass | 446 (ES) | 480 (EI) | 429 (ES) | 462 (EI) |

| Example No. | 166 | 167 * | 168 * | 169 |
|---|---|---|---|---|
| Structure | (structure with indole, pyrimidine-Br, isopropyl, CH₂OH) | (bis-sulfonamide phenyl-pyrimidine-Br-cyclohexyl-amine dimer) | (bis-sulfonamide with pyrrolidine-ethyl linker; Diastereomers 1/2 (about 6:1)) | (dihydroxymethyl benzamide, salicyl, pyrimidine-Br, isopropyl, CH₂OH) |
| NMR | 10.90 (s, 1H)<br>8.95 (s, 1H)<br>7.93 (m, 2H)<br>7.25 (m, 3H)<br>6.30 (s, 1H)<br>6.00 (d, 1H)<br>4.75 (tr, 1H)<br>4.05 (m, 1H)<br>3.60 (m, 2H)<br>2.00 (m, 1H)<br>1.00 (m, 6H) | 11.15 (br, 1H)<br>10.90 (s, 1H)<br>9.75 (br, 2H)<br>8.35 (s, 1H)<br>7.78 (m, 4H)<br>7.30 (br, 2H)<br>4.15 (m, 1H)<br>3.50 (m, 5H)<br>2.85 (s, 6H)<br>1.90 (m, 8H) | 11.30 (br, 2H)<br>11.08 (s, 1H)<br>10.92 (s, 1H)<br>9.90 (s, 1H)<br>9.70 (s, 1H)<br>8.36 (2xs, 2H)<br>8.20 (d, 1H)<br>7.93 (d, 2H)<br>7.75 (m, 6H)<br>7.35 (br, 4H)<br>7.10 (d, 1H)<br>4.15 (m, 1H)<br>3.98 (m, 1H)<br>3.64 (m, 8H)<br>3.40 (m, 5H)<br>3.10 (m, 5H)<br>1.95 (m, 26H) | 9.05 (br, 1H)<br>8.85 (s, 1H)<br>8.11 (d, 1H)<br>7.97 (s, 1H)<br>7.47 (dd, 1H)<br>6.80 (d, 1H)<br>5.95 (d, 1H)<br>4.80 (br, 2H)<br>3.90 (m, 2H)<br>3.45 (m, 6H)<br>2.00 (m, 1H) |
| Yield | 6% | 16% | 58% | 60% |
| Melting Point | | 256 | 261 | |
| Mass | 390 (ES) | 512 (ES) | 538 (ES) | 484 (ES) |

-continued
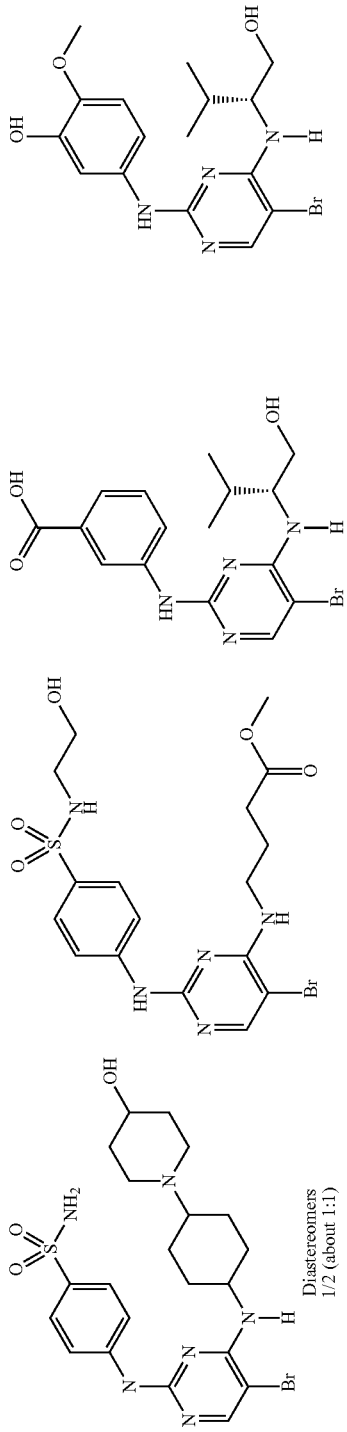
| Example No. | 170 * | 171 | 172 | 173 |
|---|---|---|---|---|
| | Diastereomers 1/2 (about 1:1) | | | |
| | 11.05 (s, 1H) | 10.45 (s, 1H) | 11.05 (s, 1H) | 8.90 (s, 1H) |
| | 10.90 (s, 1H) | 8.25 (s, 1H) | 8.35 (m, 2H) | 8.72 (s, 1H) |
| | 10.6 (br, 2H) | 8.00 (br, 1H) | 7.82 (d, 1H) | 7.95 (s, 1H) |
| | 8.35 (2xss, 2H) | 7.85 (d, 2H) | 7.65 (d, 2H) | 7.18 (m, 1H) |
| | 8.15 (d, 1H) | 7.75 (d, 2H) | 7.50 (t, 1H) | 7.05 (dd, 1H) |
| | 7.80 (m, 8H) | 7.45 (br, 1H) | 4.05 (m, 1H) | 6.75 (d, 1H) |
| | 7.30 (br, 4H) | 3.60 (m, 5H) | 3.62 (m, 2H) | 5.99 (d, 1H) |
| | 7.05 (m, 1H) | 3.35 (m, 2H) | 2.00 (m, 1H) | 4.74 (t, 1H) |
| | 4.25 (m, 1H) | 2.80 (m, 2H) | 0.96 (d, 3H) | 4.03 (m, 1H) |
| | 3.95 (m, 2H) | 2.41 (t, 2H) | 0.85 (d, 3H) | 3.70 (s, 3H) |
| | 3.65 (m, 1H) | 1.90 (m, 2H) | | 3.60 (m, 2H) |
| | 3.20 (m, 10H) | | | 2.00 (m, 1H) |
| | 1.90 (m, 24H) | | | 0.90 (m, 6H) |
| Yield | 64% | 7% | 65% | 40% |
| Melting Point | 226 | 164 | 206 | 144 |
| Mass | 525 (ES) | 488 (ES) | 395 (ES) | 397 (ES) |

-continued
| Example No. | 174 * 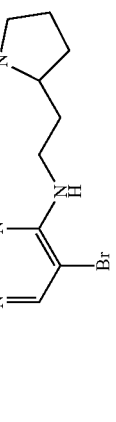 Diastereomers 1/2 (about 1:1) | 175 * 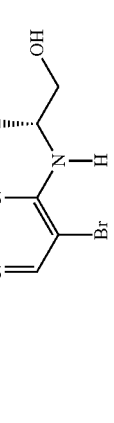 Diastereomers 3/4 (about 1:1) | 176 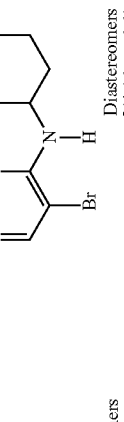 | 177 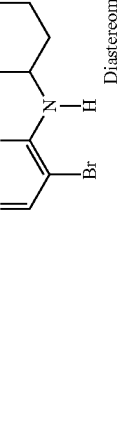 |
|---|---|---|---|---|
| | 11.05 (m, 3H)<br>10.48 (s, 1H)<br>8.38 (s, 2H)<br>7.80 (m, 8H)<br>7.10 (s, 1H)<br>6.95 (s, 1H)<br>4.42 (m, 2H)<br>4.18 (m, 2H)<br>3.70–2.90<br>(m, 10H)<br>2.40–1.60 | 11.15 (br, 1H)<br>11.05 (s, 2H)<br>10.65 (br, 1H)<br>8.30 (s, 2H)<br>8.13 (m, 2H)<br>7.88 (m, 8H)<br>7.30 (br, 4H)<br>4.40 (m, 2H)<br>4.00 (br, 2H)<br>3.70–2.90<br>(m, 10H)<br>2.40–1.40 | 8.00 (s, 1H)<br>7.80 (m, 4H)<br>4.48 (m, 1H)<br>3.65 (d, 2H)<br>1.75 (m, 1H)<br>1.59 (m, 2H)<br>1.01 (d, 3H)<br>0.92 (d, 3H) | 9.65 (s, 1H)<br>8.08 (s, 1H)<br>7.85 (d, 2H)<br>7.65 (d, 2H)<br>7.40 (br, 1H)<br>7.15 (s, 2H)<br>3.55 (m, 2H)<br>2.55 (m, 2H)<br>2.15 (m, 2H)<br>1.80 (m, 3H)<br>1.65 (m, 1H) |
| Yield Melting Point | 95% | 51% | 3% | 8% |
| Mass | 511 (ES) | 511 (ES) | 443 (EI) | 456 (EI) |

-continued

| Example No. | 178 | 179 | 180 | 181 |
|---|---|---|---|---|
|  | 9.49 (s, 1H)<br>8.25 (s, 1H)<br>7.80 (m, 4H)<br>7.32 (br, 2H)<br>4.03 (m, 2H)<br>3.75 (m, 1H)<br>3.35 (m, 2H)<br>1.80 (m, 2H)<br>1.40 (m, 2H) | 9.61 (s, 1H)<br>8.08 (s, 1H)<br>7.88 (d, 2H)<br>7.65 (d, 2H)<br>7.60 (t, 1H)<br>7.15 (s, 1H)<br>3.45 (m, 2H)<br>2.40 (t, 2H)<br>2.20 (s, 6H)<br>1.75 (t, 2H) | 9.65 (s, 1H)<br>8.11 (s, 1H)<br>7.81 (d, 2H)<br>7.63 (d, 2H)<br>7.15 (s, 2H)<br>6.64 (d, 1H)<br>4.28 (m, 3H)<br>2.00 (m, 1H)<br>1.98 (s, 3H)<br>0.98 (d, 3H)<br>0.93 (d, 3H) | 9.71 (s, 1H)<br>8.06 (s, 1H)<br>7.90 (d, 2H)<br>7.61 (d, 2H)<br>7.37 (t, 1H)<br>6.56 (d, 1H)<br>4.66 (m, 2H)<br>3.90 (m, 1H)<br>3.39 (m, 3H)<br>2.78 (q, 2H)<br>1.96 (m, 4H)<br>1.56 (m, 2H)<br>1.29 (m, 2H) |
| Yield | 17% | 9% | 27% | 24% |
| Melting Point |  |  |  |  |
| Mass | 427 (EI) | 428 (EI) | 472 (ES) | 486 (ES) |

| Example No. | 182 | 183 | 184 | 185 |
|---|---|---|---|---|
| Structure | 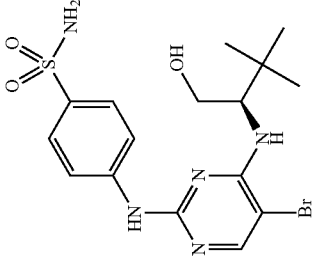 | 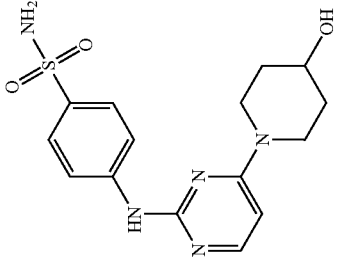 | 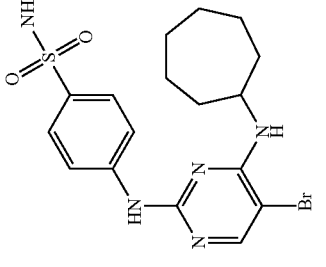 | 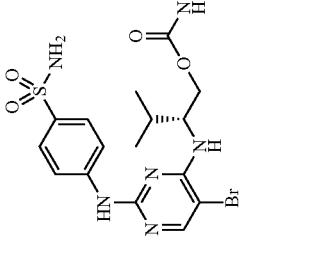 |
| NMR | 9.68 (s, 1H)<br>9.47 (s, 1H)<br>8.10 (s, 1H)<br>7.81 (d, 2H)<br>7.67 (d, 2H)<br>7.14 (s, 2H)<br>6.76 (m, 3H)<br>4.47 (m, 2H)<br>4.30 (m, 1H)<br>3.65 (s, 6H)<br>3.54 (s, 3H)<br>1.99 (m, 1H)<br>0.98 (d, 3H)<br>0.92 (d, 3H) | 10.97 (s, 1H)<br>8.30 (s, 1H)<br>8.02 (d, 1H)<br>7.81 (m, 4H)<br>7.30 (s, 2H)<br>4.14 (m, 1H)<br>1.80 (m, 12H) | 11.06 (s, 1H)<br>8.04 (m, 1H)<br>7.82 (m, 2H)<br>7.70 (m, 2H)<br>7.30 (s, 2H)<br>6.72 (m, 1H)<br>3.75 (m, 5H)<br>1.88 (m, 2H)<br>1.48 (m, 2H) | 11.01 (s, 1H)<br>8.38 (s, 1H)<br>7.82 (s, 4H)<br>7.40 (d, 1H)<br>7.32 (s, 2H)<br>4.20 (s, 1H)<br>3.70 (m, 2H)<br>0.97 (s, 9H) |
| Yield | 57% | 78% | 26% | 76% |
| Melting Point | | | | |
| Mass | 639 (ES) | 439 (EI) | 348 (EI) | 445 (EI) |

-continued
| Example No. | 186 | 187 | 188 | 189 |
|---|---|---|---|---|
| | 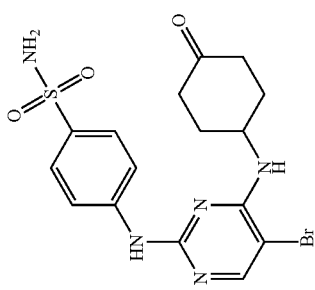 | 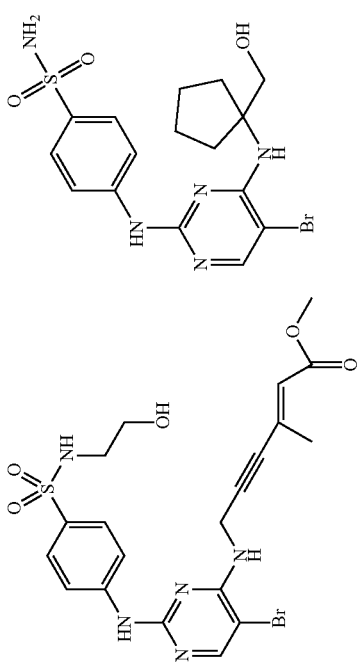 | | 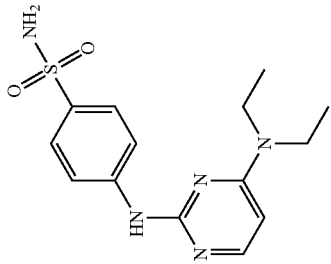 |
| | 9.71 (s, 1H)<br>8.11 (s, 1H)<br>7.90 (d, 2H)<br>7.70 (d, 2H)<br>7.12 (s, 1H)<br>6.75 (d, 1H)<br>4.45 (m, 1H)<br>2.25 (m, 6H)<br>1.90 (m, 2H) | 7.75 (s, 1H)<br>7.65 (d, 2H)<br>7.58 (d, 2H)<br>5.82 (s, 1H)<br>4.25 (s, 2H)<br>3.40 (t, 2H)<br>2.82 (t, 2H)<br>2.06 (s, 3H) | 10.60 (s, 1H)<br>8.29 (s, 1H)<br>7.79 (d, 2H)<br>7.71 (d, 2H)<br>7.28 (s, 2H)<br>6.60 (s, 1H)<br>3.58 (s, 2H)<br>2.10 (m, 2H)<br>1.78 (m, 2H)<br>1.55 (m, 4H) | 11.19 (s, 1H)<br>8.03 (d, 1H)<br>7.88 (d, 2H)<br>7.78 (d, 2H)<br>7.31 (s, 2H)<br>6.58 (d, 1H)<br>3.60 (m, 4H)<br>1.20 (m, 6H) |
| Yield | 16% | 7% | 61% | 35% |
| Melting Point | | | | |
| Mass | 440 (ES) | 480 (ES) | 443 (EI) | 321 (EI) |

| Example No. | 190 | 191 * Diastereomer 1 | 192 * Diastereomer 2 | 193 |
|---|---|---|---|---|
| | 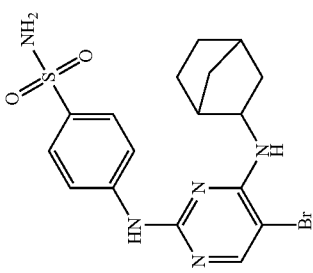 | | | |
| NMR | 10.61 (s, 1H)<br>8.28 (s, 1H)<br>7.82 (d, 2H)<br>7.73 (d, 2H)<br>7.53 (br, 1H)<br>7.25 (s, 2H)<br>4.25 (m, 1H)<br>2.59 (br, 1H)<br>2.21 (br, 1H)<br>1.94 (m, 1H)<br>1.40 (m, 7H) | 9.67 (s, 1H)<br>8.08 (s, 1H)<br>7.88 (d, 2H)<br>7.65 (d, 2H)<br>7.11 (s, 2H)<br>6.35 (d, 1H)<br>4.10 (m, 1H)<br>3.62 (m, 4H)<br>2.45 (m, 4H)<br>2.19 (m, 1H)<br>1.88 (m, 4H)<br>1.65 (m, 4H) | 9.63 (s, 1H)<br>8.06 (s, 1H)<br>7.85 (d, 2H)<br>7.65 (d, 2H)<br>7.15 (s, 2H)<br>6.55 (d, 1H)<br>3.95 (m, 1H)<br>3.58 (m, 4H)<br>2.50 (m, 4H)<br>1.96 (m, 1H)<br>1.50 (m, 4H)<br>1.30 (m, 4H) | 10.61 (s, 1H)<br>8.28 (s, 1H)<br>7.78 (m, 4H)<br>7.45 (d, 1H)<br>7.20 (s, 2H)<br>4.30 (br, 2H)<br>3.53 (m, 2H)<br>1.21 (d, 3H) |
| Yield Melting Point | 63% | 15% | 17% | 57% |
| Mass | 437 (EI) | 511 (ES) | 511 (EI) | 403 (EI) |

| Example No. | 194 | 195 | 196 | 197 |
|---|---|---|---|---|
| NMR | 9.89 (s, 1H)<br>8.21 (d, 2H)<br>7.82 (d, 2H)<br>7.65 (m, 3H)<br>7.17 (br, 2H)<br>4.30 (m, 2H) | 10.98 (s, 1H)<br>8.51 (br, 1H)<br>8.29 (s, 1H)<br>7.81 (m, 4H)<br>7.29 (br, 2H)<br>3.45 (m, 4H)<br>1.68 (m, 2H)<br>1.45 (m, 2H) | 10.39 (s, 1H)<br>8.30 (s, 1H)<br>8.04 (d, 2H)<br>7.70 (d, 2H)<br>7.21 (br, 2H)<br>6.55 (s, 1H)<br>3.49 (s, 1H)<br>2.32 (m, 2H)<br>1.85 (m, 2H)<br>1.60 (m, 5H)<br>1.29 (m, 1H) | 10.85 (s, 1H)<br>8.71 (d, 1H)<br>8.31 (s, 1H)<br>7.72 (d, 2H)<br>7.55 (d, 2H)<br>7.30 (m, 6H)<br>5.41 (m, 1H)<br>3.49 (m, 2H)<br>2.11 (m, 2H) |
| Yield<br>Melting Point | 26% | 56% | 12% | 61% |
| Mass | 476 (EI) | 417 (EI) | 450 (EI) | 479 (EI) |

-continued
| Example No | 198 | 199 | 196 | 197 |
|---|---|---|---|---|
| | 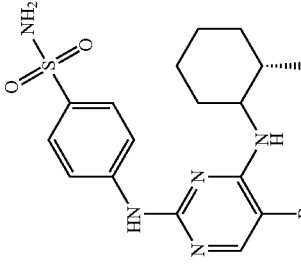 (+)-Enantiomer | 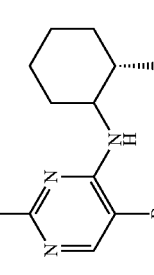 (−)-Enantiomer | 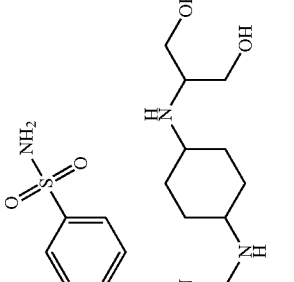 Diastereomer 1 | 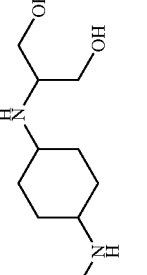 Diastereomer 2 |
| | 11.01 (s, 1H)<br>8.32 (s, 1H)<br>8.10 (d, 1H)<br>7.80 (m, 4H)<br>7.30 (br, 2H)<br>3.70 (m, 1H)<br>1.80 (m, 5H)<br>1.48 (m, 1H)<br>1.29 (m, 2H)<br>1.07 (m, 1H)<br>0.83 (d, 3H) | 11.01 (s, 1H)<br>8.32 (s, 1H)<br>8.10 (d, 1H)<br>7.80 (m, 4H)<br>7.30 (br, 2H)<br>3.70 (m, 1H)<br>1.80 (m, 5H)<br>1.48 (m, 1H)<br>1.29 (m, 2H)<br>1.07 (m, 1H)<br>0.83 (d, 3H) | | 9.16 (s, 1H)<br>8.07 (s, 1H)<br>7.89 (d, 2H)<br>7.67 (d, 2H)<br>7.15 (s, 2H)<br>6.45 (d, 1H)<br>4.35 (s, 2H)<br>3.97 (m, 1H)<br>3.40 (m, 4H)<br>2.85 (m, 1H)<br>2.55 (m, 1H)<br>1.82 (m, 2H)<br>1.61 (m, 6H) |
| Yield | 4% | 4% 7% | 2% | |
| Melting Point | | | | |
| Mass | 439 (EI) | 439 (EI) | 515 (ES) | 515 (ES) |

-continued
| Example No. | 202 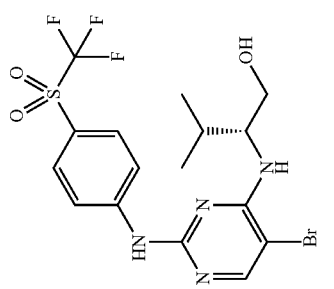 | 203 * 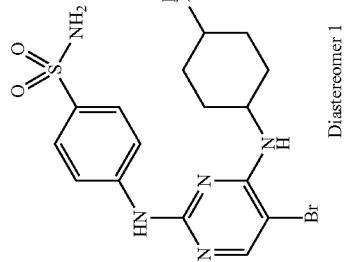 Diastereomer 1 | 204 * 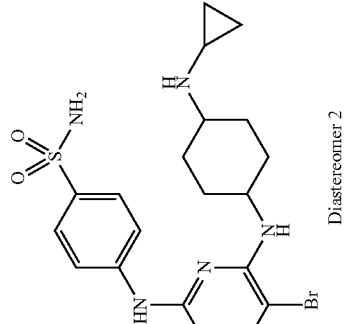 Diastereomer 2 | 205 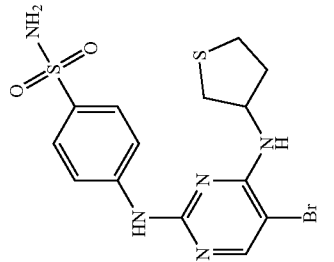 |
|---|---|---|---|---|
| | 10.21 (s, 1H)<br>8.18 (s, 1H)<br>8.10 (d, 2H)<br>7.92 (d, 2H)<br>6.39 (d, 1H)<br>4.80 (br, 1H)<br>4.05 (m, 1H)<br>3.62 (m, 2H)<br>2.00 (m, 1H)<br>0.99 (d, 3H)<br>0.92 (d, 3H) | 7.69 (d, 2H) | 9.66 (s, 1H)<br>8.08 (s, 1H)<br>7.90 (d, 2H)<br>7.65 (d, 2H)<br>7.15 (s, 2H)<br>6.53 (d, 1H)<br>3.93 (m, 1H)<br>2.05 (m, 5H)<br>1.51 (m, 2H)<br>1.15 (m, 2H)<br>0.42 (m, 2H)<br>0.25 (m, 2H) | 9.73 (s, 1H)<br>8.11 (s, 1H)<br>7.82 (d, 2H)<br>7.12 (s, 1H)<br>6.80 (d, 1H)<br>4.67 (m, 1H)<br>3.13 (m, 1H)<br>2.86 (m, 3H)<br>2.18 (m, 2H) |
| Yield | 10% | 2% | 2% 16% | |
| Melting Point | | | | |
| Mass | 483 (ES) | 480 (EI) | 480 (EI) | 430 (ES) |

-continued
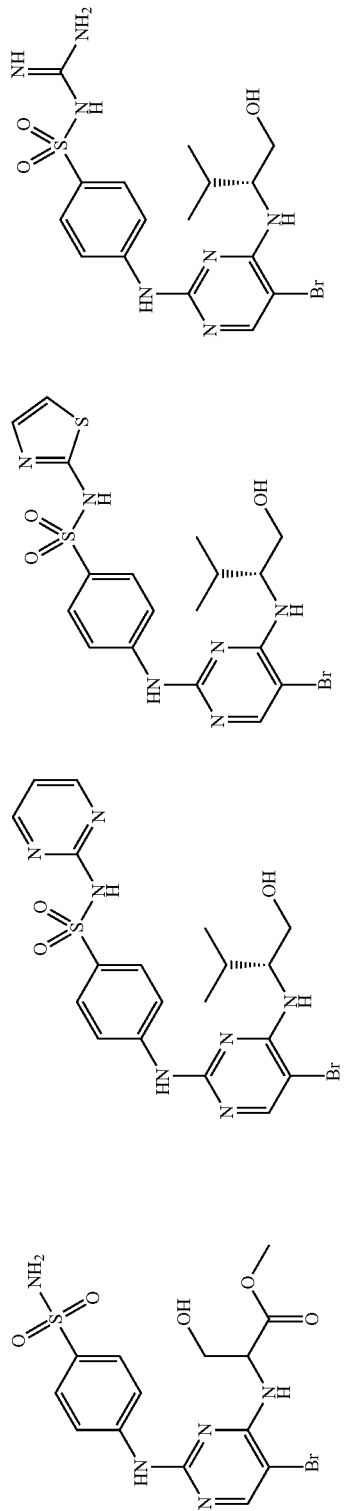
| Example No. | 206 | 207 | 208 | 209 |
|---|---|---|---|---|
| | 9.75 (s, 1H)<br>8.19 (s, 1H)<br>7.75 (d, 2H)<br>7.18 (d, 2H)<br>7.17 (s, 2H)<br>6.68 (d, 1H)<br>5.35 (t, 1H)<br>4.71 (m, 1H)<br>3.91 (m, 2H)<br>3.65 (s, 3H) | 10.98 (s, 1H)<br>8.50 (d, 2H)<br>8.31 (s, 1H)<br>7.97 (d, 2H)<br>7.78 (d, 1H)<br>7.57 (d, 1H)<br>7.00 (t, 1H)<br>4.01 (m, 1H)<br>3.62 (m, 2H)<br>1.97 (m, 1H)<br>0.98 (d, 3H)<br>0.92 (d, 3H) | 11.00 (s, 1H)<br>8.31 (s, 1H)<br>7.74 (m, 5H)<br>7.21 (d, 1H)<br>6.80 (d, 1H)<br>4.00 (m, 1H)<br>3.62 (m, 2H)<br>1.95 (m, 1H)<br>0.98 (d, 3H)<br>0.90 (d, 3H) | 9.55 (s, 1H)<br>8.08 (s, 1H)<br>7.80 (d, 2H)<br>7.60 (d, 2H)<br>6.58 (br, 4H)<br>6.20 (d, 1H)<br>4.80 (br, 1H)<br>4.04 (m, 1H)<br>3.60 (m, 2H)<br>2.00 (m, 1H)<br>0.99 (d, 3H)<br>0.92 (d, 3H) |
| Yield<br>Melting Point | 5%<br>223 | 55%<br>248 | 44%<br>228 | 77%<br>231 |
| Mass | 446 (ES) | 507 (EI) | 514 (EI) | |

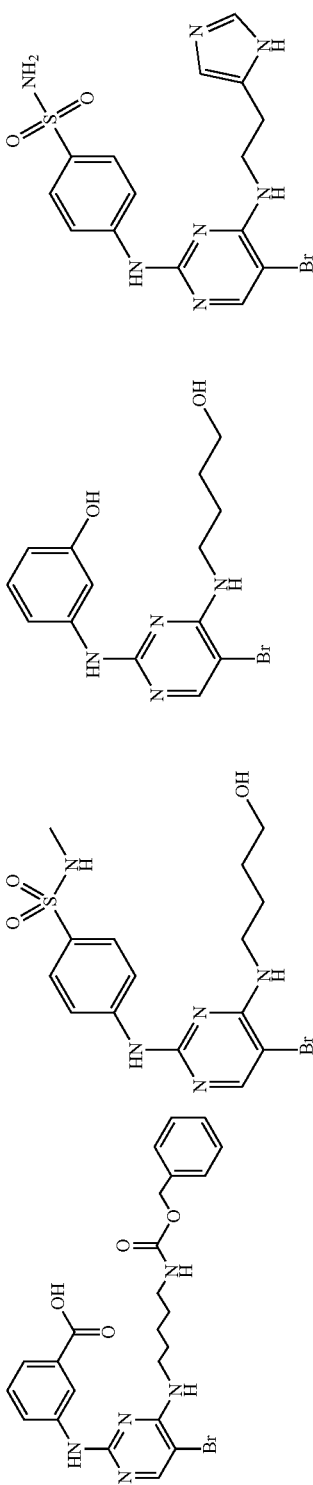

| Example No. | 213 | 61 | 214 | 215 |
|---|---|---|---|---|
| | 12.40 (br, 1H)<br>11.10 (s, 1H)<br>8.08 (d, 2H)<br>7.79 (m, 4H)<br>7.30 (s, 2H)<br>4.04 (m, 1H)<br>3.60 (m, 2H)<br>2.07 (s, 3H)<br>2.00 (m, 1H)<br>0.97 (d, 3H)<br>0.90 (d, 3H) | 12.41 (br, 1H)<br>11.11 (s, 1H)<br>8.10 (d, 1H)<br>7.80 (m, 5H)<br>7.30 (s, 2H)<br>4.08 (m, 1H)<br>3.63 (m, 2H)<br>2.50 (m, 2H)<br>2.01 (m, 1H)<br>1.15 (t, 3H)<br>0.99 (d, 3H)<br>0.92 (d, 3H) | 8.03 (s, 1H)<br>7.76 (m, 4H)<br>3.70 (s, 2H)<br>1.92 (m, 4H)<br>0.92 (m, 6H)<br>(in MeOD) | 9.55 (s, 1H)<br>8.10 (s, 1H)<br>7.80 (d, 2H)<br>7.68 (d, 2H)<br>7.15 (s, 2H)<br>5.82 (s, 1H)<br>3.74 (d, 1H)<br>3.52 (d, 1H)<br>2.72 (m, 1H)<br>1.35 (s, 3H)<br>0.97 (d, 3H)<br>0.91 (d, 3H) |
| Yield | 49% | 25% | 2% | 9% |
| Melting Point | | | | |
| Mass | 365 (EI) | 379 (EI) | 443 (ES) | 444 (ES) |

| Example No. | 216 | 217 | 218 | 219 |
|---|---|---|---|---|
| | 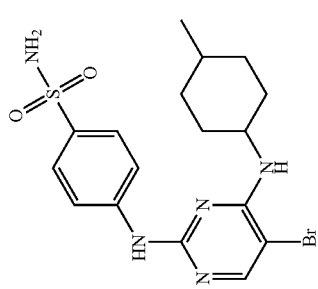 | 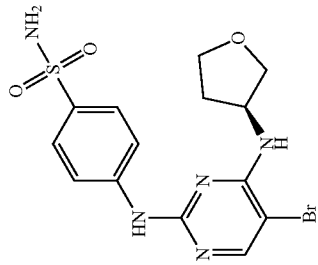 | 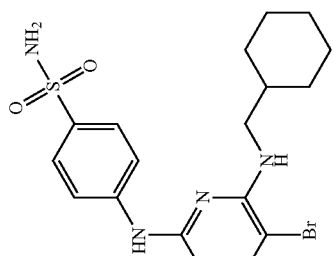 | 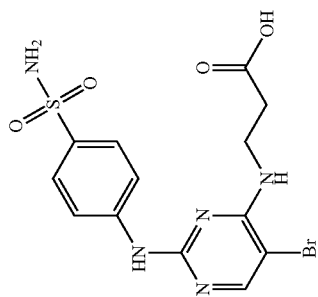 |
| | 10.88 (s, 1H)<br>8.36 (s, 1H)<br>8.03 (d2, 1H)<br>7.79 (m, 4H)<br>7.28 (br, 2H)<br>4.65 (m, 1H)<br>3.89 (m, 2H) | 10.88 (s, 1H)<br>8.36 (s, 1H)<br>8.03 (d, 1H)<br>7.79 (m, 4H)<br>7.28 (br, 2H)<br>4.65 (m, 1H)<br>3.89 (m, 2H)<br>3.71 (m, 2H)<br>2.19 (m, 2H) | 11.01 (s, 1H)<br>8.52 (br, 1H)<br>8.29 (s, 1H)<br>7.78 (m, 4H)<br>7.32 (s, 2H)<br>3.39 (m, 2H)<br>1.70 (m, 6H)<br>1.15 (m, 3H)<br>0.96 (m, 2H) | 11.11 (s, 1H)<br>8.53 (m, 1H)<br>8.36 (s, 1H)<br>7.80 (m, 4H)<br>7.31 (s, 1H)<br>3.71 (m, 2H)<br>2.65 (m, 2H) |
| Yield | 65% | 34% | 58% | 88% |
| Melting Point | 239 | 239 | 238 | 280 |
| Mass | 439 (EI) | 413 (EI) | 439 (EI) | 416 (EI) |

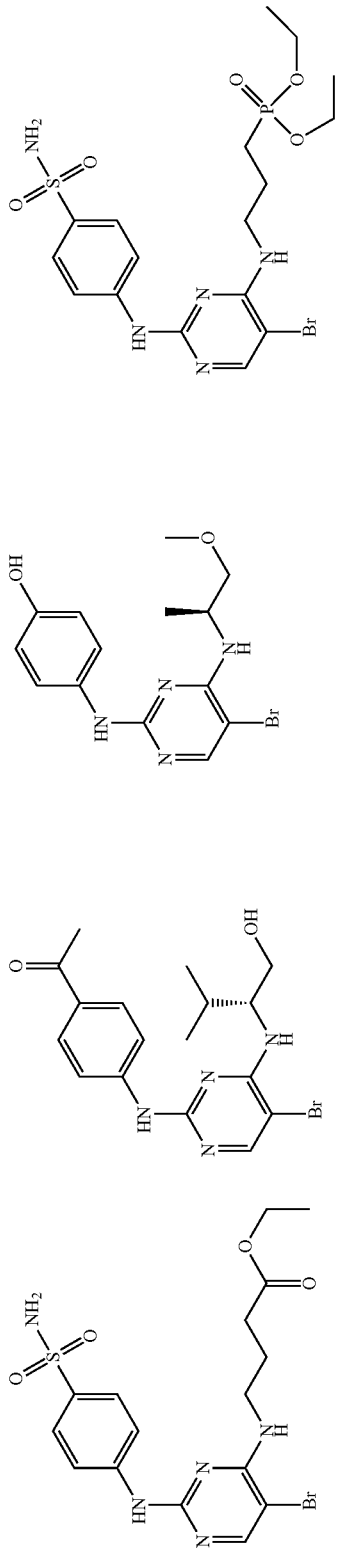
| Example No. | 74 | 56 | 220 | 221 |
|---|---|---|---|---|
| | 9.67 (s, 1H) | 9.70 (s, 1H)<br>8.11 (s, 1H)<br>7.88 (m, 4H)<br>6.25 (d, 1H)<br>4.81 (m, 1H)<br>4.05 (m, 1H)<br>3.61 (m, 2H)<br>2.01 (m, 1H)<br>0.97 (d, 3H)<br>0.92 (d, 3H) | 8.92 (m, 1H)<br>8.81 (m, 1H)<br>7.96 (s, 1H)<br>7.43 (d, 2H)<br>6.67 (d, 2H)<br>6.20 (m, 1H)<br>4.38 (m, 1H)<br>3.48 (m, 1H)<br>3.37 (m, 1H)<br>1.20 (d, 3H) | 9.66 (s, 1H)<br>8.08 (s, 1H)<br>7.83 (d, 2H)<br>7.68 (d, 2H)<br>7.22 (t, 1H)<br>7.11 (s, 2H)<br>3.95 (m, 4H)<br>3.48 (m, 2H)<br>1.79 (m, 4H)<br>1.18 (t, 6H) |
| Yield | 7% | 17% | 65% | 19% |
| Melting Point | 285 | 158 | 166 | |
| Mass | 457 (EI) | 392 (EI) | 354 (EI) | 522 (ES) |

-continued

| Example No. | 222 | 223 | 224 | 225 |
|---|---|---|---|---|
| | 9.81 (s, 1H)<br>9.08 (s, 1H)<br>8.68 (s, 1H)<br>8.35 (m, 1H)<br>8.20 (s, 1H)<br>8.02 (t, 1H)<br>7.63 (m, 5H)<br>7.17 (s, 2H)<br>7.03 (s, 1H)<br>4.82 (d, 2H) | 9.71 (s, 1H)<br>8.13 (s, 1H)<br>7.89 (d, 2H)<br>7.66 (d, 2H)<br>7.31 (t, 1H)<br>7.14 (s, 2H)<br>3.98 (m, 2H)<br>3.69 (s, 3H)<br>3.64 (s, 3H) | 9.70 (s, 1H)<br>8.08 (s, 1H)<br>7.88 (d, 2H)<br>7.65 (d, 2H)<br>7.25 (m, 3H)<br>6.11 (m, 1H)<br>3.40 (m, 5H) | 10.29 (s, 1H)<br>8.83 (m, 2H)<br>8.51 (m, 1H)<br>8.26 (s, 1H)<br>7.93 (d, 2H)<br>7.60 (d, 2H)<br>7.51 (d, 2H)<br>7.25 (br, 2H)<br>4.90 (d, 2H) |
| Yield | 54% | 23% | 7% | 43 |
| Melting Point | 300 | 300 | | 243 |
| Mass | 501 (EI) | 465 (EI) | | 434 (EI) |

-continued

| Example No. | 226 | 227 | 228 | 229 | 230 |
|---|---|---|---|---|---|
|  | 10.38 (s, 1H)<br>8.52 (br, 1H)<br>8.23 (s, 1H)<br>7.72 (m, 4H)<br>7.36 (m, 1H)<br>7.22 (s, 2H)<br>7.03 (m, 1H)<br>6.95 (m, 1H)<br>4.80 (d, 2H) | 10.30 (s, 1H)<br>8.78 (m, 1H)<br>8.36 (m, 3H)<br>7.81 (m, 2H)<br>7.60 (m, 4H)<br>7.22 (br, 2H)<br>4.94 (d, 2H) | 10.52 (s, 1H)<br>8.66 (m, 1H)<br>8.28 (s, 1H)<br>7.63 (m, 4H)<br>7.26 (m, 6H)<br>4.63 (d, 2H) | 10.88 (s, 1H)<br>8.92 (m, 1H)<br>8.33 (s, 1H)<br>7.72 (d, 2H)<br>7.62 (d, 2H)<br>7.30 (m, 4H)<br>6.89 (d, 2H)<br>4.62 (d, 2H)<br>3.70 (s, 3H) | 10.45 (s, 1H)<br>8.20 (s, 1H)<br>8.05 (m, 1H)<br>7.79 (m, 4H)<br>7.21 (s, 2H)<br>3.50 (m, 2H)<br>1.83 (m, 2H)<br>1.56 (m, 2H) |
| Yield<br>Melting Point | 47%<br>229 | 41%<br>287 | 88%<br>259 | 89%<br>233 | 58%<br>>300 |
| Mass | 440 (CI) | 434 (EI) | 451 (EI) | 463 (EI) | 466 (ES) |

-continued

| Example No. | 231 | 232 | 233 | 234 |
|---|---|---|---|---|
| | (structure with ethyl benzoate, pyrimidine-Br, propargyl NH) | (structure with hydroxymethyl phenyl, pyrimidine-Cl, propargyl NH) | (structure with sulfonamide phenyl, pyrimidine-Br, ethanolamine NH) | (structure with sulfonamide phenyl, pyrimidine-Br, 1-phenylethylamine NH) |
| | 10.3 (s, 1H)<br>8.34 (tr, 1H)<br>8.2 (s, 1H)<br>7.9 (m, 4H)<br>4.3 (q, 2H)<br>4.2 (m, 2H)<br>3.23 (tr, 1H)<br>1.32 (tr, 3H) | 9.28 (s, 1H)<br>8.0 (s, 1H)<br>7.73 (d, 2H)<br>7.63 (tr, 1H)<br>7.18 (d, 2H)<br>5.0 (m, 1H)<br>4.3 (s, 2H)<br>4.14 (m, 2H)<br>3.11 (tr, 1H) | 10.48 (s, 1H)<br>8.25 (s, 1H)<br>7.85 (m, 4H)<br>7.25 (m, 1H)<br>7.15 (s, 1H)<br>5.1 (m, 1H)<br>3.58 (m, 4H) | 9.63 (s, 1H)<br>8.12 (s, 1H)<br>7.65 (m, 4H)<br>7.42 (d, 2H)<br>7.35 (tr, 2H)<br>7.21 (m, 1H)<br>7.16 (s, 1H)<br>5.35 (m, 1H)<br>1.55 (d, 3H) |
| Yield | 85% | 35% | 33% | 25% |
| Melting Point | | | | |
| Mass | 330 (EI) | 228 (EI) | 389 (CI) | 448 (ESI) |

-continued
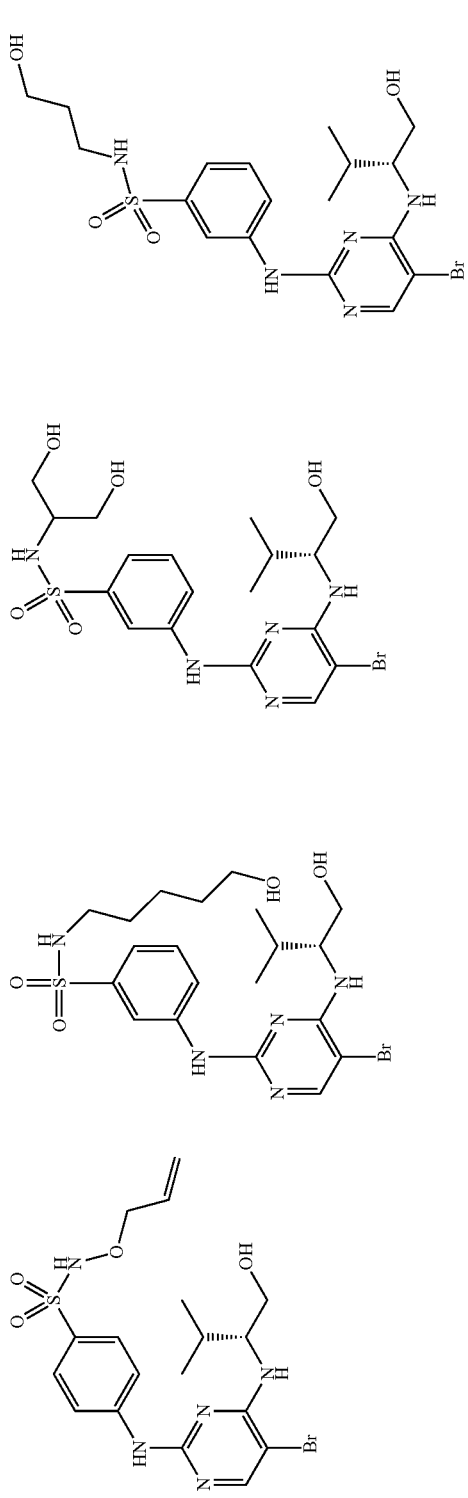
| Example No. | 235 | 236 | 237 | 238 |
|---|---|---|---|---|
| Melting Point [° C.] | | | | |
| Mass | 486 (ES) | 516 (ES) | 504 (ES) | 488 (ES) |
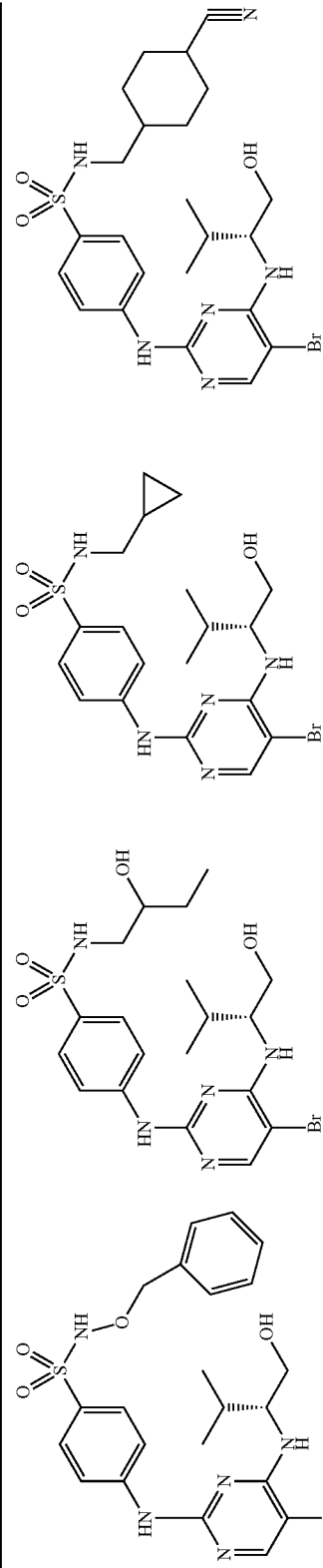
| Example No. | 239 | 240 | 241 | 242 |
|---|---|---|---|---|
| Melting Point [° C.] | | | | |
| Mass | 536 (ES) | 502 (ES) | 484 (ES) | 551 (ES) |

| Example No. | 243 | 244 | 245 | 246 | 247 | 248 | 249 |
|---|---|---|---|---|---|---|---|
| Melting Point [° C.] | | | | | | | |
| Mass | 516 (ES) | 514 (ES) | 433 (ES) | 446 (ES) | 415 (EI) | 504 (ES) | 431 (ES) |

| Example No. | 250 | 251 | 252 | 253 |
|---|---|---|---|---|
| Melting Point [°C] | 113 | 231 | 187 | — |
| Mass | 488 (ES) | 446 (ES) | 433 (ES) | — |

| No. | 254 | 255 | 256 | 257 |
|---|---|---|---|---|
| Melting Point [°C] | — | — | — | — |
| Mass | 399 (ES) | 444 (ES) | 474 (ES) | 486 (ES) |

Compounds Nos. 159, 160, 161, 163, 167, 168, 170, 174, 175, 191, 192, 203 and 204 that are identified with *) can be produced by the process variants that are described under Example No. 295.

EXAMPLE 258

Production of 4-(5-bromo-4-morpholin-4-yl-pyrimidin-2-ylamino)-phenylsulfonamide

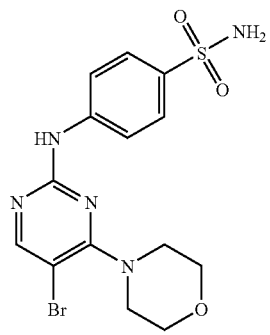

202 mg (0.60 mmol) of the compound of Example No. 122 is mixed with 1 ml of water and 0.2 g (1.2 mmol) of bromine and stirred at room temperature. After 24 hours, 0.2 g (1.2 mmol) of bromine is added again, and it is stirred for another 24 hours at room temperature. The solvent is evaporated by means of underpressure, and the remaining residue is purified by chromatography (Flashmaster II, DCM/MeOH 7:3). 17 mg (0.04 mmol,7%) of the product is obtained as a white solid.

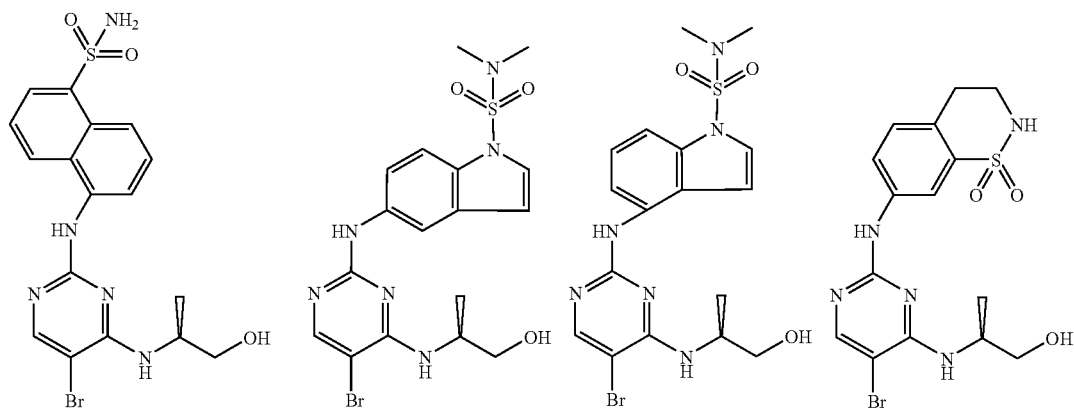

| Example No. | 259 | 260 | 261 | 262 |
|---|---|---|---|---|
| Melting Point [° C.] | | 205–207 | 202–203 | |
| Mass | MS (ES) 452, 454 (M + H, 100%) | | | 428 (ES) |

| Example No. | Compound | ESI-MS |
|---|---|---|
| 263 | 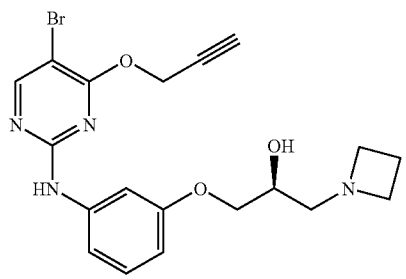 | 434 |
| 264 | 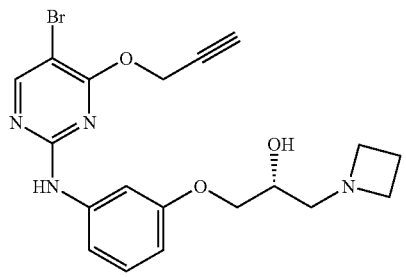 | 434 |
| 265 | 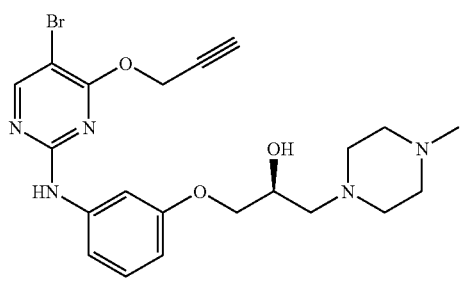 | 477 |
| 266 | 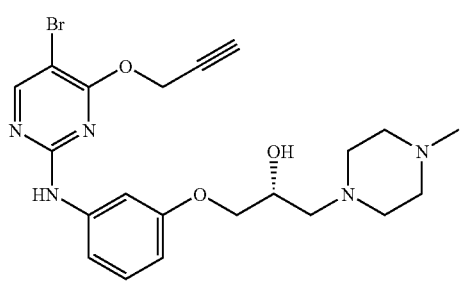 | 477 |

| Example No. | Compound | ESI-MS |
|---|---|---|
| 267 | [structure] | 552 |
| 268 | [structure] | 552 |

Analogously to the process for the production of intermediate products that is described under Example 6.0, the following compounds are also produced:

| Example No. | 269 | 270 | 271 |
|---|---|---|---|
| | [structure] | [structure] | [structure] |
| Yield | 47% | 90% | |
| Mass | ESI: MH+ 480 (100%) 478 (97%) 115 (30%) | ESI: MH+ 432 (100%) 430 (94%) 157 (43%) | ESI: MH+ 446 (18%) |

Analogously to production example 1, the following compounds are also produced:
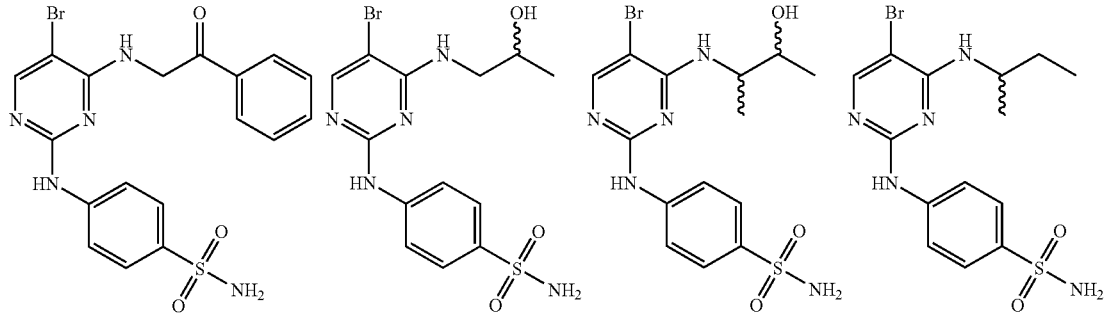
| Example No. | 272 | 273 | 274 | 275 |
|---|---|---|---|---|
| Yield | 61% | 44% | 42% | 68% |
| Mass | EI: | EI: | ESI: | EI: |
| | M+ 463 (4%) | M+ 403 (24%) | MH+ 418 | M+ 401 (33%) |
| | 277 (8%) | 358 (100%) | 100% | 372 (100%) |
| | 105 (100%) | 277 (52%) | 416 (94%) | 344 (38%) |
| | | | 346 (8%) | |
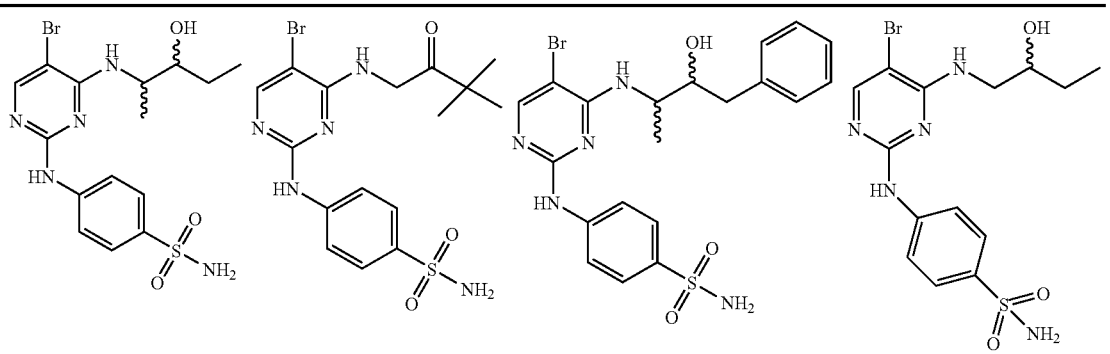
| Example No. | 276 | 277 | 278 | 279 |
|---|---|---|---|---|
| Yield | 81% | 58% | ~20% | 30% |
| Mass | EI: | ESI: | ESI: | ESI: |
| | M+ 431 (5%) | MH+ 444 | MH+ 494 | MH+ 418 |
| | 372 (100%) | (100%) | (75%) | (100%) |
| | 291 (46%) | 442 (97%) | 346 (18%) | 416 (97%) |
| | | 115 (20%) | 214 (55%) | 310 (27%) |
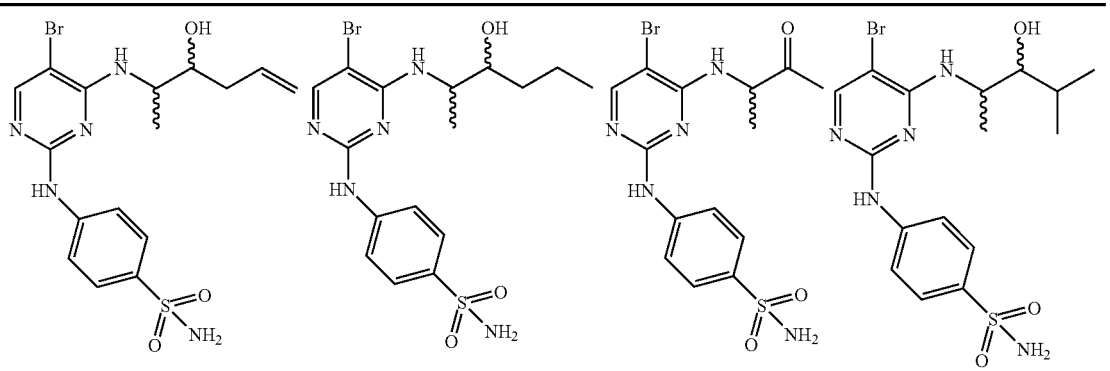
| Example No. | 280 | 281 | 282 | 283 |
|---|---|---|---|---|
| Yield | 55% | 43% | ~18% | 35% |
| Mass | ESI: | ESI: | ESI: | ESI: |

-continued

| MH+ 444 | MH+ 446 | MH+ 416 | MH+ 446 |
| (100%) | (100%) | (100%) | (100%) |
| 442 (97%) | 444 (95%) | 414 (96%) | 444 (90%) |
| 214 (12%) | 346 (5%) | 317 (4%) | |

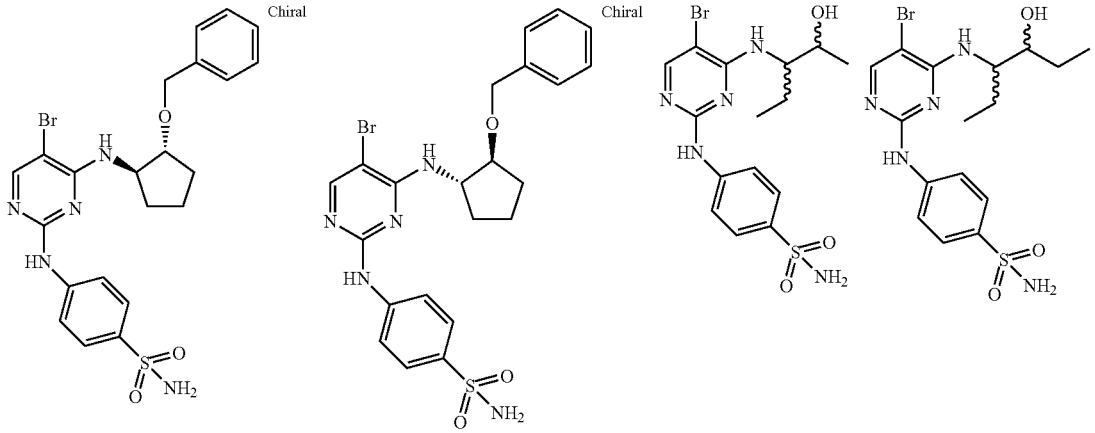

| Example No. | 284 | 285 | 286 | 287 |
|---|---|---|---|---|
| Yield | 51% | 46% | 47% | 61% |
| Mass | ESI: | ESI: | ESI. | ESI. |
| | MH+ 520 | MH+ 520 | MH+ 432 | MH+ 446 |
| | (100%) | (100%) | (100%) | (100%) |
| | 518 (97%) | 518 (97%) | 430 (95%) | 444 (93%) |
| | 115 (27%) | 115 (23%) | 346 (5%) | 115 (13%) |

According to the production variants below, the following compounds are also synthesized:

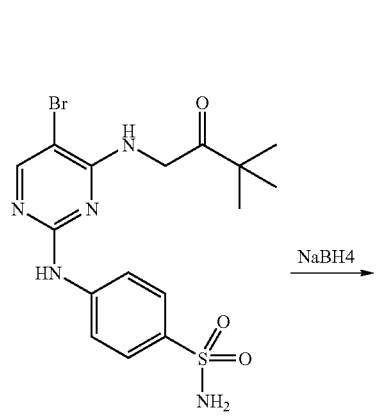

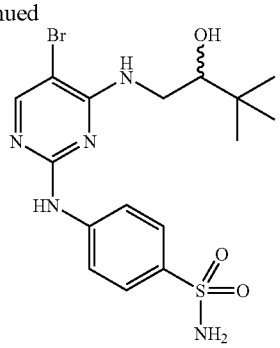

30 mg (0.0678 mmol) of compound No. 278 is dissolved in 1 ml of methanol/tetrahydrofuran 1:1. After adding ~10 mg of sodium borohydride, stirring is continued for 2 hours. Then, it is quenched with ≈3–4 drops of glacial acetic acid while being cooled, and it is concentrated by evaporation. Below, the crude product is taken up with a little water, suctioned off, rewashed with acetonitrile and dried in a vacuum at 60° C. Yield: 21 mg (70% of theory) of the desired compound.

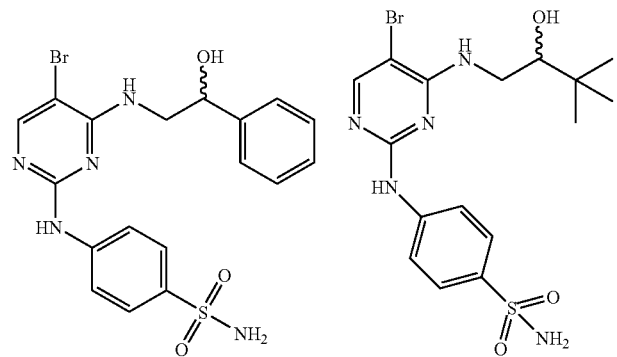

| Example No. | 288 | 289 |
|---|---|---|
| Yield | 52% | 70% |
| Mass | EI:<br>M+ 465 (5%)<br>358 (40%)<br>207 (31%) | ESI:<br>MH+ 446 (100%)<br>444 (93%)<br>117 (20%) |

EXAMPLE 290
Production of the Oxime Ether-Pyrimidine Compounds of General Formula I The production of the oxime ether is carried out according to the following general reaction diagram:

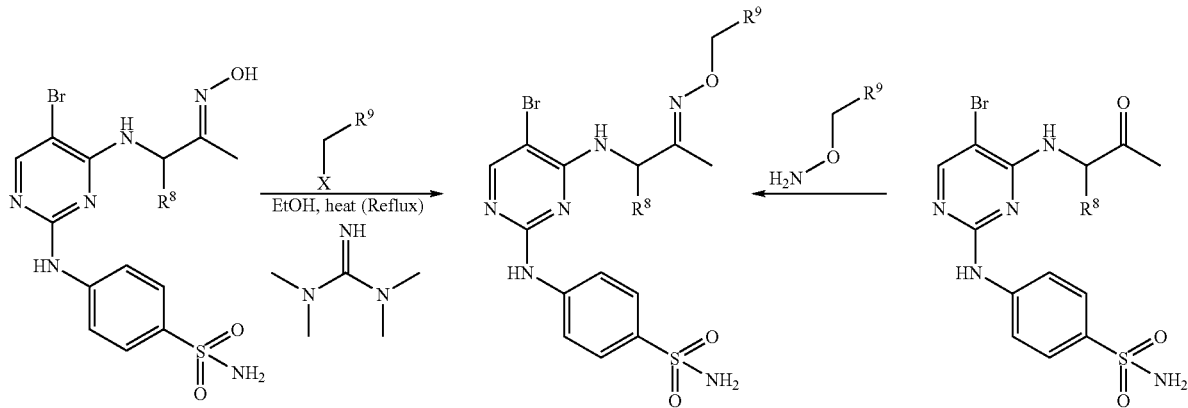

$R^8$ and $R^9$ have the meanings that are indicated in general formula I.

Production of Example 290

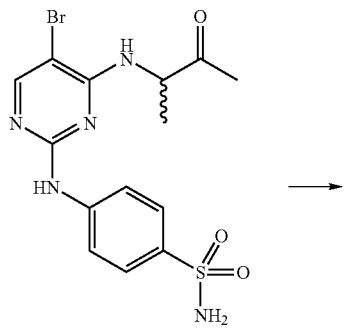

→

-continued

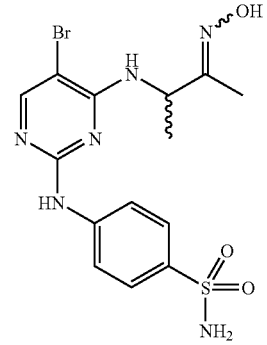

50 mg (0.12 mmol) of compound No. 282, 34 mg of hydroxylammonium chloride and 150 mg of pulverized KOH are refluxed for 2 hours in 2 ml of ethanol. Then, it is poured onto ice water and acidified with glacial acetic acid, extracted 3 times with dichloromethane/isopropanol 4:1, dried with magnesium sulfate and concentrated by evaporation. The residue is suspended with acetonitrile, suctioned off and dried at 60° C.

Yield: 28 mg (54% of theory) of the desired compound.
Mass ESI: MH$^+$429 (29%) 371 (61%) 289 (91%)
Similarly produced ar ealso the following compounds:

50 mg (0.12 mmol) of compound No. 282 and 7.5 mg (0.132 mmol) of cyclopropylamine are dissolved in 2 ml of 1,2-dichloroethane. After 9.1 mg (0.144 mmol) of sodium cyanoborohydride is added, it is allowed to stir for 12 more hours. Then, it is diluted with dichloromethane/isopropanol 4:1, washed 2× with water, dried with magnesium sulfate and concentrated by evaporation. The residue is chromatographed on silica gel with dichloromethane/methanol 95:5.

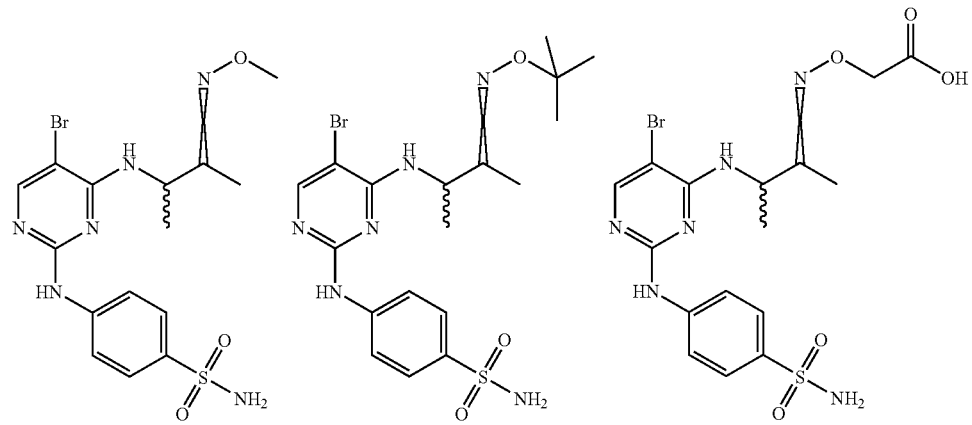

| Example No. | 291 | 292 | 293 |
|---|---|---|---|
| Yield | 34% | 36% | 40% |
| Mass | ESI:<br>MH+ 443 (95%)<br>445 (99%)<br>373 (32%) | ESI:<br>MH+ 485 (92%)<br>487 (99%) | ESI:<br>MH$^+$ 487 (91%)<br>489 (89%)<br>373 (32%) |

EXAMPLE 294
Reduced Amination

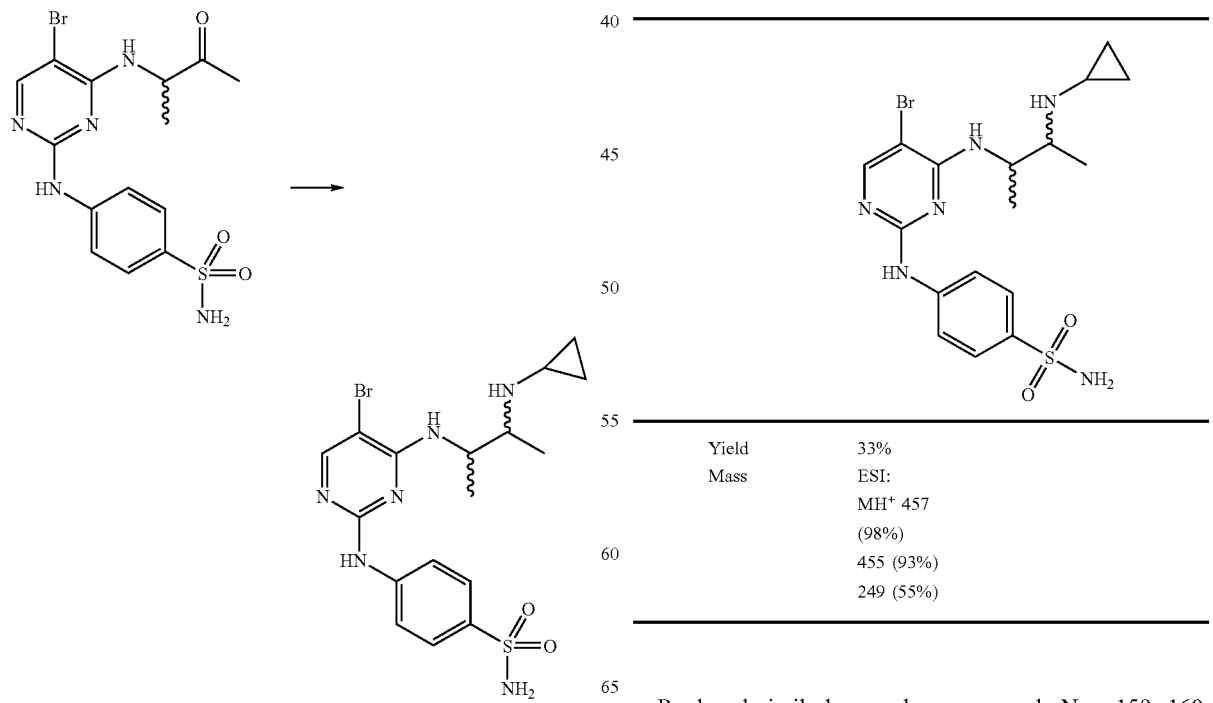

Yield: 18 mg (33% of theory) of the desired compound.

| Yield | 33% |
|---|---|
| Mass | ESI:<br>MH$^+$ 457<br>(98%)<br>455 (93%)<br>249 (55%) |

Produced similarly are also compounds Nos. 159, 160, 161, 163, 167, 168, 170, 174, 175, 191, 203 and 204.

EXAMPLES 295 and 296

Produced Similarly to Example 1 are also the Following Two Compounds:

| Example No. | 295 | 296 |
|---|---|---|
| Yield | 46% | 47% |
| Mass | ESI: MH⁺ 432 (30%) 434 (31%) 123 (100%) | ESI: MH⁺ 446 (45%) 448 (49%) 123 (90%) |

Production of General Formula I

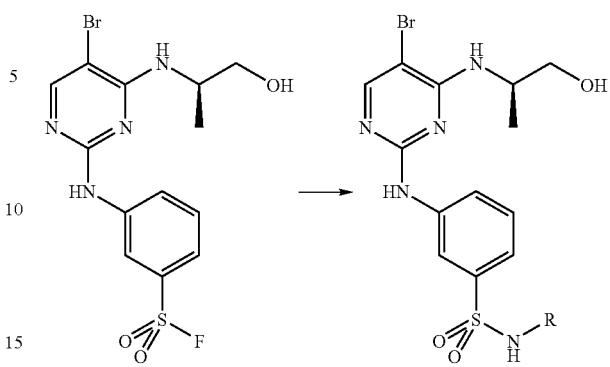

0.2 mmol of sulfonic acid fluoride is introduced into the reactor of a synthesizer. 1.0 ml of solvent, preferably 2-butanol, is added. 0.2 ml (0.2 mmol) of DMAP—dissolve in a solvent, for example DMSO or 2-butanol—and 0.2 ml (0.2 mmol) of the amine, dissolved in 2-butanol, are added in succession via a pipette. The reaction mixture is then stirred for 20 hours at 80° C. After the reaction is completed, the crude product is pipetted off, and the reactor is rewashed with 1.0 ml of THF. The solution of the crude product is then concentrated by evaporation and purified by HPLC.

The following compounds were produced:

| Example No. | Compound | Molecular Weight | ESI-MS |
|---|---|---|---|
| 297 | | 526.4968 | 526/528 |
| 298 | | 562.5298 | 562/564 |

-continued
| Example No. | Compound | Molecular Weight | ESI-MS |
|---|---|---|---|
| 299 | 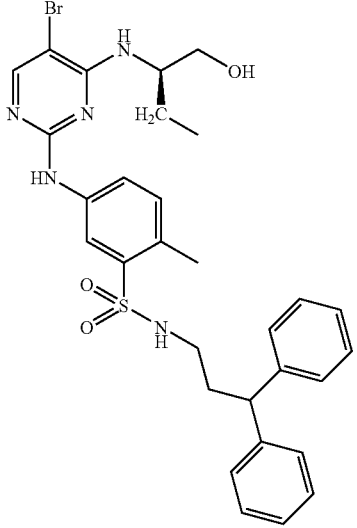 | 624.6006 | 624/626 |
| 300 | 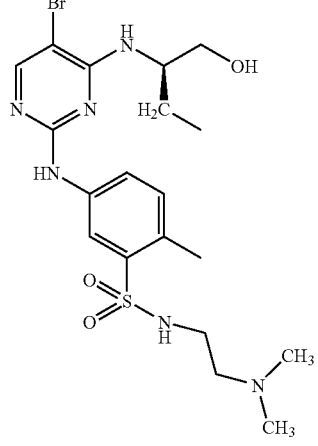 | 501.4471 | 501/503 |
| 301 | 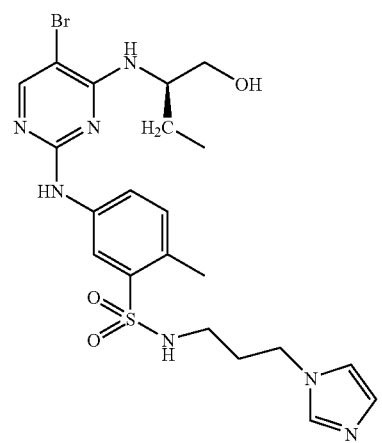 | 538.4682 | 538/540 |

-continued

| Example No. | Compound | Molecular Weight | ESI-MS |
|---|---|---|---|
| 302 | (structure: 5-bromo-4-[(1S)-1-(hydroxymethyl)propylamino]-2-[(4-methyl-3-{N-[3-(trifluoromethyl)benzyl]sulfamoyl}phenyl)amino]pyrimidine) | 588.4465 | 588/590 |
| 303 | (structure: 5-bromo-4-[(1S)-1-(hydroxymethyl)propylamino]-2-[(4-methyl-3-(N-heptylsulfamoyl)phenyl)amino]pyrimidine) | 528.5126 | 528/530 |
| 304 | (structure: 5-bromo-4-[(1S)-1-(hydroxymethyl)propylamino]-2-[(4-methyl-3-(N-octylsulfamoyl)phenyl)amino]pyrimidine) | 542.5394 | 542/544 |

-continued
| Example No. | Compound | Molecular Weight | ESI-MS |
|---|---|---|---|
| 305 | 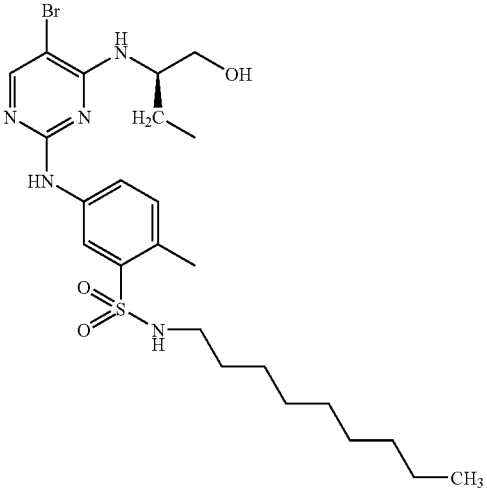 | 556.5662 | 556/558 |
| 306 | 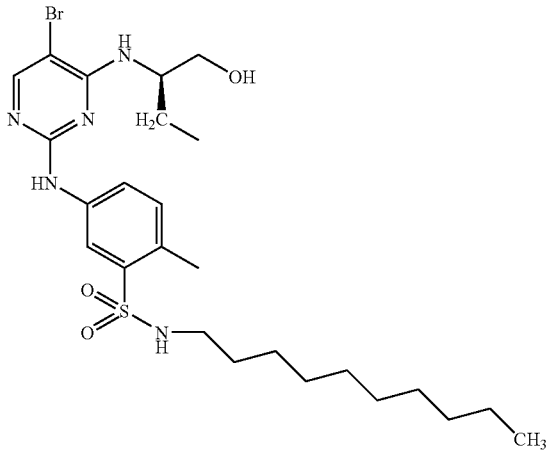 | 570.593 | 570/572 |
| 307 | 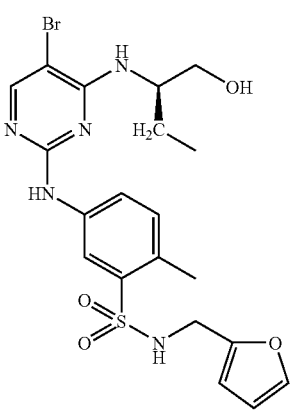 | 510.4106 | 510/512 |

-continued

| Example No. | Compound | Molecular Weight | ESI-MS |
|---|---|---|---|
| 308 | | 588.4465 | 588/590 |
| 309 | | 548.503 | 548/550 |
| 310 | | 555.4949 | 555/557 |

-continued

| Example No. | Compound | Molecular Weight | ESI-MS |
|---|---|---|---|
| 311 | | 500.459 | 500/502 |
| 312 | | 514.4858 | 514/516 |
| 313 | | 515.4739 | 515/517 |

-continued
| Example No. | Compound | Molecular Weight | ESI-MS |
|---|---|---|---|
| 314 | 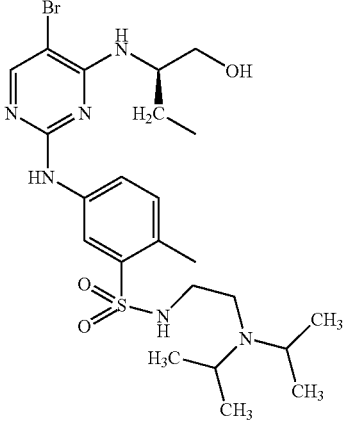 | 557.5543 | 557/559 |
| 315 | 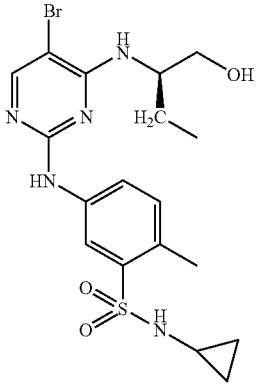 | 470.3896 | 470/472 |
| 316 | 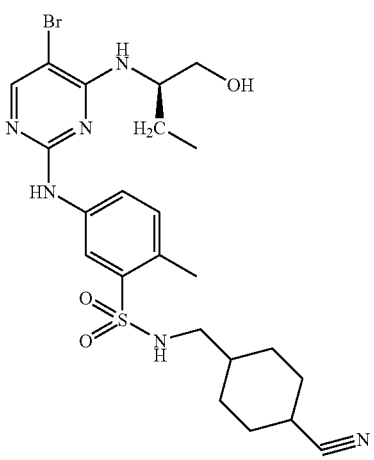 | 551.5069 | 551/553 |

-continued

| Example No. | Compound | Molecular Weight | ESI-MS |
|---|---|---|---|
| 317 | | 534.4762 | 534/536 |
| 318 | | 568.9213 | 568/570 |
| 319 | | 524.4374 | 524/526 |

-continued
| Example No. | Compound | Molecular Weight | ESI-MS |
|---|---|---|---|
| 320 | 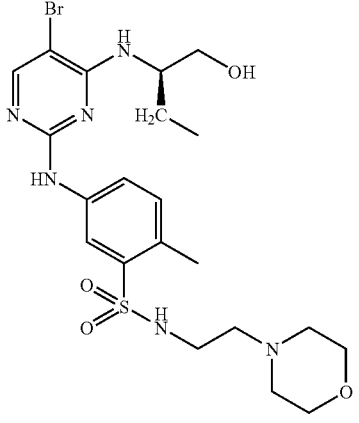 | 543.4839 | 543/545 |
| 321 | 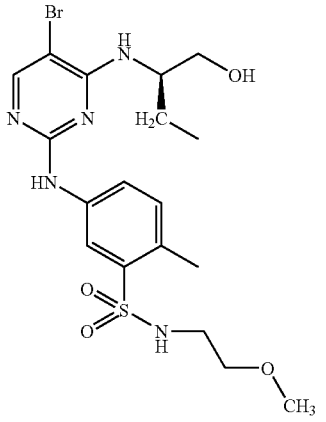 | 488.4044 | 488/490 |
| 322 | 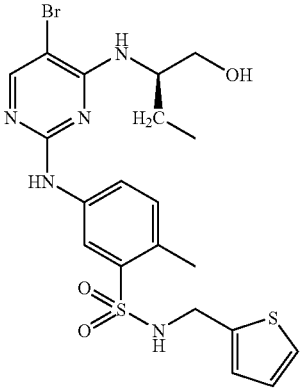 | 526.4776 | 526/528 |

-continued
| Example No. | Compound | Molecular Weight | ESI-MS |
|---|---|---|---|
| 323 | 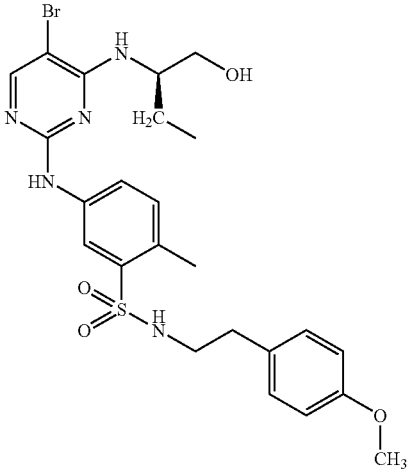 | 564.502 | 564/566 |
| 324 | 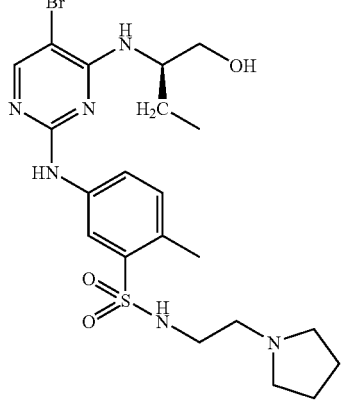 | 527.4849 | 527/529 |
| 325 | 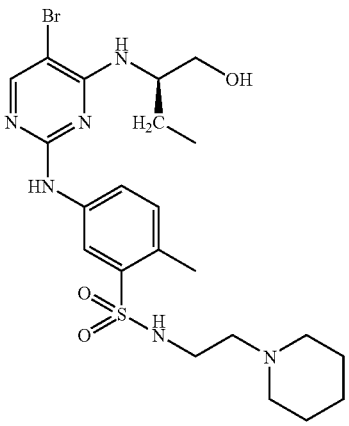 | 541.5117 | 541/543 |

-continued

| Example No. | Compound | Molecular Weight | ESI-MS |
|---|---|---|---|
| 326 | | 538.4395 | 538/540 |
| 327 | | 541.5117 | 541/543 |
| 328 | | 521.4375 | 521/523 |

-continued
| Example No. | Compound | Molecular Weight | ESI-MS |
|---|---|---|---|
| 329 | 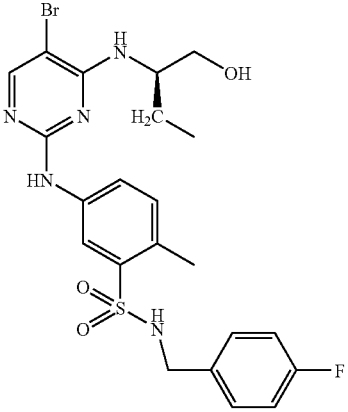 | 538.4395 | 538/540 |
| 330 | 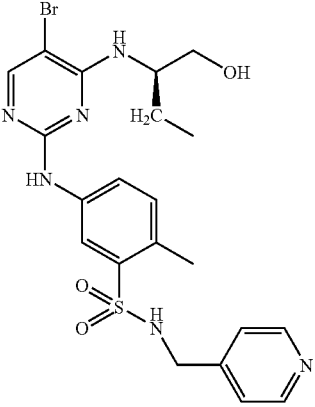 | 521.4375 | 521/523 |
| 331 | 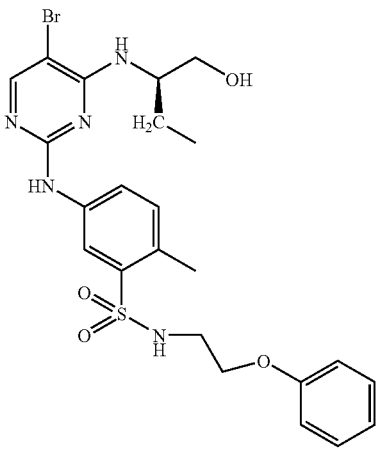 | 550.4752 | 550/552 |

-continued

| Example No. | Compound | Molecular Weight | ESI-MS |
|---|---|---|---|
| 332 | | 550.4752 | 550/552 |
| 333 | | 613.5551 | 613/615 |
| 334 | | 534.4762 | 534/536 |

-continued

| Example No. | Compound | Molecular Weight | ESI-MS |
|---|---|---|---|
| 335 | | 512.47 | 512/514 |
| 336 | | 548.503 | 548/550 |
| 337 | | 610.5738 | 610/612 |

-continued

| Example No. | Compound | Molecular Weight | ESI-MS |
|---|---|---|---|
| 338 | | 487.4203 | 487/489 |
| 339 | | 524.4414 | 524/526 |
| 340 | | 574.4197 | 574/576 |

| Example No. | Compound | Molecular Weight | ESI-MS |
|---|---|---|---|
| 341 | | 514.4858 | 516/514 |
| 342 | | 528.5126 | 528/530 |
| 343 | | 542.5394 | 542/544 |

-continued

| Example No. | Compound | Molecular Weight | ESI-MS |
|---|---|---|---|
| 344 | | 556.5662 | 556/558 |
| 345 | | 496.3838 | 496/498 |
| 346 | | 574.4197 | 574/576 |

-continued

| Example No. | Compound | Molecular Weight | ESI-MS |
|---|---|---|---|
| 347 | | 534.4762 | 534/536 |
| 348 | | 541.4681 | 541/543 |
| 349 | | 486.4322 | 486/488 |

-continued

| Example No. | Compound | Molecular Weight | ESI-MS |
|---|---|---|---|
| 350 | | 500.459 | 500/502 |
| 351 | | 501.4471 | 501/503 |
| 352 | | 543.5275 | 543/545 |

-continued

| Example No. | Compound | Molecular Weight | ESI-MS |
|---|---|---|---|
| 353 | | 456.3628 | 456/458 |
| 354 | | 537.4801 | 537/539 |
| 355 | | 520.4494 | 520/522 |

-continued
| Example No. | Compound | Molecular Weight | ESI-MS |
|---|---|---|---|
| 356 | 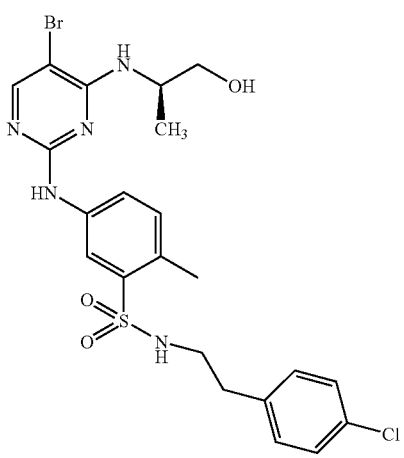 | 554.8945 | 554/556 |
| 357 | 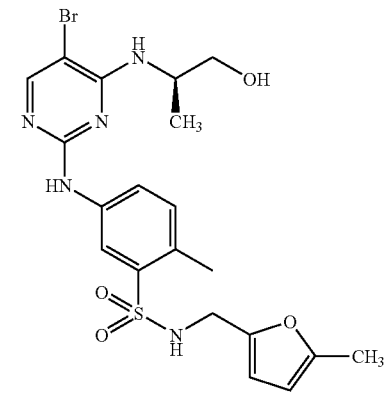 | 510.4106 | 510/512 |
| 358 | 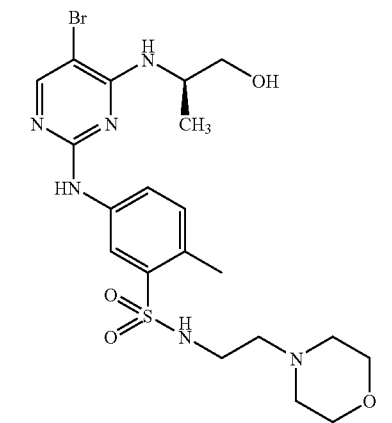 | 529.4571 | 529/531 |

-continued
| Example No. | Compound | Molecular Weight | ESI-MS |
|---|---|---|---|
| 359 | 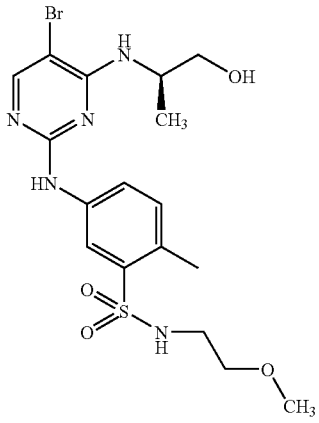 | 474.3776 | 474/476 |
| 360 | 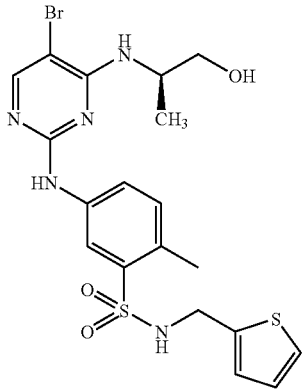 | 512.4508 | 541/514 |
| 361 | 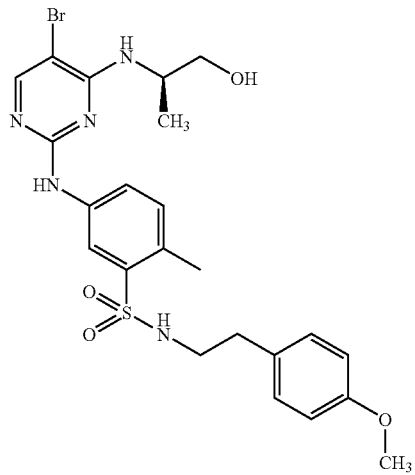 | 550.4752 | 550/552 |

-continued

| Example No. | Compound | Molecular Weight | ESI-MS |
|---|---|---|---|
| 362 | | 513.4581 | 513/515 |
| 363 | | 527.4849 | 527/529 |
| 364 | | 524.4127 | 524/526 |

-continued
| Example No. | Compound | Molecular Weight | ESI-MS |
|---|---|---|---|
| 365 | 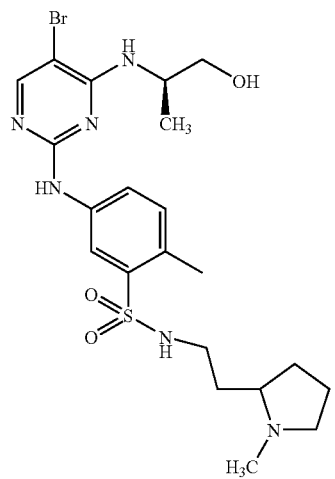 | 527.4849 | 527/529 |
| 366 | 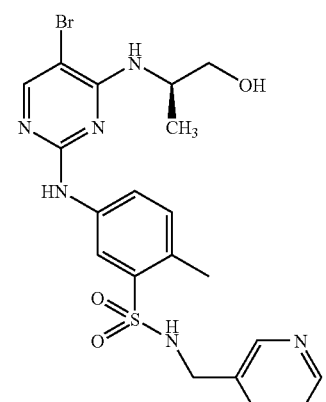 | 507.4107 | 507/509 |
| 367 | 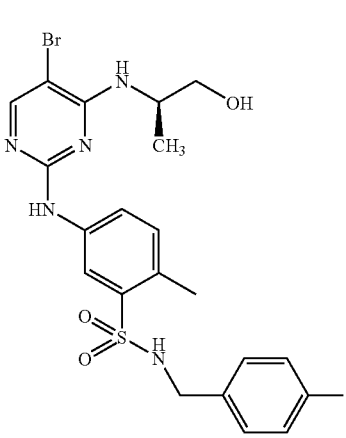 | 524.4127 | 524/526 |

-continued
| Example No. | Compound | Molecular Weight | ESI-MS |
|---|---|---|---|
| 368 | 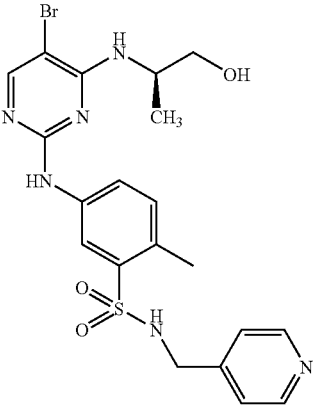 | 507.4107 | 507/509 |
| 369 | 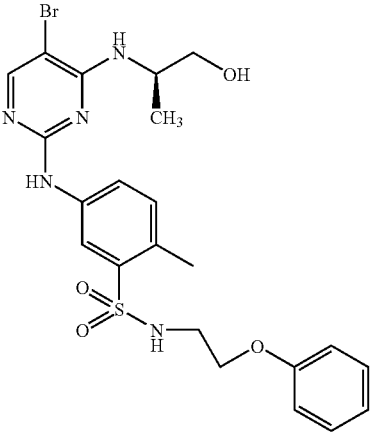 | 536.4484 | 536/538 |
| 370 | 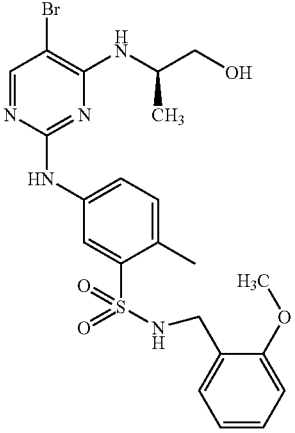 | 536.4484 | 536/538 |

-continued
| Example No. | Compound | Molecular Weight | ESI-MS |
|---|---|---|---|
| 371 | 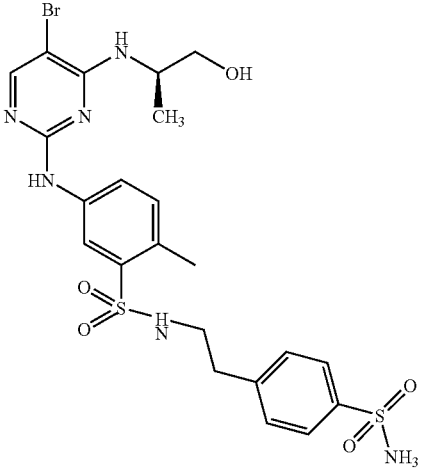 | 599.5283 | 599/601 |
| 372 | 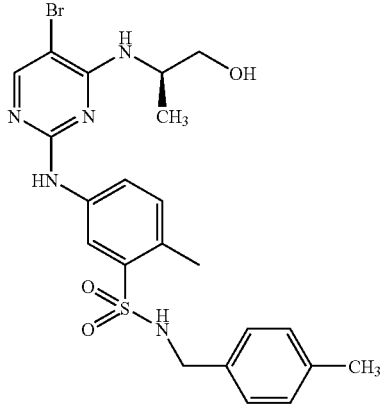 | 520.4494 | 520/522 |
| 373 | 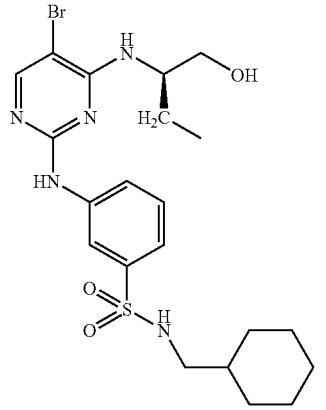 | 512.47 | 512/514 |

-continued
| Example No. | Compound | Molecular Weight | ESI-MS |
|---|---|---|---|
| 374 | 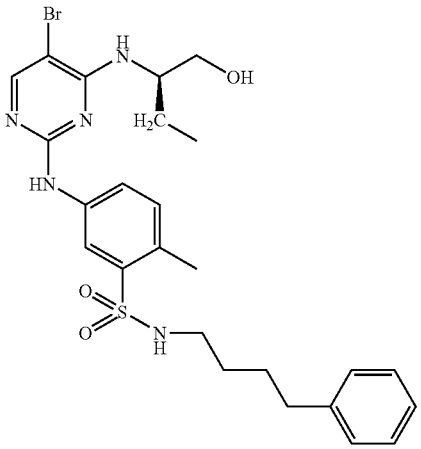 | 548.503 | 548/550 |
| 375 | 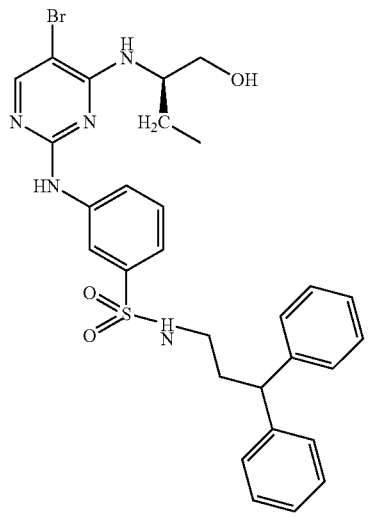 | 610.5738 | 610/612 |
| 376 | 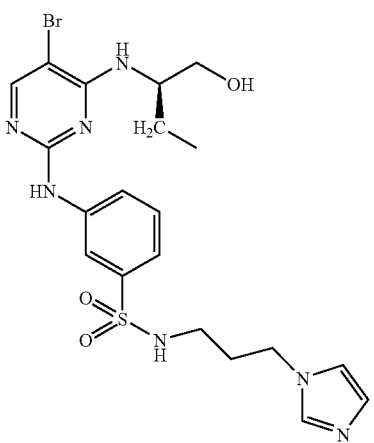 | 524.4414 | 524/526 |

-continued

| Example No. | Compound | Molecular Weight | ESI-MS |
|---|---|---|---|
| 377 | | 574.4197 | 574/576 |
| 378 | | 514.4858 | 514/516 |
| 379 | | 528.5126 | 528/530 |

-continued

| Example No. | Compound | Molecular Weight | ESI-MS |
|---|---|---|---|
| 380 | | 542.5394 | 542/544 |
| 381 | | 496.3838 | 496/498 |
| 382 | | 574.4197 | 574/576 |

-continued

| Example No. | Compound | Molecular Weight | ESI-MS |
|---|---|---|---|
| 383 | | 534.4762 | 534/536 |
| 384 | | 541.4681 | 541/543 |
| 385 | | 486.4322 | 486/488 |

-continued

| Example No. | Compound | Molecular Weight | ESI-MS |
|---|---|---|---|
| 386 | (structure) | 500.459 | 500/502 |
| 387 | (structure) | 501.4471 | 501/503 |
| 388 | (structure) | 543.5275 | 543/545 |

-continued
| Example No. | Compound | Molecular Weight | ESI-MS |
|---|---|---|---|
| 389 | 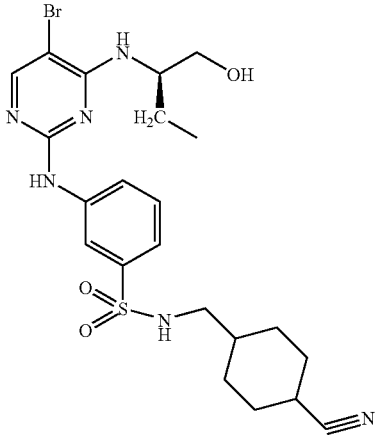 | 537.4801 | 537/539 |
| 390 | 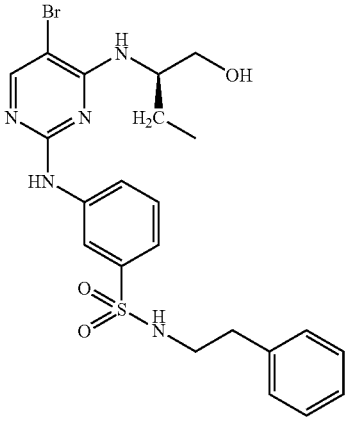 | 520.4494 | 520/522 |
| 391 | 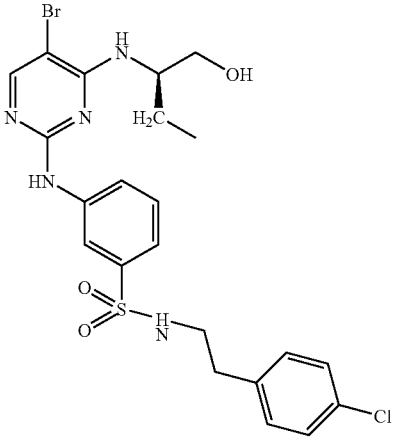 | 554.8945 | 554/556 |

-continued

| Example No. | Compound | Molecular Weight | ESI-MS |
|---|---|---|---|
| 392 | | 510.4106 | 510/512 |
| 393 | | 529.4571 | 529/531 |
| 394 | | 474.3776 | 474/476 |

-continued

| Example No. | Compound | Molecular Weight | ESI-MS |
|---|---|---|---|
| 395 | | 512.4508 | 512/514 |
| 396 | | 513.4581 | 513/515 |
| 397 | | 527.4849 | 527/529 |

-continued

| Example No. | Compound | Molecular Weight | ESI-MS |
|---|---|---|---|
| 398 | | 524.4127 | 524/526 |
| 399 | | 527.4849 | 527/529 |
| 400 | | 507.4107 | 507/509 |

-continued
| Example No. | Compound | Molecular Weight | ESI-MS |
|---|---|---|---|
| 401 | 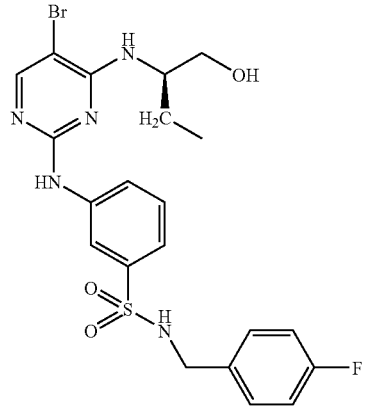 | 524.4127 | 524/526 |
| 402 | 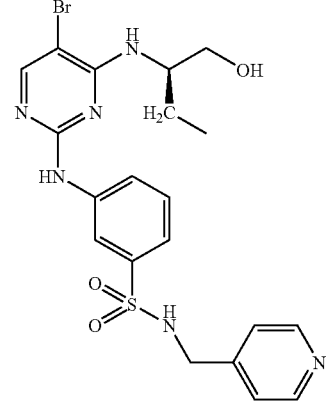 | 507.4107 | 507/509 |
| 403 | 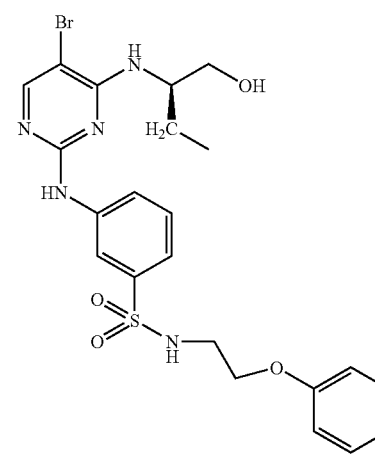 | 536.4484 | 526/538 |

| Example No. | Compound | Molecular Weight | ESI-MS |
|---|---|---|---|
| 404 | 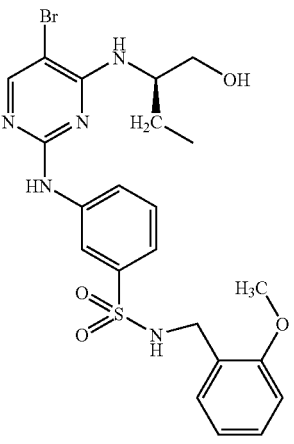 | 536.4484 | 536/538 |
| 405 | 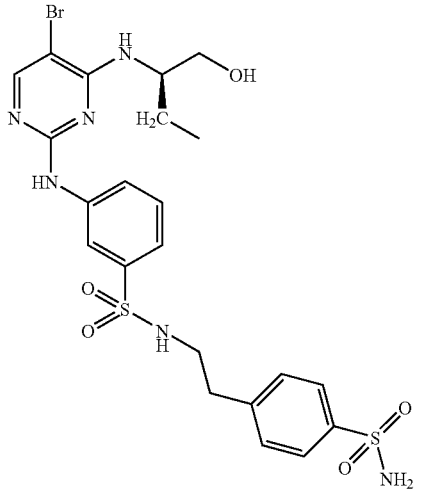 | 599.5283 | 599/601 |
| 406 | 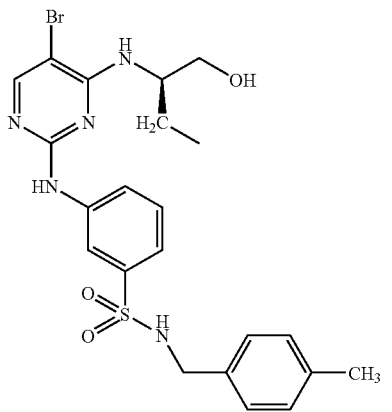 | 520.4494 | 520/522 |

-continued
| Example No. | Compound | Molecular Weight | ESI-MS |
|---|---|---|---|
| 407 | 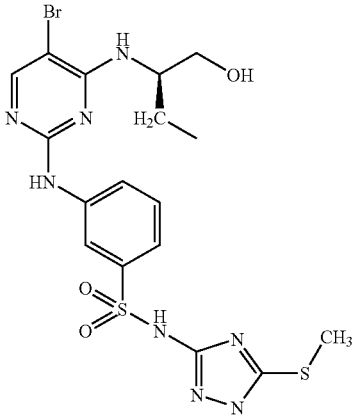 | 529.4419 | 529/531 |
| 408 | 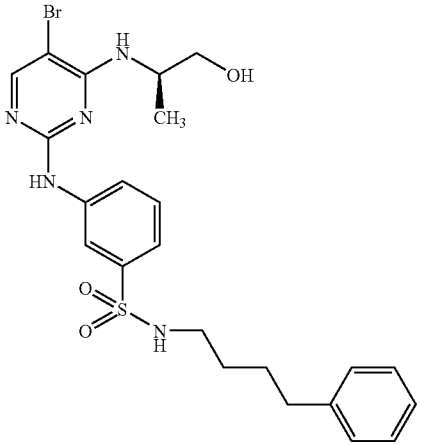 | 534.4762 | 534/536 |
| 409 | 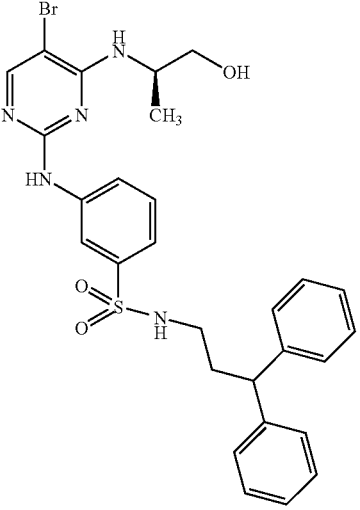 | 596.547 | 596/598 |

-continued

| Example No. | Compound | Molecular Weight | ESI-MS |
|---|---|---|---|
| 410 | | 473.3935 | 473/475 |
| 411 | | 510.4146 | 510/512 |
| 412 | | 560.3929 | 560/562 |

-continued
| Example No. | Compound | Molecular Weight | ESI-MS |
|---|---|---|---|
| 413 | 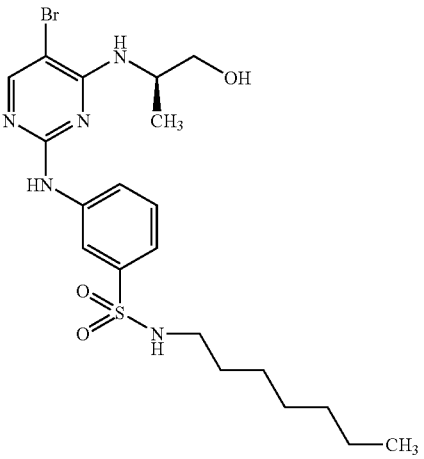 | 500.459 | 500/502 |
| 414 | 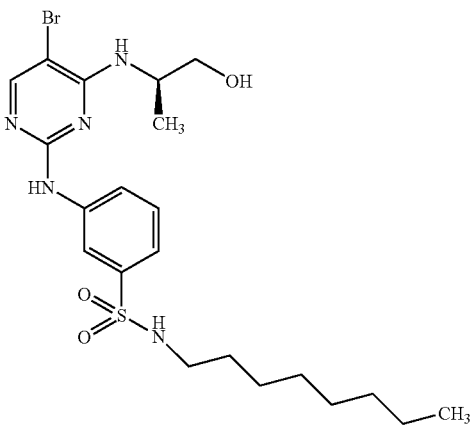 | 514.4858 | 514/516 |
| 415 | 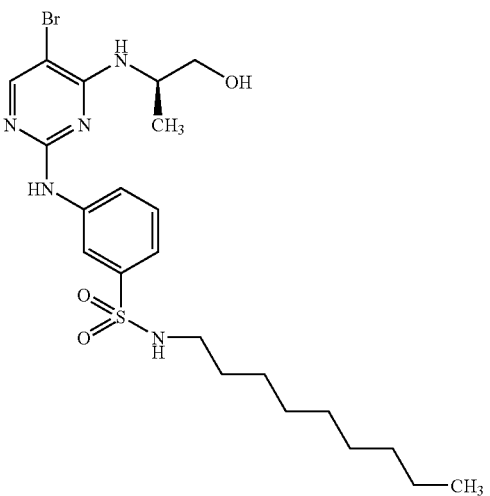 | 528.5126 | 528/530 |

-continued

| Example No. | Compound | Molecular Weight | ESI-MS |
|---|---|---|---|
| 416 | | 482.357 | 482/484 |
| 417 | | 560.3929 | 560/562 |
| 418 | | 520.4494 | 520/522 |

-continued
| Example No. | Compound | Molecular Weight | ESI-MS |
|---|---|---|---|
| 419 | 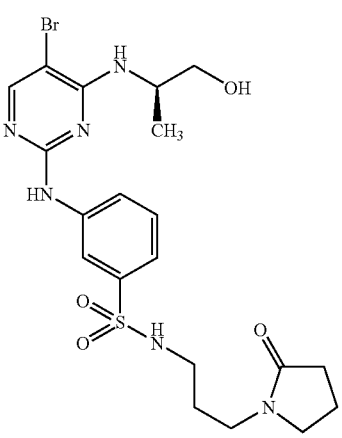 | 527.4413 | 527/529 |
| 420 | 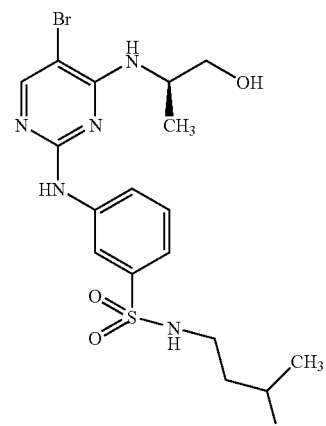 | 472.4054 | 472/474 |
| 421 | 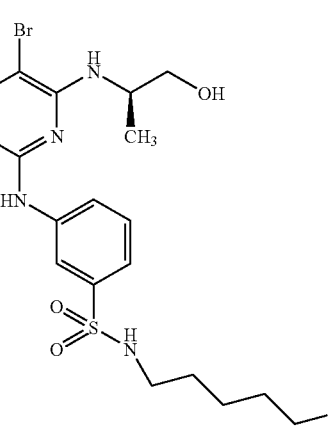 | 486.4322 | 486/488 |

-continued
| Example No. | Compound | Molecular Weight | ESI-MS |
|---|---|---|---|
| 422 | 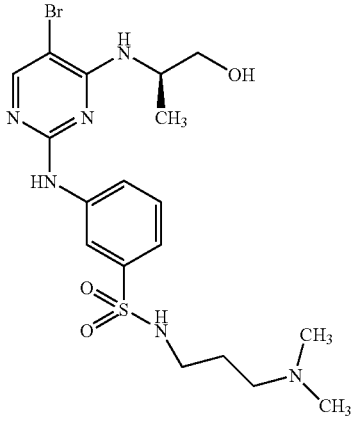 | 487.4203 | 487/489 |
| 423 | 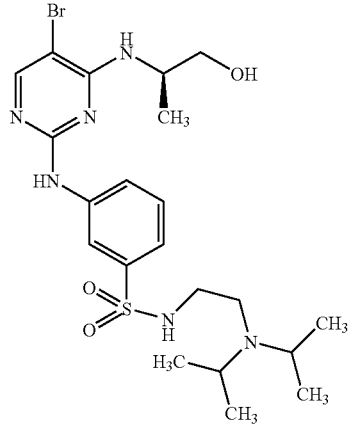 | 529.5007 | 529/531 |
| 424 | 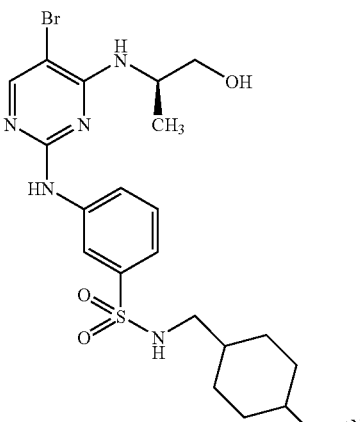 | 523.4532 | 523/525 |

-continued
| Example No. | Compound | Molecular Weight | ESI-MS |
|---|---|---|---|
| 425 | 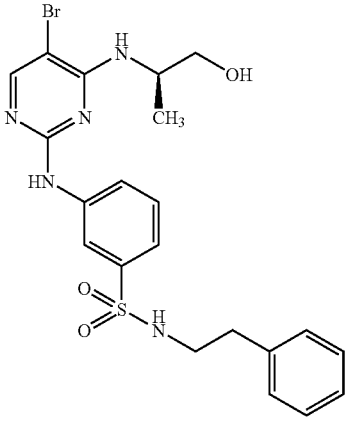 | 506.4226 | 506/508 |
| 426 | 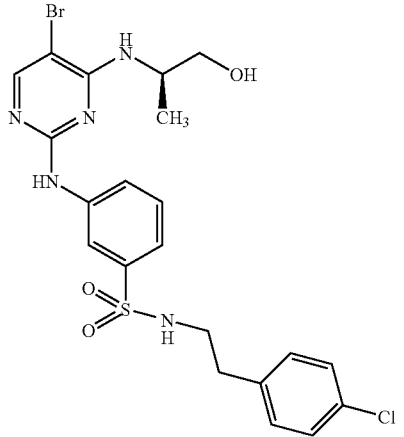 | 540.8677 | 540/542 |
| 427 | 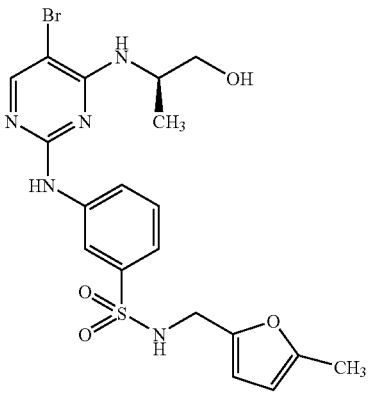 | 496.3838 | 496/498 |

-continued
| Example No. | Compound | Molecular Weight | ESI-MS |
|---|---|---|---|
| 428 | 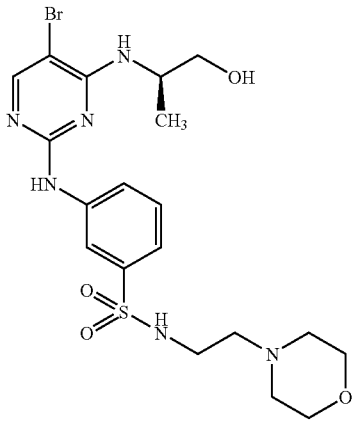 | 515.4303 | 515/517 |
| 429 | 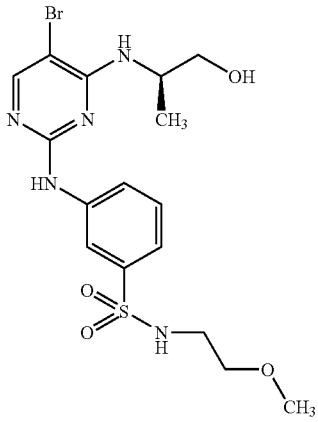 | 460.3508 | 460/462 |
| 430 | 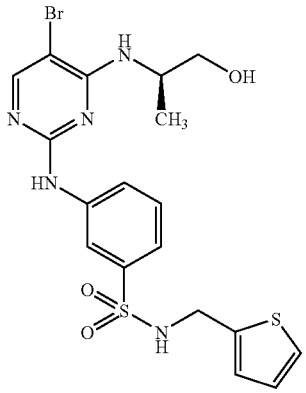 | 498.424 | 498/500 |

-continued
| Example No. | Compound | Molecular Weight | ESI-MS |
|---|---|---|---|
| 431 | 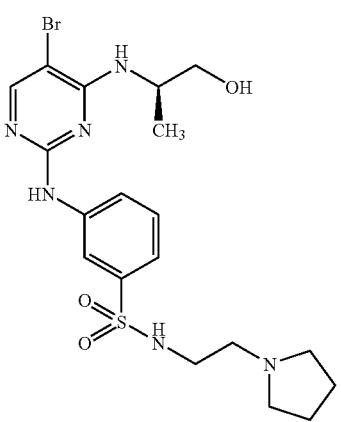 | 499.4313 | 499/501 |
| 432 | 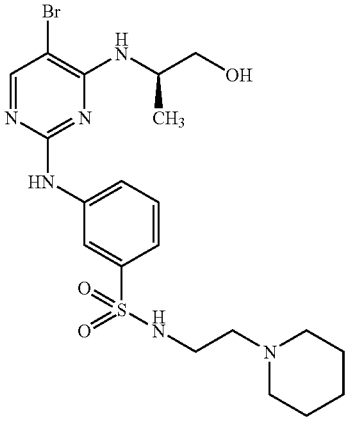 | 513.4581 | 513/515 |
| 433 | 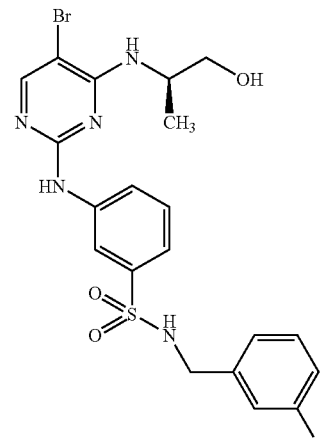 | 510.3859 | 510/512 |

-continued

| Example No. | Compound | Molecular Weight | ESI-MS |
|---|---|---|---|
| 434 | | 513.4581 | 513/515 |
| 435 | | 493.3839 | 493/495 |
| 436 | | 510.3859 | 510/512 |

-continued

| Example No. | Compound | Molecular Weight | ESI-MS |
|---|---|---|---|
| 437 | | 493.3839 | 493/495 |
| 438 | | 522.4216 | 522/524 |
| 439 | | 522.4216 | 522/524 |

-continued
| Example No. | Compound | Molecular Weight | ESI-MS |
|---|---|---|---|
| 440 | 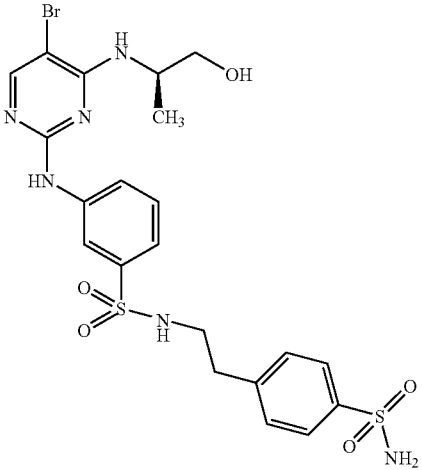 | 585.5015 | 585/587 |
| 441 | 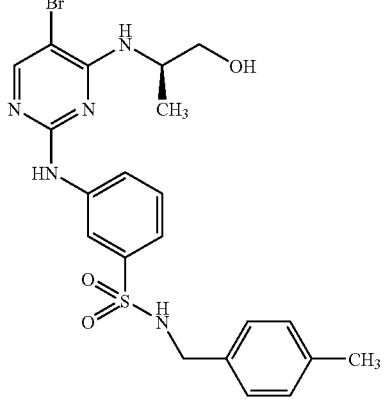 | 506.4226 | 506/508 |
| 442 | 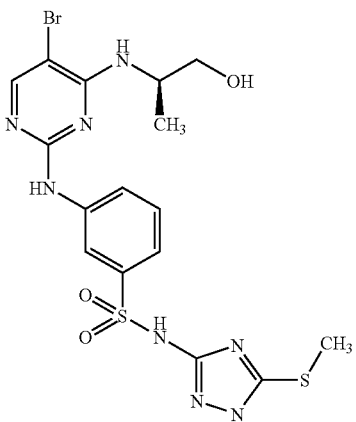 | 515.4151 | 515/517 |

| Example No. | Compound | Molecular Weight | ESI-MS |
|---|---|---|---|
| 443 *) | (structure) | 416.30 | 416/418 |

*) produced according to the process that is described ubder Sulfonamides

Production of the Pyrimidine-Sulfonyl Fluorides of General Formula I

The production of the pyrimidine-sulfonic acid fluorides is carried out analogously to the production of the sulfonic acid amides.

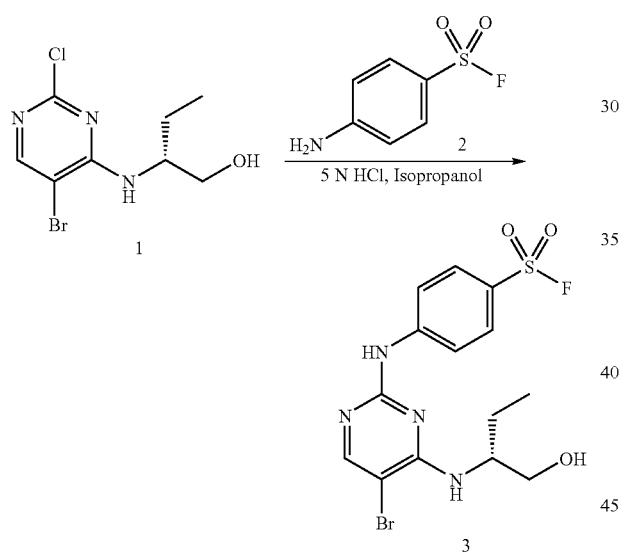

| Example No. | Compound | Molecular Weight | Melting Point [° C.] and ESI-MS |
|---|---|---|---|
| 444 | (structure) | 405.25 | 217–220 405/407 |
| 445 | (structure) | 419.27 | 196–202 419/421 |
| 446 | (structure) | 419.27 | 165–196 419/421 |
| 447 | (structure) | 433.30 | 198–204 433/435 |

-continued

| Example No. | Compound | Molecular Weight | Melting Point [° C.] and ESI-MS |
|---|---|---|---|
| 448 | | 433.30 | 144–149 433/435 |
| 449 | | 447.33 | 219–222 447/449 |
| 450 | | 405.25 | 170–173 405/407 |
| 451 | | 419.27 | 226–228 419/421 |

-continued

| Example No. | Compound | Molecular Weight | Melting Point [° C.] and ESI-MS |
|---|---|---|---|
| 452 | | 433.30 | 433/435 |
| 453 | | 447.33 | 447/449 |
| 454 | | 433.30 | 433/435 |
| 455 | | 419.27 | 419/421 |

The follwing para compunds are also produced similarly to the above-described examples:
| Example No. | Compound | Molecular Weight | ESI-MS |
|---|---|---|---|
| 456 | 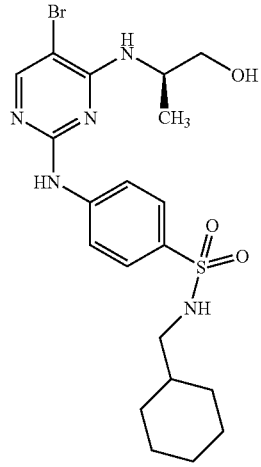 | 498.4432 | 498/500 |
| 457 | 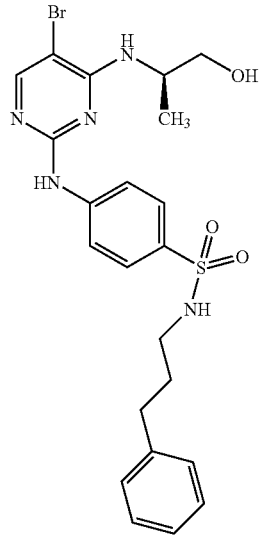 | 534.4762 | 534/536 |
| 458 | 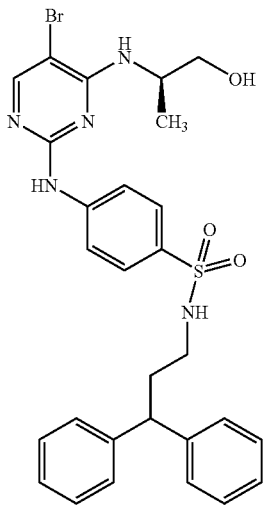 | 596.547 | 596/598 |

-continued
| Example No. | Compound | Molecular Weight | ESI-MS |
|---|---|---|---|
| 459 | 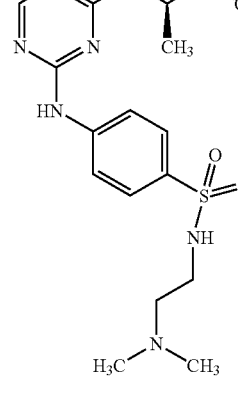 | 473.3935 | 473/475 |
| 460 | 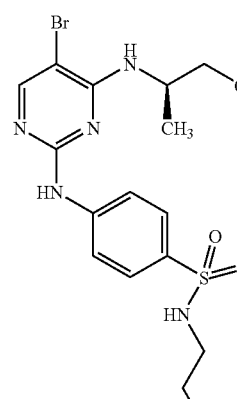 | 510.4146 | 510/512 |
| 461 | 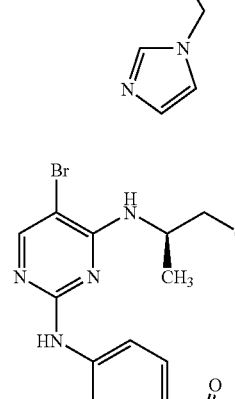 | 560.3929 | 560/562 |

| Example No. | Compound | Molecular Weight | ESI-MS |
|---|---|---|---|
| 462 | (structure) | 500.459 | 500/502 |
| 463 | (structure) | 514.4858 | 514/516 |

-continued
| Example No. | Compound | Molecular Weight | ESI-MS |
|---|---|---|---|
| 464 | 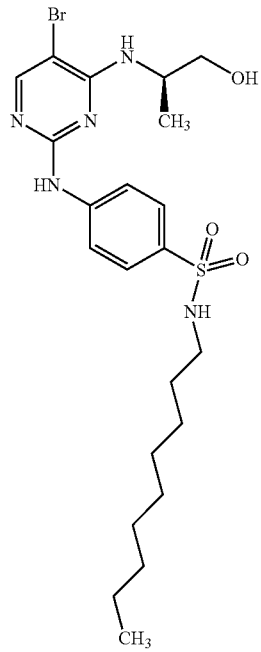 | 528.5126 | 528/530 |
| 465 | 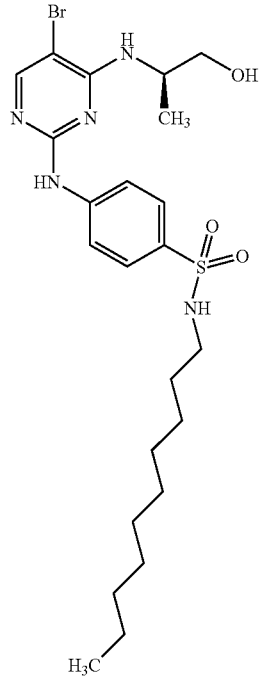 | 542.5394 | 542/544 |

-continued
| Example No. | Compound | Molecular Weight | ESI-MS |
|---|---|---|---|
| 466 | 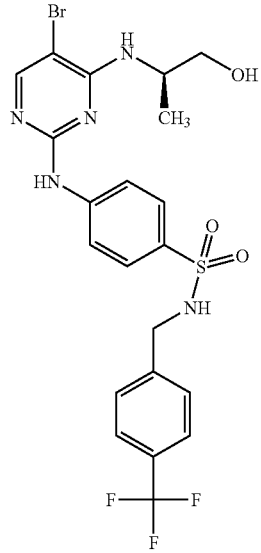 | 560.3929 | 560/562 |
| 467 | 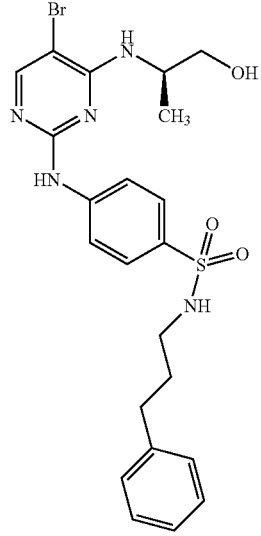 | 520.4494 | 520/522 |
| 468 | 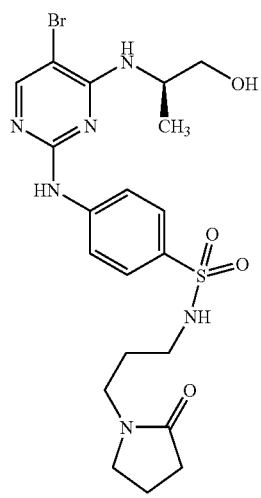 | 527.4413 | 527/529 |

-continued
| Example No. | Compound | Molecular Weight | ESI-MS |
|---|---|---|---|
| 469 | 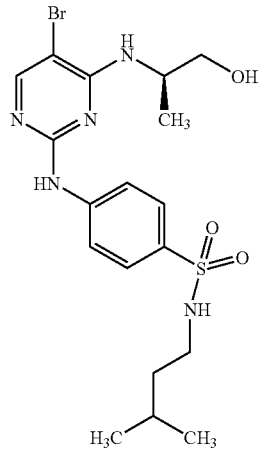 | 472.4054 | 472/474 |
| 470 | 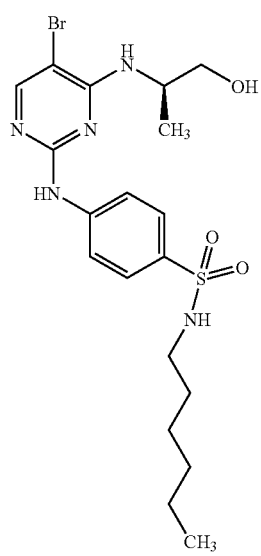 | 486.4322 | 486/488 |
| 471 | 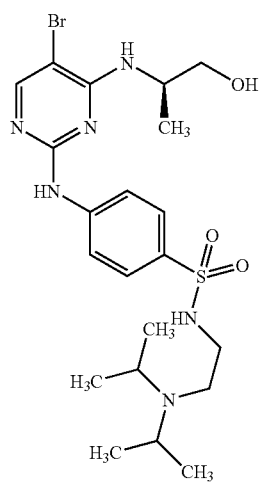 | 529.5007 | 529/531 |

-continued

| Example No. | Compound | Molecular Weight | ESI-MS |
|---|---|---|---|
| 472 | | 442.336 | 442/444 |
| 473 | | 523.4532 | 523/525 |
| 474 | | 506.4226 | 506/508 |

| Example No. | Compound | Molecular Weight | ESI-MS |
|---|---|---|---|
| 475 | *(structure)* | 540.8677 | 540/542 |
| 476 | *(structure)* | 496.3838 | 496/498 |
| 477 | *(structure)* | 515.4303 | 515/517 |

-continued
| Example No. | Compound | Molecular Weight | ESI-MS |
|---|---|---|---|
| 478 | 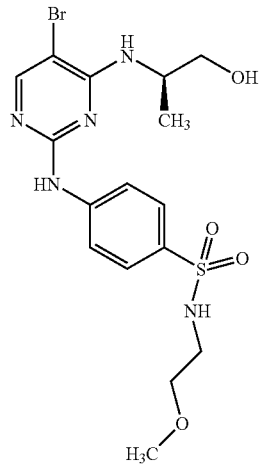 | 460.3508 | 460/462 |
| 479 | 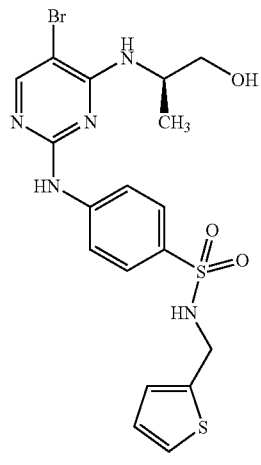 | 498.424 | 498/500 |
| 480 | 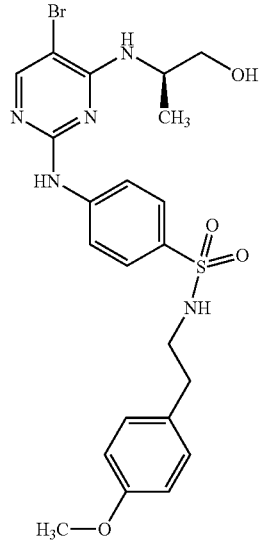 | 536.4484 | 536/538 |

-continued

| Example No. | Compound | Molecular Weight | ESI-MS |
|---|---|---|---|
| 481 | | 499.4313 | 499/501 |
| 482 | | 513.4581 | 513/515 |
| 483 | | 510.3859 | 510/512 |

| Example No. | Compound | Molecular Weight | ESI-MS |
|---|---|---|---|
| 484 | | 513.4581 | 513/515 |
| 485 | | 493.3839 | 493/495 |
| 486 | | 510.3859 | 510/512 |

| Example No. | Compound | Molecular Weight | ESI-MS |
|---|---|---|---|
| 487 | 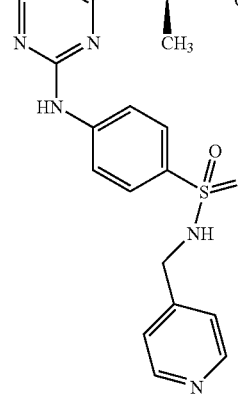 | 493.3839 | 493/495 |
| 488 | 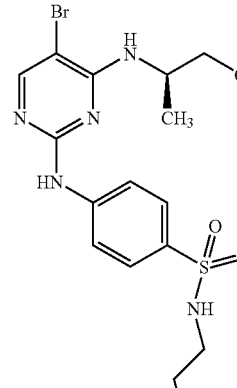 | 522.4216 | 522/524 |
| 489 | 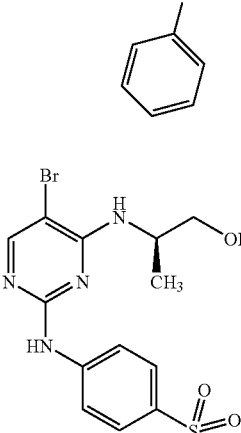 | 522.4216 | 522/524 |

| Example No. | Compound | Molecular Weight | ESI-MS |
|---|---|---|---|
| 490 | | 585.5015 | 585/587 |
| 491 | | 506.4226 | 506/508 |
| 492 | | 515.4151 | 515/517 |

-continued

| Example No. | Compound | Molecular Weight | ESI-MS |
|---|---|---|---|
| 493 | | 512.47 | |
| 494 | | 548.503 | |
| 495 | | 610.5738 | |

| Example No. | Compound | Molecular Weight | ESI-MS |
|---|---|---|---|
| 496 | | 487.4203 | |
| 497 | | 524.4414 | |
| 498 | | 574.4197 | |
| 499 | | 514.4858 | |

-continued

| Example No. | Compound | Molecular Weight | ESI-MS |
|---|---|---|---|
| 500 | | 528.5126 | |
| 501 | | 542.5394 | |
| 502 | | 556.5662 | |
| 503 | | 496.3838 | |

| Example No. | Compound | Molecular Weight | ESI-MS |
|---|---|---|---|
| 504 | | 574.4197 | |
| 505 | | 534.4762 | |
| 506 | | 541.4681 | |
| 507 | | 486.4322 | |

| Example No. | Compound | Molecular Weight | ESI-MS |
|---|---|---|---|
| 508 | | 500.459 | |
| 509 | | 501.4471 | |
| 510 | | 543.5275 | |
| 511 | | 456.3628 | |

| Example No. | Compound | Molecular Weight | ESI-MS |
|---|---|---|---|
| 512 | | 537.4801 | |
| 513 | | 520.4494 | |
| 514 | | 566.4742 | |
| 515 | | 554.8945 | |

| Example No. | Compound | Molecular Weight | ESI-MS |
|---|---|---|---|
| 516 | | 510.4106 | |
| 517 | | 529.4571 | |
| 518 | | 474.3776 | |
| 519 | | 512.4508 | |

| Example No. | Compound | Molecular Weight | ESI-MS |
|---|---|---|---|
| 520 | 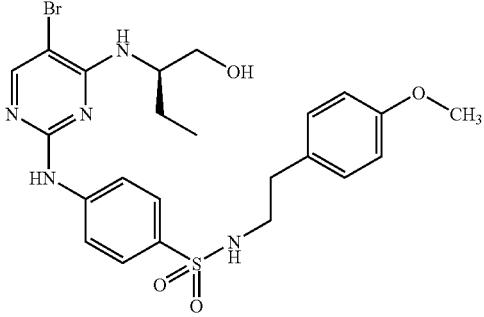 | 550.4752 | |
| 521 | 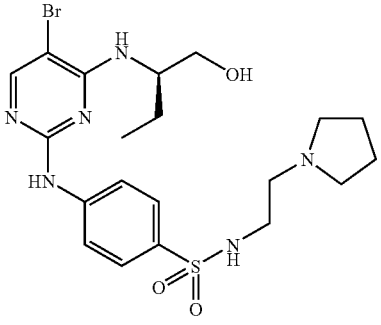 | 513.4581 | |
| 522 | 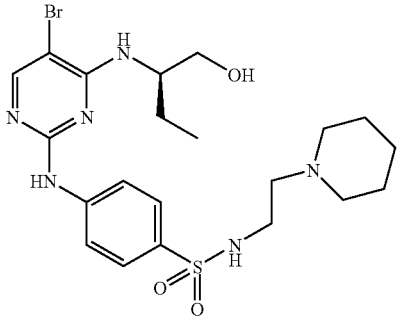 | 527.4849 | |
| 523 | 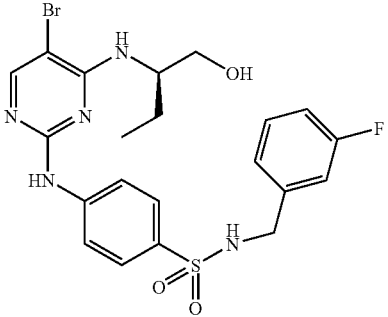 | 524.4127 | |

-continued

| Example No. | Compound | Molecular Weight | ESI-MS |
|---|---|---|---|
| 524 | | 527.4849 | |
| 525 | | 507.4107 | |
| 526 | | 524.4127 | |
| 527 | | 507.4107 | |

| Example No. | Compound | Molecular Weight | ESI-MS |
|---|---|---|---|
| 528 | | 536.4484 | |
| 529 | | 536.4484 | |
| 530 | | 599.5283 | |
| 531 | | 520.4494 | |

| Example No. | Compound | Molecular Weight | ESI-MS |
|---|---|---|---|
| 532 | | 529.4419 | |
Separation of Diastereomer Mixtures of the Compounds According to the Invention
Separation in the Example of the Diastereomer Mixture of Compound No. 274
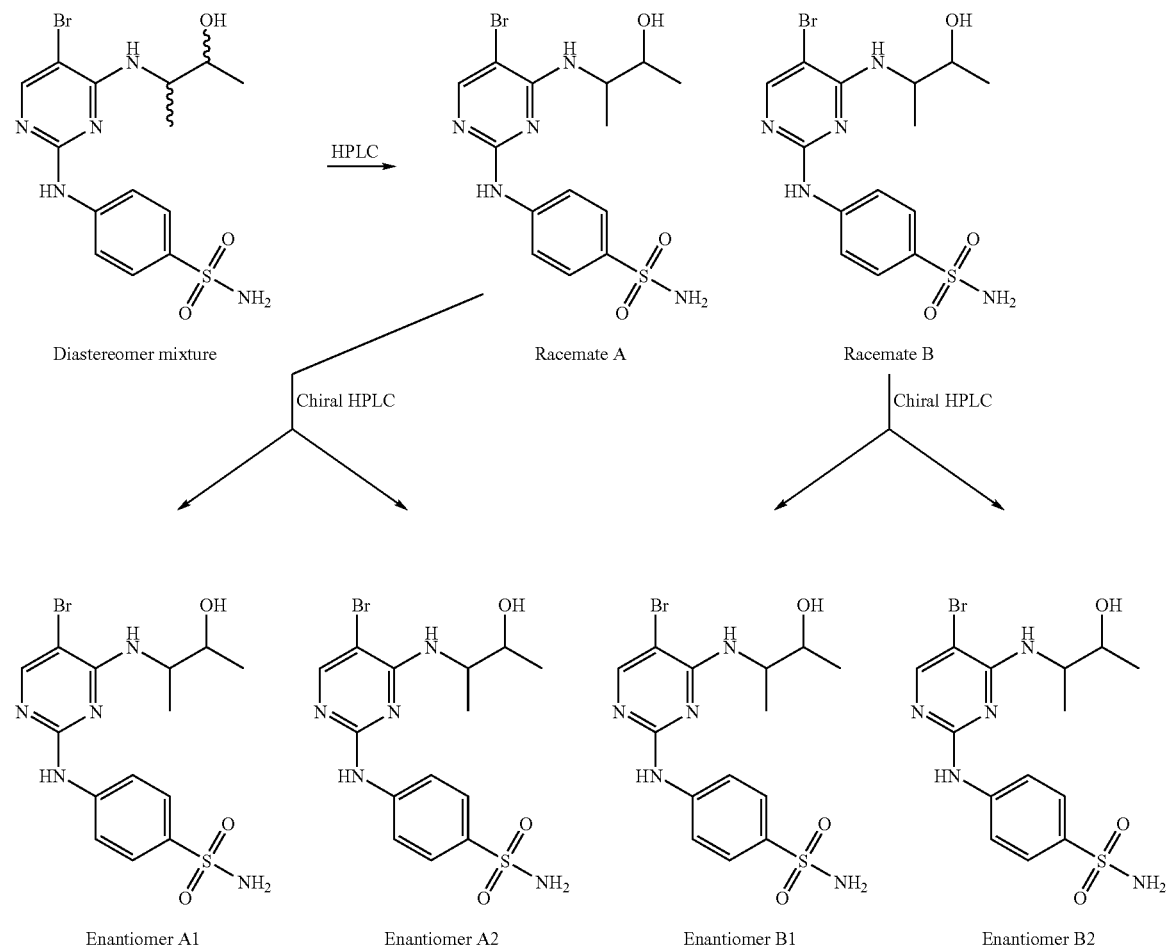

The diastereomer mixture is separated into the two corresponding racemates (A and B) by means of HPLC. Conditions:

| Conditions: | |
|---|---|
| Column: | Kromasil C18 (5 µm) 150 × 4.6 mm |
| Eluant: | 25% acetonitrile/water with 1 ml of NH3/1; |
| Flow: | 1.0 ml/min |
| Detection: | PDA 300 nm |
| Retention times: | Racemate A - 11.6 minutes |
| | Racemate B - 12.4 minutes |

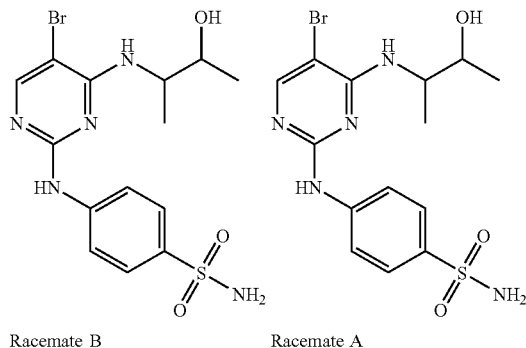

Racemate B          Racemate A

| NMR | DMSO-d6: | DMSO-d6: |
|---|---|---|
| | 9.68, s, 1H | 9.68, s, 1H |
| | 8.12, s, 1H | 8.11, s, 1H |
| | 7.87, d, 2H | 7.85, d, 2H |
| | 7.70, d, 2H | 7.69, d, 2H |
| | 7.14, s, 2H | 7.16, s, 2H |
| | 6.15, d, 1H | 6.35, d, 1H |
| | 5.01, d, 1H | 4.90, d, 1H |
| | 4.10, m, 1H | 4.08, m, 1H |
| | 3.80, m, 1H | 3.80, m, 1H |
| | 1.22, d, 3H | 1.18, d, 3H |
| | 1.1, d, 3H | 1.12, d, 3H |

Below, racemates A and B in each case are separated by means of chiral HPLC.

| Conditions: | |
|---|---|
| Column: | Chiralpak AD (10 µm) 250 × 4.6 mm |
| Eluant: | Hexane/ethanol 80:20 |
| Flow: | 1.0 ml/min |
| Detection: | PDA 300 nm |
| Retention times: | Enantiomer A1 - 16.6 minutes |
| | Enantiomer A2 - 19.6 minutes |
| | Enantiomer B1 - 16.0 minutes |
| | Enantiomer B2 - 17.8 minutes |

Conditions:

Column: Chiralpak AD (10 µm) 250×4.6 nm

Eluant: Hexane/ehanol 80:20

Flow: 1.0 ml/min

Detection: PDA 300 nm

Retention times: Enantiomer A1—16.6 minutes
  Enantiomer A1—19.6 minutes
  Enantiomer B1—16.0 minutes
  Enantiomer B2—17.8 minutes Production of the Intermediate Stages Preferably Used for the synthesis of the Compounds of General Formula I According to the Invention.

EXAMPLE 1.0

Production of N-(2-chloro-5-fluoro-4-pyrimidinyl)-N-2-propynylamine 11.1 g (66 mmol) of 2,4-dichloro-5-fluoropyrimidine is dissolved in 60 ml of acetonitrile, and 10.2 ml (73 mmol) of triethylamine and 6.0 ml (86 mmol) of propynylamine are added. The reaction mixture is stirred overnight at room temperature and then poured into water. The mixture is extracted by means of ethyl acetate, the combined organic phases are dried on $MgSO_4$, and the solvent is evaporated by means of underpressure. After the remaining material is recrystallized with diisopropyl ether/hexane, the yield is 10.6 g (87% of theory) of the product.

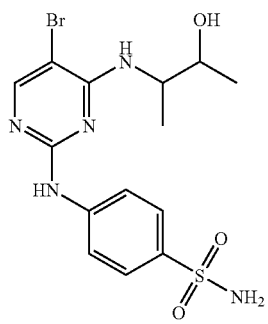

| 5-H | 8.18 (3.3 Hz, 1H) | Solvent: DMSO |
|---|---|---|
| 4CH | 4.14 (dd, 2H) | Yield: 87% |
| | 3.20 (t, 1H) | Melting point: 96° C. |
| NH | 8.65 (tb, 1H) | |

The 4-(diaminocyclohexyl) derivatives that are described below are synthesized via reductive aminations of the described keto derivative with use of triacetoxy borohydride (Abdel-Magid, Carson, Harris, Maryanoff, Sha, *J. Org. Chem.* 1996, 61, 3849). The keto derivative is obtained by TPAP oxidation (Griffith, Ley, *Aldrichimica Acta* 1990, 23, 13) of the corresponding alcohol.

Similarly produced are also the following intermediate compounds:

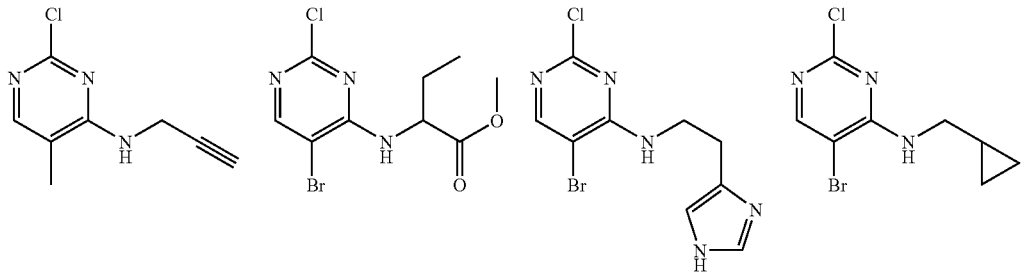

| Example No. | 1.1 | 1.2 | 1.3 | 1.4 |
|---|---|---|---|---|
| Solvent | CDCl$_3$ | DMSO | DMSO | DMSO |
| 5-H | 7.87(s, 1H) | 8.34(s, 1H) | 8.24(s, 1H) | 8.23(s, 1H) |
| 4CH | 4.32(dd, 2H) | 4.48(q, 1H) | 3.59(td, 2H) | 3.21(t, 2H) |
|  | 2.30(t, 1H) | 1.93(dq, 2H) | 2.78(t, 2H) | 1.10(mc, 1H) |
|  |  | 0.92(t, 3H) | 7.57(s, 1H) | 0.42(mc, 2H) |
| 5CH | 2.03(s, 3H) | 3.66(s, 3H) | 6.85(s, 1H) | 0.37(mc, 2H) |
|  |  |  | 7.90(tb, 1H) | 7.84(t, 1H) |
| NH | 4.91(sb, 1H) | 7.69(d, 1H) | 11.92(sb, 1H) |  |
| Yield | 80% | 42% | 33% | 74% |
| Melting Point | 121–121.5° C. | 73° C. | 90° C. |  |

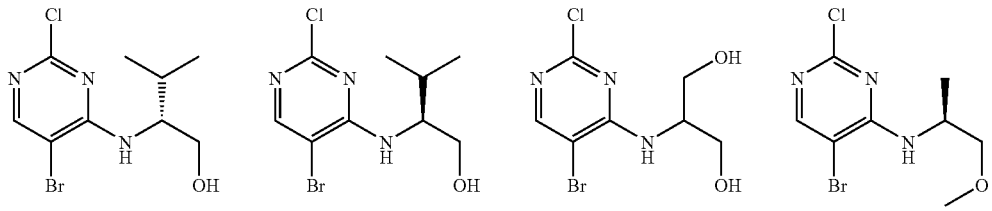

| Example No. | 1.5 | 1.6 | 1.7 | 1.8 |
|---|---|---|---|---|
| Solvent | DMSO | DMSO | DMSO | DMSO |
| 6-H | 8.26(s, 1H) | 8.26(s, 1H) | 8.27(s, 1H) | 8.37(s, 1H) |
| 4CH | 3.59(mc, 2H) | 3.58(mc, 2H) | 3.58(sb, 4H) | 4.40(m, 1H) |
|  | 3.90(mc, 1H) | 3.97(mc, 1H) | 4.14(mc, 1H) | 3.49(dd, 1H) |
|  | 1.98(mc, 1H) | 1.96(mc, 1H) |  | 3.33(dd, 1H) |
|  | 0.94(d, 3H) | 0.92(d, 3H) |  | 3.26(s, 3H) |
|  | 0.86(d, 3H) | 0.84(d, 3H) |  | 1.15(d, 3H) |
| OH | 4.67(mb, 1H) | 4.74(t, 1H) | 4.78(sb, 2H) |  |
| NH | 6.75(sb, 1H) | 6.87(d, 1H) | 6.73(sb, 1H) | 7.29(d, 1H) |
| Yield | 82% | 91% | 41% | 74% |
| Melting Point | 113–114° C. | 121–122° C. | 155–156° C. | Oil |

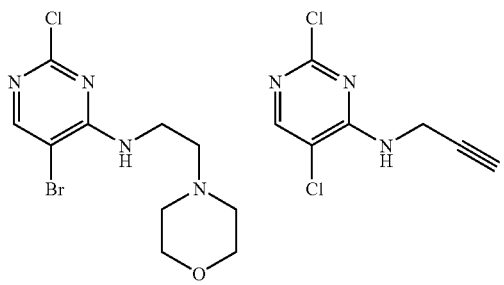

| Example No. | 1.9 | 1.10 |
|---|---|---|
| Solvent | DMSO | DMSO |
| 6-H | 8.24(s, 1H) | 8.36(s, 1H) |
| 4CH | 3.49(q, 2H) | 4.14(d, 2H) |
|  | 2.50(t, 2H) | 3.18(t, 1H) |
|  | 2.42(t, 4H) |  |
|  | 3.56(t, 4H) |  |

-continued

| | | |
|---|---|---|
| OH | | |
| NH | 7.57(sb, 1H) | 8.40(s, 1H) |
| Yield | 31% | 73 |
| Melting Point | 118–119° C. | 103–104° C. |

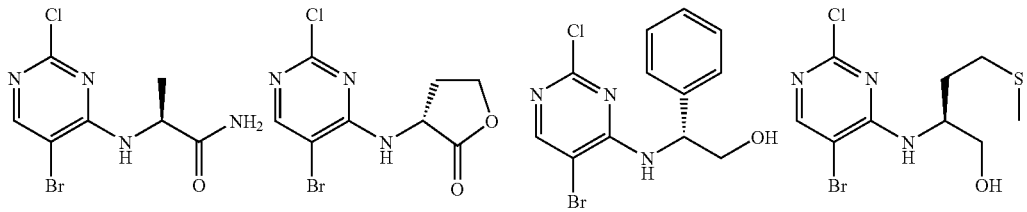

| Example No. | 1.11 | 1.12 | 1.13 | 1.14 |
|---|---|---|---|---|
| Solvent | DMSO | DMSO | DMSO | DMSO |
| 6-H | 8.30(s, 1H) | 8.32(s, 1H) | 8.29(s, 1H) | 8.24(s, 1H) |
| | 4.46(dq, 1H) | 5.04(q, 1H) | 3.7–3.9(2H) | 4.25(m, 1H) |
| | 1.38(d, 3H) | 2.39(m, 2H) | 5.19(m, 1H) | 3.48(m, 2H) |
| | | | 7.2–7.4(5H) | |
| NH | 7.60(sb, 1H) | 4.31(q, 1H) | 7.72(d, 1H) | 1.86(m, 2H) |
| | | | 5.09(t, 1H) | |
| OH | 7.29(sb, 1H) | 4.40(t, 1H) | | 2.43(m, 2H) |
| | 7.21(d, 1H) | 8.13(d, 1H) | | 2.03(s, 3H) |
| | | | | 7.13(d, 1H) |
| | | | | 4.88(t, 1H) |
| Yield | 87% | 63% | 99% | 78% |
| Melting Point | 234° C. Dec. | 210° C. Dec. | 152–153° C. | 130° C. |

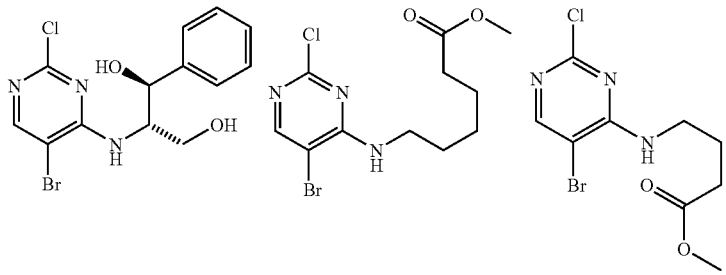

| Example No. | 1.15 | 1.16 | 1.17 |
|---|---|---|---|
| Solvent | DMSO | DMSO | DMSO |
| 6-H | 8.20(s, 1H) | 8.21(s, 1H) | 8.22(s, 1H) |
| | 3.55(m, 2H) | 3.33(q, 2H) | 3.39(q, 2H) |
| | 4.22(m, 1H) | 1.53(m, 4H) | 2.26(t, 2H) |
| | 5.03(m, 2H) | 1.28(m, 2H) | 1.79(q, 2H) |
| | 7.1–7.4(5H) | 2.29(t, 2H) | |
| NH | 6.53(d, 1H) | 7.74(t, 1H) | 7.78(t, 1H) |
| | 5.93(d, 1H) | | 12.11(sb, 1H) |
| Yield | 93% | 99% | 11% |
| Melting Point | Oil | Oil | Oil |

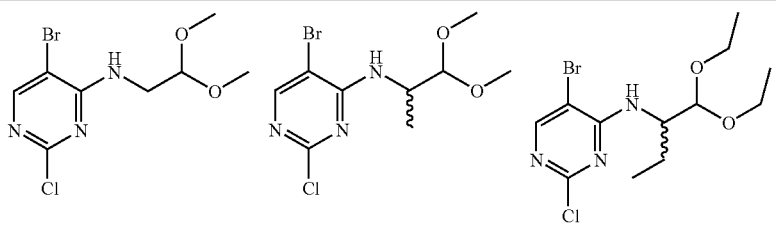

| Example No. | 1.18 | 1.19 | 1.20 |
|---|---|---|---|
| Yield | 86% | 64% | 87% |
| Mass | ESI: | ESI: | CI: |
| | MH$^+$ 297(2%) | MH$^+$ 311(2%) | M + 354(100%) |
| | 266(22%) | 248(20%) | 352(72%) |

| | | |
|---|---|---|
| 234(30%) | 236(18%) | 308(54%) |
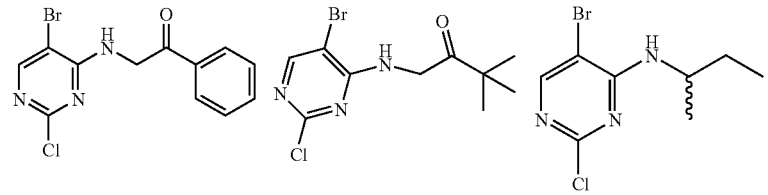
| | | | |
|---|---|---|---|
| Example No. | 1.21 | 1.22 | 1.23 |
| Yield | 26% | ~20% | 89% |
| Mass | EI: | NMR, CDCl3 | EI: |
| | M+ 327(10%) | 8, 16(s, 1H) | M+ 265(15%) |
| | 222(36%) | 6, 55(s, 1H) | 236(100%) |
| | 105(100%) | 4, 43(d, 2H) | 209(18%) |
| | | 1, 29(s, 9H) | |
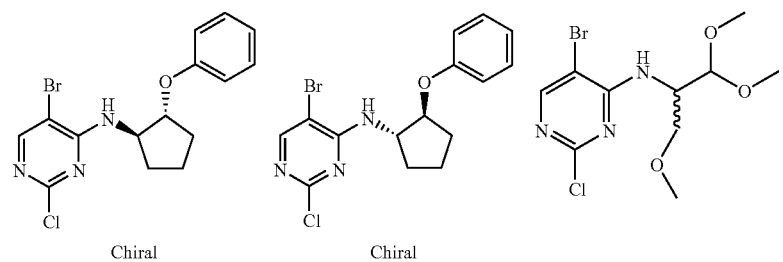
| | | | |
|---|---|---|---|
| | Chiral | Chiral | |
| Example No. | 1.24 | 1.25 | 1.26 |
| Yield | 75% | 70% | 83% |
| Mass | CI: | CI | ESI: |
| | M+ 384 | M+ 384(100%) | 319   3% |
| | (100%) | 212(21%) | 278 100% |
| | 212(21%) | 91(7%) | 220   68% |
| | 91(7%) | | |
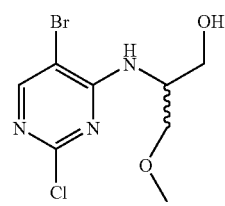
| | |
|---|---|
| Example No. | 1.27 |
| Yield | 98% |
| Mass | ESI: |
| | MH+ 296(90%) |
| | 298(100%) |
| | 210(12%) |

EXAMPLE 2.0

Production of 5-Bromo-2-chloro-4-(4,4,4-trifluorobutoxy)pyrimidine 3.19 g (14 mmol) of 5-bromo-2,4-dichloropyrimidine is mixed with 8.06 g (63 mmol) of 4,4,4-trifluorobutanol, and 0.74 ml (8.4 mmol) of trifluoromethanesulfonic acid is slowly added to it. The reaction mixture is stirred overnight at room temperature and then poured into water. The mixture is extracted by means of ethyl acetate, the combined organic phases are dried on $MgSO_2$, and the solvent is evaporated by means of underpressure. The product is always contaminated with varying amounts of 2,4-bisalkoxypyrimidine. The remaining material is therefore purified by means of gradient chromatography with silica gel as a carrier medium (eluant: hexane and hexane/ethyl acetate at a 9:1 ratio). This process results in a yield of 1.70 g (38%) and also yields 1.93 g (34%) of 5-bromo-2,4-bis-(4,4,4-trifluorobutoxy)pyrimidine (starting compound).

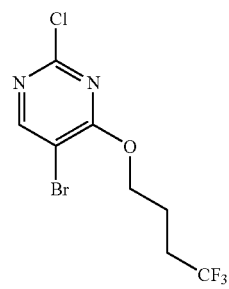

| | | | |
|---|---|---|---|
| 5-H | 8.74 (s, 1H) | Chromatography: H to H/EA 9:1 | |
| 4CH | 4.48 (t, 2H) | Yield: 38% | |
| 5CH | 2.00 (mc, 2H) | Melting point: 66.5–67.5° C. | |
| | 2.44 (mc, 2H) | | |

Similarly produced are also the following compounds:

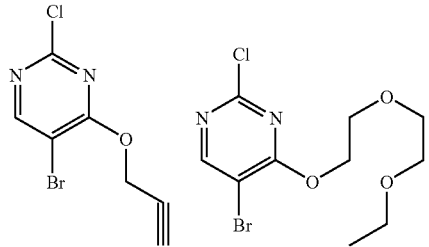

| Example No. | 2.1 | 2.2 |
|---|---|---|
| | CDCl$_3$ | DMSO |
| 5-H | 8.49 (s, 1H) | 8.75 (s, 1H) |
| 4CH | 5.10 (d, 2H) | 4.05 (mc, 2H) |
| | | 3.79 (mc, 2H) |
| | | 3.60 (mc, 2H) |
| 5CH | 2.59 (t, 1H) | 3.48 (mc, 2H) |
| | | 3.40 (t, 2H) |
| | | 1.07 (t, 3H) |
| Chrom. | H to H/EA 4:1 | DCM to DCM/MeOH 95:5 |
| Yield | 78% | 11% |
| Melting Point | 55° C. | Oil |

Analogously to process examples 1 and 2, the following intermediate products are also produced:

| Example No. | 1-2.1 | 1-2.2 | 1-2.3 | 1-2.4 |
|---|---|---|---|---|
| Structure |  | 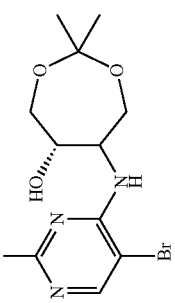 | 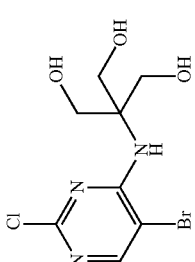 | 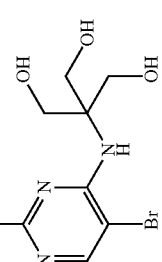 |
| Solvent | DMSO 8.26 (s, 1H) 6.65 (d, 1H) 4.70 (t, 1H) 4.10 (dt, 1H) 3.65 (at, 2H) 0.90 (s, 9H) | DMSO 8.26 (s, 1H) 6.65 (d, 1H) 4.70 (t, 1H) 4.10 (dt, 1H) 3.65 (at, 2H) 0.90 (s, 9H) | DMSO 8.29 (s, 1H) 6.32 (s, 1H) 4.89 (t, 3H) 3.74 (d, 6H) | DMSO 8.28 (s, 1H) 7.09 (d, 1H) 5.05 (d, 1H) 3.95 (m, 1H) 3.60 (m, 5H) 1.30 (s, 3H) 1.28 (s, 3H) |
| Yield | 49% | 70% | 16% | 92% |
| Mass | 309 (EI) | 309 (EI) | 314 (EI) | 354 (EI) |
| Example No. | 1-2.5 | 1-2.6 | 1-2.7 | 1-2.8 |
|---|---|---|---|---|
| Structure | 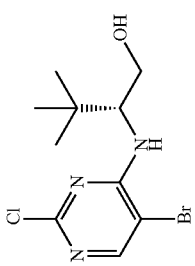 | 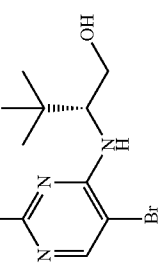 | 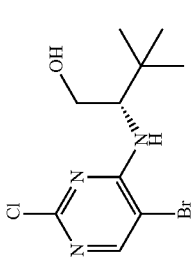 | 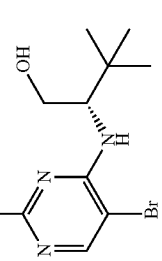 |
| Solvent | DMSO 8.15 (s, 1H) 7.25 (t, 1H) 3.16 (s, 2H) 1.90 (s, 3H) 1.61 (q, 6H) 1.41 (s, 6H) | DMSO 8.22 (s, 1H) 4.82 (t, 1H) 4.49 (br, 1H) 3.85 (m, 1H) 3.76 (m, 1H) 3.54 (m, 1H) 3.40 (m, 1H) 1.93 (m, 3H) 1.80 (m, 1H) | DMSO 8.28 (s, 1H) 6.29 (s, 1H) 5.31 (t, 1H) 3.39 (d, 2H) 1.39 (s, 6H) | DMSO 8.22 (s, 1H) 7.23 (d, 1H) 4.60 (d, 1H) 3.85 (m, 1H) 3.35 (m, 1H) 1.80 (m, 4H) 1.53 (m, 2H) 1.20 (m, 2H) |

-continued

| Yield Mass | 70% 357 (EI) | 75% 293 (EI) | 46% 281 (EI) | 24% 305 (EI) |
|---|---|---|---|---|
| Structure | 4-hydroxypiperidine on 2-chloro-5-bromopyrimidine | (S)-2-amino-propan-1-ol derivative | (S)-leucinol derivative | methyl valinate derivative |

| Example No. | 1-2.9 | 1-2.10 | 1-2.11 | 1-2.12 |
|---|---|---|---|---|
| Solvent | DMSO 8.38 (s, 1H) 4.81 (br, 1H) 3.96 (m, 2H) 3.72 (m, 1H) 3.30 (m, 2H) 1.81 (m, 2H) 1.48 (m, 2H) | DMSO 8.22 (s, 1H) 7.05 (d, 1H) 4.82 (t, 1H) 4.18 (m, 1H) 3.42 (m, 2H) 1.15 (d, 3H) | DMSO 8.38 (s, 1H) 7.06 (d, 1H) 4.81 (t, 1H) 4.22 (m, 1H) 3.47 (m, 2H) 1.51 (m, 2H) 1.37 (m, 1H) 0.88 (m, 6H) | DMSO 8.31 (s, 1H) 7.32 (d, 1H) 4.35 (s, 1H) 3.68 (s, 3H) 2.32 (m, 1H) 0.90 (dd, 6H) |

| Yield Mass | 19% 292 (EI) | 71% 266 (EI) | 99% 308 (EI) | 77% 322 (ES) |
|---|---|---|---|---|
| Structure | nonafluorobutyl amine derivative | tetrahydrofuran-3-yl amine derivative | cyclohexylmethylamine derivative | trans-2-methylcyclohexylamine derivative |

| Example No. | 1-2.13 | 1-2.14 | 1-2.15 | 1-2.16 |
|---|---|---|---|---|
| Solvent | DMSO 8.41 (s, 1H) 8.11 (s, 1H) 4.28 (t, 2H) 3.70 (dd, 1H) 3.62 (dd, 1H) 2.16 (m, 1H) 2.02 (m, 1H) | DMSO 8.25 (s, 1H) 4.53 (m, 1H) 3.88 (m, 2H) 1.62 (m, 6H) 1.16 (m, 3H) 0.90 (m, 2H) | DMSO 8.19 (s, 1H) 7.65 (t, 1H) 3.18 (t, 2H) 1.68 (m, 5H) 1.25 (m, 4H) 0.78 (d, 3H) | DMSO 8.19 (s, 1H) 7.30 (d, 1H) 3.65 (m, 1H) |

| | | | | |
|---|---|---|---|---|
| Yield-Mass | 7.56 (d, 1H) 46% 390 (FAB) | 72% 277 (EI) | 68% 303 (EI) | 31% 305 (EI) |
| Example No. | 1-2.17 | 1-2.18 | 1-2.19 | 1-2.20 |
| Solvent | DMSO 8.21 (s, 1H) 7.22 (d, 1H) 3.88 (m, 2H) 1.70 (m, 4H) 1.50 (m, 12H) 1.28 (m, 1H) 1.01 (m, 2H) 0.82 (d, 5H) | DMSO 8.35 (t, 1H) 8.19 (s, 1H) 3.40 (m, 2H) 2.97 (p, 1H) 2.22 (m, 4H) 2.08 (dd, 1H) 1.70 (m, 6H) | DMSO 8.21 (s, 1H) 7.81 (t, 1H) 3.41 (dd, 2H) 2.31 (m, 10H) 2.13 (s, 3H) 1.70 (p, 2H) | DMSO 8.20 (s, 1H) 7.71 (t, 1H) 4.45 (br, 1H) 3.40 (m, 4H) 1.60 (m, 2H) 1.44 (m, 2H) |
| Yield Mass | 22% 303 (EI) | 32% 320 (EI) | 28% 349 (EI) | 98% 281 (EI) |
| Example No. | 1-2.21 | 1-2.22 | 1-2.23 | 1-2.24 |
| Solvent | DMSO 8.25 (s, 1H) 8.08 (d, 1H) 7.35 (m, 5H) 5.30 (m, 1H) 4.81 (t, 1H) 3.45 (m, 2H) 2.05 (m, 2H) | DMSO 8.25 (s, 1H) 7.38 (d, 1H) 4.44 (m, 1H) 2.60 (m, 2H) 2.24 (m, 2H) 2.07 (m, 2H) 1.90 (m, 2H) | DMSO 8.20 (s, 1H) 7.28 (d, 1H) 4.19 (m, 1H) 2.40 (m, 6H) 1.50 (m, 4H) 1.15 (d, 3H) 0.91 (t, 6H) | DMSO 8.21 (s, 1H) 7.24 (d, 1H) 7.02 (t, 1H) 4.40 (m, 1H) 3.92 (m, 2H) 2.95 (q, 2H) 1.95 (m, 2H) 1.82 (m, 2H) |

| Example No. | 1-2.25 | 1-2.26 | 1-2.27 | 1-2.28 |
|---|---|---|---|---|
| Solvent | DMSO | DMSO<br>8.22 (s, 1H)<br>7.21 (d, 1H)<br>3.82 (m, 1H)<br>2.45 (m, 4H)<br>2.22 (m, 1H)<br>1.78 (m, 8H)<br>1.45 (m, 6H) | DMSO<br>8.25 (s, 1H)<br>6.87 (d, 1H)<br>4.02 (m, 1H)<br>2.45 (m, 4H)<br>2.22 (m, 1H)<br>1.78 (m, 8H)<br>1.45 (m, 6H) | DMSO<br>8.22 (s, 1H)<br>7.28 (d, 1H)<br>3.85 (m, 1H)<br>2.19 (s, 6H)<br>2.15 (m, 1H)<br>1.82 (m, 4H)<br>1.50 (m, 2H)<br>1.25 (m, 2H) |
| Yield<br>Mass | 97%<br>343 (EI) | 58%<br>304 (ES) | 52%<br>348 (EI) | 1.59 (m, 2H)<br>1.3 (m, 6H)<br>0.82 (t, 3H)<br>70% |

| Example No. | 1-2.29 | 1-2.30 | 1-2.31 | 1-2.32 |
|---|---|---|---|---|
| Solvent | DMSO<br>8.22 (s, 2H) | DMSO<br>8.21 (s, 1H) | DMSO<br>8.21 (s, 1H) | DMSO<br>8.71 (s, 1H) |
| Yield<br>Mass | n.b.<br>344 (EI) | 26%<br>374 (EI) | 23%<br>374 (EI) | 51%<br>334 (EI) |

-continued

| | | | |
|---|---|---|---|
| | 7.28 (d, 1H)<br>7.10 (d, 1H)<br>4.00 (m, 1H)<br>3.85 (m, 1H)<br>2.19 (s, 6H)<br>2.17 (s, 6H)<br>2.15 (m, 1H)<br>2.00 (m, 8H)<br>1.82 (m, 4H)<br>1.50 (m, 3H)<br>1.25 (m, 2H) | 7.18 (d, 1H)<br>7.10 (d, 1H)<br>4.20 (m, 1H)<br>3.95 (m, 1H)<br>2.75 (dd, 1H)<br>2.50 (m, 2H)<br>2.31 (dd, 1H)<br>2.15 (s, 1H)<br>2.00 (m, 1H)<br>1.82 (m, 4H)<br>1.50 (m, 3H)<br>1.55 (m, 5H) | 7.22 (d, 1H)<br>4.65 (s, 1H)<br>4.15 (m, 1H)<br>3.85 (m, 1H)<br>2.78 (m, 1H)<br>2.60 (m, 1H)<br>2.38 (dd, 1H)<br>1.95 (m, 3H)<br>1.80 (m, 2H)<br>1.52 (m, 3H)<br>1.20 (m, 2H) | 5.32 (m, 1H)<br>3.82 (m, 2H)<br>3.55 (m, 2H)<br>2.00 (m, 2H)<br>1.70 (m, 2H) |
| Yield | 13% | 35% | 21% | 40% |
| Mass | 334 (EI) | 374 (EI) | 374 (EI) | 292 (EI) |

| Example No. | 1–2.33 | 1–2.34 | 1–2.35 | 1–2.36 |
|---|---|---|---|---|
| Solvent | DMSO<br>8.50 (s, 1H)<br>4.10 (m, 2H)<br>3.72 (br, 1H)<br>3.30 (m, 2H)<br>1.75 (m, 2H)<br>1.35 (m, 2H) | CDCl3<br>8.08 (s, 1H)<br>6.04 (d, 1H)<br>5.71 (br, 1H)<br>4.48 (d, 2H)<br>3.71 (s, 3H)<br>2.25 (s, 3H) | DMSO<br>8.23 (s, 1H)<br>7.27 (d, 1H)<br>7.04 (t, 1H)<br>4.46 (m, 1H)<br>3.95 (m, 1H)<br>2.94 (m, 2H)<br>1.92 (m, 4H)<br>1.62 (m, 2H)<br>1.32 (m, 6H)<br>0.84 (t, 3H) | CDCl3<br>8.11 (s, 2H, 1 + 2)<br>5.55 (m, 1H, 1)<br>5.29 (m, 1H, 2)<br>4.25 (m, 1H, 1)<br>3.98 (m, 1H, 2)<br>3.72 (m, 8H, 1 + 2)<br>2.65 (m, 8H, 1 + 2)<br>1.70<br>(m, 18H, 1 + 2) |
| Yield | 3% | 30% | 70% | 66% |
| Mass | 291 (EI) | 300 (ES) | 405 (ES) | 375 (ES) |

Diastereomers 1 + 2 (about 1:1)

-continued

| Example No. | 1-2.37 | 1-2.38 | 1-2.39 | 1-2.40 |
|---|---|---|---|---|
| Solvent | CDCl3<br>8.14 (s, 1H)<br>5.41 (d, 1H)<br>4.49 (m, 1H)<br>2.44 (m, 6H)<br>1.79 (m, 2H) | CDCl3<br>8.20 (s, 1H)<br>7.71 (m, 1H)<br>7.30 (m, 6H)<br>4.97 (s, 2H)<br>3.00 (m, 2H)<br>1.40 (m, 8H) | DMSO<br>8.22 (s, 1H)<br>6.35 (s, 1H)<br>5.19 (t, 1H)<br>3.54 (d, 2H)<br>2.00 (m, 4H)<br>1.75 (m, 4H)<br>1.53 (m, 2H) | DMSO<br>8.22 (s, 1H)<br>7.12 (d, 1H)<br>4.10 (m, 1H)<br>2.20 (m, 1H)<br>1.89 (m, 1H)<br>1.35 (m, 8H) |
| Yield | 58% | 77% | 48% | 60% |
| Mass | 304 (ES) | 427 (ES) | 308 (EI) | 301 (EI) |

| Example No. | 1-2.41 | 1-2.42 | 1-2.43 | 1-2.44 |
|---|---|---|---|---|
| Solvent | DMSO<br>8.19 (s, 1H)<br>7.21 (m, 1H)<br>4.03 (m, 1H)<br>1.60 (m, 12H) | DMSO<br>8.21 (s, 1H)<br>7.03 (d, 1H)<br>4.83 (t, 1H)<br>4.13 (m, 1H)<br>3.47 (m, 2H)<br>1.12 (d, 3H) | DMSO<br>8.28 (s, 1H)<br>3.62 (q, 4H)<br>1.18 (t, 6H) | DMSO<br>8.41 (s, 1H)<br>8.15 (t, 1H)<br>4.21 (td, 2H) |
| Yield | 73% | 61% | 13% | 21% |
| Mass | 303 (EI) | 267 (EI) | 265 (EI) | 339 (EI) |

-continued

| Example No. | 1-2.45 | 1-2.46 | 1-2.47 | 1-2.48 |
|---|---|---|---|---|
| Solvent | DMSO | DMSO | DMSO | DMSO |
|  | 8.36 (s, 1H) | 8.26 (s, 1H) | 8.32 (t, 1H) | 8.15 (s, 1H) |
|  | 6.56 (s, 1H) | 8.06 (d, 1H) | 8.15 (s, 1H) | 7.06 (d, 1H) |
|  | 3.81 (m, 1H) | 7.30 (m, 5H) | 3.40 (m, 2H) | 4.65 (br, 1H) |
|  | 2.28 (m, 2H) | 5.29 (m, 1H) | 2.34 (m, 2H) | 3.79 (m, 1H) |
|  | 1.83 (m, 2H) | 4.81 (t, 1H) | 2.18 (s, 6H) | 3.52 (m, 1H) |
|  | 1.58 (m, 6H) | 3.42 (m, 2H) | 1.69 (m, 2H) | 1.86 (m, 2H) |
|  |  | 2.10 (m, 2H) |  | 1.61 (m, 2H) |
|  |  |  |  | 1.25 (m, 4H) |
| Yield | 84% | 97% | 22% | 53% |
| Mass | 314 (EI) | 343 (EI) | 294 (EI) | 307 (EI) |

| Example No. | 1-2.49 | 1-2.50 | 1-2.51 | 1-2.52 |
|---|---|---|---|---|
| Solvent mittel | DMSO | DMSO | DMSO | DMSO |
|  | 8.29 (s, 1H) | 8.18 (s, 1H) | 8.29 (s, 1H) | 8.38 (s, 1H) |
|  | 6.05 (d, 1H) | 7.25 (d, 1H) | 6.18 (s, 1H) | 7.28 (d, 1H) |
|  | 5.18 (t, 1H) | 4.15 (m, 1H) | 5.15 (t, 1H) | 5.28 (t, 1H) |
|  | 3.54 (m, 2H) | 2.40 (m, 6H) | 3.70 (m, 1H) | 4.65 (m, 1H) |
|  | 1.92 (m, 2H) | 1.50 (m, 4H) | 3.49 (m, 1H) | 3.86 (m, 2H) |
|  | 1.70 (m, 2H) | 1.17 (d, 3H) | 2.60 (m, 1H) | 3.65 (s, 3H) |
|  |  | 0.90 (dd, 6H) | 0.92 (d, 3H) |  |
|  |  |  | 0.83 (d, 3H) |  |
| Yield | 16% | 52% | 27% | 63% |
| Mass | 308 (EI) | 350 (EI) | 308 (EI) | 309 (EI) |

| Example No. | | | |
|---|---|---|---|
| Structure | 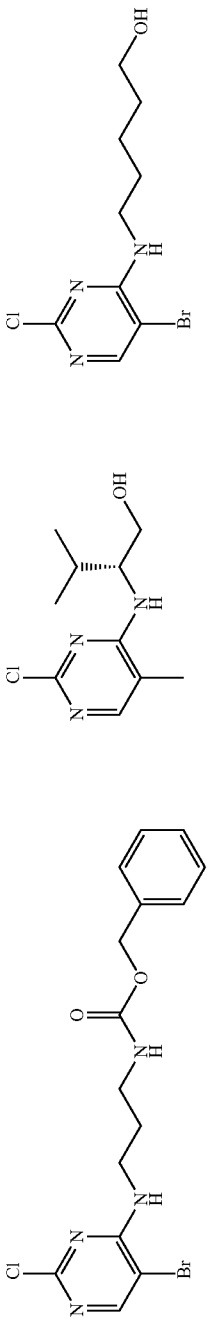 | 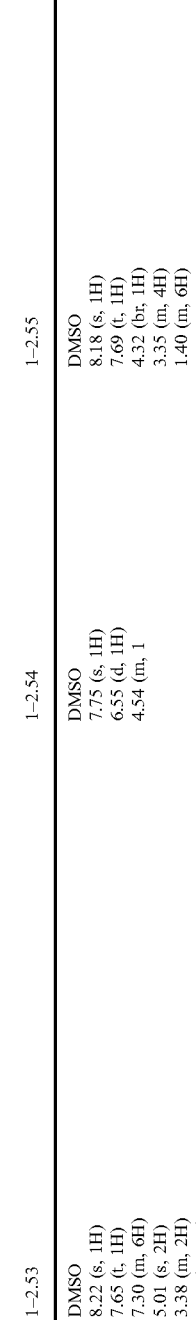 | 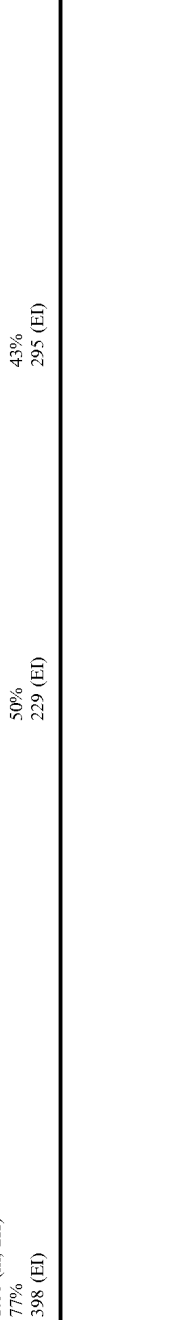 |
| | 1-2.53 | 1-2.54 | 1-2.55 |
| Solvent | DMSO<br>8.22 (s, 1H)<br>7.65 (t, 1H)<br>7.30 (m, 6H)<br>5.01 (s, 2H)<br>3.38 (m, 2H)<br>3.04 (m, 2H)<br>1.68 (m, 2H) | DMSO<br>7.75 (s, 1H)<br>6.55 (d, 1H)<br>4.54 (m, 1 | DMSO<br>8.18 (s, 1H)<br>7.69 (t, 1H)<br>4.32 (br, 1H)<br>3.35 (m, 4H)<br>1.40 (m, 6H) |
| Yield<br>Mass | 77%<br>398 (EI) | 50%<br>229 (EI) | 43%<br>295 (EI) |

EXAMPLE 3.0
Production of Amines

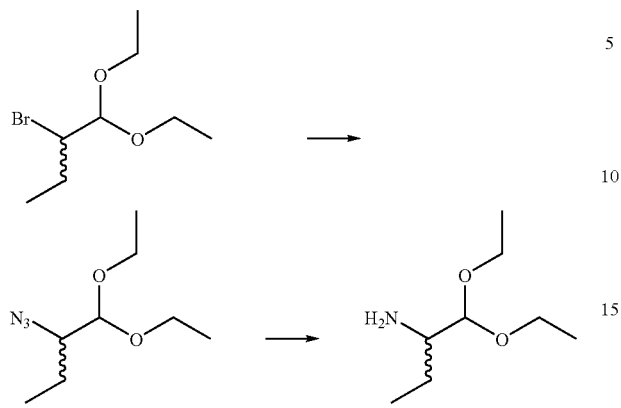

4.5 g (20 mmol) of 2-bromobutyraldehyde diethyl acetyl (Pfaltz-Bauer Company) and 5.2 g (80 mmol) of sodium azide are stirred for 5 days in 15 ml of DMF at 100° C. Then, it is poured onto cold dilute sodium bicarbonate solution, and extracted 3× with ether. The organic phase is dried with magnesium sulfate and concentrated by evaporation: raw yield 1.87 g (50% of theory).

936 mg of the crude product is dissolved in 50 ml of methanol, mixed with palladium on carbon (10%) and stirred for 12 hours under $H_2$ atmosphere. After the catalyst is filtered off and after concentration by evaporation, 457 mg (57% of theory) of the desired amine remains.

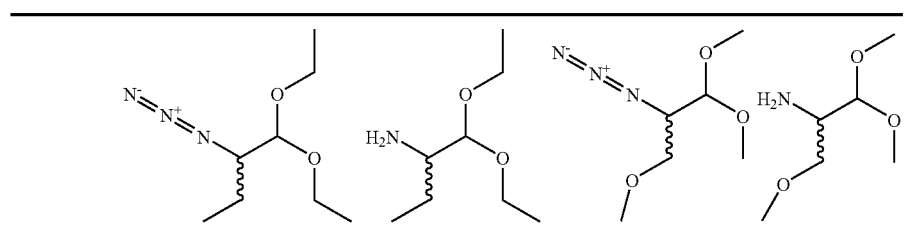

| Example No. | 3.0 | 3.1 | 3.2 | 3.3 |
|---|---|---|---|---|
| Yield | 50% | 57% | 50% | 71% |
| NMR CDCl3 | 4.38 (d, 1H) | 4.19 (d, 1H) | 4.38 (d, 1H) | 4.25 (d, 1H) |
| | 3.72 (m, 2H) | 3.68 (m, 2H) | 3.58 (m, 2H) | 3.5 (m, 1H) |
| | 3.6 (m, 2H) | 3.52 (m, 2H) | 3.5 (m, 1H) | 3.42 (s, 3H) |
| | 3.25 (m, 1H) | 2.7 (m, 1H) | 3.49 (s, 3H) | 3.41 (s, 3H) |
| | 1.7 (m, 1H) | 1.60 (m, 1H) | 3.43 (s, 3H) | 3.40 (m, 1H) |
| | 1.46 (m, 1H) | 1.25 (m, 1H) | 3,39 (s, 3H) | 3.08 (m, 1H) |
| | 1.25 (trtr, 6H) | 1.2 (trtr, 6H) | | |
| | 1.0 (tr, 3H) | 0.95 (tr, 3H) | | |

EXAMPLE 4.0
Production of the Free Aldehydes

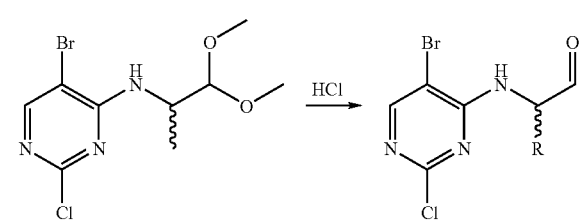

148 mg (0.5 mmol) of intermediate product compound 1.18 is dissolved in 1 ml of glacial acetic acid. At room temperature, 0.5 ml of 1N hydrochloric acid is added, and it is stirred for 12 hours. For working-up, it is poured onto ice water and carefully neutralized with pulverized sodium bicarbonate. Then, it is extracted 3× with ethyl acetate, the organic phase is dried with magnesium sulfate and concentrated by evaporation. Crude product 104 mg (83% of theory) of the aldehyde of compound 4.0 is obtained. The crude product can be used without further purification.

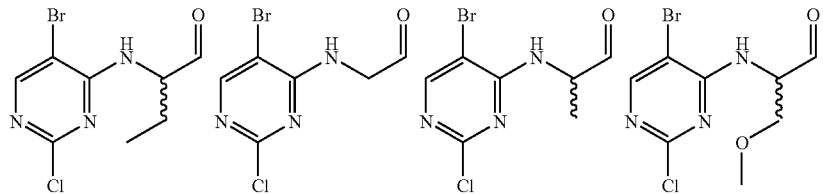

| Example No. | 4.1 | 4.0 | 4.2 | 4.3 |
|---|---|---|---|---|
| Yield | 82% | 83% | 89% | 79% |
| Mass | ESI:<br>MH$^+$ 278 (39%)<br>210 (100%) | ESI:<br>MH$^+$ 250 (9%) | ESI:<br>MH$^+$ 266 (8%) | ESI:<br>MH+ 294 (10%) |

EXAMPLE 5.0
Production of Ketones

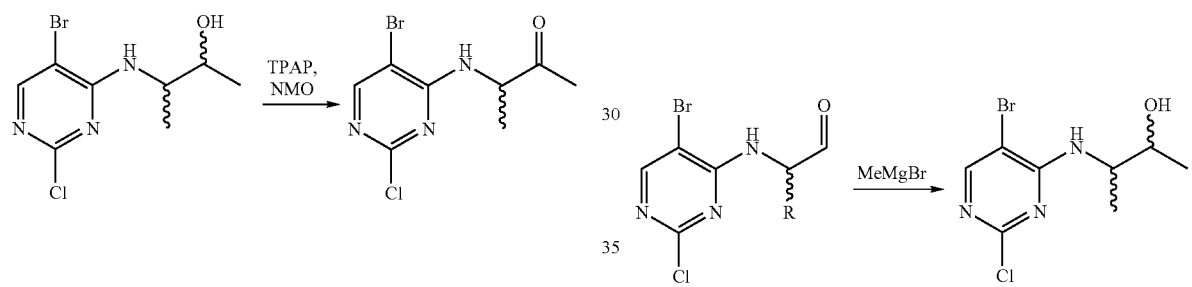

100 mg (0.356 mmol) of compound 6.0 and 126 mg of N-methylmorpholine-N-oxide are dissolved in 5 ml of dichloromethane and stirred for 10 minutes with pulverized molecular sieve (4 A). Then, 6 mg of tetrapropylammonium perruthenate is added, and it is stirred for 4 more hours at room temperature. After concentration by evaporation, it is chromatographed on silica gel (hexane/ethyl acetate 4:1>2:1). Yield: 75 mg (76% of theory) of the ketone of compound 5.0.

| Example No. | 5.0 |
|---|---|
| Yield | 76% |
| Mass | ESI:<br>MH$^+$ 280 (100%)<br>200 (37%)<br>156 (30%) |

EXAMPLE 6.0
Production of Alcohols 265 mg (1 mmol) of compound 4.2 is dissolved in 20 ml of tetrahydrofuran. While being cooled in an ice bath, 5 equivalents of methylmagnesium bromide (3 molar solution in ether) is added in portions. Then, it is stirred for 3 more hours at room temperature and then quenched with water while being cooled. Then, it is mixed with ammonium chloride solution, extracted 3× with ethyl acetate, the organic phase is dried with magnesium sulfate and concentrated by evaporation. Flash chromatography (hexane/ethyl acetate 2:1) yields 213 mg (76% of theory) of the alcohol of compound 6.0.

ESI:MH$^+$282 (100%) 276 (5%)

Similarly produced are also the following intermediate products:
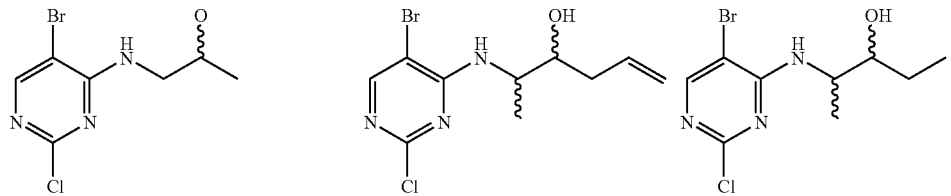
| Example No. | 6.1 | 6.2 | 6.3 |
|---|---|---|---|
| Yield | 46% | 32% | 39% |
| Mass | EI: | ESI: | ESI: |
|  | $M^+$ 267 (3%) | $MH^+$ 308 | $MH^+$ 296 |
|  | 223 (100%) | (100%) | (100%) |
|  | 132 (27%) | 306 (71%) | 294 (73%) |
|  |  | 268 (31%) | 217 (4%) |
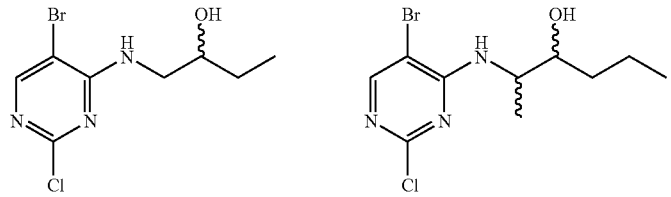
| Example No. | 6.4 | 6.5 |
|---|---|---|
| Yield | 36% | 50% |
| Mass | EI: | ESI: |
|  | M+ 281 | $MH^+$ 310 |
|  | (3%) | (100%) |
|  | 223 (100%) | 308 (87%) |
|  | 114 (38%) | 298 (9%) |
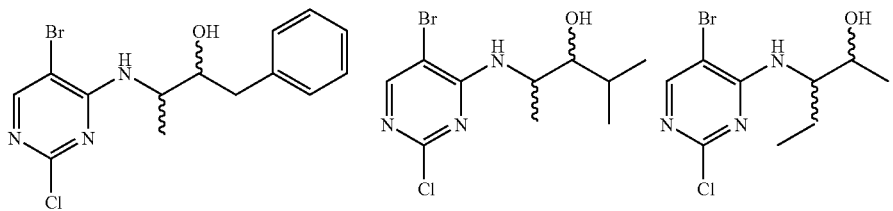
| Example No. | 6.6 | 6.7 | 6.8 |
|---|---|---|---|
| Yield | 40% | 20% | 35% |
| Mass | EI: | CI: | ESI: |
|  | $M^+$ 358 | $M^+$ 310 (100%) | $MH^+$ 294 |
|  | (100%) | 308 (84%) | (28%) |
|  | 356 (97%) | 130 (54%) | 296 (36%) |
|  | 277 (29%) |  | 210 (100%) |
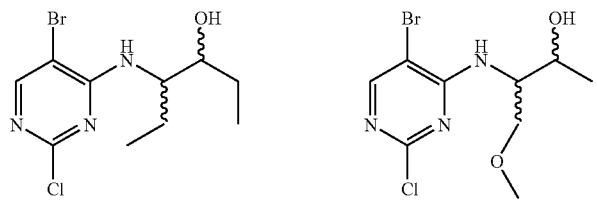
| Example No. | 6.9 | 6.10 |
|---|---|---|
| Yield | 29% | 67% |

| -continued | |
|---|---|
| Mass | ESI:<br>MH⁺ 308 (28%)<br>310 (38%)<br>210 (100%) | ESI:<br>MH+ 310 (87%)<br>312 (100%)<br>123 (24%) |

Subjects of this invention are thus also compounds of general formula Ia

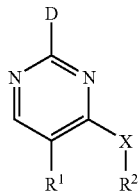

(Ia)

in which

D stands for halogen, and X, $R^1$, and $R^2$ have the meanings that are indicated in general formula (1).

Those intermediate products of general formula Ia, in which D stands for chlorine and X, $R^1$ and $R^2$ have the meanings that are indicated in the general formula, are especially valuable.

Another subject of this invention are also those compunds that fall under industrial property right DE 4029650, whose action is in the fungicide range and which are not described as CDK inhibitors, however, and also their use for treating cancer is not described.

| No. | Structure | Name |
|---|---|---|
| 5 | 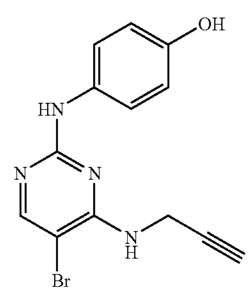 | 4-[[5-Bromo-4-(2-propynylamino)-2-pyrimidinyl]amino]-phenol |
| 6 | 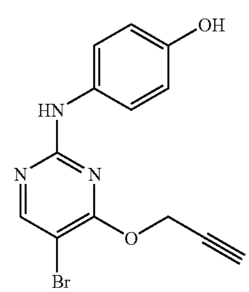 | 4-[[5-Bromo-4-(2-propynyloxy)-2-pyrimidinyl]amino]-phenol |
| 16 | 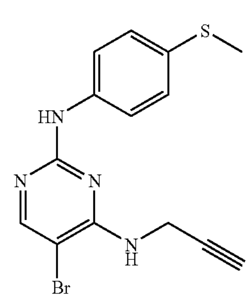 | 5-Bromo-N2-(4-methylthiophenyl)-N4-2-propynyl-2,4-pyrimidine diamine |

-continued

| No. | Structure | Name |
|---|---|---|
| 22 | 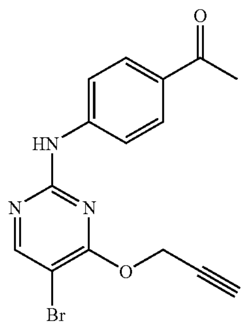 | 1-[4-[(5-Bromo-4-(2-propynyloxy)-2-pyrimidinyl)amino]phenyl]-ethanone |
| 23 | 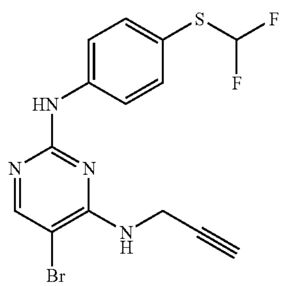 | 5-Bromo-N2-(4-difluoromethylthiophenol)-N4-2-propynyl-2,4-pyrimidine diamine |
| 24 | 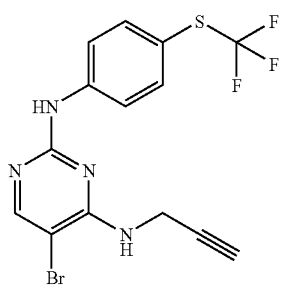 | 5-Bromo-N4-2-propynyl-N2-(4-trifluoromethylthiophenyl)-2,4-pyrimidine diamine |
| 35 | 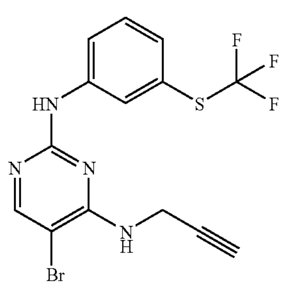 | 5-Bromo-N4-2-propynyl-N2-(3-trifluoromethylthiophenyl)-2,4-pyrimidine diamine |
| 37 | 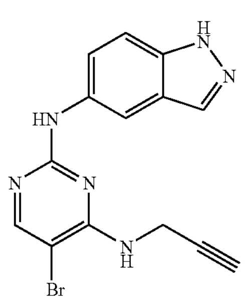 | N-[5-Bromo-4-(2-propynylamino)-2-pyrimidinyl]-indazol-5-amine |

-continued

| No. | Structure | Name |
|---|---|---|
| 38 | 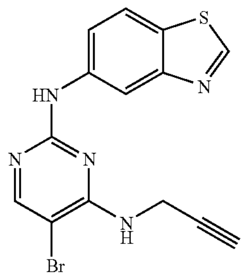 | N-[5-Bromo-4-(2-propynylamino)-2-pyrimidinyl]-benzothiazole-5-amine |
| 42 | 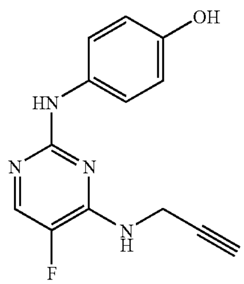 | 4-[[5-Fluoro-4-(2-propynyloxy)-2-pyrimidinyl]amino]-phenol |
| 43 | 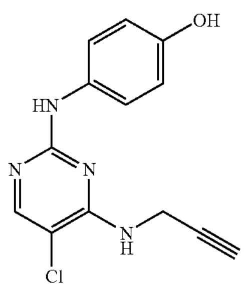 | 4-[[5-Chloro-4-(2-propynyloxy)-2-pyrimidinyl]amino]-phenol |
| 50 | 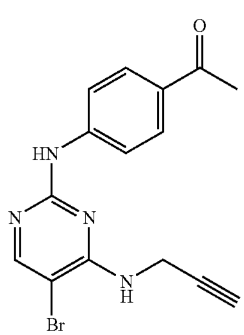 | 1-[4-[(5-Bromo-4-(2-propynylamino)-2-pyrimidinyl)amino]phenyl]-ethanone |
| 54 | 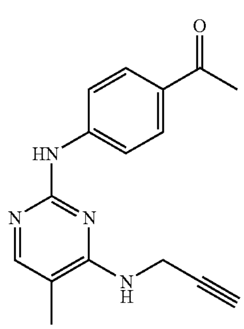 | 1-[4-[(5-Iodo-4-(2-propynylamino)-2-pyrimidinyl)amino]phenyl]-ethanone |

-continued

| No. | Structure | Name |
|---|---|---|
| 70 | 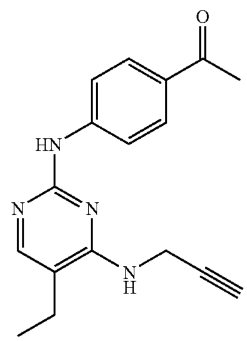 | 1-[4-[(5-Ethyl-4-(2-propynylamino)-2-pyrimidinyl)amino]phenyl]-ethanone |
| 81 | 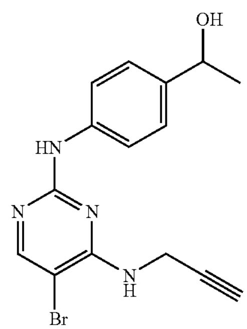 | 1-[4-[(5-Bromo-4-(2-propynylamino)-2-pyrimidinyl)amino]phenyl]-ethanol |
| 82 | 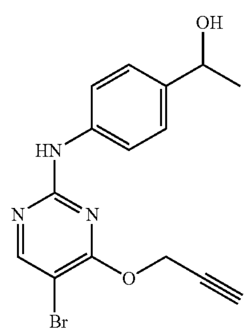 | 1-[4-[(5-Bromo-4-(2-propynyloxy)-2-pyrimidinyl)amino]phenyl]-ethanol |

The invention thus relates in addition to pharmaceutical agents that comprise a compound of general formula I in which $R^1$ stands for halogen or $C_1$–$C_3$-alkyl X stands for oxygen or —NH, A stands for hydrogen B stands for hydroxy, —CO-alkyl-$R^7$, —S—$CHF_2$, —S—$(CH_2)_n$CH(OH)$CH_2$N—$R^3R^4$, —S—$CF_3$, or —CH—(OH)—$CH_3$, or A and B, independently of one another, can form a group

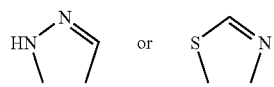

$R^2$, $R^3$, $R^4$, $R^7$ and $R^8$ have the meanings that are indicated in general formula I, as well as isomers, diastereomers, enantiomers and salts thereof.

The agents according to the invention can also be used for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arterioscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS dementia and Alzheimer's disease; acute neurodegenerative diseases are defined as isehemias of the brain and neurotraumas; and viral infections are defined as cytomegalic infections, herpes, hepatitis B or C, and HIV diseases.

The following examples describe the biological action of the compounds according to the invention without limiting the invention to these examples.

EXAMPLE 1

CDK2/CycE Kinase Assay

Recombinant CDK2- and CycE-GST-fusion proteins, purified from baculovirus-infected insect cells (Sf9), are obtained by Dr. Dieter Marmé, Klinik für Tumorbiologie [Clinic for Tumor Biology], Freiburg. Histone IIIS, which is used as a kinase substrate, is purchased by the Sigma Company.

CDK2/CycE (50 ng/measuring point) is incubated for 15 minutes at 22° C. in the presence of various concentrations of test substances (0 μm, as well as within the range of 0.01–100 μm) in assay buffer [50 mmol of tris/HCl pH 8.0, 10 mmol of $MgCl_2$, 0.1 mmol of Na ortho-vanadate, 1.0 mmol of dithiothreitol, 0.5 μm of adenosine triphosphate (ATP), 10 μg/measuring point of histone IIIS, 0.2 μCi/measuring point of $^{33}$P-gammna ATP, 0.05% NP40, 12.5% dimethyl sulfoxide]. The reaction is stopped by adding EDTA solution (250 mmol, pH 8.0, 14 μl/measuring point).

From each reaction batch, 10 μl is applied to P30 filter strips (Wallac Company), and non-incorporated $^{33}$P-ATP is removed by subjecting the filter strips to three washing cycles for 10 minutes each in 0.5% phosphoric acid. After the filter strips are dried for one hour at 70° C., the filter strips are covered with scintillator strips (MeltiLex™ A, Wallac Company) and baked for one hour at 90° C. The amount of incorporated $^{33}$P (substrate phosphorylation) is determined by scintillation measurement in a gamma-radiation measuring device (Wallac).

EXAMPLE 2

Proliferation Assay

Cultivated human tumor cells (as indicated) are flattened out at a density of 5000 cells/measuring point in a 96-hole multititer plate in 200 μl of the corresponding growth medium. After 24 hours, the cells of one plate (zero-point plate) are colored with crystal violet (see below), while the medium of the other plates is replaced by fresh culture medium (200 μl), to which the test substances are added at various concentrations (0 μm, as well as in the range of 0.01–30 μm; the final concentration of the solvent dimethyl sulfoxide is 0.5%). The cells are incubated for 4 days in the presence of test substances. The cell proliferation is determined by coloring the cells with crystal violet: the cells are fixed by adding 20 μl/measuring point of a 11% glutaric aldehyde solution for 15 minutes at room temperature. After three washing cycles of the fixed cells with water, the plates are dried at room temperature. The cells were are colored by adding 100 μl/measuring point of a 0.1% crystal violet solution (pH is set at 3 by adding acetic acid). After three washing cycles of the colored cells with water, the plates are dried at room temperature. The dye is dissolved by adding 100 μ/measuring point of a 10% acetic acid solution. The extinction is determined by photometry at a wavelength of 595 nm. The change of cell growth, in percent, is calculated by standardization of the measured values to the extinction values of the zero-point plate (=0%) and the extinction of the untreated (0 μm) cells (=100%).

The results of Examples 1 and 2 are cited in the following tables.

| Example Number | Inhibition $IC_{50}$ [nM] CDK2/CycE | Proliferation $IC_{50}$ [μM] MCF7 | H460 | HCT116 | DU145 | Sw (g/l) |
|---|---|---|---|---|---|---|
| 22 | 40 | 1.2 | 1.5 | 1.5 | 1.5 | 0.003 |
| 37 | 70 | 4 | | | | 0.006 |
| 6 | 70 | 4 | 6 | | | 0.008 |
| 40 | 20 | 1 | 3 | 3 | 9 | 0.002 |

-continued

| Example Number | Inhibition $IC_{50}$ [nM] CDK2/CycE | Proliferation $IC_{50}$ [μM] MCF7 | H460 | HCT116 | DU145 | Sw (g/l) |
|---|---|---|---|---|---|---|
| 51 | 70 | 8 | | | | |
| 20 | 60 | 4 | | | | |
| 21 | 400 | 2 | | | | |
| 1 | 300 | 8 | | | | |
| 2 | 700 | | | | | |
| 16 | 300 | 3 | | | | |
| 24 | 400 | 5 | | | | |
| 26 | 300 | 3 | | | | |
| 35 | 120 | >10 | | | | |
| 23 | 180 | 3 | | | | |
| 11 | 6 | 0.2 | 0.5 | 0.3 | 0.2 | |
| 38 | 80 | >10 | | | | |
| 34 | 1800 | | | | | |
| 10 | 4 | 0.2 | 0.5 | 0.5 | 0.5 | |
| 12 | 400 | 4 | | | | |
| 25 | 70 | 1.2 | 1.5 | 1.1 | 1.2 | 0.017 |
| 9 | 7 | 0.9 | | 3 | 3 | |
| 7 | 6 | 0.7 | 1.5 | 1.2 | 0.5 | 0.028 |
| 31 | 800 | 7 | | | | 0.0023 |
| 14 | 200 | 3 | | | | 0.013 |
| 18 | 2000 | | | | | 0.039 |
| 3 | 200 | 8 | | | | 0.039 |
| 19 | 800 | >10 | | | | 0.041 |
| 13 | 2000 | >10 | | | | |
| 17 | 1000 | >10 | | | | 0.04 |
| 4 | 40 | 8 | | | | 0.042 |
| 15 | 300 | >10 | | | | 0.024 |
| 8 | <10 | 4 | | | | 0.007 |
| 43 | 200 | 6 | | | | 0.04 |
| 36 | 30 | 0.4 | 0.6 | 0.5 | 0.6 | 0.018 |
| 27 | >10000 | | | | | |
| 42 | 2000 | | | | | 0.043 |
| 39 | 300 | | | | | 0.0016 |
| 44 | 8 | 1.2 | 0.4 | 0.4 | 0.3 | 0.005 |
| 45 | 10 | 2 | 1.7 | 1.2 | 0.5 | 0.0094 |
| 50 | 150 | | | | | |
| 5 | 90 | 10 | | | | 0.043 |
| 46 | 7 | 2 | | | | 0.0069 |
| 52 | 200 | 0.2 | 1.6 | 1.2 | 2 | 0.0005 |
| 53 | 300 | 1.6 | | | | 0.026 |
| 54 | 100 | 1.1 | | | | 0.0015 |
| 47 | 12 | 0.7 | 1.8 | 1.3 | 0.9 | |
| 56 | 80 | 4 | | | | 0.023 |
| 49 | 50 | >10 | | | | 0.044 |
| 48 | 4 | 0.2 | 1 | 0.4 | 0.3 | 0.042 |
| 96 | 400 | | | | | 0.0005 |
| 98 | 2000 | | | | | |
| 85 | 2000 | | | | | 0.001 |
| 84 | 400 | | | | | 0.0005 |
| 86 | 3000 | | | | | |
| 87 | 250 | 0.8 | | | | 0.003 |
| 22 | 40 | 1.2 | 1.5 | 1.5 | 1.5 | 0.003 |
| 37 | 70 | 4 | | | | 0.006 |
| 6 | 70 | 4 | 6 | | | 0.008 |
| 16 | 300 | 3 | | | | |
| 24 | 400 | 5 | | | | |
| 35 | 120 | >10 | | | | |
| 23 | 180 | 3 | | | | |
| 38 | 80 | >10 | | | | |
| 43 | 200 | 6 | | | | 0.04 |
| 42 | 2000 | | | | | 0.043 |
| 50 | 150 | | | | | |
| 5 | 90 | 10 | | | | 0.043 |
| 54 | 100 | 1.1 | | | | 0.0015 |

Proof of Superiority of the Compounds According to the Invention Compared to the Known Compounds To prove the superiority of the compounds according to the invention compared to the known compounds, the compounds according to the invention are compared to known reference compounds and structurally-similar known compounds in the enzyme test. The result is cited in the following table:

| Example No. | R² | A | CDK2/CycE IC$_{50}$ [nM] | MCF-7 IC$_{50}$ [µM] | Solubility (g/l) |
|---|---|---|---|---|---|
| 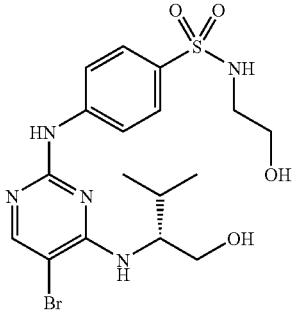 No. 48 | CH(C$_3$H$_7$)—  CH$_2$—OH— | —SO$_2$—N— (CH$_2$)$_2$—OH | 4 | 0.2 | 0.042 |
| 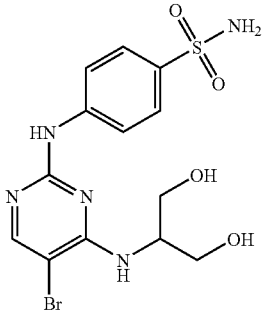 No. 9 | CH(CH$_2$OH)$_2$ | SO$_2$NH$_2$ | 7 | 0.9 | 0.009 |
| 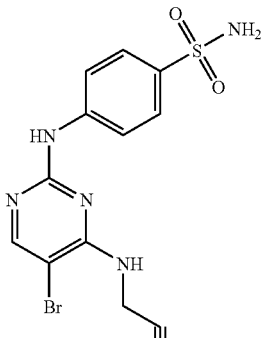 No. 11 | Propargyl-NH— | SO$_2$NH$_2$ | 6 | 0.2 | |
| 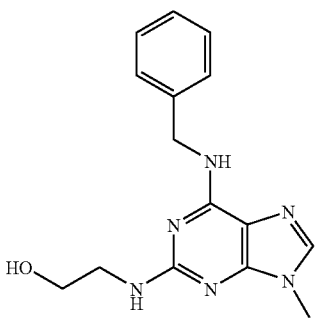 Olomoucine | | | 7000 | 30 | |

-continued
| Example No. | R² | A | CDK2/CycE IC$_{50}$ [nM] | MCF-7 IC$_{50}$ [μM] | Solubility (g/l) |
|---|---|---|---|---|---|
| Roscovitine 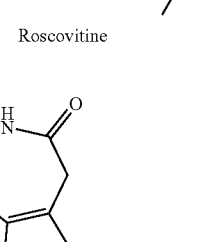 Chiral | | | 1500 | 8 | |
| Kenpaullone 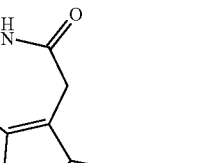 | | | 1800 | 6 | |
| Alsterpaullone 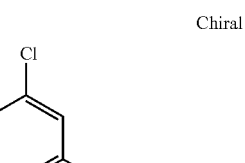 | | | 90 | 1.2 | |
| Purvalanol A  Chiral | | | 10 | 2 | |

| Example No. | R² | A | CDK2/CycE IC₅₀ [nM] | MCF-7 IC₅₀ [μM] | Solubility (g/l) |
|---|---|---|---|---|---|
| Example 11 from WO01/14375 (Page 38) | 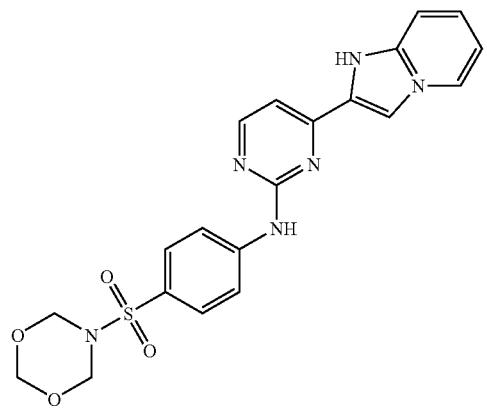 | | 190 | | |

It can be seen from the results of the table that both in the enzyme test and in the cell test, the compounds according to the invention have significantly higher activities in the enzyme and in the MCF-7 cells than the compounds that are known from the prior art. The compounds according to the invention are thus far superior to the known compounds.

What is claimed is:

1. A compound of formula I

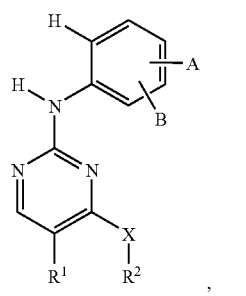

(I)

wherein

R¹ stands for hydrogen, halogen, $C_1$–$C_6$-alkyl, or —(CH₂)ₙR⁵,

R² stands for $C_1$–$C_{10}$-alkyl, $C_2$–$C_{10}$-alkenyl, $C_2$–$C_{10}$-alkynyl, or $C_3$–$C_{10}$-cycloalkyl; or for $C_1$–$C_{10}$-alkyl, $C_2$–$C_{10}$-alkenyl, $C_2$–$C_{10}$-alkynyl, or $C_3$–$C_{10}$-cycloalkyl each of which is substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—(CH₂)ₙ—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —NH$C_1$–$C_6$-alkyl, —N($C_1$–$C_6$-alkyl)₂, —SO($C_1$–$C_6$-alkyl), SO₂($C_1$–$C_6$-alkyl), $C_1$–$C_6$-alkanoyl, —CONR³R⁴, —COR⁵, $C_1$–$C_6$-alkylOAc, carboxy, aryl, —(CH₂)ₙ-aryl, phenyl-(CH₂)ₙ—R⁵, —(CH₂)ₙPO₃(R⁵)₂ or with the group or —NR³R⁴, and the phenyl, $C_3$–$C_{10}$-cycloalkyl, aryl and —(CH2)ₙ-aryl groups themselves optionally can be substituted in one or more places in the same way or differently with halogen, hydroxy, $C_1$–$C_6$-alkyl, $C_1$–$C_6$-alkoxy, benzoxy or with the group —CF₃ or —OCF₃; and the ring of $C_3$–$C_{10}$-cycloalkyl can be interrupted by one or more ═C═O groups in the ring and/or optionally one or more possible double bonds can be contained in the ring;

and $C_1$–$C_{10}$ alkyl optionally can be interrupted by one or more nitrogen, oxygen and/or sulfur atoms, or R² stands for the group

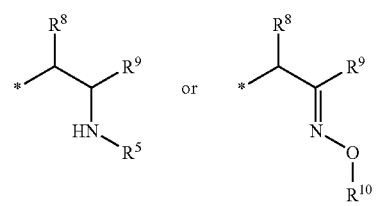

X stands for the group —NH—, or —N($C_1$–$C_3$-alkyl),

A independently of B stands for —SO₂NR³R⁴,

B independently of A stands for hydrogen, hydroxy, $C_1$–$C_3$ alkyl, $C_1$–$C_6$ alkoxy, —SR⁷, —S(O)R⁷, —SO₂R⁷, —NHSO₂ R⁷, —CH(OH)R⁷, —CR⁷(OH)—R⁷, $C_1$–$C_6$-alkylP(O)OR³OR⁴ or —COR⁷;

R³ R⁴, in each case independently of one another, stand for hydrogen, phenyl, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, $C_3$–$C_6$-cycloalkyl-$C_1$–$C_3$-alkyl that is optionally substituted with cyano, or for $C_1$–$C_6$-alkyl that is optionally substituted in one or more places in the same way or differently with phenyl, phenyloxy, $C_3$–$C_6$-cycloalkyl, $C_1$–$C_6$-alkyl or $C_1$–$C_6$-alkoxy, wherein the phenyl itself can be substituted in one or more places in the same way or differently with halogen, $C_1$–$C_6$-alkyl, $C_1$–$C_6$-alkoxy or —SO₂NR³R⁴, R⁵ stands for hydroxy, phenyl, $C_1$–$C_6$-alkyl, $C_3$–$C_6$-cycloalkyl, benzoxy, $C_1$–$C_6$-alkylthio or $C_1$–$C_6$-alkoxy, 6 stands for a $C_3$–$C_{10}$-cycloalkyl ring, optionally can be interrupted by one or more =C=O groups in the ring and/or optionally one or more possible double bonds can be contained in the ring, $R^7$ stands for halogen, hydroxy, phenyl, $C_1$–$C_6$-alkyl, $C_2$–$C_6$-alkenyl, $C_2$–$C_6$-alkynyl, $C_3$–$C_{10}$-cycloalkyl, with the above-indicated meaning for $R^6$, or for the group —$NR^3R^4$, or for a $C_1$–$C_{10}$-alkyl, $C_2$–$C_{10}$-alkenyl, $C_2$–$C_{10}$-alkynyl or $C_3$–$C_7$-cycloalkyl that is substituted in one or more places in the same way or differently with hydroxy, $C_1$–$C_6$-alkoxy, halogen, —$NR^3R^4$ or phenyl which itself can be substituted in one or more places in the same way or differently with halogen, hydroxy, $C_1$–$C_6$-alkyl, $C_1$–$C_6$-alkoxy, halo-$C_1$–$C_6$-alkyl, halo-$C_1$–$C_6$-alkoxy; or $R^7$ stands for phenyl, which itself can be substituted in one or more places in the same way or differently with halogen, hydroxy, $C_1$–$C_6$-alkyl or $C_1$–$C_6$-alkoxy, halo-$C_1$–$C_6$-alkyl, or halo-$C_1$–$C_6$-alkoxy, $R^8$, $R^9$ and $R^{10}$, in each case independently of one another, stand for hydrogen, hydroxy, $C_1$–$C_{10}$-alkyl, $C_2$–$C_{10}$-alkenyl, $C_2$–$C_{10}$-alkynyl, $C_3$–$C_{10}$-cycloalkyl, or aryl, or for $C_1$–$C_{10}$-alkyl, $C_2$–$C_{10}$-alkenyl, $C_2$–$C_{10}$-alkynyl or $C_3$–$C_{10}$-cycloalkyl, each of which is optionally substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—$(CH_2)_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —NHC$_1$–$C_6$-alkyl, —N($C_1$–$C_6$-alkyl)$_2$, —SO($C_1$–$C_6$-alkyl), —SO$_2$($C_1$–$C_6$-alkyl), $C_1$–$C_6$-alkanoyl, —CONR$^3$R$^4$, —COR$^5$, $C_1$–$C_6$-alkylOAc, carboxy, aryl, —$(CH_2)_n$-aryl, phenyl-$(CH_2)_n$—R$^5$, —$(CH_2)_n$PO$_3$(R$^5$)$_2$ or with the group —R$^6$ or —NR$^3$R$^4$, and the phenyl, $C_3$–$C_{10}$-cycloalkyl, aryl, and —$(CH_2)_n$-aryl itself optionally can be substituted in one or more places in the same way or differently with halogen, hydroxy, $C_1$–$C_6$-alkyl, $C_1$–$C_6$-alkoxy or with the group —CF$_3$ or —OCF$_3$; and the ring of $C_3$–$C_{10}$-cycloalkyl optionally can be interrupted by one or more =C=O groups in the ring and/or optionally one or more possible double bonds can be contained in the ring, and $C_1$–$C_{10}$alkyl optionally can be interrupted by one or more nitrogen, oxygen and/or sulfur atoms, and n stands for 0–6, or a pharmaceutically acceptable salt thereof.

2. A compound of claim 1 wherein $R^7$ stands for halogen, hydroxy, phenyl, $C_1$–$C_6$-alkyl, —$C_2H_4OH$, or —$NR^3R^4$, $R^8$, $R^9$ and $R^{10}$, in each case independently of one another, stand for hydrogen, hydroxy, $C_1$–$C_6$-alkyl, $C_3$–$C_6$-cycloalkyl or for the group

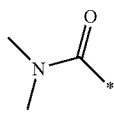 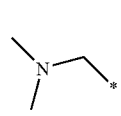 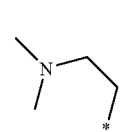

-continued

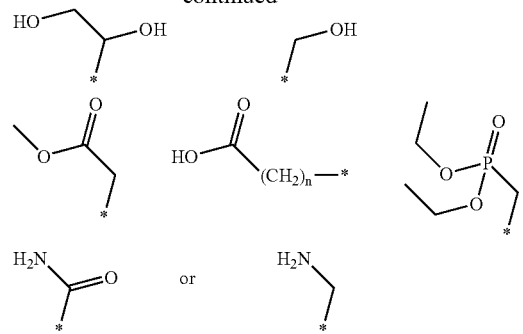

and n stands for 0–6.

3. A compound according to claim 1, wherein $R^1$ stands for hydrogen, halogen, $C_1$–$C_{-3}$-alkyl, or for the group —$(CH_2)_nR^5$, $R^2$ stands for —CH(CH$_3$)—$(CH_2)_n$—R$^5$, —CH—(CH$_2$OH)$_2$, —$(CH_2)_n$R$^7$, —CH(C$_3$H$_7$)—$(CH_2)_n$—R$^5$, —CH(C$_2$H$_5$)—$(CH_2)_n$—R$^5$, —CH$_2$—CN, —CH(CH$_3$)COCH$_3$, —CH(CH$_3$)—C(OH)(CH$_3$)$_2$, —CH(CH(OH)CH$_3$)OCH$_3$, —CH(C$_2$H$_5$)CO—R$^5$, C$_2$–C$_4$-alkynyl, —$(CH_2)_n$—COR$^5$, —$(CH_2)_n$—CO—C$_1$–C$_6$-alkyl, —$(CH_2)_n$—C(OH)(CH$_3$)-phenyl, —CH(CH$_3$)—C(CH$_3$)—R$^5$, —CH(CH$_3$)—C(CH$_3$)(C$_2$H$_5$)—R$^5$, —CH(OCH$_3$)—CH$_2$—R$^5$, —CH$_2$—CH(OH)—R$^5$, —CH(OCH$_3$)—CHR$^5$—CH$_3$, —CH(CH$_3$)—CH(OH)—CH$_2$—CH=CH$_2$, —CH(C$_2$H$_5$)—CH(OH)—(CH$_2$)$_n$—CH$_3$, —CH(CH$_3$)—CH(OH)—(CH$_2$)—CH$_3$, —CH(CH$_3$)—CH(OH)—CH(CH$_3$)$_2$, (CH$_2$OAc)$_2$, —(CH$_2$)$_n$—R$^6$, —(CH$_2$)$_n$—(CF$_2$)—CF$_3$, —CH((CH$_2$)$_n$—R$^5$)$_2$, —CH(CH$_3$)—CO—NH$_2$, —CH(CH$_2$OH)-phenyl, —CH(CH$_2$OH)—CH(OH)—(CH$_2$)$_n$R$^5$, —CH(CH$_2$OH)—CH(OH)-phenyl, —CH(CH$_2$OH)—C$_2$H$_4$—R$^5$, —(CH$_2$)$_n$—C≡C—C(CH$_3$)=CH—COR$^5$, —CH(Ph)—(CH$_2$)$_n$—R$^5$, —(CH$_2$)$_n$PO$_3$(R$^5$)$_2$, —CH((CH$_2$)$_n$OR$^5$)CO—R$^5$, —(CH$_2$)$_n$CONHCH((CH$_2$)$_n$ R$^5$)$_2$, —(CH$_2$)NH—COR$^5$, —CH(CH$_2$)$_n$R$^5$—(CH$_2$)$_n$C$_3$–C$_{10}$-cycloalkyl, —(CH$_2$)$_n$—C$_3$–C$_{10}$-cycloalkyl or, C$_3$–C$_{10}$-cycloalkyl, C$_1$–C$_6$-alkyl, C$_3$–C$_{10}$-cycloalkyl, —(CH$_2$)$_n$—O—(CH$_2$)$_n$—R$^5$, or —(CH$_2$)$_n$—NR$^3$R$^4$, —CH(C$_3$H$_7$H)—(CH$_2$)$_n$—OC(O)—(CH$_2$)—CH$_3$, —(CH$_2$)$_n$—R$^5$, —C(CH$_3$)$_2$—(CH$_2$)$_n$—R$^5$, —C(CH$_2$)$_n$(CH$_3$)—(CH$_2$)$_n$R$^5$, —C(CH$_2$)$_n$—(CH$_2$)$_n$R$^5$, —CH(t-butyl)—CH$_{2)n}$—R$^5$, —CCH$_3$(C$_3$H$_7$)—(CH$_2$)$_n$R$^5$, —(CH$_2$)$_n$—R$^3$, —CH(C$_3$H$_7$)—COR$^5$, —CH(C$_3$H$_7$)—(CH$_2$)$_n$—OC(O)—NH—Ph, —CH((CH$_2$)$_n$(C$_3$H$_7$))—(CH$_2$)$_n$R$^5$, —CH(C$_3$H$_7$)—(CH$_2$)$_n$—OC(O)—NH—Ph(OR$^5$)$_3$, R$^5$—(CH$_2$)$_n$—C*H—CH(R$^5$)—(CH$_2$)$_n$R$^5$, —(CH$_2$)$_n$—CO—NH—(CH$_2$)$_n$—CO—R$^5$, or —(CH$_2$)$_n$—CO—NH—(CH$_2$)$_n$—CH—((CH$_2$)$_n$R$^5$)$_2$, each of which is optionally substituted in one or more places in the same way or differently with hydroxy, $C_1$–$C_6$-alkyl or the group —NR$^3$R$^4$, or for $C_3$–$C_{10}$-cycloalkyl, which is substituted with the group

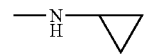

or for the group

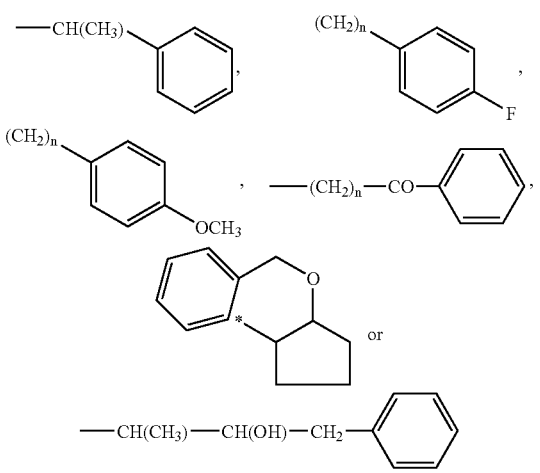

or for

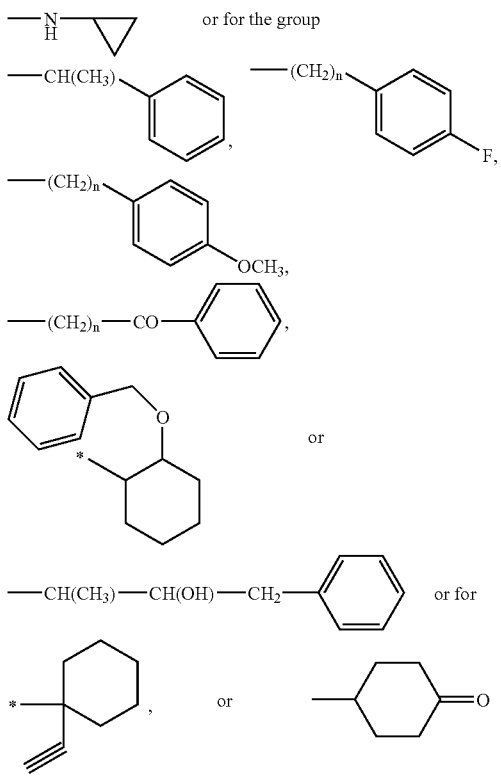

X stands for the group —NH—, or —N(C$_1$–C$_3$-alkyl) or R$^2$ stands for the group

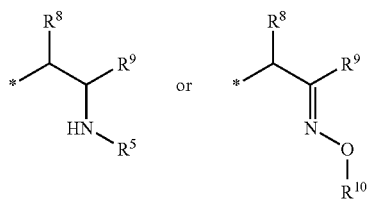

B stands for hydrogen, hydroxy, C$_1$–C$_3$-alkyl, C$_1$–C$_6$-alkoxy or for the group —S—CH$_3$, —SO$_2$—C$_2$H$_4$—

OH, —CO—CH$_3$, —S—CF$_2$, —S(CH$_2$)$_n$CH(OH)CH$_2$N-R$^3$R$^4$, —CH$_2$PO(OC$_2$H$_5$)$_2$, —S—CF$_3$, —SO—OH$_3$, —SO$_2$CF$_3$, —SO$_2$(CH$_2$)$_n$—N—R$^3$R$^4$, —SO$_2$—NR$^3$R$^4$, —SO$_2$R$^7$, —CH(OH)—CH$_3$, —COOH, —CH((CH$_2$)$_n$R$^5$)$_2$, —(CH$_2$)$_n$R$^5$, —COO—C$_1$–C$_6$-alkyl, or —CONR$^3$R$^4$, R$^7$ stands for halogen, hydroxy, phenyl, C$_1$–C$_6$-alkyl, —(CH$_2$)$_n$OH, or —NR$^3$R$^4$ R$^8$, R$^9$ and R$^{10}$ stand for hydrogen, hydroxy, C$_1$–C$_6$-alkyl or for the group —(CH$_2$)$_n$—COOH, and n stands for 1–6.

4. A composition comprising a compound of claim 1 and a pharmaceutically acceptable carrier.

5. A compound according to claim 1, wherein B is H, OH, or CH$_3$; and X is —NH— or —N(C$_1$–C$_3$-alkyl).

6. A compound according to claim 1, wherein B is H and X is —NH—.

7. A compound according to claim 1, wherein B is CH$_3$ and X is —NH—.

8. A compound according to claim 1, in the form of a diastereomer or an enantiomer.

9. A compound according to claim 1, wherein X is —NH—.

10. A compound according to claim 9, wherein one of R$^3$ and R$^4$ is H or methyl and the other is hydrogen, hydroxy, methyl, butyl, hexyl, heptyl, octyl, nonyl, decyl, 1-hydroxyethyl, 2-hydroxyethyl, 1-hydroxymethyl-2-hydroxyethyl, ethoxy, 2-methoxyethyl, prop-2-eneoxy, benzyloxy, 3-hydroxypropyl, 3-hydroxybutyl, 5-hydroxypentyl, cyclopropylmethyl, 4-cyanocyclohexylmethyl, cyclohexylmethyl, 2-methoxyphenylmethyl, 4-methylphenylmethyl, 2-fluorophenylmethyl, 3-fluorophenylmethyl, 4-fluorophenylmethyl, 2-methoxyphenylmethyl, 3,4-dimethoxyphenylmethyl, 2-phenyloxyethyl, 3,3-diphenyipropyl, phenylmethyl, 2-phenylethyl, 3-phenyipropyl, 4-phenylbutyl, 2-phenoxyethyl, 4-chloro-2-phenylethyl, 4-methoxyphenylethyl, 3-methylbutyl, cyclopropyl, or 4-sulfoaminophenylethyl.

11. A compound according to claim 10, wherein one of R$^3$ and R$^4$ is H or methyl and the other is hydrogen, methyl, hexyl, heptyl, octyl, nonyl, 2-hydroxyethyl, 2-methoxyethyl, 4-cyanocyclohexylmethyl, cyclohexylmethyl, 4-methylphenylmethyl, 2-methoxyphenylmethyl, 3,3-diphenylpropyl, 2-phenylethyl, 3-phenylpropyl, 4-phenylbutyl, 4-chloro-2-phenylethyl, or 3-methylbutyl.

12. A compound according to claim 11, wherein both R$^3$ and R$^4$ are hydrogen.

13. A compound according to claims 9, 10, 11, or 12 wherein B is H or methyl.

14. A compound according to claim 13, wherein B is H.

15. A compound according to claims 9, 10, 11, or 12 wherein R$^1$ is fluorine, bromine, chlorine, iodine, hydrogen, methyl, or ethyl.

16. A compound according to claim 13, wherein R$^1$ is fluorine, bromine, chlorine, iodine, hydrogen, methyl, or ethyl.

17. A compound according to claim 14, wherein R$^1$ is fluorine, bromine, chlorine, iodine, hydrogen, methyl, or ethyl.

18. A compound according to claim 15, wherein R$^1$ is bromine, chlorine, iodine, or methyl.

19. A compound according to claim 16, wherein R$^1$ is bromine, chlorine, iodine, or methyl.

20. A compound according to claim 17, wherein R$^1$ is bromine, chlorine, iodine, or methyl.

21. A compound according to claim 18, wherein $R^1$ is bromine.

22. A compound according to claim 19, wherein $R^1$ is bromine.

23. A compound according to claim 20, wherein $R^1$ is bromine.

24. A compound according to claims 9, 10, 11, or 12, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

25. A compound according to claim 13, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

26. A compound according to claim 14, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

27. A compound according to claim 15, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

28. A compound according to claim 16, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

29. A compound according to claim 17, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

30. A compound according to claim 18, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

31. A compound according to claim 19, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

32. A compound according to claim 20, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

33. A compound according to claim 21, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

34. A compound according to claim 22, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

35. A compound according to claim 23, wherein $R^2$ is (2R)-1-hydroxy-3-methylbut-2-yl, 2-propynyl, 1-hydroxybut-2-yl, 2-hydroxybut-3-yl, 1-hydroxyprop-2-yl, or methyl prop-2-yl ether.

36. A compound according to claim 24, wherein $R^2$ is 1-hydroxybut-2-yl or 1-hydroxyprop-2-yl.

37. A compound according to claim 25, wherein $R^2$ is 1-hydroxybut-2-yl or 1-hydroxyprop-2-yl.

38. A compound according to claim 26, wherein $R^2$ is 1-hydroxybut-2-yl or 1-hydroxyprop-2-yl.

39. A compound according to claim 27, wherein $R^2$ is 1-hydroxybut-2-yl or 1-hydroxyprop-2-yl.

40. A compound according to claim 28, wherein $R^2$ is 1-hydroxybut-2-yl or 1-hydroxyprop-2-yl.

41. A compound according to claim 29, wherein $R^2$ is 1-hydroxybut-2-yl or 1-hydroxyprop-2-yl.

42. A compound according to claim 30, wherein $R^2$ is 1-hydroxybut-2-yl or 1-hydroxyprop-2-yl.

43. A compound according to claim 31, wherein $R^2$ is 1-hydroxybut-2-yl or 1-hydroxyprop-2-yl.

44. A compound according to claim 32, wherein $R^2$ is 1-hydroxybut-2-yl or 1-hydroxyprop-2-yl.

45. A compound according to claim 33, wherein $R^2$ is 1-hydroxybut-2-yl or 1-hydroxyprop-2-yl.

46. A compound according to claim 34, wherein $R^2$ is 1-hydroxybut-2-yl or 1-hydroxyprop-2-yl.

47. A compound according to claim 35, wherein $R^2$ is 1-hydroxybut-2-yl or 1-hydroxyprop-2-yl.

48. A compound according to claim 1, wherein one of $R^3$ and $R^4$ is H or methyl and the other is hydrogen, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, $C_3$–$C_6$-cycloalkyl-$C_1$–$C_3$-alkyl that is optionally substituted with cyano, or $C_1$–$C_6$-alkyl that is optionally substituted in one or more places in the same way or differently with phenyl, phenyloxy, $C_3$–$C_6$-cycloalkyl, $C_1$–$C_6$-alkyl or $C_1$–$C_6$-alkoxy, wherein the phenyl groups can be substituted in one or more places in the same way or differently with halogen, $C_1$–$C_6$-alkyl, $C_1$–$C_6$-alkoxy or with the group —$SO_2NR^3R^4$.

49. A compound according to claim 9, wherein one of $R^3$ and $R^4$ is H.

50. A compound according to claim 10, wherein one of $R^3$ and $R^4$ is H.

51. A composition comprising a compound of claim 13 and a pharmaceutically acceptable carrier.

52. A composition comprising a compound of claim 15 and a pharmaceutically acceptable carrier.

53. A composition comprising a compound of claim 24 and a pharmaceutically acceptable carrier.

54. A compound of the formula:

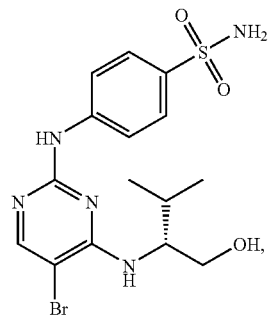

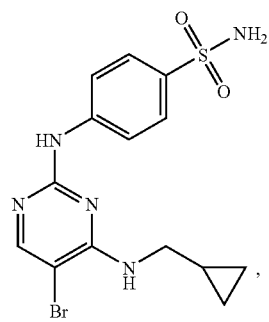

-continued
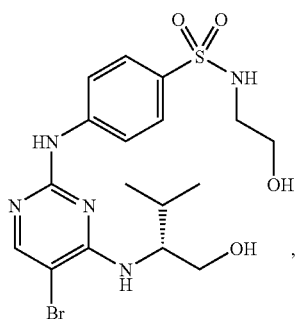
,
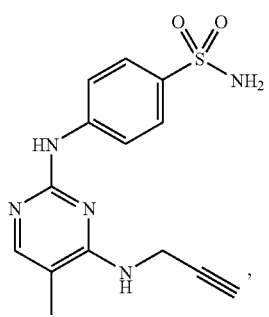
,
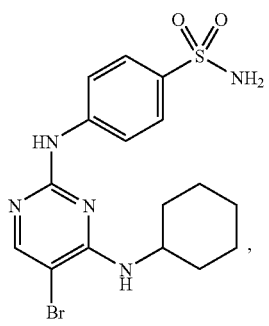
,
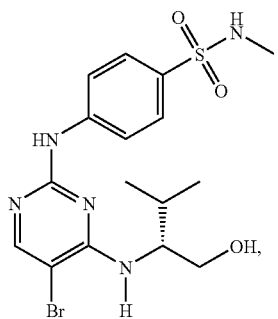
,
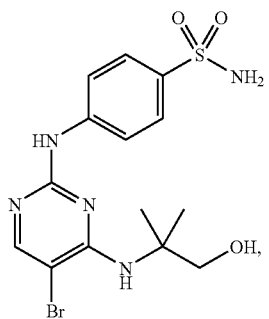
-continued
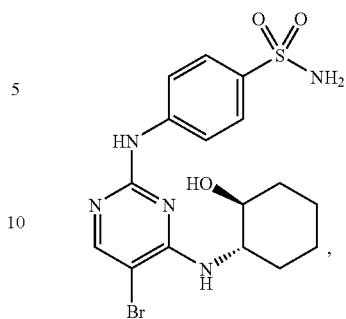
,
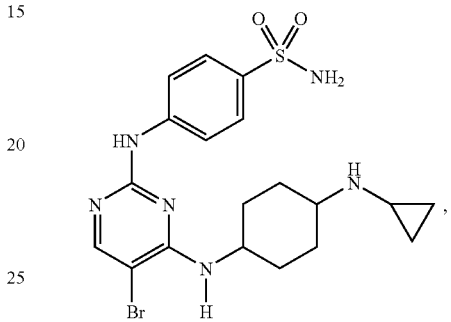
,
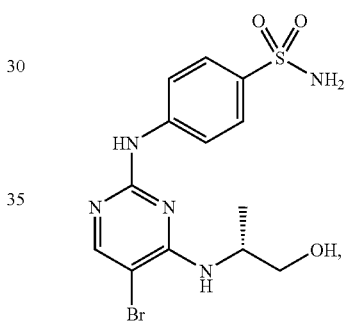
,
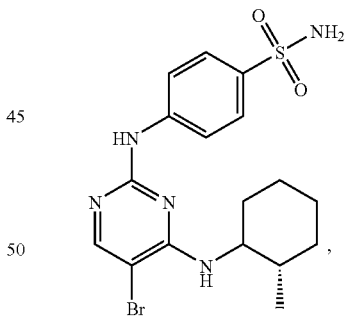
,
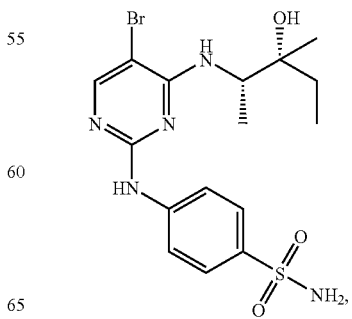

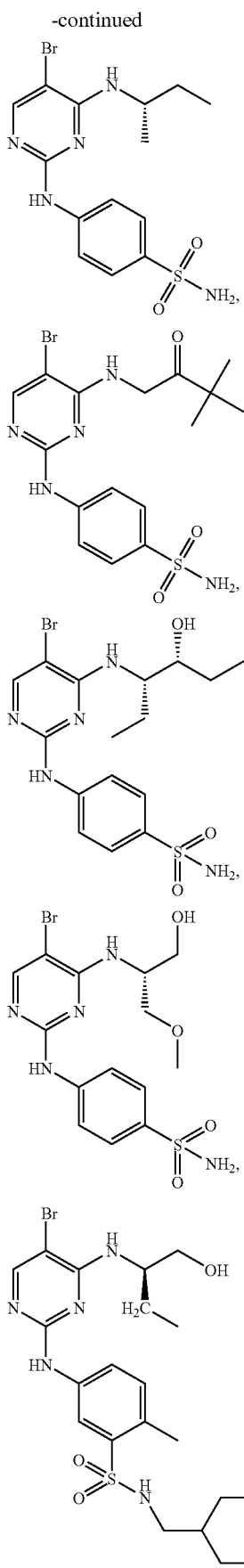

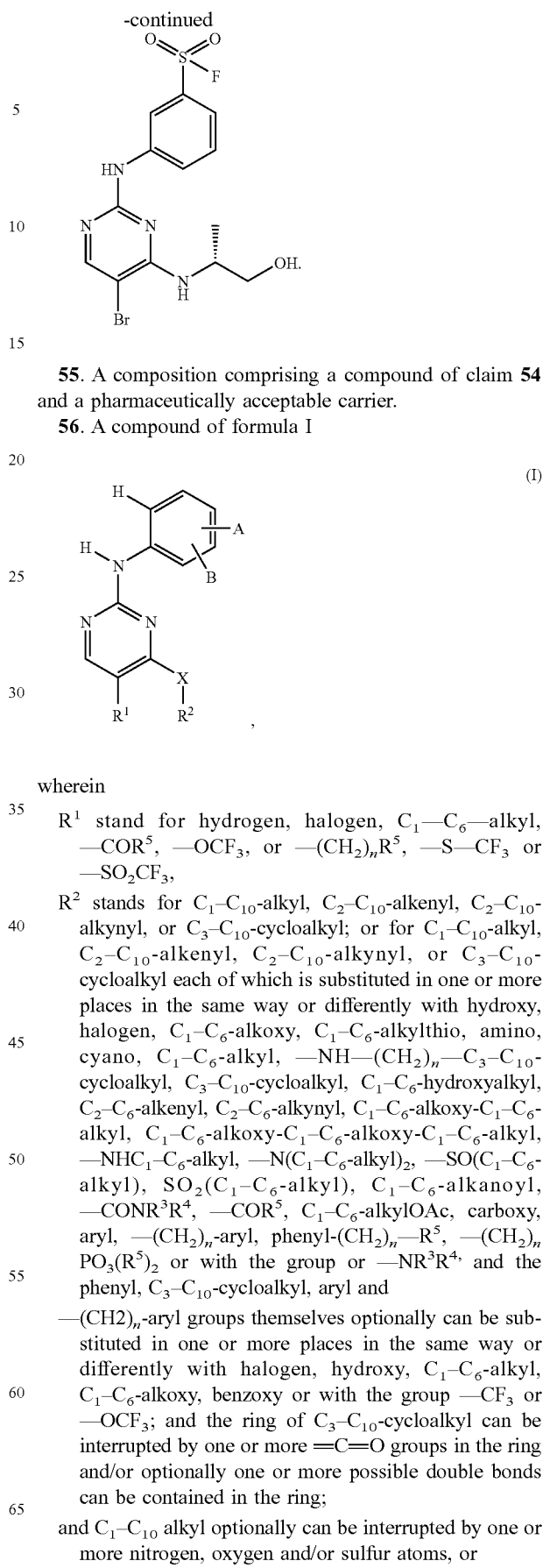

55. A composition comprising a compound of claim 54 and a pharmaceutically acceptable carrier.

56. A compound of formula I wherein

R$^1$ stand for hydrogen, halogen, C$_1$–C$_6$–alkyl, —COR$^5$, —OCF$_3$, or —(CH$_2$)$_n$R$^5$, —S—CF$_3$ or —SO$_2$CF$_3$, R$^2$ stands for C$_1$–C$_{10}$-alkyl, C$_2$–C$_{10}$-alkenyl, C$_2$–C$_{10}$-alkynyl, or C$_3$–C$_{10}$-cycloalkyl; or for C$_1$–C$_{10}$-alkyl, C$_2$–C$_{10}$-alkenyl, C$_2$–C$_{10}$-alkynyl, or C$_3$–C$_{10}$-cycloalkyl each of which is substituted in one or more places in the same way or differently with hydroxy, halogen, C$_1$–C$_6$-alkoxy, C$_1$–C$_6$-alkylthio, amino, cyano, C$_1$–C$_6$-alkyl, —NH—(CH$_2$)$_n$—C$_3$–C$_{10}$-cycloalkyl, C$_3$–C$_{10}$-cycloalkyl, C$_1$–C$_6$-hydroxyalkyl, C$_2$–C$_6$-alkenyl, C$_2$–C$_6$-alkynyl, C$_1$–C$_6$-alkoxy-C$_1$–C$_6$-alkyl, C$_1$–C$_6$-alkoxy-C$_1$–C$_6$-alkoxy-C$_1$–C$_6$-alkyl, —NHC$_1$–C$_6$-alkyl, —N(C$_1$–C$_6$-alkyl)$_2$, —SO(C$_1$–C$_6$-alkyl), SO$_2$(C$_1$–C$_6$-alkyl), C$_1$–C$_6$-alkanoyl, —CONR$^3$R$^4$, —COR$^5$, C$_1$–C$_6$-alkylOAc, carboxy, aryl, —(CH$_2$)$_n$-aryl, phenyl-(CH$_2$)$_n$—R$^5$, —(CH$_2$)$_n$PO$_3$(R$^5$)$_2$ or with the group or —NR$^3$R$^4$, and the phenyl, C$_3$–C$_{10}$-cycloalkyl, aryl and —(CH2)$_n$-aryl groups themselves optionally can be substituted in one or more places in the same way or differently with halogen, hydroxy, C$_1$–C$_6$-alkyl, C$_1$–C$_6$-alkoxy, benzoxy or with the group —CF$_3$ or —OCF$_3$; and the ring of C$_3$–C$_{10}$-cycloalkyl can be interrupted by one or more =C=O groups in the ring and/or optionally one or more possible double bonds can be contained in the ring;

and C$_1$–C$_{10}$ alkyl optionally can be interrupted by one or more nitrogen, oxygen and/or sulfur atoms, or $R^2$ stands for the group

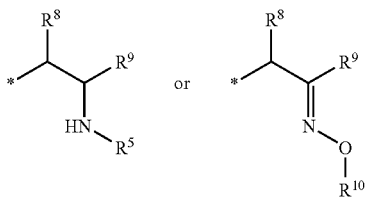

X stands for the group —NH—, or —N($C_1$–$C_3$-alkyl),

A independently of B stands for —$SO_2NR^3R^4$,

B independently of A stands for hydrogen, hydroxy, $C_1$–$C_3$ alkyl, $C_1$–$C_6$ alkoxy, —$SR^7$, —S(O)$R^7$, —$SO_2R^7$, —$NHSO_2$ $R^7$, —CH(OH)$R^7$, —$CR^7$(OH)—$R^7$, $C_1$–$C_6$-alkylP(O)O$R^3$O$R^4$ or —$COR^7$;

$R^3$ $R^4$, in each case independently of one another, stand for hydrogen, phenyl, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, $C_3$–$C_6$-cycloalkyl-$C_1$–$C_3$-alkyl that is optionally substituted with cyano, or for $C_1$–$C_6$-alkyl that is optionally substituted in one or more places in the same way or differently with phenyl, phenyloxy, $C_3$–$C_6$-cycloalkyl, $C_1$–$C_6$-alkyl or $C_1$–$C_6$-alkoxy, wherein the phenyl itself can be substituted in one or more places in the same way or differently with halogen, $C_1$–$C_6$-alkyl, $C_1$–$C_6$-alkoxy or —$SO_2NR^3R^4$, $R^5$ stands for hydroxy, phenyl, $C_1$–$C_6$-alkyl, $C_3$–$C_6$-cycloalkyl, benzoxy, $C_1$–$C_6$-alkylthio or $C_1$–$C_6$-alkoxy, 6 stands for a $C_3$–$C_{10}$-cycloalkyl ring, optionally can be interrupted by one or more =C=O groups in the ring and/or optionally one or more possible double bonds can be contained in the ring, $R^7$ stands for halogen, hydroxy, phenyl, $C_1$–$C_6$-alkyl, $C_2$–$C_6$-alkenyl, $C_2$–$C_6$-alkynyl, $C_3$–$C_{10}$-cycloalkyl, with the above-indicated meaning for $R^6$, or for the group —$NR^3R^4$, or for a $C_1$–$C_{10}$-alkyl, $C_2$–$C_{10}$-alkenyl, $C_2$–$C_{10}$-alkynyl or $C_3$–$C_7$-cycloalkyl that is substituted in one or more places in the same way or differently with hydroxy, $C_1$–$C_6$-alkoxy, halogen, —$NR^3R^4$ or phenyl which itself can be substituted in one or more places in the same way or differently with halogen, hydroxy, $C_1$–$C_6$-alkyl, $C_1$–$C_6$-alkoxy, halo-$C_1$–$C_6$-alkyl, halo-$C_1$–$C_6$-alkoxy; or $R^7$ stands for phenyl, which itself can be substituted in one or more places in the same way or differently with halogen, hydroxy, $C_1$–$C_6$-alkyl or $C_1$–$C_6$-alkoxy, halo-$C_1$–$C_6$-alkyl, or halo-$C_1$–$C_6$-alkoxy, $R^8$, $R^9$ and $R^{10}$, in each case independently of one another, stand for hydrogen, hydroxy, $C_1$–$C_{10}$-alkyl, $C_2$–$C_{10}$-alkenyl, $C_2$–$C_{10}$-alkynyl, $C_3$–$C_{10}$-cycloalkyl, or aryl, or for $C_1$–$C_{10}$-alkyl, $C_2$–$C_{10}$-alkenyl, $C_2$–$C_{10}$-alkynyl or $C_3$–$C_{10}$-cycloalkyl, each of which is optionally substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—(CH$_2$)$_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —NHC$_1$–$C_6$-alkyl, —N($C_1$–$C_6$-alkyl)$_2$, —SO($C_1$–$C_6$-alkyl), —$SO_2$($C_1$–$C_6$-alkyl), $C_1$–$C_6$-alkanoyl, —CON$R^3R^4$, —$COR^5$, $C_1$–$C_6$-alkylOAc, carboxy, aryl, —(CH$_2$)$_n$-aryl, phenyl-(CH$_2$)$_n$—$R^5$, —(CH$_2$)$_n$PO$_3$($R^5$)$_2$ or with the group —$R^6$ or —$NR^3R^4$, and the phenyl, $C_3$–$C_{10}$-cycloalkyl, aryl, and —(CH$_2$)$_n$-aryl itself optionally can be substituted in one or more places in the same way or differently with halogen, hydroxy, $C_1$–$C_6$-alkyl, $C_1$–$C_6$-alkoxy or with the group —$CF_3$ or —$OCF_3$; and the ring of $C_3$–$C_{10}$-cycloalkyl optionally can be interrupted by one or more =C=O groups in the ring and/or optionally one or more possible double bonds can be contained in the ring, and $C_1$–$C_{10}$alkyl optionally can be interrupted by one or more nitrogen, oxygen and/or sulfur atoms, and n stands for 0–6, or a pharmaceutically acceptable salt thereof.

57. A compound of formula I

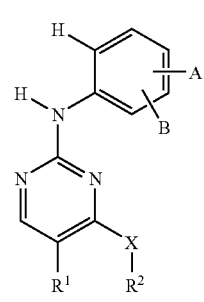

(I)

wherein $R^1$ stand for hydrogen, halogen, $C_1$—$C_6$—alkyl, nitro, —$COR^5$, —$OCF_3$, or —(CH$_2$)$_n$$R^5$, —S—$CF_3$ or —$SO_2CF_3$, $R^2$ stands for $C_1$–$C_{10}$-alkyl, $C_2$–$C_{10}$-alkenyl, $C_2$–$C_{10}$-alkynyl, or $C_3$–$C_{10}$-cycloalkyl; or for $C_1$–$C_{10}$-alkyl, $C_2$–$C_{10}$-alkenyl, $C_2$–$C_{10}$-alkynyl, or $C_3$–$C_{10}$-cycloalkyl each of which is substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—(CH$_2$)$_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —NHC$_1$–$C_6$-alkyl, —N($C_1$–$C_6$-alkyl)$_2$, —SO($C_1$–$C_6$-alkyl), $SO_2$($C_1$–$C_6$-alkyl), $C_1$–$C_6$-alkanoyl, —CON$R^3R^4$, —$COR^5$, $C_1$–$C_6$-alkylOAc, carboxy, aryl, —(CH$_2$)$_n$-aryl, phenyl-(CH$_2$)$_n$—$R^5$, —(CH$_2$)$_n$PO$_3$($R^5$)$_2$ or with the group or —$NR^3R^4$, and the phenyl, $C_3$–$C_{10}$-cycloalkyl, aryl and —(CH2)$_n$-aryl groups themselves optionally can be substituted in one or more places in the same way or differently with halogen, hydroxy, $C_1$–$C_6$-alkyl, $C_1$–$C_6$-alkoxy, benzoxy or with the group —$CF_3$ or —$OCF_3$; and the ring of $C_3$–$C_{10}$-cycloalkyl can be interrupted by one or more =C=O groups in the ring and/or optionally one or more possible double bonds can be contained in the ring;

and $C_1$–$C_{10}$ alkyl optionally can be interrupted by one or more nitrogen, oxygen and/or sulfur atoms, or $R^2$ stands for the group

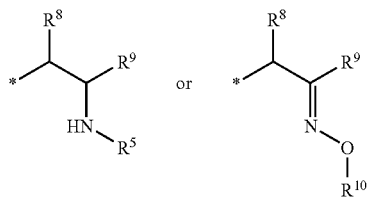

X stands for the group —NH—, or —N($C_1$–$C_3$-alkyl),

A independently of B stands for —$SO_2NR^3R^4$,

B independently of A stands for hydrogen, hydroxy, $C_1$–$C_3$ alkyl, $C_1$–$C_6$ alkoxy, —$SR^7$, —S(O)$R^7$, —$SO_2R^7$, —NHSO$_2$ $R^7$, —CH(OH)$R^7$, —$CR^7$(OH)—$R^7$, $C_1$–$C_6$-alkylP(O)O$R^3$O$R^4$ or —$COR^7$;

$R^3$ $R^4$, in each case independently of one another, stand for hydrogen, phenyl, benzyloxy, $C_1$–$C_{12}$-alkyl, $C_1$–$C_6$-alkoxy, $C_2$–$C_4$-alkenyloxy, $C_3$–$C_6$-cycloalkyl, hydroxy, hydroxy-$C_1$–$C_6$-alkyl, dihydroxy-$C_1$–$C_6$-alkyl, $C_3$–$C_6$-cycloalkyl-$C_1$–$C_3$-alkyl that is optionally substituted with cyano, or for $C_1$–$C_6$-alkyl that is optionally substituted in one or more places in the same way or differently with phenyl, phenyloxy, $C_3$–$C_6$-cycloalkyl, $C_1$–$C_6$-alkyl or $C_1$–$C_6$-alkoxy, wherein the phenyl itself can be substituted in one or more places in the same way or differently with halogen, $C_1$–$C_6$-alkyl, $C_1$–$C_6$-alkoxy or —$SO_2NR^3R^4$, $R^5$ stands for hydroxy, phenyl, $C_1$–$C_6$-alkyl, $C_3$–$C_6$-cycloalkyl, benzoxy, $C_1$–$C_6$-alkylthio or $C_1$–$C_6$-alkoxy, 6 stands for a $C_3$–$C_{10}$-cycloalkyl ring, optionally can be interrupted by one or more =C=O groups in the ring and/or optionally one or more possible double bonds can be contained in the ring, $R^7$ stands for halogen, hydroxy, phenyl, $C_1$–$C_6$-alkyl, $C_2$–$C_6$-alkenyl, $C_2$–$C_6$-alkynyl, $C_3$–$C_{10}$-cycloalkyl, with the above-indicated meaning for $R^6$, or for the group —$NR^3R^4$, or for a $C_1$–$C_{10}$-alkyl, $C_2$–$C_{10}$-alkenyl, $C_2$–$C_{10}$-alkynyl or $C_3$–$C_7$-cycloalkyl that is substituted in one or more places in the same way or differently with hydroxy, $C_1$–$C_6$-alkoxy, halogen, —$NR^3R^4$ or phenyl which itself can be substituted in one or more places in the same way or differently with halogen, hydroxy, $C_1$–$C_6$-alkyl, $C_1$–$C_6$-alkoxy, halo-$C_1$–$C_6$-alkyl, halo-$C_1$–$C_6$-alkoxy; or $R^7$ stands for phenyl, which itself can be substituted in one or more places in the same way or differently with halogen, hydroxy, $C_1$–$C_6$-alkyl or $C_1$–$C_6$-alkoxy, halo-$C_1$–$C_6$-alkyl, or halo-$C_1$–$C_6$-alkoxy, $R^8$, $R^9$ and $R^{10}$, in each case independently of one another, stand for hydrogen, hydroxy, $C_1$–$C_{10}$-alkyl, $C_2$–$C_{10}$-alkenyl, $C_2$–$C_{10}$-alkynyl, $C_3$–$C_{10}$-cycloalkyl, or aryl, or for $C_1$–$C_{10}$-alkyl, $C_2$–$C_{10}$-alkenyl, $C_2$–$C_{10}$-alkynyl or $C_3$–$C_{10}$-cycloalkyl, each of which is optionally substituted in one or more places in the same way or differently with hydroxy, halogen, $C_1$–$C_6$-alkoxy, $C_1$–$C_6$-alkylthio, amino, cyano, $C_1$–$C_6$-alkyl, —NH—($CH_2$)$_n$—$C_3$–$C_{10}$-cycloalkyl, $C_3$–$C_{10}$-cycloalkyl, $C_1$–$C_6$-hydroxyalkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, —NH$C_1$–$C_6$-alkyl, —N($C_1$–$C_6$-alkyl)$_2$, —SO($C_1$–$C_6$-alkyl), —$SO_2$($C_1$–$C_6$-alkyl), $C_1$–$C_6$-alkanoyl, —$CONR^3R^4$, —$COR^5$, $C_1$–$C_6$-alkylOAc, carboxy, aryl, —($CH_2$)$_n$-aryl, phenyl-($CH_2$)$_n$—$R^5$, —($CH_2$)$_n$PO$_3$($R^5$)$_2$ or with the group —$R^6$ or —$NR^3R^4$, and the phenyl, $C_3$–$C_{10}$-cycloalkyl, aryl, and —($CH_2$)$_n$-aryl itself optionally can be substituted in one or more places in the same way or differently with halogen, hydroxy, $C_1$–$C_6$-alkyl, $C_1$–$C_6$-alkoxy or with the group —CF$_3$ or —OCF$_3$; and the ring of $C_3$–$C_{10}$-cycloalkyl optionally can be interrupted by one or more =C=O groups in the ring and/or optionally one or more possible double bonds can be contained in the ring, and $C_1$–$C_{10}$alkyl optionally can be interrupted by one or more nitrogen, oxygen and/or sulfur atoms, and n stands for 0–6, or a pharmaceutically acceptable salt thereof with the proviso that said compound is not 2-(4-aminosulfonyl-phenylamino)--methylamino-5-nitro-pyrimidine.

58. A compound according to claim 1, wherein $R^1$ stands for hydrogen, halogen, $C_1$–$C_{-3}$-alkyl, or for the group —($CH_2$)$_n$$R^5$, $R^2$ stands for —CH($CH_3$)—($CH_2$)$_n$—$R^5$, —CH—($CH_2OH$)$_2$, —($CH_2$)$_n$$R^7$, —CH($C_3H_7$)—($CH_2$)$_n$—$R^5$, —CH($C_2H_5$)—($CH_2$)$_n$—$R^5$, —CH$_2$—CN, —CH($CH_3$)COCH$_3$, —CH($CH_3$)—C(OH)(CH$_3$)$_2$, —CH(CH(OH)CH$_3$)OCH$_3$, —CH($C_2H_5$)CO—$R^5$, $C_2$–$C_4$-alkynyl, —($CH_2$)$_n$—$COR^5$, —($CH_2$)$_n$—CO—$C_1$–$C_6$-alkyl, —($CH_2$)$_{n-C(OH)(CH3)}$-phenyl, —CH($CH_3$)—C($CH_3$)—$R^5$, —CH($CH_3$)—C($CH_3$)($C_2H_5$)—$R^5$, —CH(OCH$_3$)—CH$_2$—$R^5$, —CH$_2$—CH(OH)—$R^5$, —CH(OCH$_3$)—CH$R^5$—CH$_3$, —CH($CH_3$)—CH(OH)—CH$_2$—CH=CH$_2$, —CH($C_2H_5$)—CH(OH)—($CH_2$)$_n$—CH$_3$, —CH($CH_3$)—CH(OH)—($CH_2$)$_n$—CH$_3$, —CH($CH_3$)—CH(OH)—CH($CH_3$)$_2$, ($CH_2OAc$)$_2$, —($CH_2$)$_n$—$R^6$, —($CH_2$)$_n$—($CF_2$)—CF$_3$, —CH(($CH_2$)$_n$—$R^5$)$_2$, —CH($CH_3$)—CO—NH$_2$, —CH($CH_2OH$)-phenyl, —CH($CH_2OH$)—CH(OH)—($CH_2$)$_n$$R^5$, —CH($CH_2OH$)—CH(OH)-phenyl, —CH($CH_2OH$)—$C_2H_4$—$R^5$, —($CH_2$)$_n$—C≡C—C($CH_3$)=CH—$COR^5$, —CH(Ph)—($CH_2$)$_n$—$R^5$, —($CH_2$)$_n$PO$_3$($R^5$)$_2$, —CH(($CH_2$)$_n$O$R^5$)CO—$R^5$, —($CH_2$)$_n$CONHCH(($CH_2$)$_n$ $R^5$)$_2$, —($CH_2$)NH—$COR^5$, —CH($CH_2$)$_n$$R^5$—($CH_2$)$_n$$C_3$–$C_{10}$-cycloalkyl, —($CH_2$)$_n$—$C_3$–$C_{10}$-cycloalkyl, or, $C_3$–$C_{10}$-cycloalkyl, $C_1$–$C_6$-alkyl, $C_3$–$C_{10}$-cycloalkyl, —($CH_2$)$_n$—O—($CH_2$)$_n$—$R^5$, or —($CH_2$)$_n$—$NR^3R^4$, —CH($C_3H_7H$)—($CH_2$)$_n$—OC(O)—($CH_2$)—CH$_3$, —($CH_2$)$_n$—$R^5$, —C($CH_3$)$_2$—($CH_2$)$_n$—$R^5$, —C($CH_2$)$_n$(CH$_3$)—($CH_2$)$_n$$R^5$, —C($CH_2$)$_n$—($CH_2$)$_n$$R^5$, —CH(t-butyl)—CH$_{2n}$—$R^5$, —CCH$_3$($C_3H_7$)—($CH_2$)$_n$$R^5$, —($CH_2$)$_n$—$R^3$, —CH($C_3H_7$)—$COR^5$, —CH($C_3H_7$)—($CH_2$)$_n$—OC(O)—NH—Ph, —CH(($CH_2$)$_n$($C_3H_7$))—($CH_2$)$_n$$R^5$, —CH($C_3H_7$)—($CH_2$)$_n$—OC(O)—NH—Ph(O$R^5$)$_3$, $R^5$—($CH_2$)$_n$—C*H—CH($R^5$)—($CH_2$)$_n$$R^5$, —($CH_2$)$_n$—CO—NH—($CH_2$)$_n$—CO—$R^5$, or —($CH_2$)$_n$—CO—NH—($CH_2$)$_n$—CH—(($CH_2$)$_n$$R^5$)$_2$, each of which is optionally substituted in one or more places in the same way or differently with hydroxy, $C_1$–$C_6$-alkyl or the group or —$NR^3R^4$, or for $C_3$–$C_{10}$-cycloalkyl, which is substituted with the group

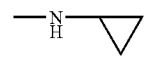

or for the group

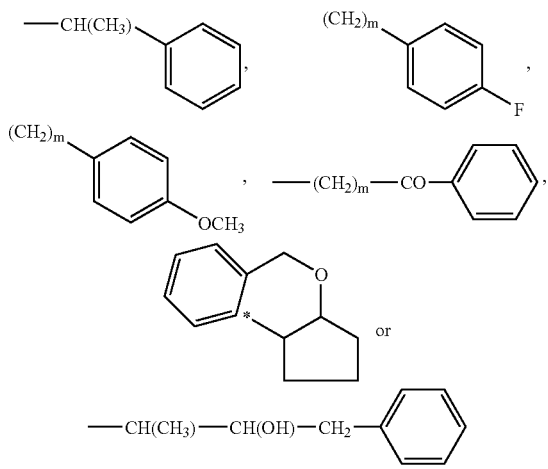

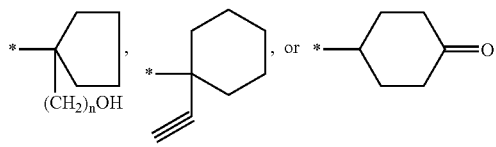

or for

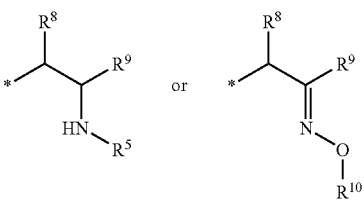

X stands for the group —NH—, or —N($C_1$–$C_3$-alkyl) or $R^2$ stands for the group

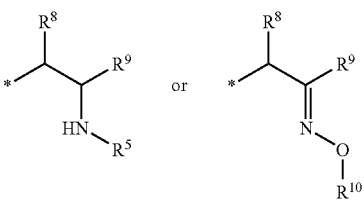

B stands for hydrogen, hydroxy, $C_1$–$C_3$-alkyl, $C_1$–$C_6$-alkoxy or for the group —S—$CH_3$, —$SO_2$—$C_2H_4$—OH, —CO—$CH_3$, —S—$CF_2$, —S($CH_2$)$_n$CH(OH)$CH_2$N-$R^3R^4$, —$CH_2$PO(O$C_2H_5$)$_2$, —S—$CF_3$, —SO—$OH_3$, —$SO_2CF_3$, —$SO_2$($CH_2$)$_n$—N—$R^3R^4$, —$SO_2$—$NR^3R^4$, —$SO_2R^7$, —CH(OH)—$CH_3$, —COOH, —CH(($CH_2$)$_nR^5$)$_2$, —($CH_2$)$_nR^5$, —COO—$C_1$–$C_6$-alkyl, or —$CONR^3R^4$, $R^7$ stands for halogen, hydroxy, phenyl, $C_1$–$C_6$-alkyl, —($CH_2$)$_n$OH, or —$NR^3R^4$ $R^8$, $R^9$ $R^{10}$ stand for hydrogen, hydroxy, $C_1$–$C_6$-alkyl or for the group —($CH_2$)$_n$—COOH, n stands for 0–6 m stands for 1–6.

* * * * *

UNITED STATES PATENT AND TRADEMARK OFFICE
CERTIFICATE OF CORRECTION

PATENT NO. : 7,235,561 B2
APPLICATION NO. : 10/156759
DATED : June 26, 2007
INVENTOR(S) : Thomas Brumby It is certified that error appears in the above-identified patent and that said Letters Patent is hereby corrected as shown below:

Column 359, line 49, reads "-$CH_2)_n$" should read -- -$(CH_2)_n$ --
Column 359, line 64, reads "group or –$NR^3R^4$," should read -- group –$R^6$ or –$NR^3R^4$, --
Column 359, line 66, reads "-$(CH2)_n$-aryl" should read -- -$(CH_2)_n$-aryl --
Column 360, line 28, begin new line after "-$OCF_3$;"
Column 360, line 32, reads "$C_1$-$C_{10}$ alkyl" should read -- $C_1$-$C_{10}$-alkyl --
Column 360, line 48, reads "$C_1$-$C_3$ alkyl, $C_1$-$C_6$ alkyloxy," should read
-- $C_1$-$C_3$-alkyl, $C_1$-$C_6$-alkyloxy, --
Column 360, line 51, reads "$R^3$ $R^4$" should read -- $R^3$ and $R^4$ --
Column 361, line 1, reads "6 stands for" should read -- $R^6$ stands for --
Column 361, line 1, reads "ring, optionally" should read -- ring, that optionally --
Column 361, line 16, begin new line after "halo-$C_1$-$C_6$-alkoxy; or"
Column 361, line 48, reads "$C_1$-$C_{10}$ alkyl" should read -- $C_1$-$C_{10}$-alkyl --
Column 362, line 45, reads "$C_3$-$C_{10}$-cycloalkyl or," should read -- $C_3$-$C_{10}$-cycloalkyl, or --
Column 362, line 47, reads "-$CH(C_3H_7H)$..." should read -- -$CH(C_3H_7)$... --
Column 362, line 48, reads "$OC(O)$-$(CH_2)$-$CH_3$," should read -- $OC(O)$-$(CH_2)_n$-$CH_3$, --
Column 362, line 50, reads "-$CH(t\text{-butyl})$-$CH_{2)n}$-$R^5$," should read
-- -$CH(t\text{-butyl})$-$(CH_2)_n$-$R^5$, --
Column 362, line 51, reads "-$CH_2)_n$-$R^5$," should read -- -$CH(C_3H_7)$-$(CH_2)_n$-$R^5$, --
Column 363, delete lines 23 to 46
Column 364, line 1, reads "-S-$CF_2$," should read -- -S-$CHF_2$, --
Column 364, line 3, reads "$OH_3$," should read -- $CH_3$, --
Column 364, line 37, reads "diphenyipropyl," should read -- diphenylpropyl, --
Column 364, line 38, reads "3-phenyipropyl," should read -- 3-phenylpropyl, --
Column 366, line 21, begin new line after "$C_1$-$C_6$-alkoxy,"
Column 370, line 54, reads "with the group or" should read -- with the group –$R^6$ or --
Column 370, line 54, reads "-$NR^3R^4$," should read -- -$NR^3R^4$, --
Column 370, line 61, begin new line after "-$OCF_3$;"

UNITED STATES PATENT AND TRADEMARK OFFICE
CERTIFICATE OF CORRECTION

PATENT NO. : 7,235,561 B2
APPLICATION NO. : 10/156759
DATED : June 26, 2007
INVENTOR(S) : Thomas Brumby It is certified that error appears in the above-identified patent and that said Letters Patent is hereby corrected as shown below:

Column 371, line 15, reads "$C_1$-$C_3$ alkyl, $C_1$-$C_6$ alkoxy," should read -- $C_1$-$C_3$-alkyl, $C_1$-$C_6$-alkoxy, --
Column 371, line 18, reads "$R^3R^4$," should read -- $R^3$ and $R^4$, --
Column 371, line 36, reads "6" should read -- $R^6$ --
Column 371, line 36, reads "ring, optionally" should read -- ring, that optionally --
Column 372, line 14, reads "$C_1$-$C_{10}$alkyl" should read -- $C_1$-$C_{10}$-alkyl --
Column 372, line 55, reads "the group or" should read -- the group –$R^6$ or --
Column 372, lines 56-57, delete line break between "and" and "-$(CH_2)_n$-aryl"
Column 372, line 57, reads "-(CH2)$_n$-aryl" should read -- -$(CH_2)_n$-aryl --
Column 372, line 61, begin new line after "-$OCF_3$;"

Signed and Sealed this

Fourteenth Day of October, 2008

JON W. DUDAS
*Director of the United States Patent and Trademark Office*